US009562052B2

(12) United States Patent
Buettelmann et al.

(10) Patent No.: US 9,562,052 B2
(45) Date of Patent: Feb. 7, 2017

(54) BICYCLICPYRIDINE DERIVATIVES

(71) Applicant: Hoffmann-La Roche Inc., Little Falls, NJ (US)

(72) Inventors: Bernd Buettelmann, Schopfheim (DE); Aurelia Conte, Shanghai (CN); Holger Kuehne, Loerrach (DE); Bernd Kuhn, Reinach BL (CH); Werner Neidhart, Hagenthal-le-Bas (FR); Ulrike Obst Sander, Reinach BL (CH); Hans Richter, Grenzach-Wyhlen (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/627,358

(22) Filed: Feb. 20, 2015

(65) Prior Publication Data

US 2015/0368256 A1 Dec. 24, 2015

Related U.S. Application Data

(63) Continuation of application No. PCT/EP2013/067220, filed on Aug. 19, 2013.

(30) Foreign Application Priority Data

Aug. 24, 2012 (EP) .................................... 12181739

(51) Int. Cl.

| | |
|---|---|
| ***C07D 215/54*** | (2006.01) |
| ***C07D 491/052*** | (2006.01) |
| ***C07D 401/14*** | (2006.01) |
| ***C07D 405/14*** | (2006.01) |
| ***C07D 413/14*** | (2006.01) |
| ***C07D 401/04*** | (2006.01) |
| ***C07D 409/14*** | (2006.01) |
| ***C07D 495/04*** | (2006.01) |
| ***C07D 221/04*** | (2006.01) |
| ***C07D 471/04*** | (2006.01) |

(52) U.S. Cl.

CPC ......... *C07D 491/052* (2013.01); *C07D 215/54* (2013.01); *C07D 221/04* (2013.01); *C07D 401/04* (2013.01); *C07D 401/14* (2013.01); *C07D 405/14* (2013.01); *C07D 409/14* (2013.01); *C07D 413/14* (2013.01); *C07D 471/04* (2013.01); *C07D 495/04* (2013.01)

(58) Field of Classification Search

CPC ... C07D 215/54; C07D 221/04; C07D 471/04; C07D 495/04; C07D 491/052; C07D 409/14; C07D 401/04; C07D 401/14; C07D 413/14; C07D 405/14

See application file for complete search history.

(56) References Cited

U.S. PATENT DOCUMENTS

| | | | | | |
|---|---|---|---|---|---|
| 5,436,247 | A * | 7/1995 | Sohda | C07D 231/12 514/266.23 |
| 5,719,157 | A * | 2/1998 | Sohda | A61K 31/47 514/266.2 |
| 5,770,602 | A * | 6/1998 | Sohda | C07D 231/12 514/266.23 |
| 5,852,039 | A * | 12/1998 | Sohda | A61K 31/47 514/311 |
| 5,932,592 | A * | 8/1999 | Sohda | C07D 231/12 514/266.24 |
| 5,948,782 | A * | 9/1999 | Sohda | A61K 31/47 514/248 |
| 9,199,938 | B2 * | 12/2015 | Ceccarelli | C07D 401/14 |
| 2012/0122837 | A1 | 5/2012 | Cheng et al. | |

OTHER PUBLICATIONS

ISR for PCT/EP2013/067220.

* cited by examiner

*Primary Examiner* — D M Seaman

(57) ABSTRACT

The invention provides novel compounds having the general formula (I)

(I)

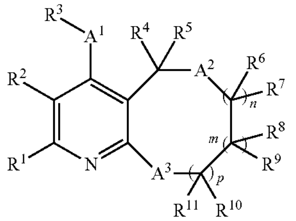

wherein $R^1$, $R^2$, $R^3$, $R^4$, $R^5$, $R^6$, $R^7$, $R^8$, $R^9$, $R^{10}$, $R^{11}$, $A^1$, $A^2$, $A^3$, m, n and p are as described herein, compositions including the compounds and methods of using the compounds.

30 Claims, No Drawings

BICYCLICPYRIDINE DERIVATIVES

CROSS REFERENCE TO RELATED APPLICATIONS

This Application is a continuation of International Application No. PCT/EP2013/067220 filed on Aug. 19, 2013, which is entitled to the priority of EP Application 12181739.9 filed on Aug. 24, 2012, the disclosures of which are incorporated herein by reference.

BACKGROUND OF THE INVENTION

FABP4 (aP2) and FABP5 (mal1) are members of the fatty acid binding protein family. FABPs are proteins of 14-15 KDa that act as chaperones for fatty acids in the aqueous cytosolic environment and facilitate their movement between cellular compartments. So far at least nine members of this family have been identified with a tissue-specific pattern of expression. FABP4 is mainly expressed in adipose tissue and macrophages, but also in other cell types, whereas FABP5 is expressed in a wide range of tissues and organs. FABPs are responsible for the transfer of fatty acids to different cell compartments and are thus implicated in key cellular functions such as lipid storage in adipocytes, fatty acid oxidation in mitochondria, ER signaling, fatty acid-dependent gene expression, regulation of cytosolic enzymes activity, modulation of inflammatory response and leukotriene synthesis. Plasma FABP4 is secreted by adipose tissue in mice and secretion is de-regulated in obesity and blocking of plasma FABP4 in vivo by antibodies improves insulin sensitivity.

Several genetic evidences in human support a role of FABP4 and FABP5 in metabolic diseases. A mutation in the FABP4 promoter (SNP T-87C) leading to 50% reduction in gene expression is associated to reduced cardiovascular diseases (CVDs) and type 2 diabetes (T2D) risk and to reduced plasma triglycerides (TGs). Two mutations in FABP5 gene, one in the 5'UTR (rs454550), one in the promoter (nSNP), are associated, respectively to increased (OR 4.24) and decreased risk (OR 0.48) of T2D. In addition, it was shown that FABP4 protein and mRNA levels in atherosclerotic plaque macrophages are associated to plaques instability and CV death. Finally, a large number of publications report an association between FABP4 and FABP5 plasma levels and severity of metabolic diseases. Elevated FABP4 plasma levels are associated with atherogenic dyslipidemia, reduced endothelial function, increased intima-media (IM) thickness, metabolic syndrome, obesity and insulin resistance IR. Elevated FABP5 plasma levels are associated to metabolic syndrome.

Genetic and pharmacological studies in mice largely confirm the human evidences. It was demonstrated that loss-of-function in FABP4 and FABP5 improves insulin sensitivity, lowers glucose, and protects against atherosclerosis. FABP4 knockout mice on high fat diet showed metabolic improvement that was tempered by compensatory up-regulation of FABP5 in adipose. Mice with a deletion of FABP5 gene on high fat (HF) diet showed body weight reduction and improved glucose and insulin tolerance. The FABP4/FABP5 double-knockout mice were strongly protected from hyperglycemia, insulin resistance, and hepatic steatosis. In addition, in an ApoE deficient background, FABP4 and FABP5 deletion was highly protective against the development of atherosclerosis and increased longevity. A specific FABP4 inhibitor (BMS309403), showed in a clamp study in ob/ob mice a reduction of hepatic glucose production, increased glucose uptake in muscle and adipose and reduction in hepatic steatosis, but no change in body weight and energy consumption. Also, it showed a decrease in atherosclerotic plaques formation in ApoE KO mice. A dual FABP4/5 inhibitor, Compound 3 described in J. Lipid Res. 2011, 52, 646, showed in mice under HF diet a reduction in plasma triglycerides and free fatty acids, but no improvement in insulin and glucose tolerance.

SUMMARY OF THE INVENTION

The present invention relates to organic compounds useful for therapy or prophylaxis in a mammal, and in particular to fatty acid binding protein (FABP) 4 and/or 5 inhibitors, more particularly dual FABP 4/5 inhibitors for the treatment or prophylaxis of e.g. type 2 diabetes, atherosclerosis, chronic kidney diseases, non-alcoholic steatohepatitis and cancer.

The present invention provides novel compounds of formula (I)

(I)

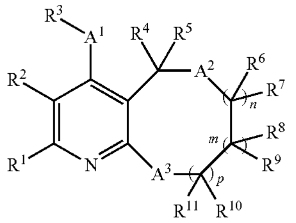

wherein $R^1$ is alkyl, haloalkyl, cycloalkyl, substituted cycloalkyl, alkoxy, alkoxyalkyl, alkoxyalkoxy, alkoxycarbonyl, alkoxycarbonylalkyl, carboxy, carboxyalkyl, haloalkyl, haloalkoxy, haloalkoxyalkyl, cycloalkoxy, substituted cycloalkoxy, cycloalkoxylalkyl, substituted cycloalkoxyalkyl, hydroxyalkyl, aryl, substituted aryl, heterocycloalkyl, substituted heterocycloalkyl, heterocycloalkoxy, substituted heterocycloalkoxy, heterocycloalkylalkoxy, substituted heterocycloalkylalkoxy, heteroaryl, substituted heteroaryl, amino, substituted amino, aminocarbonyl or substituted aminocarbonyl, wherein substituted cycloalkyl, substituted cycloalkoxy, substituted cycloalkoxyalkyl, substituted aryl, substituted heterocycloalkyl, substituted heterocycloalkoxy, substituted heterocycloalkylalkoxy and substituted heteroaryl are substituted with one to three substituents independently selected from hydroxy, oxo, halogen, alkyl, cycloalkyl, haloalkyl, alkylcycloalkyl, cycloalkylalkyl, alkylcycloalkylalkyl, hydroxyalkyl, alkylsulfonyl, alkylsulfonylalkyl, alkoxycarbonyl, alkoxy and alkoxyalkyl and wherein substituted amino and substituted aminocarbonyl are substituted on the nitrogen atom with one to two substituents independently selected from alkyl, cycloalkyl, haloalkyl, alkylcycloalkyl, cycloalkylalkyl, alkylcycloalkylalkyl, hydroxyalkyl and alkoxyalkyl;

$R^2$ is —COOH, tetrazol-5-yl, [1,3,4]oxadiazol-2-on-5-yl, [1,3,4]oxadiazole-2-thion-5-yl, [1,2,4]oxadiazol-5-on-3-yl, [1,2,4]oxadiazole-5-thion-3-yl, [1,2,3,5]oxathiadiazole-2-oxide-4-yl, [1,2,4]thiadiazol-5-on-3-yl, isoxazol-3-ol-5-yl, 5-alkylisoxazol-3-ol-4-yl, 5-cycloalkylisoxazol-3-ol-4-yl, furazan-3-ol-4-yl, 5-alkylsulfonylamino-[1,3,4]oxadiazol-2-yl, 5-cycloalkylsulfonylamino-[1,3,4]oxadiazol-2-yl, 5-alkylsulfonylamino-[1,2,4]triazol-3-yl, 5-cycloalkylsulfonylamino-[1,2,4]triazol-3-yl, 5-alkylisothiazol-3-ol-4-yl, 5-cycloalkylisothiazol-3-ol-4-yl, [1,2,5]thiadiazol-3-ol-4-yl, 1,4-dihydro-tetrazol-5-on-1-yl, tetrazol-5-ylcarbamoyl, tetrazole-5-carbonyl, [1,2,4]oxadiazolidine-3,5-dion-2-y, [1,2,4]oxadiazol-5-on-3-yl, 2,4-dihydro-[1,2,4]triazol-3-on-5-sulfanyl, [1,2,4]triazole-3-sulfanyl, [1,2,4]triazole-3-sulfinyl, [1,2,4]triazole-3-sulfonyl, 4-alkyl-pyrazol-1-ol-5-yl, 4-cycloalkyl-pyrazol-1-ol-5-yl, 4-alkyl-[1,2,3]triazol-1-ol-5-yl, 4-cycloalkyl-[1,2,3]triazol-1-ol-5-yl, 5-alkyl-imidazol-1-ol-2-yl, 5-cycloalkyl-imidazol-1-ol-2-yl, 4-alkyl-imidazol-1-ol-5-yl, 4-cycloalkyl-imidazol-1-ol-5-yl, 4-alkyl-1,1-dioxo-1$\lambda^6$-[1,2,5]thiadiazolidin-3-on-5-yl, 4,4-dialkyl-1,1-dioxo-1$\lambda^6$-[1,2,5]thiadiazolidin-3-on-5-yl, 4-cycloalkyl-1,1-dioxo-1$\lambda^6$-[1,2,5]thiadiazolidin-3-on-5-yl, 4,4-dicycloalkyl-1,1-dioxo-1$\lambda^6$-[1,2,5]thiadiazolidin-3-on-5-yl, thiazolidine-2,4-dion-5-yl, oxazolidine-2,4-dion-5-yl, 3-[1-hydroxy-meth-(E)-ylidene]-pyrrolidine-2,4-dion-1-yl, 3-[1-hydroxy-meth-(Z)-ylidene]-pyrrolidine-2,4-dion-1-yl, 5-methyl-4-hydroxyfuran-2-on-3-yl, 5,5-dialkyl-4-hydroxyfuran-2-on-3-yl, 5-cycloalkyl-4-hydroxyfuran-2-on-3-yl, 5,5-dicycloalkyl-4-hydroxyfuran-2-on-3-yl, 3-hydroxycyclobut-3-ene-1,2-dion-4-yl or 3-hydroxycyclobut-3-ene-1,2-dion-4-amino;

$R^3$ is phenyl, substituted phenyl, substituted dihydropyridinyl, heteroaryl or substituted heteroaryl, wherein substituted phenyl, substituted dihydropyridinyl and substituted heteroaryl are substituted with one to three substituents independently selected from hydroxy, oxo, halogen, alkyl, cycloalkyl, haloalkyl, haloalkoxy, alkylcycloalkyl, cycloalkylalkyl, alkylcycloalkylalkyl, hydroxyalkyl, hydroxyalkoxy, alkoxy, alkoxyalkyl, alkylsulfonyl, amino and amino substituted on the nitrogen atom with one to two substituents independently selected from alkyl, cycloalkyl, haloalkyl, alkylcycloalkyl, cycloalkylalkyl, alkylcycloalkylalkyl, hydroxyalkyl and alkoxyalkyl;

$A^1$ is a bond or $CR^{12}R^{13}$;

$A^2$ is $—CR^{14}R—$, $—NR^{16}—$, —O—, —S—, —S(O)— or $—S(O)_2—$;

$A^3$ is $—CR^{17}R^{18}—$, $—C(O)NR^{19}—$, $—NR^{19}—$, —O—, —S—, —S(O)— or $—S(O)_2—$;

$R^4$, $R^5$, $R^6$, $R^7$, $R^8$, $R^9$, $R^{10}$, $R^{11}$, $R^{14}$, $R^{15}$, $R^{17}$ and $R^{18}$ are independently selected from H, halogen, alkyl, alkoxy, cycloalkyl, cycloalkylalkoxy, haloalkoxy and haloalkyl.

$R^{12}$ and $R^{13}$ are independently selected from hydrogen, alkyl, cycloalkyl and haloalkyl.

$R^{16}$ and $R^{19}$ are independently selected from hydrogen, alkyl, cycloalkyl, haloalkyl and alkylcarbonyl.

n, m and p are independently selected from zero and 1; or pharmaceutically acceptable salts.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of type 2 diabetes, metabolic syndrome, atherosclerosis, dyslipidemia, liver diseases involving inflammation, steatosis and/or fibrosis, such as non-alcoholic fatty liver disease, in particular non-alcoholic steatohepatitis, obesity, lipodystrophy, such as genetic and iatrogenic lipodystrophy, cancer, eye diseases supported by endothelial proliferation and angiogenesis, such as macular degeneration and retinopathy, lung diseases, such as asthma, bronchopulmonary dysplasia and chronic obstructive pulmonary disease, sarcoidosis, chronic renal diseases, such as vasculitis, focal segmental glomerulosclerosis, diabetic nephropathy, lupus nephritis, polycystic kidney disease and drug or toxin-induced chronic tubulointerstitial nephritis, chronic inflammatory and autoimmune inflammatory diseases, preeclampsia and polycystic ovary syndrome, and the use of the said compounds, salts or esters for the production of medicaments for the treatment or prophylaxis of of type 2 diabetes, metabolic syndrome, atherosclerosis, dyslipidemia, liver diseases involving inflammation, steatosis and/or fibrosis, such as non-alcoholic fatty liver disease, in particular non-alcoholic steatohepatitis, obesity, lipodystrophy, such as genetic and iatrogenic lipodystrophy, cancer, eye diseases supported by endothelial proliferation and angiogenesis, such as macular degeneration and retinopathy, lung diseases, such as asthma, bronchopulmonary dysplasia and chronic obstructive pulmonary disease, sarcoidosis, chronic renal diseases, such as vasculitis, focal segmental glomerulosclerosis, diabetic nephropathy, lupus nephritis, polycystic kidney disease and drug or toxin-induced chronic tubulointerstitial nephritis, chronic inflammatory and autoimmune inflammatory diseases, preeclampsia and polycystic ovary syndrome.

Compounds of the present invention are FABP 4 and/or 5 inhibitors, more particularly dual FABP 4 and 5 inhibitors. Some particular compounds of formula (I) of the present invention are also selective FABP 4 and/or 5 inhibitors compared to FABP 3 and/or 1.

DETAILED DESCRIPTION OF THE INVENTION

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include methoxy, ethoxy and isopropoxy. More particular, alkoxy group is methoxy.

The term "alkoxyalkoxy" denotes an alkoxy group wherein at least one of the hydrogen atoms of the alkoxy group has been replaced by another alkoxy group. Example of alkoxyalkoxy group includes methoxyethoxy, The term "alkoxyalkyl" denotes an alkyl group wherein at least one of the hydrogen atoms of the alkyl group has been replaced by an alkoxy group. Exemplary alkoxyalkyl groups include methoxymethyl, ethoxymethyl, methoxyethyl, methoxydimethylethyl, methoxymethylpentanyl, methoxymethylpropanyl, ethoxyethyl, methoxypropyl and ethoxypropyl. Particular alkoxyalkyl groups include methoxymethyl and 2-methoxy-1,1-dimethylethyl.

The term "alkoxycarbonyl" denotes a group of the formula —C(O)—R', wherein R' is an alkoxy group. Examples of alkoxycarbonyl groups include groups of the formula —C(O)—R', wherein R' is methoxy, ethoxy, n-propoxy, isopropoxy, n-butoxy, isobutoxy and tert-butoxy. Particular alkoxycarbonyl group is a group of the formula —C(O)—R', wherein R' is tert-butoxy.

The term "alkoxycarbonylalkyl" denotes an alkyl group wherein one of the hydrogen atoms of the alkyl group has been replaced by an alkoxycarbonyl group. Particular alkoxycarbonylalkyl includes 2-tert-butoxy-1,1-dimethyl-2-oxo-ethyl.

The term "alkyl" denotes a monovalent linear or branched saturated hydrocarbon group of 1 to 12 carbon atoms, in particular of 1 to 7 carbon atoms, more particular of 1 to 4 carbon atoms, for example, methyl, ethyl, propyl, isopropyl, n-butyl, iso-butyl, sec-butyl, tert-butyl, ethylpropyl and dimethylpropyl. Particular alkyl groups include methyl, ethyl, propyl, isopropyl, n-butyl, sec-butyl, tert-butyl, ethylpropyl and dimethylpropyl. Further particular alkyl groups include methyl and ethylpropyl.

The term "alkylcarbonyl" denotes a group of the formula —C(O)—R', wherein R' is an alkyl group. Examples of alkylcarbonyl groups include groups of the formula —C(O)—R', wherein R' is methyl, ethyl, propyl, isopropyl, n-butyl, iso-butyl, sec-butyl and tert-butyl. Particular alkylcarbonyl group is a group of the formula —C(O)—R', wherein R' is methyl.

The term "alkylcycloalkyl" denotes a cycloalkyl group wherein at least one of the hydrogen atoms of the cycloalkyl group is replaced by an alkyl group. Examples of alkylcycloalkyl include methyl-cyclopropyl, dimethyl-cyclopropyl, methyl-cyclobutyl, dimethyl-cyclobutyl, methyl-cyclopentyl, dimethyl-cyclopentyl, methyl-cyclohexyl and dimethyl-cyclohexyl. Particular alkylcycloalkyl groups include methyl-cyclopropyl and dimethyl-cyclopropyl.

The term "alkylcycloalkylalkyl" denotes an alkyl group wherein at least one of the hydrogen atoms of the alkyl group is replaced by an alkylcycloalkyl group. Examples of alkylcycloalkylalkyl include methyl-cyclopropylmethyl, dimethyl-cyclopropylmethyl, methyl-cyclopropylethyl, dimethyl-cyclopropylethyl, methyl-cyclobutylmethyl, dimethyl-cyclobutylmethyl, methyl-cyclobutylethyl, dimethyl-cyclobutylethyl, methyl-cylopentylmethyl, dimethyl-cylopentylmethyl, methyl-cyclopentylethyl, dimethyl-cyclopentylethyl, methyl-cyclohexylmethyl, dimethyl-cyclohexylmethyl, methyl-cyclohexylethyl, dimethyl-cyclohexylethyl, methyl-cycloheptylmethyl, dimethyl-cycloheptylmethyl, methyl-cycloheptylethyl, dimethyl-cycloheptylethyl, methyl-cyclooctylmethyl, dimethyl-cyclooctylmethyl, methyl-cyclooctylethyl and dimethyl-cyclooctylethyl.

The term "alkylsulfonyl" denotes a group of the formula —$S(O)_2$—R', wherein R' is an alkyl group. Examples of alkylsulfonyl groups include groups of the formula —$S(O)_2$—R', wherein R' is methyl, ethyl, n-propyl, isopropyl, n-butyl, isobutyl and tert-butyl. Particular example is a group of the formula —$S(O)_2$—R', wherein R' is methyl.

The term "alkylsulfonylalkyl" denotes an alkyl group wherein one of the hydrogen atoms of the alkyl group has been replaced by an alkylsulfonyl group. Particular example of alkylsulfonylalkyl is methylsulfonylmethyl. The term "alkylsulfonylamino" denotes a group of formula —NH—$S(O)_2$—R' wherein R' is an alkyl group. Examples of alkylsulfonylamino include methylsulfonylamino, ethylsulfonylamino, propylsulfonylamino, isopropylsulfonylamino, n-butylsulfonylamino, iso-butylsulfonylamino, sec-butylsulfonylamino, and tert-butylsulfonylamino The term "amino" denotes a —$NH_2$ group.

The term "aminocarbonyl" denotes a group of the formula —C(O)—$NH_2$

The term "aryl" denotes a monovalent aromatic carbocyclic mono- or bicyclic ring system comprising 6 to 10 carbon ring atoms. Examples of aryl moieties include phenyl and naphthyl. Particular aryl group is phenyl.

The term "carbonyl" denotes a —C(O)— group.

The term "cycloalkoxy" denotes a group of the formula —O—R', wherein R' is a cycloalkyl group. Examples of cycloalkoxy group include cyclopropoxy, cyclobutoxy, cyclopentyloxy, cyclohexyloxy, cycloheptyloxy and cyclooctyloxy. Particular cycloalkoxy group is cyclopentyloxy.

The term "cycloalkoxyalkyl" denotes an alkyl group wherein at least one of the hydrogen atoms of the alkyl group has been replaced by a cycloalkoxy group. Examples of cycloalkoxyalkyl group include cyclopropoxymethyl, cyclopropoxyethyl, cyclobutoxymethyl, cyclobutoxyethyl, cyclopentyloxymethyl, cyclopentyloxyethyl, cyclohexyloxymethyl, cyclohexyloxyethyl, cycloheptyloxymethyl, cycloheptyloxyethyl, cyclooctyloxymethyl and cyclooctyloxyethyl.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. Bicyclic means consisting of two saturated or partially saturated carbocycles having two carbon atoms in common. Particular cycloalkyl groups are cyclopropyl, cyclobutyl, cyclopentyl, cyclohexyl and cycloheptenyl. Further particular cycloalkyl groups are cyclobutyl, cyclopentyl and cyclohexyl.

The term "cycloalkylalkoxy" denotes an alkoxy group wherein at least one of the hydrogen atoms of the alkoxy group is replaced by a cycloalkyl group. Examples of cycloalkylalkoxy include cyclopropylmethoxy, cyclobutylmethoxy, cyclopentylmethoxy, cyclohexylmethoxy, cycloheptylmethoxy and cyclooctylmethoxy.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclobutylpropyl and cyclopentylbutyl.

The term "cycloalkylsulfonylamino" denotes a group of formula —NH—$S(O)_2$—R' wherein R' is a cycloalkyl group. Examples of cycloalkylsulfonylamino include cyclopropylsulfonylamino, cyclobutanylsulfonylamino, cyclopentylsulfonylamino or cyclohexylsulfonylamino.

The term "haloalkoxy" denotes an alkoxy group wherein at least one of the hydrogen atoms of the alkoxy group has been replaced by same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups are trifluoromethoxy, trifluoroethoxy and trifluoromethylethoxy.

The term "haloalkoxyalkyl" denotes an alkyl group wherein at least one of the hydrogen atoms of the alkyl group has been replaced by a haloalkoxy group. Examples of haloalkoxyalkyl include fluoromethoxymethyl, difluoromethoxymethyl, trifluoromethoxymethyl, fluoroethoxymethyl, difluoroethoxymethyl, trifluoroethoxymethyl, fluoromethoxyethyl, difluoromethoxyethyl, trifluoromethoxyethyl, fluoroethoxyethyl, difluoroethoxyethyl, trifluoroethoxyethyl, fluoromethoxypropyl, difluoromethoxypropyl, trifluoromethoxypropyl, fluoroethoxypropyl, difluoroethoxypropyl and trifluoroethoxypropyl. Particular haloalkoxyalkyl group is 2,2-difluoroethoxyethyl.

The term "haloalkyl" denotes an alkyl group wherein at least one of the hydrogen atoms of the alkyl group has been replaced by same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl groups are trifluoromethyl and trifluoroethyl.

The term "halogen" and "halo" are used interchangeably herein and denote fluoro, chloro, bromo, or iodo. Particular halogens are chloro and fluoro. More particular halogen is fluoro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzisoxazolyl, benzothiazolyl, benzisothiazolyl, benzoxadiazolyl, benzothiadiazolyl, benzotriazolyl, purinyl, quinolinyl, isoquinolinyl, quinazolinyl, or quinoxalinyl. Particular heteroaryl groups are furanyl, thienyl, imidazolyl, thiazolyl, triazolyl, tetrazolyl, pyridinyl, pyrazolyl, pyridazinyl, pyrimidinyl and isoxazolyl.

In the case of $R^1$, particular heteroaryl is furanyl.

In the case of $R^3$, particular heteroaryl are thienyl, imidazolyl, thiazolyl, triazolyl, tetrazolyl, pyridinyl, pyrazolyl, pyridazinyl, pyrimidinyl and isoxazolyl. Also particular heteroaryl are oxazolyl, indolyl, pyridinonyl and indazolyl, The term "heterocycloalkoxy" denotes a group of the formula —O—R', wherein R' is a heterocycloalkyl group. Particular R' are tetrahydrofuranyl and tetrahydro-2H-pyranyl. Further particular R' is tetrahydrofuranyl.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are 4,5-dihydro-oxazolyl, oxetanyl, azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Particular examples of heterocycloalkyl group are azetidinyl, pyrrolidinyl, tetrahydrofuranyl, piperidinyl and tetrahydropyranyl. Further particular examples of heterocycloalkyl group are tetrahydrofuranyl and piperidinyl.

The term "heterocycloalkylalkoxy" denotes an alkoxy group wherein at least one of the hydrogen atoms of the alkoxy group is replaced by a heterocycloalkyl group. Particular example of heterocycloalkylalkoxy is tetrahydrofuranylmethyl.

The term "hydroxy" denotes a —OH group.

The term "hydroxyalkoxy" denotes an alkoxy group wherein at least one of the hydrogen atoms of the alkoxy group has been replaced by a hydroxy group. Examples of hydroxyalkoxy include hydroxyethoxy, hydroxypropoxy, hydroxymethylpropoxy and dihydroxypropoxy. Particular example of hydroxyalkoxy group is hydroxyethoxy.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxypropyl, hydroxymethylpropyl and dihydroxypropyl. Particular examples are hydroxymethyl and hydroxyethyl.

The term "carboxy" denotes a COOH group.

The term "carboxyalkyl" denotes an alkyl group wherein one of the hydrogen atoms of the alkyl group has been replaced by a carboxy group. Particular carboxyalkyl group is 1-carboxy-1-methyl-ethyl.

The term "oxo" denotes a =O group.

The term "sulfonyl" denotes a $-S(O)_2-$ group.

The term "pharmaceutically acceptable salts" refers to those salts which retain the biological effectiveness and properties of the free bases or free acids, which are biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts. Particular pharmaceutically acceptable salts of compounds of formula (I) are also the sodium and potassium salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the tert-butoxycarbonyl (Boc).

The compounds of formula (I) can contain several asymmetric centers and/or stereoaxis and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

An embodiment of the present invention are compounds of formula (I)

(I)

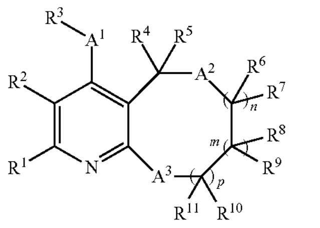

wherein $R^1$ is alkyl, haloalkyl, cycloalkyl, substituted cycloalkyl, alkoxy, alkoxyalkyl, haloalkoxy, haloalkoxyalkyl, cycloalkoxy, substituted cycloalkoxy, cycloalkoxylalkyl, substituted cycloalkoxyalkyl, hydroxyalkyl, aryl, substituted aryl, heterocycloalkyl, substituted heterocycloalkyl, heteroaryl, substituted heteroaryl, amino, substituted amino, aminocarbonyl or substituted aminocarbonyl, wherein substituted cycloalkyl, substituted cycloalkoxy, substituted cycloalkoxyalkyl, substituted aryl, substituted heterocycloalkyl and substituted heteroaryl are substituted with one to three substituents independently selected from hydroxy, oxo, halogen, alkyl, cycloalkyl, haloalkyl, alkylcycloalkyl, cycloalkylalkyl, alkylcycloalkylalkyl, hydroxyalkyl, alkoxy and alkoxyalkyl and wherein substituted amino and substituted aminocarbonyl are substituted on the nitrogen atom with one to two substituents independently selected from alkyl, cycloalkyl, haloalkyl, alkylcycloalkyl, cycloalkylalkyl, alkylcycloalkylalkyl, hydroxyalkyl and alkoxyalkyl;

$R^2$ is —COOH, tetrazol-5-yl, [1,3,4]oxadiazol-2-on-5-yl, [1,3,4]oxadiazole-2-thion-5-yl, [1,2,4]oxadiazol-5-on-3-yl, [1,2,4]oxadiazole-5-thion-3-yl, [1,2,3,5]oxathiadiazole-2-oxide-4-yl, [1,2,4]thiadiazol-5-on-3-yl, isoxazol-3-ol-5-yl, 5-alkylisoxazol-3-ol-4-yl, 5-cycloalkylisoxazol-3-ol-4-yl, furazan-3-ol-4-yl, 5-alkylsulfonylamino-[1,3,4]oxadiazol-2-yl, 5-cycloalkylsulfonylamino-[1,3,4]oxadiazol-2-yl, 5-alkylsulfonylamino-[1,2,4]triazol-3-yl, 5-cycloalkylsulfonylamino-[1,2,4]triazol-3-yl, 5-alkylisothiazol-3-ol-4-yl, 5-cycloalkylisothiazol-3-ol-4-yl, [1,2,5]thiadiazol-3-ol-4-yl, 1,4-dihydro-tetrazol-5-on-1-yl, tetrazol-5-ylcarbamoyl, tetrazole-5-carbonyl, [1,2,4]oxadiazolidine-3,5-dion-2-y, [1,2,4]oxadiazol-5-on-3-yl, 2,4-dihydro-[1,2,4]triazol-3-on-5-sulfanyl, [1,2,4]triazole-3-sulfanyl, [1,2,4]triazole-3-sulfinyl, [1,2,4]triazole-3-sulfonyl, 4-alkyl-pyrazol-1-ol-5-yl, 4-cycloalkyl-pyrazol-1-ol-5-yl, 4-alkyl-[1,2,3]triazol-1-ol-5-yl, 4-cycloalkyl-[1,2,3]triazol-1-ol-5-yl, 5-alkyl-imidazol-1-ol-2-yl, 5-cycloalkyl-imidazol-1-ol-2-yl, 4-alkyl-imidazol-1-ol-5-yl, 4-cycloalkyl-imidazol-1-ol-5-yl, 4-alkyl-1,1-dioxo-1λ$^6$-[1,2,5]thiadiazolidin-3-on-5-yl, 4,4-dialkyl-1,1-dioxo-1λ$^6$-[1,2,5]thiadiazolidin-3-on-5-yl, 4-cycloalkyl-1,1-dioxo-1λ$^6$-[1,2,5]thiadiazolidin-3-on-5-yl, 4,4-dicycloalkyl-1,1-dioxo-1λ$^6$-[1,2,5]thiadiazolidin-3-on-5-yl, thiazolidine-2,4-dion-5-yl, oxazolidine-2,4-dion-5-yl, 3-[1-hydroxy-meth-(E)-ylidene]-pyrrolidine-2,4-dion-1-yl, 3-[1-hydroxy-meth-(Z)-ylidene]-pyrrolidine-2,4-dion-1-yl, 5-methyl-4-hydroxyfuran-2-on-3-yl, 5,5-dialkyl-4-hydroxyfuran-2-on-3-yl, 5-cycloalkyl-4-hydroxyfuran-2-on-3-yl, 5,5-dicycloalkyl-4-hydroxyfuran-2-on-3-yl, 3-hydroxycyclobut-3-ene-1,2-dion-4-yl or 3-hydroxycyclobut-3-ene-1,2-dion-4-amino;

$R^3$ is phenyl, substituted phenyl, substituted dihydropyridinyl, heteroaryl or substituted heteroaryl, wherein substituted phenyl, substituted dihydropyridinyl and substituted heteroaryl are substituted with one to three substituents independently selected from hydroxy, oxo, halogen, alkyl, cycloalkyl, haloalkyl, alkylcycloalkyl, cycloalkylalkyl, alkylcycloalkylalkyl, hydroxyalkyl, hydroxyalkoxy, alkoxy, alkoxyalkyl, amino and amino substituted on the nitrogen atom with one to two substituents independently selected from alkyl, cycloalkyl, haloalkyl, alkylcycloalkyl, cycloalkylalkyl, alkylcycloalkylalkyl, hydroxyalkyl and alkoxyalkyl;

$A^1$ is a bond or $CR^{12}R^{13}$;

$A^2$ is —$CR^{14}R$—, —$NR^{16}$—, —O—, —S—, —S(O)— or —$S(O)_2$—;

$A^3$ is —$CR^{17}R^{18}$—, —$C(O)NR^{19}$—, —$NR^{19}$—, —O—, —S—, —S(O)— or —$S(O)_2$—;

$R^4$, $R^5$, $R^6$, $R^7$, $R^8$, $R^9$, $R^{10}$, $R^{11}$, $R^{14}$, $R^{15}$, $R^{17}$ and $R^{18}$ are independently selected from H, halogen, alkyl, alkoxy, cycloalkyl, cycloalkylalkoxy, haloalkoxy and haloalkyl.

$R^{12}$ and $R^{13}$ are independently selected from hydrogen, alkyl, cycloalkyl and haloalkyl.

$R^{16}$ and $R^{19}$ are independently selected from hydrogen, alkyl, cycloalkyl, haloalkyl and alkylcarbonyl.

n, m and p are independently selected from zero and 1;

and pharmaceutically acceptable salts.

Also further embodiment of the present invention are compounds according to formula (I) as described herein, wherein $R^1$ is alkyl, cycloalkyl, substituted cycloalkyl, alkoxy, alkoxyalkyl, alkoxyalkoxy, alkoxycarbonylalkyl, carboxyalkyl, haloalkyl, haloalkoxy, substituted aryl, heterocycloalkyl, substituted heterocycloalkyl, heterocycloalkoxy, substituted heterocycloalkylalkoxy, heteroaryl, substituted heteroaryl, amino or substituted amino, wherein substituted cycloalkyl, substituted aryl, substituted heterocycloalkyl, substituted heterocycloalkylalkoxy and substituted heteroaryl are substituted with one to three substituents independently selected from halogen, alkyl, haloalkyl, hydoxyalkyl, alkylsulfonylalkyl, alkoxycarbonyl and alkoxyalkyl and wherein substituted amino is substituted on the nitrogen atom with two alkyl.

A further embodiment of the present invention are compounds according to formula (I) as described herein, wherein $R^1$ is alkyl, cycloalkyl, substituted cycloalkyl, alkoxyalkyl, substituted aryl, heterocycloalkyl, substituted heterocycloalkyl, heteroaryl, amino or substituted amino, wherein substituted cycloalkyl, substituted aryl and substituted heterocycloalkyl are substituted with one to three substituents independently selected from halogen, alkyl, haloalkyl and alkoxyalkyl and wherein substituted amino is substituted on the nitrogen atom with two alkyl.

A particular embodiment of the present invention are compounds according to formula (I) as described herein, wherein $R^1$ is cycloalkyl, substituted cycloalkyl, heterocycloalkyl, substituted heterocycloalkyl, heterocycloalkylalkoxy or substituted amino, wherein substituted cycloalkyl and substituted heterocycloalkyl are substituted with one alkyl or alkoxyalkyl and wherein substituted amino is substituted on the nitrogen atom with two alkyl.

A particular embodiment of the present invention are compounds according to formula (I) as described herein, wherein $R^1$ is cycloalkyl, substituted cycloalkyl, heterocycloalkyl or substituted amino, wherein substituted cycloalkyl is substituted with one alkoxyalkyl and wherein substituted amino is substituted on the nitrogen atom with two substituents independently selected alkyl.

A further particular embodiment of the present invention are compounds according to formula (I) as described herein, wherein $R^1$ is cyclopentyl, substituted cyclopentyl, tetrahydrofuranyl, substituted tetrahydrofuranyl, tetrahydrofuranyloxy, piperidinyl or substituted amino, wherein substituted cyclopentyl and substituted tetrahydrofuranyl are substituted with one alkyl or alkoxyalkyl and wherein substituted amino is substituted on the nitrogen atom with two alkyl.

A particular embodiment of the present invention are compounds according to formula (I) as described herein, wherein $R^1$ is cyclopentyl, substituted cyclopentyl, tetrahydrofuranyl, piperidinyl or substituted amino, wherein substituted cyclopentyl is substituted with one alkoxyalkyl and wherein substituted amino is substituted on the nitrogen atom with two substituents independently selected alkyl.

In a further embodiment of the present invention are compounds according to formula (I) as described herein, wherein $R^2$ is —COOH, tetrazol-5-yl or [1,3,4]oxadiazol-2-thion-5-yl.

Another further embodiment of the present invention are compounds according to formula (I) as described herein, wherein $R^2$ is tetrazol-5-yl.

Another embodiment of the present invention are compounds according to formula (I) as described herein, wherein $R^3$ is phenyl, substituted phenyl, substituted dihydropyridinyl, heteroaryl or substituted heteroaryl, wherein substituted phenyl, substituted dihydropyridinyl and substituted heteroaryl are substituted with one to three substituents independently selected from hydroxy, oxo, halogen, alkyl, cycloalkyl, haloalkyl, haloalkoxy, hydroxyalkoxy, alkoxy, alkylsulfonyl and amino substituted on the nitrogen atom with one to two substituents independently selected from alkyl, cycloalkyl, haloalkyl, alkylcycloalkyl, cycloalkylalkyl, alkylcycloalkylalkyl, hydroxyalkyl and alkoxyalkyl.

Another embodiment of the present invention are compounds according to formula (I) as described herein, wherein $R^3$ is phenyl, substituted phenyl, substituted dihydropyridinyl, heteroaryl or substituted heteroaryl, wherein substituted phenyl, substituted dihydropyridinyl and substituted heteroaryl are substituted with one to three substituents independently selected from oxo, halogen, alkyl, cycloalkyl, haloalkyl, hydroxyalkoxy and alkoxy.

Another particular embodiment of the present invention are compounds according to formula (I) as described herein, wherein $R^3$ is phenyl, substituted phenyl or substituted heteroaryl, wherein substituted phenyl and substituted heteroaryl are substituted with one to three substituents independently selected from halogen and alkyl.

The present invention also relates to compounds according to formula (I) as described herein, wherein $R^3$ is phenyl, substituted phenyl, substituted pyrazolyl or substituted pyridinyl, wherein substituted phenyl, substituted pyrazolyl and substituted pyridinyl are substituted with one to three substituents independently selected from halogen and alkyl.

A further particular embodiment of the present invention are compounds according to formula (I) as described herein, wherein $R^3$ is substituted pyrazolyl or substituted pyridinyl, wherein substituted pyrazolyl and substituted pyridinyl are substituted with one alkyl.

A particular embodiment of the present invention are compounds according to formula (I) as described herein, wherein $R^3$ is pyridinyl substituted with one alkyl or halogen.

A more particular embodiment of the present invention are compounds according to formula (I) as described herein, wherein $R^3$ is pyridinyl substituted with one alkyl.

Also an embodiment of the present invention are compounds according to formula (I) as described herein, wherein A is a bond.

The present invention also relates to compounds according to formula (I) as described herein, wherein $A^2$ is $—CR^{14}R^{15}—$, $—NR^{16}—$, —O— or —S—.

The present invention also relates to compounds according to formula (I) as described herein, wherein $A^2$ is $—CR^{14}R^{15}—$, $—NR^{16}—$ or —O—.

Another embodiment of the present invention are compounds according to formula (I) as described herein, wherein $A^2$ is $—CR^{14}R^{15}$.

A further particular embodiment of the present invention are compounds according to formula (I) as described herein, wherein is $A^3$ is $—CR^{17}R^{18}—$, $—C(O)NR^{19}—$ or $—NR^{19}$.

A further particular embodiment of the present invention are compounds according to formula (I) as described herein, wherein is $A^3$ is $—CR^{17}R^{18}—$ or $—NR^{19}$.

A particular embodiment of the present invention are compounds according to formula (I) as described herein, wherein $A^3$ is $—CR^{17}R^{18}—$.

Also an embodiment of the present invention are compounds according to formula (I) as described herein, wherein n is 1.

A further particular embodiment of the present invention are compounds according to formula (I) as described herein, wherein p is zero.

The present invention also relates to compounds according to formula (I) as described herein, wherein $R^4$, $R^5$, $R^6$, $R^7$, $R^8$, $R^9$, $R^{10}$ and $R^{11}$ are H.

Another embodiment of the present invention are compounds according to formula (I) as described herein, wherein $R^4$ and $R^5$ are H.

The present invention also relates to compounds according to formula (I) as described herein, wherein $R^6$ and $R^7$ are H.

Also an embodiment of the present invention are compounds according to formula (I) as described herein, wherein $R^8$ and $R^9$ are H.

Also an embodiment of the present invention are compounds according to formula (I) as described herein, wherein $R^{10}$ and $R^{11}$ are H.

Another embodiment of the present invention are compounds according to formula (I) as described herein, wherein $R^{14}$ is H, halogen, alkyl, alkoxy or haloalkyl.

A particular embodiment of the present invention are compounds according to formula (I) as described herein, wherein $R^{15}$ is H, halogen or alkyl.

A further particular embodiment of the present invention are compounds according to formula (I) as described herein, wherein $R^{14}$ and $R^{15}$ are independently selected from H, halogen and alkyl.

A particular embodiment of the present invention are compounds according to formula (I) as described herein, wherein $R^{17}$ and $R^{18}$ are independently selected from H and alkyl.

A more particular embodiment of the present invention are compounds according to formula (I) as described herein, wherein $R^{17}$ and $R^{18}$ are H.

Also a particular embodiment of the present invention are compounds according to formula (I) as described herein, wherein $R^{16}$ is haloalkyl or alkylcarbonyl.

Also a particular embodiment of the present invention are compounds according to formula (I) as described herein, wherein $R^{19}$ is alkyl or alkylcarbonyl.

Also an embodiment of the present invention are compounds according to formula (I) as described herein, wherein $R^{16}$ and $R^{17}$ are halogen.

Particular examples of compounds of formula (I) as described herein are selected from 2-isopropyl-6,8-dimethyl-4-phenyl-5,6,7,8-tetrahydro-1,8-naphthyridine-3-carboxylic acid;

8-acetyl-2-isopropyl-6-methyl-4-phenyl-5,6,7,8-tetrahydro-1,8-naphthyridine-3-carboxylic acid;

8-ethyl-2-isopropyl-6-methyl-4-phenyl-5,6,7,8-tetrahydro-1,8-naphthyridine-3-carboxylic acid;

4-(3-chlorophenyl)-2-cyclohexyl-8-ethyl-5,6,7,8-tetrahydro-1,8-naphthyridine-3-carboxylic acid;

2-cyclohexyl-8-ethyl-4-phenyl-5,6,7,8-tetrahydro-1,8-naphthyridine-3-carboxylic acid;

2-cyclopentyl-8-ethyl-4-phenyl-5,6,7,8-tetrahydro-1,8-naphthyridine-3-carboxylic acid;

2-cyclopentyl-8-ethyl-6-methyl-4-phenyl-5,6,7,8-tetrahydro-1,8-naphthyridine-3-carboxylic acid;

2-cyclopentyl-6,8-dimethyl-4-phenyl-5,6,7,8-tetrahydro-1,8-naphthyridine-3-carboxylic acid;

2-isopropyl-6-methyl-4-phenyl-5,6,7,8-tetrahydroquinoline-3-carboxylic acid;

6-ethyl-2-isopropyl-4-phenyl-5,6,7,8-tetrahydroquinoline-3-carboxylic acid;

2-isopropyl-6,6-dimethyl-4-phenyl-5,6,7,8-tetrahydro-quinoline-3-carboxylic acid;

2-cyclopentyl-4-(6-methoxypyridin-2-yl)-6,7,8,9-tetrahydro-5H-cyclohepta[b]pyridine-3-carboxylic acid;

2-cyclopentyl-4-(6-oxo-1,6-dihydropyridin-2-yl)-6,7,8,9-tetrahydro-5H-cyclohepta[b]pyridine-3-carboxylic acid;

4-phenyl-2-(piperidin-1-yl)-6,7,8,9-tetrahydro-5H-cyclohepta[b]pyridine-3-carboxylic acid;

2-(2-methylpyrrolidin-1-yl)-4-phenyl-6,7,8,9-tetrahydro-5H-cyclohepta[b]pyridine-3-carboxylic acid;

6-methyl-4-phenyl-2-(piperidin-1-yl)-5,6,7,8-tetrahydroquinoline-3-carboxylic acid;

2-(diethylamino)-4-phenyl-6,7,8,9-tetrahydro-5H-cyclohepta[b]pyridine-3-carboxylic acid;

6-methyl-2-(2-methylpyrrolidin-1-yl)-4-phenyl-5,6,7,8-tetrahydroquinoline-3-carboxylic acid;

2-(diethylamino)-6-methyl-4-phenyl-5,6,7,8-tetrahydroquinoline-3-carboxylic acid;

4-(3-chlorophenyl)-6-methyl-2-(pyrrolidin-1-yl)-5,6,7,8-tetrahydroquinoline-3-carboxylic acid;

4-phenyl-2-(piperidin-1-yl)-6,7-dihydro-5H-cyclopenta[b]pyridine-3-carboxylic acid;

2-(diethylamino)-4-phenyl-6,7-dihydro-5H-cyclopenta[b]pyridine-3-carboxylic acid;

4-(3-chlorophenyl)-6-methyl-2-(piperidin-1-yl)-5,6,7,8-tetrahydroquinoline-3-carboxylic acid;

5-(6-methyl-4-phenyl-2-(piperidin-1-yl)-5,6,7,8-tetrahydroquinolin-3-yl)-1,3,4-oxadiazole-2(3H)-thione;

6-methyl-4-phenyl-2-(piperidin-1-yl)-3-(2H-tetrazol-5-yl)-5,6,7,8-tetrahydroquinoline;

N,N-diethyl-6-methyl-4-phenyl-3-(2H-tetrazol-5-yl)-5,6,7,8-tetrahydroquinolin-2-amine;

4-phenyl-2-(piperidin-1-yl)-3-(2H-tetrazol-5-yl)-6-(trifluoromethyl)-5,6,7,8-tetrahydroquinoline;

N,N-diethyl-4-phenyl-3-(2H-tetrazol-5-yl)-6-(trifluoromethyl)-5,6,7,8-tetrahydroquinolin-2-amine;

6-methyl-4-(1-methyl-1H-pyrazol-5-yl)-2-(piperidin-1-yl)-3-(2H-tetrazol-5-yl)-5,6,7,8-tetrahydroquinoline;

4-phenyl-2-(piperidin-1-yl)-3-(2H-tetrazol-5-yl)-6,7,8,9-tetrahydro-5H-cyclohepta[b]pyridine;

N,N-diethyl-4-phenyl-3-(2H-tetrazol-5-yl)-6,7,8,9-tetrahydro-5H-cyclohepta[b]pyridin-2-amine;

4-(3-chlorophenyl)-2-(piperidin-1-yl)-3-(1H-tetrazol-5-yl)-6,7,8,9-tetrahydro-5H-cyclohepta[b]pyridine;

4-(3-chlorophenyl)-N,N-diethyl-3-(1H-tetrazol-5-yl)-6,7,8,9-tetrahydro-5H-cyclohepta[b]pyridin-2-amine;

4-(1-methyl-1H-pyrazol-5-yl)-2-(piperidin-1-yl)-3-(1H-tetrazol-5-yl)-6,7,8,9-tetrahydro-5H-cyclohepta[b]pyridine;

4-(4-fluorophenyl)-6-methyl-2-(piperidin-1-yl)-3-(1H-tetrazol-5-yl)-5,6,7,8-tetrahydroquinoline;

4-(4-fluorophenyl)-2-(piperidin-1-yl)-3-(1H-tetrazol-5-yl)-7,8-dihydro-5H-pyrano[4,3-b]pyridine;

4-(1-methyl-1H-pyrazol-5-yl)-2-(2-methylpyrrolidin-1-yl)-3-(1H-tetrazol-5-yl)-6,7,8,9-tetrahydro-5H-cyclohepta[b]pyridine;

4-(5-chlorothiophen-2-yl)-N,N-diethyl-3-(1H-tetrazol-5-yl)-6,7,8,9-tetrahydro-5H-cyclohepta[b]pyridin-2-amine;

4-(5-chlorothiophen-2-yl)-2-(piperidin-1-yl)-3-(1H-tetrazol-5-yl)-6,7,8,9-tetrahydro-5H-cyclohepta[b]pyridine;

N,N-diethyl-4-(1-methyl-1H-pyrazol-5-yl)-3-(1H-tetrazol-5-yl)-6,7,8,9-tetrahydro-5H-cyclohepta[b]pyridin-2-amine;

5-methyl-3-(2-(piperidin-1-yl)-3-(1H-tetrazol-5-yl)-6,7,8,9-tetrahydro-5H-cyclohepta[b]pyridin-4-yl)isoxazole;

N,N-diethyl-4-(5-methylisoxazol-3-yl)-3-(1H-tetrazol-5-yl)-6,7,8,9-tetrahydro-5H-cyclohepta[b]pyridin-2-amine;

4-(1-methyl-1H-pyrazol-5-yl)-2-(2-methylpyrrolidin-1-yl)-3-(1H-tetrazol-5-yl)-6,7,8,9-tetrahydro-5H-cyclohepta[b]pyridine;

2-(piperidin-1-yl)-4-(pyridin-4-yl)-3-(1H-tetrazol-5-yl)-6,7,8,9-tetrahydro-5H-cyclohepta[b]pyridine;

N,N-diethyl-4-(pyridin-4-yl)-3-(1H-tetrazol-5-yl)-6,7,8,9-tetrahydro-5H-cyclohepta[b]pyridin-2-amine;

4-(5-methylfuran-2-yl)-2-(piperidin-1-yl)-3-(1H-tetrazol-5-yl)-6,7,8,9-tetrahydro-5H-cyclohepta[b]pyridine;

N,N-diethyl-4-(5-methylfuran-2-yl)-3-(1H-tetrazol-5-yl)-6,7,8,9-tetrahydro-5H-cyclohepta[b]pyridin-2-amine;

4-(1,5-dimethyl-1H-pyrazol-4-yl)-2-(piperidin-1-yl)-3-(1H-tetrazol-5-yl)-6,7,8,9-tetrahydro-5H-cyclohepta[b]pyridine;

4-(1,5-dimethyl-1H-pyrazol-4-yl)-N,N-diethyl-3-(1H-tetrazol-5-yl)-6,7,8,9-tetrahydro-5H-cyclohepta[b]pyridin-2-amine;

4-(5-chlorothiophen-2-yl)-2-(3-fluoropiperidin-1-yl)-3-(1H-tetrazol-5-yl)-6,7,8,9-tetrahydro-5H-cyclohepta[b]pyridine;

4-(5-chlorothiophen-2-yl)-2-(3,3-difluoropiperidin-1-yl)-3-(1H-tetrazol-5-yl)-6,7,8,9-tetrahydro-5H-cyclohepta[b]pyridine;

4-(5-chlorothiophen-2-yl)-2-(4,4-difluoropiperidin-1-yl)-3-(1H-tetrazol-5-yl)-6,7,8,9-tetrahydro-5H-cyclohepta[b]pyridine;
4-(5-chlorothiophen-2-yl)-2-(4-fluoropiperidin-1-yl)-3-(1H-tetrazol-5-yl)-6,7,8,9-tetrahydro-5H-cyclohepta[b]pyridine;
4-(5-chlorothiophen-2-yl)-3-(1H-tetrazol-5-yl)-2-(4-(trifluoromethyl)piperidin-1-yl)-6,7,8,9-tetrahydro-5H-cyclohepta[b]pyridine;
4-(5-chlorothiophen-2-yl)-2-(3,3-difluoroazetidin-1-yl)-3-(1H-tetrazol-5-yl)-6,7,8,9-tetrahydro-5H-cyclohepta[b]pyridine;
N,N-diethyl-4-(4-methylthiazol-5-yl)-3-(1H-tetrazol-5-yl)-6,7,8,9-tetrahydro-5H-cyclohepta[b]pyridin-2-amine;
4-methyl-5-(2-(piperidin-1-yl)-3-(1H-tetrazol-5-yl)-6,7,8,9-tetrahydro-5H-cyclohepta[b]pyridin-4-yl)thiazole;
N,N-diethyl-4-(1-methyl-1H-pyrazol-5-yl)-3-(1H-tetrazol-5-yl)-5,6,7,8,9,10-hexahydrocycloocta[b]pyridin-2-amine;
4-(5-chlorothiophen-2-yl)-2-(3,3-difluoropyrrolidin-1-yl)-3-(1H-tetrazol-5-yl)-6,7,8,9-tetrahydro-5H-cyclohepta[b]pyridine;
4-(1-methyl-1H-pyrazol-5-yl)-2-(piperidin-1-yl)-3-(1H-tetrazol-5-yl)-5,6,7,8,9,10-hexahydrocycloocta[b]pyridine;
diethyl-[4-pyrimidin-5-yl-3-(1H-tetrazol-5-yl)-6,7,8,9-tetrahydro-5H-cyclohepta[b]pyridin-2-yl]-amine;
N,N-diethyl-4-(3-fluoropyridin-4-yl)-3-(1H-tetrazol-5-yl)-6,7,8,9-tetrahydro-5H-cyclohepta[b]pyridin-2-amine;
N,N-diethyl-4-(2-methoxypyridin-4-yl)-3-(1H-tetrazol-5-yl)-6,7,8,9-tetrahydro-5H-cyclohepta[b]pyridin-2-amine;
4-phenyl-3-(1H-tetrazol-5-yl)-6,7,8,9-tetrahydro-5H-cyclohepta[b]pyridin-2-amine;
2-propyl-4-(pyridin-4-yl)-3-(1H-tetrazol-5-yl)-6,7,8,9-tetrahydro-5H-cyclohepta[b]pyridine;
4-(1-methyl-1H-pyrazol-5-yl)-2-(pentan-3-yl)-3-(1H-tetrazol-5-yl)-6,7,8,9-tetrahydro-5H-cyclohepta[b]pyridine;
4-(3-chlorophenyl)-2-cyclobutyl-3-(1H-tetrazol-5-yl)-6,7,8,9-tetrahydro-5H-cyclohepta[b]pyridine;
2-cyclohexyl-4-pyridin-4-yl-3-(1H-tetrazol-5-yl)-6,7,8,9-tetrahydro-H-cyclohepta[b]pyridine;
4-(3-chloro-phenyl)-2-cyclopentyl-3-(1H-tetrazol-5-yl)-6,7,8,9-tetrahydro-H-cyclohepta[b]pyridine;
2-cyclohexyl-4-(2-methylpyridin-4-yl)-3-(1H-tetrazol-5-yl)-6,7,8,9-tetrahydro-5H-cyclohepta[b]pyridine;
5-(2-cyclohexyl-3-(1H-tetrazol-5-yl)-6,7,8,9-tetrahydro-5H-cyclohepta[b]pyridin-4-yl)pyridin-2(1H)-one;
5-(2-cyclohexyl-3-(1H-tetrazol-5-yl)-6,7,8,9-tetrahydro-5H-cyclohepta[b]pyridin-4-yl)-1-ethylpyridin-2(1H)-one;
5-(2-cyclohexyl-3-(1H-tetrazol-5-yl)-6,7,8,9-tetrahydro-5H-cyclohepta[b]pyridin-4-yl)-1-methylpyridin-2(1H)-one;
2-cyclohexyl-4-(1-methyl-1H-pyrazol-5-yl)-3-(1H-tetrazol-5-yl)-6,7,8,9-tetrahydro-5H-cyclohepta[b]pyridine;
2-cyclopentyl-4-(pyridin-4-yl)-3-(1H-tetrazol-5-yl)-6,7,8,9-tetrahydro-5H-cyclohepta[b]pyridine;
2-cyclopentyl-4-(1-methyl-1H-pyrazol-5-yl)-3-(1H-tetrazol-5-yl)-6,7,8,9-tetrahydro-5H-cyclohepta[b]pyridine;
1-(4-(3-chlorophenyl)-2-cyclobutyl-3-(1H-tetrazol-5-yl)-7,8-dihydro-1,6-naphthyridin-6(5H)-yl)ethanone;
2-cyclopentyl-4-(6-methoxypyridin-2-yl)-3-(1H-tetrazol-5-yl)-6,7,8,9-tetrahydro-5H-cyclohepta[b]pyridine;
4-phenyl-2-(tetrahydro-2H-pyran-2-yl)-3-(1H-tetrazol-5-yl)-6,7,8,9-tetrahydro-5H-cyclohepta[b]pyridine;
2-cyclopentyl-4-(2-methylpyridin-4-yl)-3-(1H-tetrazol-5-yl)-6,7,8,9-tetrahydro-5H-cyclohepta[b]pyridine;
4-phenyl-2-(tetrahydrofuran-3-yl)-3-(1H-tetrazol-5-yl)-6,7,8,9-tetrahydro-5H-cyclohepta[b]pyridine;
2-cyclopentyl-4-(2-methoxypyridin-4-yl)-3-(1H-tetrazol-5-yl)-6,7,8,9-tetrahydro-5H-cyclohepta[b]pyridine;
2-cyclohexyl-4-phenyl-3-(1H-tetrazol-5-yl)-6,7,8,9-tetrahydro-5H-cyclohepta[b]pyridine;
2-cyclopentyl-4-phenyl-3-(1H-tetrazol-5-yl)-6,7,8,9-tetrahydro-5H-cyclohepta[b]pyridine;
4-phenyl-2-(tetrahydrofuran-2-yl)-3-(1H-tetrazol-5-yl)-6,7,8,9-tetrahydro-5H-cyclohepta[b]pyridine;
2-cyclohexyl-4-(3-fluoropyridin-4-yl)-3-(1H-tetrazol-5-yl)-6,7,8,9-tetrahydro-5H-cyclohepta[b]pyridine;
2-cyclopentyl-4-(3-fluoropyridin-4-yl)-3-(1H-tetrazol-5-yl)-6,7,8,9-tetrahydro-5H-cyclohepta[b]pyridine;
4-phenyl-2-(tetrahydro-2H-pyran-4-yl)-3-(1H-tetrazol-5-yl)-6,7,8,9-tetrahydro-5H-cyclohepta[b]pyridine;
2-cyclohexyl-4-(2-methylpyrimidin-4-yl)-3-(1H-tetrazol-5-yl)-6,7,8,9-tetrahydro-5H-cyclohepta[b]pyridine;
5-(2-cyclobutyl-3-(1H-tetrazol-5-yl)-6,7,8,9-tetrahydro-5H-cyclohepta[b]pyridin-4-yl)-1-methylpyridin-2(1H)-one;
2-cyclohexyl-4-(pyrimidin-4-yl)-3-(1H-tetrazol-5-yl)-6,7,8,9-tetrahydro-5H-cyclohepta[b]pyridine;
2-cyclopentyl-4-(pyrimidin-4-yl)-3-(1H-tetrazol-5-yl)-6,7,8,9-tetrahydro-5H-cyclohepta[b]pyridine;
2-cyclopentyl-4-(2-methylpyrimidin-4-yl)-3-(1H-tetrazol-5-yl)-6,7,8,9-tetrahydro-5H-cyclohepta[b]pyridine;
2-(1-(methoxymethyl)cyclopentyl)-4-(2-methylpyridin-4-yl)-3-(1H-tetrazol-5-yl)-6,7,8,9-tetrahydro-5H-cyclohepta[b]pyridine;
2-cyclopentyl-4-(pyridazin-4-yl)-3-(1H-tetrazol-5-yl)-6,7,8,9-tetrahydro-5H-cyclohepta[b]pyridine;
2-cyclopentyl-4-(6-methylpyridin-2-yl)-3-(1H-tetrazol-5-yl)-6,7,8,9-tetrahydro-5H-cyclohepta[b]pyridine;
2-cyclopentyl-4-(pyridin-2-yl)-3-(1H-tetrazol-5-yl)-6,7,8,9-tetrahydro-5H-cyclohepta[b]pyridine;
2-isopropyl-4-(2-isopropylpyridin-4-yl)-3-(1H-tetrazol-5-yl)-6,7,8,9-tetrahydro-5H-cyclohepta[b]pyridine;
2-cyclopentyl-4-(pyrimidin-2-yl)-3-(1H-tetrazol-5-yl)-6,7,8,9-tetrahydro-5H-cyclohepta[b]pyridine;
2-(2-(2-cyclopentyl-3-(1H-tetrazol-5-yl)-6,7,8,9-tetrahydro-5H-cyclohepta[b]pyridin-4-yl)phenoxy)ethanol;
2-cyclopentyl-4-(2-isopropylpyrimidin-4-yl)-3-(1H-tetrazol-5-yl)-6,7,8,9-tetrahydro-5H-cyclohepta[b]pyridine;
2-isopropyl-4-(2-isopropylpyrimidin-4-yl)-3-(1H-tetrazol-5-yl)-6,7,8,9-tetrahydro-5H-cyclohepta[b]pyridine;
4-(2-chloropyridin-4-yl)-2-cyclopentyl-3-(1H-tetrazol-5-yl)-6,7,8,9-tetrahydro-5H-cyclohepta[b]pyridine;
2-(1-(methoxymethyl)cyclopentyl)-4-(2-methoxypyridin-4-yl)-3-(1H-tetrazol-5-yl)-6,7,8,9-tetrahydro-5H-cyclohepta[b]pyridine;
4-(2-isopropylpyridin-4-yl)-2-(pentan-3-yl)-3-(1H-tetrazol-5-yl)-6,7,8,9-tetrahydro-5H-cyclohepta[b]pyridine;
4-(1-methyl-1H-pyrazol-5-yl)-2-(pentan-3-yl)-3-(2H-tetrazol-5-yl)-6-(trifluoromethyl)-5,6,7,8-tetrahydroquinoline;
2-cyclohexyl-4-(2-methylpyridin-4-yl)-3-(2H-tetrazol-5-yl)-6-(trifluoromethyl)-5,6,7,8-tetrahydroquinoline;
2-cyclohexyl-4-(1-methyl-1H-pyrazol-5-yl)-3-(2H-tetrazol-5-yl)-6-(trifluoromethyl)-5,6,7,8-tetrahydroquinoline;
2-cyclohexyl-6-methyl-4-(1-methyl-1H-pyrazol-5-yl)-3-(2H-tetrazol-5-yl)-5,6,7,8-tetrahydroquinoline;
2-cyclohexyl-6-methyl-4-(2-methylpyridin-4-yl)-3-(2H-tetrazol-5-yl)-5,6,7,8-tetrahydroquinoline;
2-cyclopentyl-4-(1-methyl-1H-pyrazol-5-yl)-3-(2H-tetrazol-5-yl)-6-(trifluoromethyl)-5,6,7,8-tetrahydroquinoline;
2-cyclopentyl-6,6-difluoro-4-phenyl-3-(2H-tetrazol-5-yl)-5,6,7,8-tetrahydroquinoline;

2-cyclopentyl-6-methyl-4-(2-methylpyridin-4-yl)-3-(2H-tetrazol-5-yl)-5,6,7,8-tetrahydroquinoline;
4-(2-cyclohexyl-3-(2H-tetrazol-5-yl)-6-(trifluoromethyl)-5,6,7,8-tetrahydroquinolin-4-yl)-3,5-dimethylisoxazole;
4-(2-cyclohexyl-6-methyl-3-(2H-tetrazol-5-yl)-5,6,7,8-tetrahydroquinolin-4-yl)-3,5-dimethylisoxazole;
2-cyclopentyl-4-(2-methylpyridin-4-yl)-3-(2H-tetrazol-5-yl)-6-(trifluoromethyl)-5,6,7,8-tetrahydroquinoline;
2-cyclopentyl-4-phenyl-3-(2H-tetrazol-5-yl)-6-(2,2,2-trifluoroethyl)-5,6,7,8-tetrahydro-1,6-naphthyridine;
2-cyclopentyl-6,6-dimethyl-4-(2-methylpyridin-4-yl)-3-(2H-tetrazol-5-yl)-5,6,7,8-tetrahydroquinoline;
2-cyclopentyl-6-methoxy-4-(2-methylpyridin-4-yl)-3-(2H-tetrazol-5-yl)-5,6,7,8-tetrahydroquinoline;
6-methyl-4-(2-methylpyridin-4-yl)-2-tert-pentyl-3-(2H-tetrazol-5-yl)-5,6,7,8-tetrahydroquinoline;
2-cyclopentyl-4-(2-methylpyridin-4-yl)-3-(2H-tetrazol-5-yl)-5,6,7,8-tetrahydroquinoline;
2-cyclohexyl-4-(2-methylpyridin-4-yl)-3-(2H-tetrazol-5-yl)-5,6,7,8-tetrahydroquinoline;
2-(1-methoxy-2-methylpropan-2-yl)-6-methyl-4-(2-methylpyridin-4-yl)-3-(2H-tetrazol-5-yl)-5,6,7,8-tetrahydroquinoline;
2-cyclopentyl-4-(2-methylpyridin-4-yl)-3-(2H-tetrazol-5-yl)-6,7-dihydro-5H-cyclopenta[b]pyridine;
2-cyclohexyl-4-(2-methylpyridin-4-yl)-3-(2H-tetrazol-5-yl)-6,7-dihydro-5H-cyclopenta[b]pyridine;
2-tert-butyl-4-phenyl-3-(1H-tetrazol-5-yl)-6,7,8,9-tetrahydro-5H-cyclohepta[b]pyridine;
2-tert-butyl-4-(3-fluorophenyl)-3-(1H-tetrazol-5-yl)-6,7,8,9-tetrahydro-5H-cyclohepta[b]pyridine;
2-tert-butyl-3-(1H-tetrazol-5-yl)-4-(4-(trifluoromethyl)phenyl)-6,7,8,9-tetrahydro-5H-cyclohepta[b]pyridine;
2-tert-butyl-3-(1H-tetrazol-5-yl)-4-(3-(trifluoromethyl)phenyl)-6,7,8,9-tetrahydro-5H-cyclohepta[b]pyridine;
2-tert-butyl-4-(2-methylpyridin-4-yl)-3-(1H-tetrazol-5-yl)-6,7,8,9-tetrahydro-5H-cyclohepta[b]pyridine;
2-(3,3-difluorocyclobutyl)-4-phenyl-3-(1H-tetrazol-5-yl)-6,7,8,9-tetrahydro-5H-cyclohepta[b]pyridine;
2-tert-butyl-4-(4-fluoro-phenyl)-3-(1H-tetrazol-5-yl)-6,7,8,9-tetrahydro-5H-cyclohepta[b]pyridine;
4-(2-tert-butyl-3-(1H-tetrazol-5-yl)-6,7,8,9-tetrahydro-5H-cyclohepta[b]pyridin-4-yl)oxazole;
2-tert-butyl-4-(1-methyl-1H-pyrazol-3-yl)-3-(1H-tetrazol-5-yl)-6,7,8,9-tetrahydro-5H-cyclohepta[b]pyridine;
2-tert-butyl-4-(4-methyl-1H-pyrazol-5-yl)-3-(1H-tetrazol-5-yl)-6,7,8,9-tetrahydro-5H-cyclohepta[b]pyridine;
2-tert-butyl-4-(3-cyclopropyl-1H-pyrazol-5-yl)-3-(1H-tetrazol-5-yl)-6,7,8,9-tetrahydro-5H-cyclohepta[b]pyridine;
4-(2-tert-butyl-3-(1H-tetrazol-5-yl)-6,7,8,9-tetrahydro-5H-cyclohepta[b]pyridin-4-yl)-2-methyloxazole;
2-tert-butyl-4-(4-chloro-1H-pyrazol-3-yl)-3-(1H-tetrazol-5-yl)-6,7,8,9-tetrahydro-5H-cyclohepta[b]pyridine;
2-tert-butyl-3-(1H-tetrazol-5-yl)-4-(4-(trifluoromethyl)-1H-imidazol-2-yl)-6,7,8,9-tetrahydro-5H-cyclohepta[b]pyridine;
2-tert-butyl-3-(1H-tetrazol-5-yl)-4-(1H-1,2,3-triazol-5-yl)-6,7,8,9-tetrahydro-5H-cyclohepta[b]pyridine;
2-tert-butyl-4-(2-butyl-1H-imidazol-4-yl)-3-(1H-tetrazol-5-yl)-6,7,8,9-tetrahydro-5H-cyclohepta[b]pyridine;
2-furan-2-yl-4-phenyl-3-(1H-tetrazol-5-yl)-6,7,8,9-tetrahydro-5H-cyclohepta[b]pyridine;
2-sec-butyl-4-phenyl-3-(1H-tetrazol-5-yl)-6,7,8,9-tetrahydro-5H-cyclohepta[b]pyridine;
2-(3-fluorophenyl)-4-phenyl-3-(1H-tetrazol-5-yl)-6,7,8,9-tetrahydro-5H-cyclohepta[b]pyridine;
2-sec-butyl-4-(2-methylpyridin-4-yl)-3-(1H-tetrazol-5-yl)-6,7,8,9-tetrahydro-5H-cyclohepta[b]pyridine;
and pharmaceutically acceptable salts thereof.

Also particular examples of compounds of formula (I) as described herein are selected from
4-phenyl-2-(R)-tetrahydro-furan-2-yl-3-(1H-tetrazol-5-yl)-6,7,8,9-tetrahydro-5H-cyclohepta[b]pyridine;
4-phenyl-2-(S)-tetrahydro-furan-2-yl-3-(1H-tetrazol-5-yl)-6,7,8,9-tetrahydro-5H-cyclohepta[b]pyridine;
(R)-4-(2-chloropyridin-4-yl)-2-(tetrahydrofuran-2-yl)-3-(1H-tetrazol-5-yl)-6,7,8,9-tetrahydro-5H-cyclohepta[b]pyridine;
(S)-4-(2-chloropyridin-4-yl)-2-(tetrahydrofuran-2-yl)-3-(1H-tetrazol-5-yl)-6,7,8,9-tetrahydro-5H-cyclohepta[b]pyridine;
4-phenyl-2-(tetrahydrofuran-2-yl)-3-(1H-tetrazol-5-yl)-5,6,7,8,9,10-hexahydrocycloocta[b]pyridine;
(S)-4-phenyl-2-(tetrahydrofuran-2-yl)-3-(1H-tetrazol-5-yl)-5,6,7,8,9,10-hexahydrocycloocta[b]pyridine;
(R)-4-phenyl-2-(tetrahydrofuran-2-yl)-3-(1H-tetrazol-5-yl)-5,6,7,8,9,10-hexahydrocycloocta[b]pyridine;
2-(2-methyltetrahydrofuran-2-yl)-4-phenyl-3-(1H-tetrazol-5-yl)-6,7,8,9-tetrahydro-5H-cyclohepta[b]pyridine;
2-((S)-2-methyl-tetrahydro-furan-2-yl)-4-phenyl-3-(1H-tetrazol-5-yl)-6,7,8,9-tetrahydro-5H-cyclohepta[b]pyridine;
2-((R)-2-methyl-tetrahydro-furan-2-yl)-4-phenyl-3-(1H-tetrazol-5-yl)-6,7,8,9-tetrahydro-5H-cyclohepta[b]pyridine;
4-(3-methoxyphenyl)-2-(2-methyltetrahydrofuran-2-yl)-3-(1H-tetrazol-5-yl)-6,7,8,9-tetrahydro-5H-cyclohepta[b]pyridine;
4-(3-methoxy-phenyl)-2-((S)-2-methyl-tetrahydro-furan-2-yl)-3-(1H-tetrazol-5-yl)-6,7,8,9-tetrahydro-5H-cyclohepta[b]pyridine;
4-(3-methoxy-phenyl)-2-((R)-2-methyl-tetrahydro-furan-2-yl)-3-(1H-tetrazol-5-yl)-6,7,8,9-tetrahydro-5H-cyclohepta[b]pyridine;
4-(2-methylpyridin-4-yl)-2-(2-methyltetrahydrofuran-2-yl)-3-(1H-tetrazol-5-yl)-6,7,8,9-tetrahydro-5H-cyclohepta[b]pyridine;
2-[(2S)-2-methyloxolan-2-yl]-4-(2-methylpyridin-4-yl)-3-(1H-tetrazol-5-yl)-6,7,8,9-tetrahydro-5H-cyclohepta[b]pyridine;
2-[(2R)-2-methyloxolan-2-yl]-4-(2-methylpyridin-4-yl)-3-(1H-tetrazol-5-yl)-6,7,8,9-tetrahydro-5H-cyclohepta[b]pyridine;
4-(3-chlorophenyl)-2-(2-methyltetrahydrofuran-2-yl)-3-(1H-tetrazol-5-yl)-6,7,8,9-tetrahydro-5H-cyclohepta[b]pyridine;
4-(3-chloro-phenyl)-2-((S)-2-methyl-tetrahydro-furan-2-yl)-3-(1H-tetrazol-5-yl)-6,7,8,9-tetrahydro-5H-cyclohepta[b]pyridine;
4-(3-chloro-phenyl)-2-((R)-2-methyl-tetrahydro-furan-2-yl)-3-(1H-tetrazol-5-yl)-6,7,8,9-tetrahydro-5H-cyclohepta[b]pyridine;
2-(1-methylcyclopentyl)-4-(2-methylpyridin-4-yl)-3-(1H-tetrazol-5-yl)-6,7,8,9-tetrahydro-5H-cyclohepta[b]pyridine;
2-(1-methylcyclopentyl)-4-phenyl-3-(1H-tetrazol-5-yl)-6,7,8,9-tetrahydro-5H-cyclohepta[b]pyridine;
4-(2-methoxypyridin-4-yl)-2-(1-methylcyclopentyl)-3-(1H-tetrazol-5-yl)-6,7,8,9-tetrahydro-5H-cyclohepta[b]pyridine;
4-(2-(1-methylcyclopentyl)-3-(1H-tetrazol-5-yl)-6,7,8,9-tetrahydro-5H-cyclohepta[b]pyridin-4-yl)pyridin-2(1H)-one;
4-(3-chloro-phenyl)-2-(1-methyl-cyclopentyl)-3-(1H-tetrazol-5-yl)-6,7,8,9-tetrahydro-5H-cyclohepta[b]pyridine;

4-(1-methyl-1H-pyrazol-5-yl)-2-(1-methylcyclohexyl)-3-(1H-tetrazol-5-yl)-6,7,8,9-tetrahydro-5H-cyclohepta[b]pyridine;

2-(1-methylcyclohexyl)-4-(2-methylpyridin-4-yl)-3-(1H-tetrazol-5-yl)-6,7,8,9-tetrahydro-5H-cyclohepta[b]pyridine;

2-(1-methoxymethyl-cyclopentyl)-4-(2-methyl-2H-pyrazol-3-yl)-3-(1H-tetrazol-5-yl)-6,7,8,9-tetrahydro-5H-cyclohepta[b]pyridine;

4-(3-fluoropyridin-4-yl)-2-(1-(methoxymethyl)cyclopentyl)-3-(1H-tetrazol-5-yl)-6,7,8,9-tetrahydro-5H-cyclohepta[b]pyridine;

2-(1-(methoxymethyl)cyclopentyl)-4-(4-methyl-1H-pyrazol-3-yl)-3-(1H-tetrazol-5-yl)-6,7,8,9-tetrahydro-5H-cyclohepta[b]pyridine;

4-(1H-indol-4-yl)-2-(1-(methoxymethyl)cyclopentyl)-3-(1H-tetrazol-5-yl)-6,7,8,9-tetrahydro-5H-cyclohepta[b]pyridine;

4-(2-chloropyridin-4-yl)-2-(1-(methoxymethyl)cyclopentyl)-3-(1H-tetrazol-5-yl)-6,7,8,9-tetrahydro-5H-cyclohepta[b]pyridine;

4-(2-ethylpyridin-4-yl)-2-(1-(methoxymethyl)cyclopentyl)-3-(1H-tetrazol-5-yl)-6,7,8,9-tetrahydro-5H-cyclohepta[b]pyridine;

3-(2-(1-(methoxymethyl)cyclopentyl)-3-(1H-tetrazol-5-yl)-6,7,8,9-tetrahydro-5H-cyclohepta[b]pyridin-4-yl)-2-methylphenol;

4-(2-(1-(methoxymethyl)cyclopentyl)-3-(1H-tetrazol-5-yl)-6,7,8,9-tetrahydro-5H-cyclohepta[b]pyridin-4-yl)-2-methyloxazole;

4-(1H-indazol-4-yl)-2-(1-(methoxymethyl)cyclopentyl)-3-(1H-tetrazol-5-yl)-6,7,8,9-tetrahydro-5H-cyclohepta[b]pyridine;

2-(1-(methoxymethyl)cyclopentyl)-3-(1H-tetrazol-5-yl)-4-(2-(trifluoromethyl)pyridin-4-yl)-6,7,8,9-tetrahydro-5H-cyclohepta[b]pyridine;

2-(1-(methoxymethyl)cyclopentyl)-3-(1H-tetrazol-5-yl)-4-(2-(2,2,2-trifluoroethoxyl)pyridin-4-yl)-6,7,8,9-tetrahydro-5H-cyclohepta[b]pyridine;

2-(1-(methoxymethyl)cyclopentyl)-4-phenyl-3-(1H-tetrazol-5-yl)-6,7,8,9-tetrahydro-5H-cyclohepta[b]pyridine;

4-(2-ethoxypyridin-4-yl)-2-(1-(methoxymethyl)cyclopentyl)-3-(1H-tetrazol-5-yl)-6,7,8,9-tetrahydro-5H-cyclohepta[b]pyridine;

4-(4-fluoro-3-methoxyphenyl)-2-(1-(methoxymethyl)cyclopentyl)-3-(1H-tetrazol-5-yl)-6,7,8,9-tetrahydro-5H-cyclohepta[b]pyridine;

4-(4-fluorophenyl)-2-(1-(methoxymethyl)cyclopentyl)-3-(1H-tetrazol-5-yl)-6,7,8,9-tetrahydro-5H-cyclohepta[b]pyridine;

2-(1-(methoxymethyl)cyclopentyl)-4-(3-methoxyphenyl)-3-(1H-tetrazol-5-yl)-6,7,8,9-tetrahydro-5H-cyclohepta[b]pyridine;

4-(2-fluoro-5-methoxyphenyl)-2-(1-(methoxymethyl)cyclopentyl)-3-(1H-tetrazol-5-yl)-6,7,8,9-tetrahydro-5H-cyclohepta[b]pyridine;

4-(3-chloro-phenyl)-2-(1-methoxymethyl-cyclopentyl)-3-(1H-tetrazol-5-yl)-6,7,8,9-tetrahydro-5H-cyclohepta[b]pyridine;

2-(3-(methoxymethyl)pentan-3-yl)-4-(1-methyl-1H-pyrazol-5-yl)-3-(1H-tetrazol-5-yl)-6,7,8,9-tetrahydro-5H-cyclohepta[b]pyridine;

2-(3-(methoxymethyl)pentan-3-yl)-4-phenyl-3-(1H-tetrazol-5-yl)-6,7,8,9-tetrahydro-5H-cyclohepta[b]pyridine;

2-cyclopentyl-4-(2-ethylpyridin-4-yl)-3-(1H-tetrazol-5-yl)-6,7,8,9-tetrahydro-5H-cyclohepta[b]pyridine;

4-(2-cyclopentyl-3-(1H-tetrazol-5-yl)-6,7,8,9-tetrahydro-5H-cyclohepta[b]pyridin-4-yl)-N-methylpyridin-2-amine;

2-cyclopentyl-3-(1H-tetrazol-5-yl)-4-(2-(trifluoromethyl)pyridin-4-yl)-6,7,8,9-tetrahydro-5H-cyclohepta[b]pyridine;

4-(1-methyl-1H-pyrazol-5-yl)-2-(3-methylpentan-3-yl)-3-(1H-tetrazol-5-yl)-6,7,8,9-tetrahydro-5H-cyclohepta[b]pyridine;

4-(2-ethylpyridin-4-yl)-2-isopropyl-3-(1H-tetrazol-5-yl)-6,7,8,9-tetrahydro-5H-cyclohepta[b]pyridine;

2-isopropyl-3-(1H-tetrazol-5-yl)-4-(2-(2,2,2-trifluoroethoxyl)pyridin-4-yl)-6,7,8,9-tetrahydro-5H-cyclohepta[b]pyridine;

4-(2-ethoxypyridin-4-yl)-2-isopropyl-3-(1H-tetrazol-5-yl)-6,7,8,9-tetrahydro-5H-cyclohepta[b]pyridine;

2-(1-methoxycyclopentyl)-4-phenyl-3-(1H-tetrazol-5-yl)-6,7,8,9-tetrahydro-5H-cyclohepta[b]pyridine;

2-(1-methoxycyclopentyl)-4-phenyl-3-(1H-tetrazol-5-yl)-5,6,7,8-tetrahydroquinoline;

2-(1-methoxycyclopentyl)-4-(2-methoxypyridin-4-yl)-3-(1H-tetrazol-5-yl)-6,7,8,9-tetrahydro-5H-cyclohepta[b]pyridine;

4-(2-chloropyridin-4-yl)-2-(1-methoxycyclopentyl)-3-(1H-tetrazol-5-yl)-6,7,8,9-tetrahydro-5H-cyclohepta[b]pyridine;

2-(1-methoxycyclopentyl)-4-(2-methylpyridin-4-yl)-3-(1H-tetrazol-5-yl)-6,7,8,9-tetrahydro-5H-cyclohepta[b]pyridine;

(1-(4-phenyl-3-(1H-tetrazol-5-yl)-6,7,8,9-tetrahydro-5H-cyclohepta[b]pyridin-2-yl)cyclopentyl)methanol;

(1-(4-phenyl-3-(1H-tetrazol-5-yl)-5,6,7,8-tetrahydroquinolin-2-yl)cyclopentyl)methanol;

(1-(4-(2-methylpyridin-4-yl)-3-(1H-tetrazol-5-yl)-6,7,8,9-tetrahydro-5H-cyclohepta[b]pyridin-2-yl)cyclopentyl)methanol;

(1-(4-(3-chlorophenyl)-3-(1H-tetrazol-5-yl)-6,7,8,9-tetrahydro-5H-cyclohepta[b]pyridin-2-yl)cyclopentyl)methanol;

(1-(4-(4-fluorophenyl)-3-(1H-tetrazol-5-yl)-6,7,8,9-tetrahydro-5H-cyclohepta[b]pyridin-2-yl)cyclopentyl)methanol;

(S)-tert-butyl 2-(4-phenyl-3-(1H-tetrazol-5-yl)-6,7,8,9-tetrahydro-5H-cyclohepta[b]pyridin-2-yl)pyrrolidine-1-carboxylate;

(S)-4-phenyl-2-(pyrrolidin-2-yl)-3-(1H-tetrazol-5-yl)-6,7,8,9-tetrahydro-5H-cyclohepta[b]pyridine 2,2,2-trifluoroacetate;

2-cyclopentyl-4-phenyl-3-(1H-tetrazol-5-yl)-7,8-dihydro-5H-pyrido[2,3-c]azepin-9(6H)-one;

2-(1-methoxy-2-methylpropan-2-yl)-6,6-dimethyl-4-(1-methyl-1H-pyrazol-5-yl)-3-(2H-tetrazol-5-yl)-5,6,7,8-tetrahydroquinoline;

6,6-dimethyl-4-(1-methyl-1H-pyrazol-5-yl)-2-tert-pentyl-3-(2H-tetrazol-5-yl)-5,6,7,8-tetrahydroquinoline;

2-(1-methoxy-2-methylpropan-2-yl)-6,6-dimethyl-4-(2-methylpyridin-4-yl)-3-(2H-tetrazol-5-yl)-5,6,7,8-tetrahydroquinoline;

2-(1-(methoxymethyl)cyclopentyl)-4-phenyl-3-(2H-tetrazol-5-yl)-5,6,7,8-tetrahydroquinoline;

6,6-difluoro-2-(1-(methoxymethyl)cyclopentyl)-4-phenyl-3-(2H-tetrazol-5-yl)-5,6,7,8-tetrahydroquinoline;

6,6-difluoro-2-(1-methoxymethyl-cyclohexyl)-4-phenyl-3-(1H-tetrazol-5-yl)-5,6,7,8-tetrahydro-quinoline;

6,6-difluoro-2-(1-(methoxymethyl)cyclopentyl)-4-(2-methylpyridin-4-yl)-3-(2H-tetrazol-5-yl)-5,6,7,8-tetrahydroquinoline;

2-(4-methyltetrahydro-2H-pyran-4-yl)-4-phenyl-3-(2H-tetrazol-5-yl)-5,6,7,8-tetrahydroquinoline;

6,6-difluoro-2-(4-methyltetrahydro-2H-pyran-4-yl)-4-phenyl-3-(2H-tetrazol-5-yl)-5,6,7,8-tetrahydroquinoline;

2-(1-(methoxymethyl)cyclopentyl)-6-methyl-4-(2-methylpyridin-4-yl)-3-(2H-tetrazol-5-yl)-5,6,7,8-tetrahydroquinoline;

2-(1-(methoxymethyl)cyclohexyl)-4-phenyl-3-(2H-tetrazol-5-yl)-5,6,7,8-tetrahydroquinoline;

6,6-difluoro-2-(1-(methoxymethyl)cyclopentyl)-4-(1-methyl-1H-pyrazol-5-yl)-3-(2H-tetrazol-5-yl)-5,6,7,8-tetrahydroquinoline;

2-(1-(methoxymethyl)cyclopentyl)-6,6-dimethyl-4-(1-methyl-1H-pyrazol-5-yl)-3-(2H-tetrazol-5-yl)-5,6,7,8-tetrahydroquinoline;

2-(2-methyltetrahydrofuran-2-yl)-4-phenyl-3-(2H-tetrazol-5-yl)-5,6,7,8-tetrahydroquinoline;

6,6-difluoro-2-(2-methyltetrahydrofuran-2-yl)-4-phenyl-3-(2H-tetrazol-5-yl)-5,6,7,8-tetrahydroquinoline;

6,6-dimethyl-2-(2-methyltetrahydrofuran-2-yl)-4-phenyl-3-(2H-tetrazol-5-yl)-5,6,7,8-tetrahydroquinoline;

4-(1-methyl-1H-pyrazol-5-yl)-2-(2-methyltetrahydrofuran-2-yl)-3-(2H-tetrazol-5-yl)-5,6,7,8-tetrahydroquinoline;

6,6-dimethyl-4-(1-methyl-1H-pyrazol-5-yl)-2-(2-methyltetrahydrofuran-2-yl)-3-(2H-tetrazol-5-yl)-5,6,7,8-tetrahydroquinoline;

(R)-2-(2-methyltetrahydrofuran-2-yl)-4-phenyl-3-(2H-tetrazol-5-yl)-5,6,7,8-tetrahydroquinoline;

(S)-2-(2-methyltetrahydrofuran-2-yl)-4-phenyl-3-(2H-tetrazol-5-yl)-5,6,7,8-tetrahydroquinoline;

(R)-6,6-difluoro-2-(2-methyltetrahydrofuran-2-yl)-4-phenyl-3-(2H-tetrazol-5-yl)-5,6,7,8-tetrahydroquinoline;

(S)-6,6-difluoro-2-(2-methyltetrahydrofuran-2-yl)-4-phenyl-3-(2H-tetrazol-5-yl)-5,6,7,8-tetrahydroquinoline;

(R)-6,6-dimethyl-2-(2-methyltetrahydrofuran-2-yl)-4-phenyl-3-(2H-tetrazol-5-yl)-5,6,7,8-tetrahydroquinoline;

(S)-6,6-dimethyl-2-(2-methyltetrahydrofuran-2-yl)-4-phenyl-3-(2H-tetrazol-5-yl)-5,6,7,8-tetrahydroquinoline;

2-(1-(methoxymethyl)cyclopentyl)-4-(1-methyl-1H-pyrazol-5-yl)-3-(2H-tetrazol-5-yl)-5,6,7,8-tetrahydroquinoline;

2-(1-(methoxymethyl)cyclohexyl)-4-(1-methyl-1H-pyrazol-5-yl)-3-(2H-tetrazol-5-yl)-5,6,7,8-tetrahydroquinoline;

2-(1-(methoxymethyl)cyclohexyl)-6,6-dimethyl-4-(1-methyl-1H-pyrazol-5-yl)-3-(2H-tetrazol-5-yl)-5,6,7,8-tetrahydroquinoline;

6,6-difluoro-2-(1-(methoxymethyl)cyclohexyl)-4-(1-methyl-1H-pyrazol-5-yl)-3-(2H-tetrazol-5-yl)-5,6,7,8-tetrahydroquinoline;

6,6-difluoro-4-(1-methyl-1H-pyrazol-5-yl)-2-(2-methyltetrahydrofuran-2-yl)-3-(2H-tetrazol-5-yl)-5,6,7,8-tetrahydroquinoline;

2-(2-(methoxymethyl)tetrahydrofuran-2-yl)-4-phenyl-3-(2H-tetrazol-5-yl)-5,6,7,8-tetrahydroquinoline;

2-(1-(methoxymethyl)cyclohexyl)-4-(1-methyl-1H-pyrazol-4-yl)-3-(2H-tetrazol-5-yl)-5,6,7,8-tetrahydroquinoline;

2-(2-(methoxymethyl)tetrahydrofuran-2-yl)-6,6-dimethyl-4-phenyl-3-(2H-tetrazol-5-yl)-5,6,7,8-tetrahydroquinoline;

6,6-difluoro-2-(2-(methoxymethyl)tetrahydrofuran-2-yl)-4-phenyl-3-(2H-tetrazol-5-yl)-5,6,7,8-tetrahydroquinoline;

2-(2-ethyltetrahydrofuran-2-yl)-4-phenyl-3-(2H-tetrazol-5-yl)-5,6,7,8-tetrahydroquinoline;

2-(2-ethyltetrahydrofuran-2-yl)-6,6-dimethyl-4-phenyl-3-(2H-tetrazol-5-yl)-5,6,7,8-tetrahydroquinoline;

2-(2-ethyltetrahydrofuran-2-yl)-6,6-difluoro-4-phenyl-3-(2H-tetrazol-5-yl)-5,6,7,8-tetrahydroquinoline;

(R)-2-(2-(methoxymethyl)tetrahydrofuran-2-yl)-4-phenyl-3-(2H-tetrazol-5-yl)-5,6,7,8-tetrahydroquinoline;

(S)-2-(2-(methoxymethyl)tetrahydrofuran-2-yl)-4-phenyl-3-(2H-tetrazol-5-yl))-5,6,7,8-tetrahydroquinoline;

(R)-6,6-difluoro-2-(2-(methoxymethyl)tetrahydrofuran-2-yl)-4-phenyl-3-(2H-tetrazol-5-yl)-5,6,7,8-tetrahydroquinoline;

(S)-6,6-difluoro-2-(2-(methoxymethyl)tetrahydrofuran-2-yl)-4-phenyl-3-(2H-tetrazol-5-yl)-5,6,7,8-tetrahydroquinoline;

(R)-2-(2-(methoxymethyl)tetrahydrofuran-2-yl)-6,6-dimethyl-4-phenyl-3-(2H-tetrazol-5-yl)-5,6,7,8-tetrahydroquinoline;

(S)-2-(2-(methoxymethyl)tetrahydrofuran-2-yl)-6,6-dimethyl-4-phenyl-3-(2H-tetrazol-5-yl)-5,6,7,8-tetrahydroquinoline;

2-(2-ethyltetrahydrofuran-2-yl)-4-(1-methyl-1H-pyrazol-5-yl)-3-(2H-tetrazol-5-yl)-5,6,7,8-tetrahydroquinoline;

2-(1-(methoxymethyl)cyclopentyl)-4-(1-methyl-1H-pyrazol-4-yl)-3-(2H-tetrazol-5-yl)-5,6,7,8-tetrahydroquinoline;

4-(3-chlorophenyl)-2-(2-(methoxymethyl)tetrahydrofuran-2-yl)-3-(2H-tetrazol-5-yl)-5,6,7,8-tetrahydroquinoline;

4-(3-chlorophenyl)-2-(2-methyltetrahydrofuran-2-yl)-3-(2H-tetrazol-5-yl)-5,6,7,8-tetrahydroquinoline;

2-(2-(methoxymethyl)tetrahydrofuran-2-yl)-4-(3-methoxyphenyl)-3-(2H-tetrazol-5-yl)-5,6,7,8-tetrahydroquinoline;

4-(4-fluoro-3-methoxyphenyl)-2-(2-(methoxymethyl)tetrahydrofuran-2-yl)-3-(2H-tetrazol-5-yl)-5,6,7,8-tetrahydroquinoline;

2-(1-(methylsulfonylmethyl)cyclopentyl)-4-phenyl-3-(2H-tetrazol-5-yl)-5,6,7,8-tetrahydroquinoline;

(R)-4-(4-fluoro-3-methoxyphenyl)-2-(2-(methoxymethyl)tetrahydrofuran-2-yl)-3-(2H-tetrazol-5-yl)-5,6,7,8-tetrahydroquinoline;

(S)-4-(4-fluoro-3-methoxyphenyl)-2-(2-(methoxymethyl)tetrahydrofuran-2-yl)-3-(2H-tetrazol-5-yl)-5,6,7,8-tetrahydroquinoline;

2-(1-(methoxymethyl)cyclopentyl)-4-(3-(methylsulfonyl)phenyl)-3-(2H-tetrazol-5-yl)-5,6,7,8-tetrahydroquinoline;

2-(1-(methoxymethyl)cyclopentyl)-4-(3-methoxyphenyl)-3-(2H-tetrazol-5-yl)-5,6,7,8-tetrahydroquinoline;

4-(2-fluoro-5-methoxyphenyl)-2-(2-(methoxymethyl)tetrahydrofuran-2-yl)-3-(2H-tetrazol-5-yl)-5,6,7,8-tetrahydroquinoline;

4-(2-fluoro-5-methoxyphenyl)-2-(2-(methoxymethyl)tetrahydrofuran-2-yl)-3-(2H-tetrazol-5-yl)-5,6,7,8-tetrahydroquinoline;

2-(1-(ethoxymethyl)cyclopentyl)-4-phenyl-3-(2H-tetrazol-5-yl)-5,6,7,8-tetrahydroquinoline;

(R)-4-(3-chlorophenyl)-2-(2-(methoxymethyl)tetrahydrofuran-2-yl)-6,6-dimethyl-3-(2H-tetrazol-5-yl)-5,6,7,8-tetrahydroquinoline;

(S)-4-(3-chlorophenyl)-2-(2-(methoxymethyl)tetrahydrofuran-2-yl)-6,6-dimethyl-3-(2H-tetrazol-5-yl)-5,6,7,8-tetrahydroquinoline;

2-(3,3-difluorocyclobutyl)-4-(1-methyl-1H-pyrazol-4-yl)-3-(1H-tetrazol-5-yl)-6,7,8,9-tetrahydro-5H-cyclohepta[b]pyridine;

2-(1,5-dimethyl-1H-pyrazol-4-yl)-4-phenyl-3-(2H-tetrazol-5-yl)-6,7,8,9-tetrahydro-5H-cyclohepta[b]pyridine;

2-tert-butyl-4-(1-methyl-1H-pyrazol-4-yl)-3-(1H-tetrazol-5-yl)-6,7,8,9-tetrahydro-5H-cyclohepta[b]pyridine;

2-(3,3-difluorocyclobutyl)-4-(2-methylpyridin-4-yl)-3-(1H-tetrazol-5-yl)-6,7,8,9-tetrahydro-5H-cyclohepta[b]pyridine;

2-sec-butyl-4-(1-methyl-1H-pyrazol-4-yl)-3-(1H-tetrazol-5-yl)-6,7,8,9-tetrahydro-5H-cyclohepta[b]pyridine;

2-tert-butyl-6,6-difluoro-4-(2-methyl-pyridin-4-yl)-3-(1H-tetrazol-5-yl)-5,6,7,8-tetrahydro-quinoline;

2-tert-butyl-6,6-difluoro-4-(1-methyl-1H-pyrazol-4-yl)-3-(1H-tetrazol-5-yl)-5,6,7,8-tetrahydro-quinoline;

2-tert-butyl-6,6-difluoro-4-(2-methyl-2H-pyrazol-3-yl)-3-(1H-tetrazol-5-yl)-5,6,7,8-tetrahydro-quinoline;

2-tert-butyl-4-phenyl-3-(1H-tetrazol-5-yl)-7,8-dihydro-5H-thiopyrano[4,3-b]pyridine;

2-tert-butyl-8,8-dimethyl-4-phenyl-3-(1H-tetrazol-5-yl)-5,6,7,8-tetrahydroquinoline;

2-tert-butyl-7,7-dimethyl-4-phenyl-3-(1H-tetrazol-5-yl)-6,7-dihydro-5H-cyclopenta[b]pyridine;

2-tert-butyl-8,8-dimethyl-4-(2-methylpyridin-4-yl)-3-(1H-tetrazol-5-yl)-5,6,7,8-tetrahydroquinoline;

2-tert-butyl-8,8-dimethyl-4-(1-methyl-1H-pyrazol-4-yl)-3-(1H-tetrazol-5-yl)-5,6,7,8-tetrahydroquinoline;

2-(1-(methoxymethyl)cyclobutyl)-4-phenyl-3-(1H-tetrazol-5-yl)-6,7,8,9-tetrahydro-5H-cyclohepta[b]pyridine;

2-(1-(methoxymethyl)cyclobutyl)-4-(2-methylpyridin-4-yl)-3-(1H-tetrazol-5-yl)-6,7,8,9-tetrahydro-5H-cyclohepta[b]pyridine;

2-(1-(methoxymethyl)cyclobutyl)-4-(1-methyl-1H-pyrazol-4-yl)-3-(1H-tetrazol-5-yl)-6,7,8,9-tetrahydro-5H-cyclohepta[b]pyridine;

2-(perfluoroethyl)-4-phenyl-3-(1H-tetrazol-5-yl)-6,7,8,9-tetrahydro-5H-cyclohepta[b]pyridine;

2-tert-butyl-8,8-dimethyl-4-(1-methyl-1H-pyrazol-5-yl)-3-(1H-tetrazol-5-yl)-5,6,7,8-tetrahydroquinoline;

2,4-bis(2-methylpyridin-4-yl)-3-(1H-tetrazol-5-yl)-6,7,8,9-tetrahydro-5H-cyclohepta[b]pyridine;

2-isopropoxy-4-phenyl-3-(1H-tetrazol-5-yl)-6,7,8,9-tetrahydro-5H-cyclohepta[b]pyridine;

2-methoxy-4-phenyl-3-(1H-tetrazol-5-yl)-6,7,8,9-tetrahydro-5H-cyclohepta[b]pyridine;

2-ethoxy-4-phenyl-3-(1H-tetrazol-5-yl)-6,7,8,9-tetrahydro-5H-cyclohepta[b]pyridine;

(S)-4-phenyl-2-(tetrahydrofuran-3-yloxy)-6,7,8,9-tetrahydro-5H-cyclohepta[b]pyridine-3-carbonitrile;

(R)-4-phenyl-2-(tetrahydrofuran-3-yloxy)-6,7,8,9-tetrahydro-5H-cyclohepta[b]pyridine-3-carbonitrile;

2-ethoxy-4-(1-methyl-H-pyrazol-4-yl)-3-(1H-tetrazol-5-yl)-6,7,8,9-tetrahydro-5H-cyclohepta[b]pyridine;

2-isopropoxy-4-(1-methyl-1H-pyrazol-4-yl)-3-(1H-tetrazol-5-yl)-6,7,8,9-tetrahydro-5H-cyclohepta[b]pyridine;

2-ethoxy-4-(2-methylpyridin-4-yl)-3-(1H-tetrazol-5-yl)-6,7,8,9-tetrahydro-5H-cyclohepta[b]pyridine;

2-(2-methoxyethoxy)-4-phenyl-3-(1H-tetrazol-5-yl)-6,7,8,9-tetrahydro-5H-cyclohepta[b]pyridine;

4-phenyl-2-((tetrahydrofuran-2-yl)methoxy)-3-(1H-tetrazol-5-yl)-6,7,8,9-tetrahydro-5H-cyclohepta[b]pyridine;

2-(3-fluoropropoxy)-4-phenyl-3-(1H-tetrazol-5-yl)-6,7,8,9-tetrahydro-5H-cyclohepta[b]pyridine;

2-(2,2-difluoroethoxy)-4-phenyl-3-(1H-tetrazol-5-yl)-6,7,8,9-tetrahydro-5H-cyclohepta[b]pyridine;

(S)-4-phenyl-2-(tetrahydrofuran-3-yloxy)-3-(1H-tetrazol-5-yl)-5,6,7,8-tetrahydroquinoline;

4-(2-methylpyridin-4-yl)-2-(tetrahydro-2H-pyran-4-yloxy)-3-(1H-tetrazol-5-yl)-6,7,8,9-tetrahydro-5H-cyclohepta[b]pyridine;

(S)-4-(2-methylpyridin-4-yl)-2-(tetrahydrofuran-3-yloxy)-3-(1H-tetrazol-5-yl)-6,7,8,9-tetrahydro-5H-cyclohepta[b]pyridine;

(S)-4-(2-methylpyridin-4-yl)-2-(tetrahydrofuran-3-yloxy)-3-(1H-tetrazol-5-yl)-5,6,7,8-tetrahydroquinoline;

2-(2-methoxyethoxy)-3-(1H-tetrazol-5-yl)-4-(4-(trifluoromethyl)phenyl)-6,7,8,9-tetrahydro-5H-cyclohepta[b]pyridine;

4-(3-fluorophenyl)-2-(2-methoxyethoxy)-3-(1H-tetrazol-5-yl)-6,7,8,9-tetrahydro-5H-cyclohepta[b]pyridine;

(S)-4-(3-fluorophenyl)-2-(tetrahydrofuran-3-yloxy)-3-(1H-tetrazol-5-yl)-5,6,7,8-tetrahydroquinoline;

4-(3,5-difluorophenyl)-2-(2-methoxyethoxy)-3-(1H-tetrazol-5-yl)-6,7,8,9-tetrahydro-5H-cyclohepta[b]pyridine;

(S)-4-(3-fluorophenyl)-2-(tetrahydrofuran-3-yloxy)-3-(1H-tetrazol-5-yl)-6,7,8,9-tetrahydro-5H-cyclohepta[b]pyridine;

(S)-4-(3,5-difluorophenyl)-2-(tetrahydrofuran-3-yloxy)-3-(1H-tetrazol-5-yl)-6,7,8,9-tetrahydro-5H-cyclohepta[b]pyridine;

4-(2-fluorophenyl)-2-((S)-tetrahydrofuran-3-yloxy)-3-(1H-tetrazol-5-yl)-6,7,8,9-tetrahydro-5H-cyclohepta[b]pyridine;

4-(2-fluorophenyl)-2-(2-methoxyethoxy)-3-(1H-tetrazol-5-yl)-6,7,8,9-tetrahydro-5H-cyclohepta[b]pyridine;

(S)-2-(tetrahydrofuran-3-yloxy)-3-(1H-tetrazol-5-yl)-4-(thiophen-2-yl)-6,7,8,9-tetrahydro-5H-cyclohepta[b]pyridine;

2-(3-fluoropropoxy)-3-(1H-tetrazol-5-yl)-4-(thiophen-2-yl)-6,7,8,9-tetrahydro-5H-cyclohepta[b]pyridine;

(S)-2-(tetrahydrofuran-3-yloxy)-3-(1H-tetrazol-5-yl)-4-(thiophen-3-yl)-6,7,8,9-tetrahydro-5H-cyclohepta[b]pyridine;

4-phenyl-2-(tetrahydro-2H-pyran-4-yloxy)-3-(1H-tetrazol-5-yl)-6,7,8,9-tetrahydro-5H-cyclohepta[b]pyridine;

2-(1-methylcyclopentyl)-4-phenyl-6,7,8,9-tetrahydro-5H-cyclohepta[b]pyridine-3-carboxylic acid;

4-(3-chlorophenyl)-2-(1-methylcyclopentyl)-6,7,8,9-tetrahydro-5H-cyclohepta[b]pyridine-3-carboxylic acid;

4-(1-methyl-1H-pyrazol-5-yl)-2-(1-methylcyclohexyl)-6,7,8,9-tetrahydro-5H-cyclohepta[b]pyridine-3-carboxylic acid;

2-(1-methylcyclohexyl)-4-phenyl-6,7,8,9-tetrahydro-5H-cyclohepta[b]pyridine-3-carboxylic acid;

2-cyclohexyl-4-phenyl-6,7,8,9-tetrahydro-5H-cyclohepta[b]pyridine-3-carboxylic acid;

2-(1-methylcyclohexyl)-4-(2-methylpyridin-4-yl)-6,7,8,9-tetrahydro-5H-cyclohepta[b]pyridine-3-carboxylic acid;

2-cyclohexyl-4-(2-methylpyridin-4-yl)-6,7,8,9-tetrahydro-5H-cyclohepta[b]pyridine-3-carboxylic acid;

2-cyclopentyl-4-phenyl-5,6,7,8-tetrahydroquinoline-3-carboxylic acid;

2-(1-(methoxymethyl)cyclopentyl)-6-pentyl-4-phenyl-3-(1H-tetrazol-5-yl)-5,6,7,8-tetrahydroquinoline;

tert-butyl 2-methyl-2-(4-(2-methylpyridin-4-yl)-3-(1H-tetrazol-5-yl)-6,7,8,9-tetrahydro-5H-cyclohepta[b]pyridin-2-yl)propanoate;

2-methyl-2-(4-(2-methylpyridin-4-yl)-3-(1H-tetrazol-5-yl)-6,7,8,9-tetrahydro-5H-cyclohepta[b]pyridin-2-yl)propanoic acid;

and pharmaceutically acceptable salts thereof.

Further particular examples of compounds of formula (I) as described herein are selected from 6-methyl-4-(1-methyl-1H-pyrazol-5-yl)-2-(piperidin-1-yl)-3-(2H-tetrazol-5-yl)-5,6,7,8-tetrahydroquinoline;

4-(3-chlorophenyl)-N,N-diethyl-3-(1H-tetrazol-5-yl)-6,7,8,9-tetrahydro-5H-cyclohepta[b]pyridin-2-amine;

2-cyclopentyl-4-(2-methylpyridin-4-yl)-3-(1H-tetrazol-5-yl)-6,7,8,9-tetrahydro-5H-cyclohepta[b]pyridine;

4-phenyl-2-(tetrahydrofuran-2-yl)-3-(1H-tetrazol-5-yl)-6,7,8,9-tetrahydro-5H-cyclohepta[b]pyridine;

2-(1-(methoxymethyl)cyclopentyl)-4-(2-methylpyridin-4-yl)-3-(1H-tetrazol-5-yl)-6,7,8,9-tetrahydro-5H-cyclohepta[b]pyridine;

2-cyclopentyl-6,6-difluoro-4-phenyl-3-(2H-tetrazol-5-yl)-5,6,7,8-tetrahydroquinoline;

2-cyclopentyl-6-methyl-4-(2-methylpyridin-4-yl)-3-(2H-tetrazol-5-yl)-5,6,7,8-tetrahydroquinoline;

2-cyclopentyl-6,6-dimethyl-4-(2-methylpyridin-4-yl)-3-(2H-tetrazol-5-yl)-5,6,7,8-tetrahydroquinoline;

and pharmaceutically acceptable salts thereof.

Also further particular examples of compounds of formula (I) as described herein are selected from 2-((R)-2-methyl-tetrahydro-furan-2-yl)-4-phenyl-3-(1H-tetrazol-5-yl)-6,7,8,9-tetrahydro-5H-cyclohepta[b]pyridine;

2-(1-methylcyclopentyl)-4-(2-methylpyridin-4-yl)-3-(1H-tetrazol-5-yl)-6,7,8,9-tetrahydro-5H-cyclohepta[b]pyridine;

4-(2-chloropyridin-4-yl)-2-(1-(methoxymethyl)cyclopentyl)-3-(1H-tetrazol-5-yl)-6,7,8,9-tetrahydro-5H-cyclohepta[b]pyridine;

(R)-6,6-dimethyl-2-(2-methyltetrahydrofuran-2-yl)-4-phenyl-3-(2H-tetrazol-5-yl)-5,6,7,8-tetrahydroquinoline;

(R)-2-(2-(methoxymethyl)tetrahydrofuran-2-yl)-4-phenyl-3-(2H-tetrazol-5-yl)-5,6,7,8-tetrahydroquinoline;

(S)-4-phenyl-2-(tetrahydrofuran-3-yloxy)-6,7,8,9-tetrahydro-5H-cyclohepta[b]pyridine-3-carbonitrile;

2-(1-methylcyclohexyl)-4-(2-methylpyridin-4-yl)-6,7,8,9-tetrahydro-5H-cyclohepta[b]pyridine-3-carboxylic acid;

and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the person skilled in the art such as e.g. chiral chromatography or crystallization. In case one of the starting materials or compounds of formula (I) contain one or more functional groups which are not stable or are reactive under the reaction conditions of one or more reaction steps, appropriate protecting groups can be introduced before the critical step applying methods well known in the art. Such protecting groups can be removed at a later stage of the synthesis using standard methods described in the literature. The substituents and indices used in the following description of the processes have the significance given herein.

Abbreviations

The following abbreviations are used in the present text: d=days, DCM=dichloromethane, DMA=N,N-dimethylacetamide, DMF=N,N-dimethylformamide, DMSO=dimethylsulfoxide, EtOAc=ethyl acetate, ESP=Electrospray Ionisation, positive ions, ESN=Electrospray Ionisation, negative ions, EtOH=ethanol, h=hours, HCl=hydrochloric acid, MeOH=methanol, min=minutes, NaOH=sodium hydroxide, $Na_2SO_4$=sodium sulfate, OTf=$CF_3$—$SO_2$—O—, THF=tetrahydrofuran.

Compounds of formula (I), wherein $R^2$ is 5-tetrazolyl may be prepared as illustrated in scheme 1.

Scheme 1

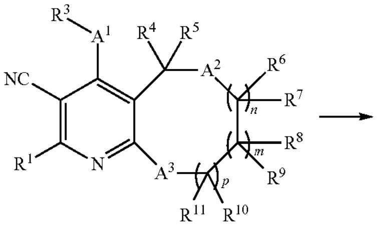

(II)

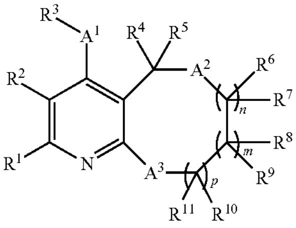

(I) $R^2$ is tetrazolyl

Nitrile derivatives of formula (II) can be converted into formula (I) compounds, wherein $R^2$ is 5-tetrazolyl, by reaction with azide reagents M-$N_3$, wherein M represents sodium, trialkyltin or trialkylsilyl, optionally in presence of additives such as zinc salts or dibutyltin oxide. Typical conditions include sodium azide in the presence of zinc chloride in a solvent such as DMF at elevated temperature, trimethyltin azide in a solvent such as xylene at elevated temperature or trimethylsilyl azide in the presence of dibutyltin oxide in a solvent such as dioxane at elevated temperature.

Compounds of formula (I), wherein $R^2$ is —COOH may be prepared as illustrated in scheme 2.

Scheme 2

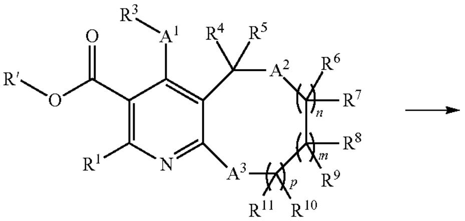

(III) R′ is alkyl, e.g. Me, Et or t-Bu

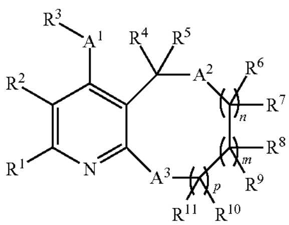

(I) $R^2$ is —$CO_2H$

Ester derivatives of formula (III) can be converted into compounds of formula (I), wherein $R^2$ is —COOH, by reaction with a metal hydroxide such as lithium, sodium or potassium hydroxide in solvent mixtures containing DMSO-water, ethanol-water, THF-methanol-water or methanol-water at elevated temperature. Alternatively, ester cleavage can also be accomplished by reaction with a nucleophile such as lithium iodide in pyridine at elevated temperatures. Ester derivatives of formula (III), wherein R' is tert-butyl can be converted into compounds of formula (I), wherein $R^2$ is —COOH by reaction with an acid such as HCl in a solvent such as dioxane or with TFA in a solvent such as DCM. Other methods for cleavage of esters can be found in the literature.

Alternatively, compounds of formula (I), wherein $R^2$ is —COOH may be prepared as illustrated in scheme 3.

Scheme 3

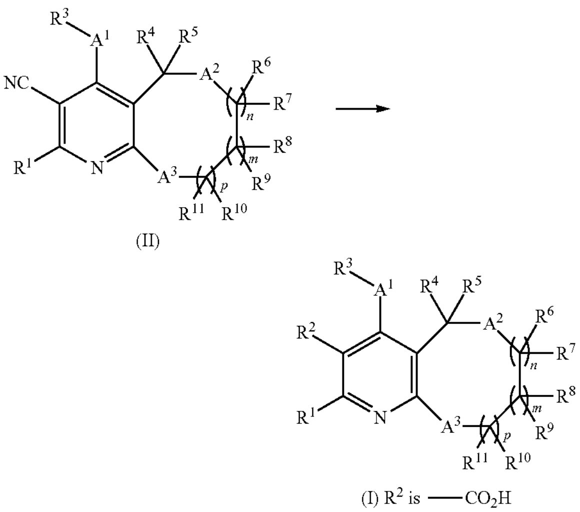

(II)

(I) $R^2$ is —$CO_2H$

Nitrile derivatives of formula (II) can be treated with aqueous acid such as HCl or alternatively with an aqueous base such as potassium hydroxide at elevated temperature to obtain compounds of formula (I), wherein $R^2$ is —COOH. Nitriles of formula (II) can also be converted to compounds of formula (I), wherein $R^2$ is —COOH by conversion to the corresponding iminoether by addition of alcoholic solutions of acids such as HCl, HBr or the like at various temperatures, preferably ranging from 0 to 100° C., followed by hydrolysis of the iminoether to the corresponding ester and hydrolysis of the ester as described above.

Nitrile intermediates of formula (II) wherein $A^3$ is —$CR^{17}R^{18}$— can be obtained as illustrated in scheme 4.

Scheme 4

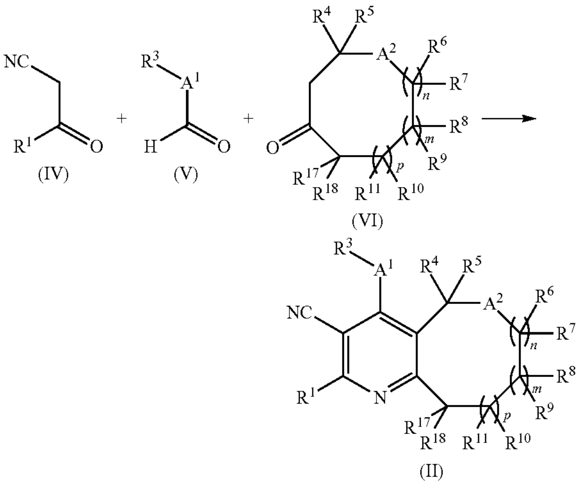

(IV) (V) (VI)

(II)

Four component reaction of suitable 0-keto nitriles (IV), aldehydes (V), cyclic ketones of formula (VI) and ammonium acetate in an inert solvent such as toluene at elevated temperature optionally with removal of water affords dihydropyridine compounds that can be oxidized to derivatives of formula (II) using oxidizing agents such as ceric ammonium nitrate.

An alternative preparation of intermediates of formula (II) wherein $A^3$ is —$CR^{17}R^{18}$— is illustrated in scheme 5.

Scheme 5

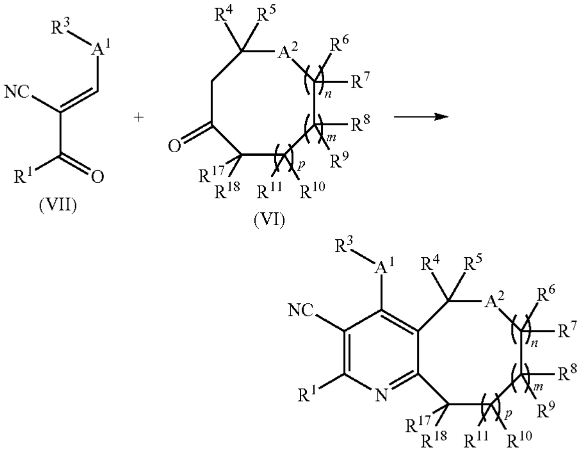

(VII) (VI)

(II)

Three component reaction of α,β-unsaturated keto nitriles (VII), cyclic ketones of formula (VI) and ammonium acetate at elevated temperature under air atmosphere affords intermediates of formula (II). Compounds of formula (VII) can be prepared by Knoevenagel condensation using suitable 0-keto nitriles (IV) and aldehydes (V). Typical conditions for this transformation include the reaction of compounds of formula (IV) and (V) in an alcoholic solvent such as ethanol or methanol, optionally in presence of L-proline at room temperature or the reaction of compounds of formula (IV) and (V) in presence of an amine such as piperidine in toluene as a solvent at reflux temperature optionally with removal of water.

Ester intermediates of formula (III) wherein $A^3$ is —$CR^{17}R^{18}$— and R' is alkyl such as methyl, ethyl or tert-butyl can be obtained as illustrated in scheme 6.

Scheme 6

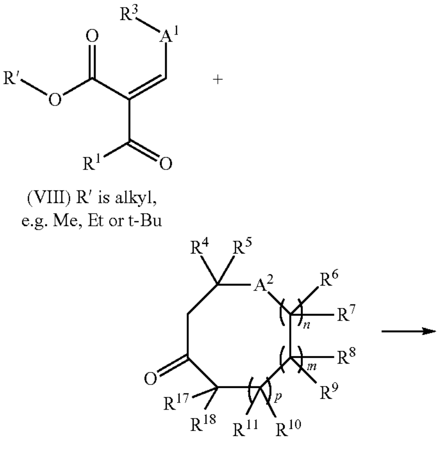

(VIII) R' is alkyl, e.g. Me, Et or t-Bu (VI)

-continued

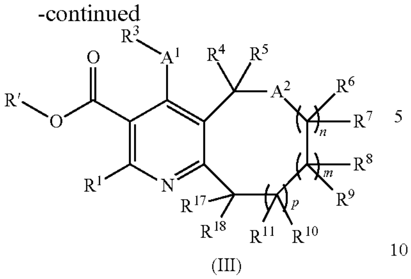

(III)

Michael addition of enolates derived from cyclic ketones of formula (VI) with α,β-unsaturated keto esters (VIII) and subsequent reaction with ammonium actetate and oxidation affords ester intermediates of formula (III). Enolate formation from ketones of formula (VI) can be accomplished with bases such as LDA, LiHMDS and NaHMDS in an inert solvent such as THF at low temperature. Cyclization of the resulting Michael adducts with ammonium acetate in presence of a catalytic amount of an acid such as p-toluenesulfonic acid in an alcoholic solvent such as ethanol at elevated temperature affords dihydropyridines that can be oxidized to derivatives of formula (III) using oxidizing agents such as DDQ.

Ester intermediates of formula (III), wherein $A^3$ is N—$R^{19}$ and R' is alkyl such as methyl, ethyl or tert-butyl can be obtained as illustrated in scheme 7.

Scheme 7

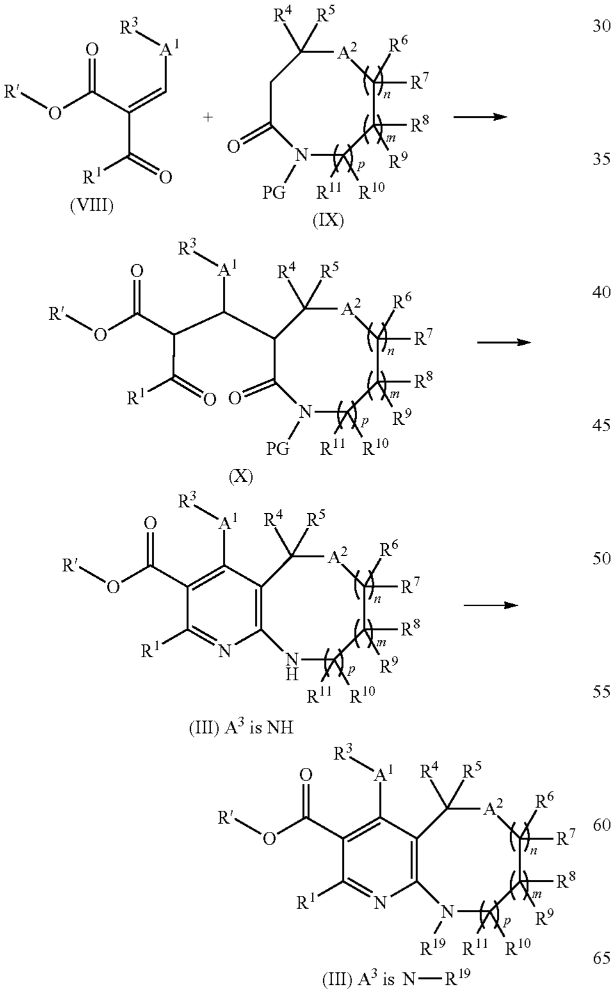

(VIII) (IX) (X) (III) $A^3$ is NH (III) $A^3$ is N—$R^{19}$

Michael addition of enolates derived from lactams of formula (IX) with α,β-unsaturated keto esters (VIII) affords compounds of formula (X). The enolate formation can be accomplished by reacting lactams of formula (IX) with a base such as LDA, LiHMDS or NaHMDS in a solvent such as THF at low temperature. Conversion of compounds of formula (X) into formula (III) compounds wherein $A^3$ is NH requires stepwise reaction with phosphorus pentachloride, ammonium acetate and copper (I) acetate. Derivatives of formula (III), wherein $A^3$ is NH can be elaborated into compounds of formula (III), wherein $A^3$ is N—$R^{19}$ and $R^{19}$ represents alkyl, cycloalkyl and haloalkyl by reaction with an appropriate reagent $R^{19}$—X wherein X is Br or I in presence of a base such as sodium hydride. In a similar manner, compounds of formula (III), wherein $A^3$ is N—$R^{19}$ and $R^{19}$ represents alkylcarbonyl can be obtained by reaction with a suitable carboxylic acid anhydride in presence of a base such as triethylamine.

Alternatively to the preparations described in schemes 4 and 5, nitrile intermediates of formula (II) wherein $A^3$ is —$CR^7R^8$— can be obtained as illustrated in scheme 8.

Scheme 8

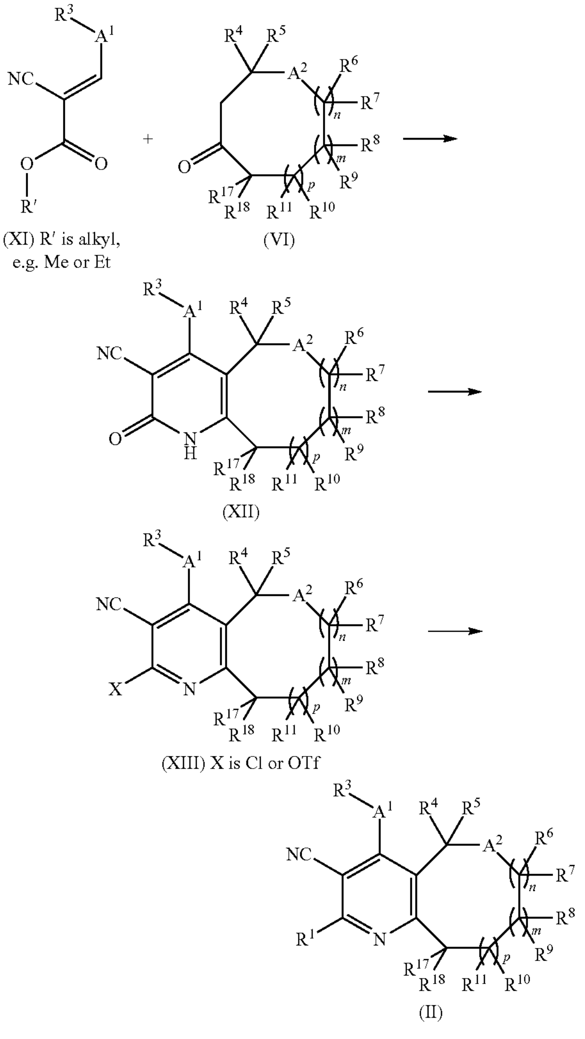

(XI) R' is alkyl, e.g. Me or Et (VI) (XII) (XIII) X is Cl or OTf (II)

Reaction of α,β-unsaturated ester nitriles (XI) with ketones of formula (VI) and ammonium acetate at elevated temperature under air atmosphere affords compounds of formula (XII). α,β-Unsaturated ester nitriles (XI) can be prepared by Knoevenagel condensation using alkyl cyanoacetates and aldehydes (V). Typical conditions for this transformation include the reaction of both components in an alcoholic solvent such as ethanol or methanol at room temperature or the reaction of both components in presence of an amine such as piperidine in toluene as a solvent at reflux temperature optionally with removal of water. Compounds of formula (XII) can be elaborated into derivatives of formula (II) in 2 steps. Reaction of compounds of formula (XII) with phosphorus oxychloride delivers pyridines of formula (XIII), wherein X is Cl. Alternatively, compounds of formula (XII) can be reacted with N-phenylbis(trifluoromethanesulphonimide) in presence of a base such as sodium hydride to obtain derivatives of formula (XIII), wherein X is OTf. Compounds of formula (XIII), wherein X is Cl or OTf can be reacted with alcohols in presence of a base such as sodium hydride to obtain compounds of formula (II), wherein $R^1$ represents alkoxy, haloalkoxy, cycloalkoxy or halocycloalkoxy. Compounds of formula (XIII), wherein X is Cl or OTf can also be reacted with amines or amides, optionally in presence of a base such as triethylamine, potassium carbonate or sodium hydride to obtain compounds of formula (II), wherein $R^1$ represents heterocycloalkyl, substituted heterocycloalkyl or substituted amino.

Alternatively to the preparations described in schemes 6 and 7, ester intermediates of formula (III) wherein $A^3$ is —$CR^{17}R^{18}$— and R' is alkyl such as methyl, ethyl or tert-butyl can be obtained as illustrated in scheme 9.

Scheme 9

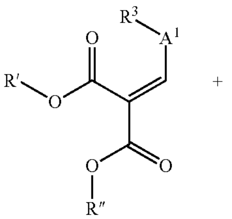

(XIV)
R′ is alkyl,
e.g. Me, Et or t-Bu
R″ is alkyl,
e.g. Me, Et or t-Bu

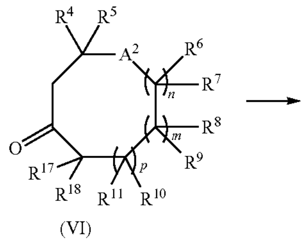

(VI)

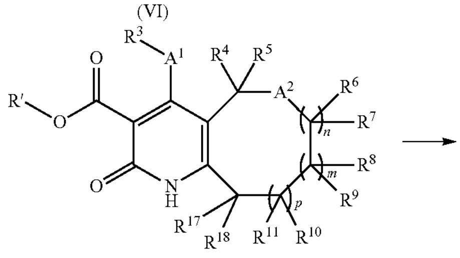

(XV)

-continued

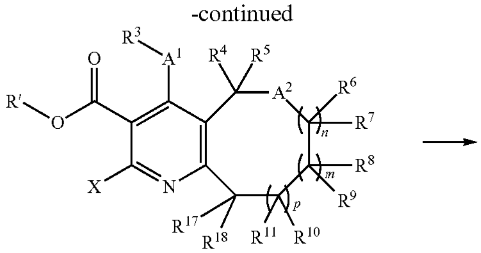

(XVI) X is Cl or OTf

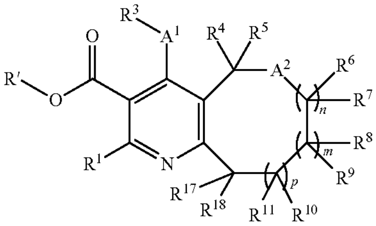

(III)

Pyridone derivatives of formula (XV) are accessible from α,β-unsaturated diesters (XIV) and ketones of formula (VI) in 3 steps. The Michael adducts that result from reaction of enolates derived from ketones of formula (VI) and a, 3-unsaturated diesters (XIV) can be cyclized with ammonium acetate at elevated temperature. Final oxidation using an oxidizing agent such as $FeCl_3$ in refluxing propionic acid delivers pyridines of formula (XV). Compounds of formula (XV) can be elaborated into derivatives of formula (III) in 2 steps. Reaction of compounds of formula (XV) with phosphorus oxychloride delivers pyridines of formula (XVI), wherein X is Cl.

Alternatively, compounds of formula (XV) can be reacted with N-phenylbis(trifluoromethanesulphonimide) in presence of a base such as sodium hydride to obtain derivatives of formula (XVI), wherein X is OTf. Compounds of formula (XVI), wherein X is Cl or OTf can be reacted with alcohols in presence of a base such as sodium hydride to obtain compounds of formula (III), wherein $R^1$ represents alkoxy, haloalkoxy, cycloalkoxy or halocycloalkoxy. Compounds of formula (XVI), wherein X is Cl or OTf can also be reacted with amines or amides, optionally in presence of a base such as triethylamine, potassium carbonate or sodium hydride to obtain compounds of formula (III), wherein $R^1$ represents heterocycloalkyl, substituted heterocycloalkyl or substituted amino.

Nitrile intermediates of formula (II) wherein $A^3$ is —$CR^{17}R^{18}$— and $R^2$ is —$NH_2$ can be obtained as illustrated in scheme 10.

Scheme 10

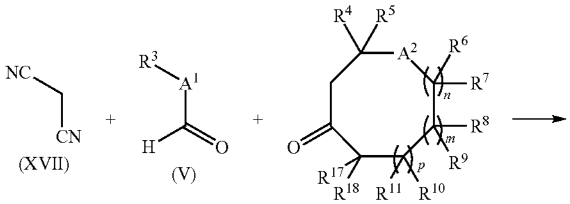

(XVII) (V) (VI)

-continued

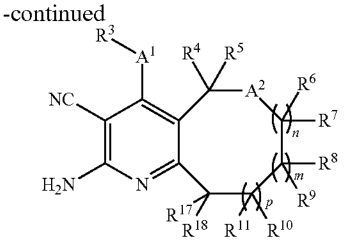

(II) $R^1$ is —$NH_2$

Four component reaction of malononitrile (XVII) with suitable aldehydes (V), cyclic ketones of formula (VI) and ammonium acetate in an inert solvent such as benzene at elevated temperature affords compounds of formula (II) wherein $R^2$ is —$NH_2$.

Alternatively to the preparation described in scheme 8, intermediates of formula (XII) wherein $A^3$ is —$CR^{17}R^{18}$— can also be obtained as illustrated in scheme 11.

Scheme 11

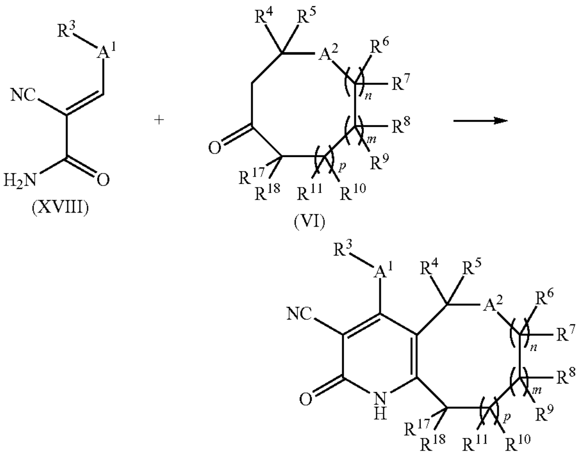

(XVIII) (VI) (XII)

α,β-Unsaturated nitrile amides (XVIII) can be reacted with ketones of formula (VI) in the presence of potassium tert-butoxide in a polar aprotic solvent such as DMSO at room temperature under air or oxygen atmosphere (R. Jain et. al., *Tetrahedron Lett.* 1995, 36, 3307) to obtain compounds of formula (XII).

Compounds of formula (I), wherein $A^3$ is —$CR^{17}R^{18}$— and $R^2$ is [1,3,4]-oxadiazol-2-on-yl or [1,3,4]-oxadiazol-2-thion-yl may be prepared as described in scheme 12.

Scheme 12

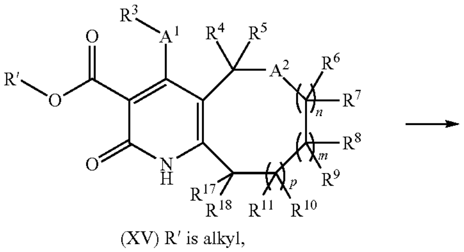

(XV) R′ is alkyl,
e.g. Me, Et or t-Bu

-continued

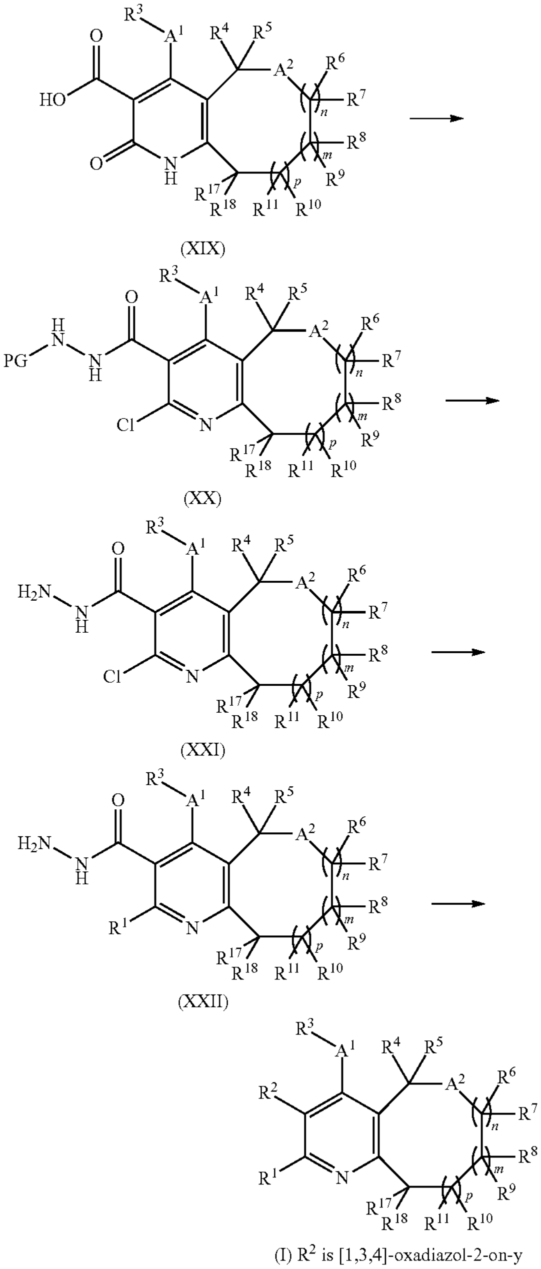

(XIX) (XX) (XXI) (XXII)

(I) $R^2$ is [1,3,4]-oxadiazol-2-on-y or [1,3,4]-oxadiazol-2-thion-yl

Derivatives of formula (XV) can be reacted with lithium, sodium or potassium hydroxide in a solvent such as methanol or ethanol at elevated temperatures to obtain carboxylic acids of formula (XIX). To elaborate compounds of formula (XIX) into derivatives of formula (XX), wherein PG is a protecting group they can be reacted first with phenylphosphonic dichloride and then with suitably protected hydrazine. If PG represents a 9-fluorenylmethoxycarbonyl (Fmoc) group and acyclic or cyclic secondary amines are introduced as $R^1$ substituents, cleavage of the protecting group and nucleophilic displacement can be performed stepwise via compounds of formula (XXI) or in one step to obtain compounds of formula (XXII). Compounds of formula (XXII) can be reacted with N,N'-carbonyldiimidazole or 1,1'-thiocarbonyldiimidazole in presence of a base such as triethylamine and in a solvent such as THF to obtain compounds of formula (I), wherein $R^2$ is [1,3,4]-oxadiazol-2-on-yl or [1,3,4]-oxadiazol-2-thion-yl.

Compounds of formula (I) wherein $A^3$ is $—CR^{17}R^{18}—$ and $R^2$ is —COOH can also be prepared as illustrated in scheme 13.

Scheme 13

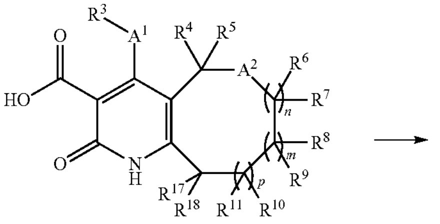

(XIX)

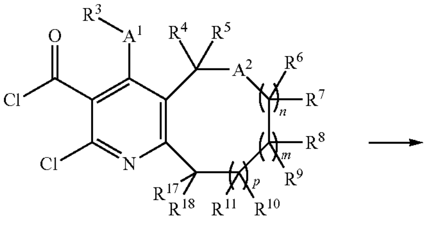

(XXIII)

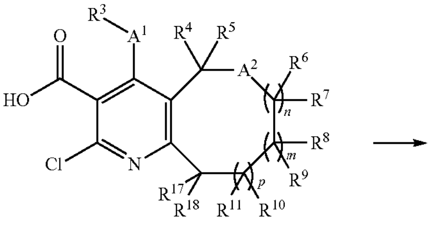

(XXIV)

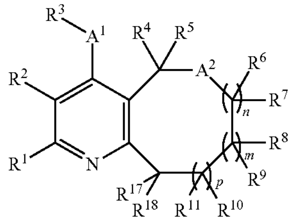

(I) $R^2$ is —$CO_2H$

Reaction of derivatives of formula (XIX) with phenylphosphonic dichloride at elevated temperature affords dichloro intermediates of formula (XXIII). Derivatives of formula (XXIV) can be obtained by hydrolysis of the acid chloride moiety of (XXIII) to a carboxylic acid with water in a co-solvent such as THF at room temperature or elevated temperature. Derivatives of formula (XXIV) can be reacted with amines in the presence of copper powder, copper (I) bromide and potassium carbonate in a solvent such as DMA at elevated temperature to obtain compounds of formula (I), wherein $R^1$ represents heterocycloalkyl, substituted heterocycloalkyl or substituted amino.

Also an embodiment of the present invention is a process to prepare a compound of formula (I) as defined above comprising the reaction of a compound of formula (II) in the presence of a compound of formula (XXV), wherein M is sodium, trialkyltin, such as trimethyltin, or trialkylsilyl, such as trimethylsilyl, optionally in presence of additives such as zinc salts or dibutyltin oxide, in a solvent such as DMF, xylene or dioxane, at elevated temperature.

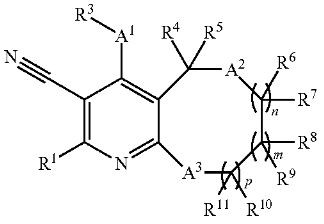

(II)

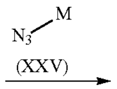

(XXV)

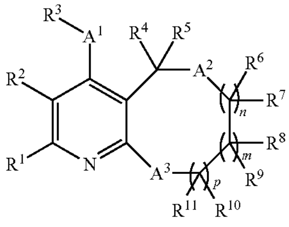

(I)

Also an object of the present invention is a compound according to formula (I) as described herein for use as therapeutically active substance.

Likewise an object of the present invention is a pharmaceutical composition comprising a compound according to formula (I) as described herein and a therapeutically inert carrier.

In accordance with the invention, the compounds of formula (I) or their pharmaceutically acceptable salts and esters can be used for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome.

Particular liver diseases are liver diseases involving inflammation, steatosis and/or fibrosis, such non-alcoholic fatty liver disease, more particularly non-alcoholic steatohepatitis.

Particular lipodystrophy are genetic and iatrogenic lipodystrophy.

Particular eye diseases are eye diseases supported by endothelial proliferation and angiogenesis, particularly macular degeneration and retinopathy.

Particular lung diseases are asthma, bronchopulmonary dysplasia and chronic obstructive pulmonary disease.

Particular chronic renal diseases are vasculitis, focal segmental glomerulosclerosis, diabetic nephropathy, lupus nephritis, polycystic kidney disease and drug or toxin-induced chronic tubulointerstitial nephritis.

The present invention also relates to the use of a compound according to formula (I) as described herein for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome.

The present invention particularly relates to the use of a compound according to formula (I) as described herein for the treatment or prophylaxis of type 2 diabetes, atherosclerosis, cancer, chronic renal disease and non-alcoholic steatohepatitis.

The present invention also relates to the use of a compound according to formula (I) as described herein for the treatment or prophylaxis of non-alcoholic steatohepatitis.

A particular embodiment of the present invention is a compound according to formula (I) as described herein for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome.

Another particular embodiment of the present invention is a compound according to formula (I) as described herein for the treatment or prophylaxis of type 2 diabetes, atherosclerosis, cancer, chronic renal disease and non-alcoholic steatohepatitis.

Also a particular embodiment of the present invention is a compound according to formula (I) as described herein for the treatment or prophylaxis of non-alcoholic steatohepatitis.

The present invention also relates to the use of a compound according to formula (I) as described herein for the preparation of a medicament for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome.

The present invention particularly relates to the use of a compound according to formula (I) as described herein for the preparation of a medicament for the treatment or prophylaxis of type 2 diabetes, atherosclerosis, cancer, chronic renal disease and non-alcoholic steatohepatitis.

Also an embodiment of the present invention is the use of a compound according to formula (I) as described herein for the preparation of a medicament for the treatment or prophylaxis of non-alcoholic steatohepatitis.

Also an object of the invention is a method for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome, which method comprises administering an effective amount of a compound according to formula (I) as described herein.

Another object of the invention is a method for the treatment or prophylaxis of type 2 diabetes, atherosclerosis, cancer, chronic renal disease and non-alcoholic steatohepatitis, which method comprises administering an effective amount of a compound according to formula (I) as described herein.

Also an embodiment of the present invention is a method for the treatment or prophylaxis of non-alcoholic steatohepatitis, which method comprises administering an effective amount of a compound according to formula (I) as described herein.

Also an embodiment of the present invention is a method for the treatment or prophylaxis of lipodystrophy, which method comprises administering an effective amount of a compound according to formula (I) as described herein.

Also a particular embodiment of the present invention is a compound according to formula (I) as described herein, when manufactured according to any one of the described processes.

Assay Procedures

Compounds were profiled for activity against human FABP4 (huFABP4) and/or human FABP5 (huFABP5) in Terbium (Tb) time resolved-fluorescence energy transfer (TR-FRET) assays monitoring the direct binding of Bodipy labeled fatty acid to His6 tagged FABP proteins (huFABP4 was expressed in house in *E. coli* and purified, huFABP5 was purchased from Cayman Chemical Co., cat. no. 10010364), bound to Terbium labeled anti His6 tag antibody. Assay read-outs reflected energy transfer, upon binding of the ligand to the FABP protein, from the Terbium donor molecule to the acceptor Bodipy moiety. Final ligand concentration (125 nM) approximated the Kd for each protein.

Stock DMSO solutions (1.8 mM) of compounds were serially diluted 3-fold for ten concentrations with 100% DMSO (50M to 0.003 M final compound concentration). 1 μl of these compound dilutions and 1 μl of Bodipy labeled fatty acid 4.5 μM in 100% DMSO (Bodipy FL C11, cat. no. D3862, Invitrogen) were sequentially pipetted in wells of 384-well black polypropylene plates (Thermo Matrix cat. no. 4344). FABP4 or FABP5 protein was then added (28 μl of 64 nM protein in 25 mM Tris pH 7.5, 0.4 mg/ml γ-globulin, 1 mM DTT, 0.012% NP40, final protein concentration: 50 nM). Assay blanks contained ligand, but no protein. Neutral controls contained ligand, but no compound. After adding the detection reagent (Tb antiHis6 antibody, Columbia Biosciences, TB-110, 6 μl of a 24 nM Ab solution in 25 mM Tris pH 7.5, 0.4 mg/ml γ-globulin, final Tb antiHis6 Ab concentration: 4 nM), plates were spun one minute at 1000 rpm. Following an incubation at room temperature with shaking for 30 minutes, plates were read using an Envision reader (Perkin Elmer, Extinction wavelength: 340 nm, Emission: 490 nm and 520 nm, time delay: 100 μs; time window: 200 μs, 50 flashes).

Final assay conditions were: 50 nM FABP protein, 125 nM Bodipy labeled fatty acid, 0.009% (vol/vol) NP40, 5.5% (vol/vol) DMSO in a total final assay volume of 36 μl. The assay was performed in triplicate.

The relative fluorescence units (RFU) ratio (520 nm*10000/488 nm) were used to calculate the percent inhibition: 100−(RFU ratio compound−blank)/neutral control−blank)*100. These percent inhibition values were then fit to dose response curves using a 4 parameter logistic model (Hill sigmoidal dose-response model). $IC_{50}$s reflected compound concentrations associated with 50% inhibition of protein activity compared to that of neutral controls.

| Example | IC50 h-fabp4-ecoli-r μM | IC50 h-fabp5-ecoli-r μM |
|---|---|---|
| 1 | 0.23 | 10.98 |
| 2 | 2.06 | |
| 3 | 0.06 | 0.95 |
| 4 | 0.42 | 1.36 |
| 5 | 0.07 | 0.75 |
| 6 | 0.22 | 0.73 |
| 7 | 0.01 | 0.61 |
| 8 | 0.03 | 1.38 |
| 9 | 0.11 | 33.73 |
| 10 | 0.33 | 8.68 |
| 11 | 0.96 | |
| 12 | 0.3 | 12.09 |
| 13 | 9.96 | 13.82 |
| 14 | 0.26 | 6.13 |
| 15 | 0.23 | 10.14 |
| 16 | 0.32 | |
| 17 | 0.16 | 6.01 |
| 18 | 0.28 | 12.24 |
| 19 | 0.05 | 2.25 |
| 20 | 0.42 | 6.52 |
| 21 | 2.97 | 26.94 |
| 22 | 3.95 | |
| 23 | 0.33 | 1.83 |
| 24 | 0.02 | 0.07 |
| 25 | 0.06 | 0.19 |
| 26 | 0.01 | 0.13 |
| 27 | 0.11 | 0.17 |
| 28 | 0.02 | 0.12 |

-continued

| Example | IC50 h-fabp4-ecoli-r μM | IC50 h-fabp5-ecoli-r μM |
|---|---|---|
| 29 | 0.04 | 0.27 |
| 30 | 0.03 | 0.38 |
| 31 | 0.02 | 0.19 |
| 32 | 0.04 | 0.25 |
| 33 | 0.02 | 0.23 |
| 34 | 0.32 | 1.04 |
| 35 | 0.04 | 0.13 |
| 36 | 0.42 | 11.1 |
| 37 | 0.02 | 0.25 |
| 38 | 0.01 | 0.26 |
| 39 | 0.08 | 0.38 |
| 40 | 0.04 | 0.57 |
| 41 | 4.63 | 7.94 |
| 42 | 1.46 | 10.96 |
| 43 | 0.17 | 0.82 |
| 44 | 0.05 | 0.42 |
| 45 | 0.03 | 0.31 |
| 46 | 0.52 | 2.01 |
| 47 | 0.13 | 0.86 |
| 48 | 3.33 | 4.34 |
| 49 | 1.19 | 3.21 |
| 50 | 0.07 | 0.28 |
| 51 | 0.18 | 0.43 |
| 52 | 0.25 | 2.16 |
| 53 | 0.09 | 1.51 |
| 54 | 4.17 | 10.34 |
| 55 | 0.05 | 1.09 |
| 56 | 0.04 | 0.24 |
| 57 | 0.04 | 0.12 |
| 58 | 0.03 | 0.7 |
| 59 | 0.07 | 0.97 |
| 60 | 0.04 | 0.77 |
| 61 | 0.14 | 5.36 |
| 62 | 0.03 | 0.13 |
| 63 | 0.03 | 0.78 |
| 64 | 0.23 | |
| 65 | 0.03 | 3.74 |
| 66 | 0.04 | 3.1 |
| 67 | 0.01 | 0.52 |
| 68 | 0.11 | 1.24 |
| 69 | 0.02 | 0.26 |
| 70 | 0.12 | 0.63 |
| 71 | 0.31 | 10.53 |
| 72 | 1.41 | 46.17 |
| 73 | 3.46 | |
| 74 | 0.15 | 0.74 |
| 75 | 0.03 | 0.2 |
| 76 | 0.08 | 1.76 |
| 77 | 13.01 | |
| 78 | 0.04 | 1.32 |
| 79 | 0.18 | 2.13 |
| 80 | 0.04 | 0.22 |
| 81 | 0.06 | 1.75 |
| 82 | 0.004 | 0.167 |
| 83 | 0.086 | 0.18 |
| 84 | 0.012 | 0.074 |
| 85 | 0.024 | 0.54 |
| 86 | 0.11 | 0.38 |
| 87 | 0.03 | 0.4 |
| 88 | 0.14 | 1.54 |
| 89 | 16.37 | 16.43 |
| 90 | 0.22 | 21.12 |
| 91 | 2.9833 | 7.6219 |
| 92 | 0.2621 | 6.5653 |
| 93 | 0.7122 | 4.2287 |
| 94 | 0.026 | 0.0996 |
| 95 | 0.9872 | 3.5918 |
| 96 | 0.86 | 4.71 |
| 97 | 0.28 | 1.81 |
| 98 | 0.08 | 7.53 |
| 99 | 2.78 | 11.46 |
| 100 | 0.29 | 0.97 |
| 101 | 3.22 | 16.2 |
| 102 | 1.06 | 21.81 |
| 103 | 0.08 | 0.44 |

-continued

| Example | IC50 h-fabp4-ecoli-r μM | IC50 h-fabp5-ecoli-r μM |
|---|---|---|
| 104 | 0.04 | 0.37 |
| 105 | 0.15 | 1.6 |
| 106 | 0.59 | 1.61 |
| 107 | 1.29 | 0.09 |
| 108 | 1.8 | 1.67 |
| 109 | 0.08 | 0.37 |
| 110 | 0.02 | 0.31 |
| 111 | 0.69 | 0.71 |
| 112 | 0.042 | 0.726 |
| 113 | 0.01 | 0.066 |
| 114 | 2.097 | 2.104 |
| 115 | 0.206 | 1.097 |
| 116 | 0.16 | 0.1 |
| 117 | 5.03 | 1.23 |
| 118 | 0.06 | 0.2835 |
| 119 | 0.24 | 1.49 |
| 120 | 0.02 | 0.05 |
| 121 | 0.02 | 0.3 |
| 122 | 0.19 | 0.48 |
| 123 | 0.04 | 0.37 |
| 124 | 0.09 | 2.47 |
| 125 | 0.77 | 1.67 |
| 126 | 0.01 | 0.07 |
| 127 | 0.015 | 0.051 |
| 128 | 0.046 | 0.462 |
| 129 | 0.01 | 0.13 |
| 130 | 0.01 | 0.08 |
| 131 | 0.03 | 0.37 |
| 132 | 0.02 | 0.05 |
| 133 | 0.03 | 0.61 |
| 134 | 0.0591 | 2.4221 |
| 135 | 0.0165 | 0.3187 |
| 136 | 0.0979 | 5.6834 |
| 137 | 0.043 | 2.3478 |
| 138 | 0.02 | 0.09 |
| 139 | 0.2 | 19.85 |
| 140 | 0.08 | 9.35 |
| 141 | 0.17 | 5.08 |
| 142 | 0.93 | 2.46 |
| 143 | 0.01 | 0.28 |
| 144 | 0.77 | 3.56 |
| 145 | 0.03 | 0.57 |
| 146 | 0.05 | 0.86 |
| 147 | 0.04 | 0.98 |
| 149 | 0.06 | 0.86 |
| 150 | 0.12 | 6.74 |
| 151 | 0.17 | 2.58 |
| 152 | 0.1 | 1.68 |
| 153 | 0.09 | 1.04 |
| 154 | 0.01 | 0.09 |
| 155 | 0.02 | 0.14 |
| 156 | 0.02 | 0.06 |
| 157 | 0.02 | 0.17 |
| 158 | 0.01 | 0.09 |
| 159 | 0.01 | 0.2 |
| 160 | 0.04 | 0.16 |
| 161 | 0.02 | 0.17 |
| 162 | 0.02 | 0.13 |
| 163 | 0.02 | 0.13 |
| 164 | 0.02 | 0.09 |
| 165 | 0.02 | 0.18 |
| 166 | 0.01 | 0.04 |
| 167 | 0.02 | 0.04 |
| 168 | 0.02 | 0.05 |
| 169 | 0.24 | 0.26 |
| 170 | 0.01 | 0.05 |
| 171 | 0.01 | 0.25 |
| 172 | 0.01 | 0.06 |
| 173 | 0.09 | 1.96 |
| 174 | 0.02 | 0.14 |
| 175 | 0.15 | 2.19 |
| 176 | 0.05 | 0.09 |
| 177 | 0.03 | 0.66 |
| 178 | 0.02 | 0.28 |
| 179 | 0.05 | 0.36 |

-continued

| Example | IC50 h-fabp4-ecoli-r μM | IC50 h-fabp5-ecoli-r μM |
|---|---|---|
| 180 | 3.44 | 20.61 |
| 181 | 0.04 | 0.1 |
| 182 | 0.07 | 1.35 |
| 183 | 4.15 | 23.2 |
| 184 | 0.01 | 0.1 |
| 185 | 0.11 | 0.87 |
| 186 | 0.01 | 0.11 |
| 187 | 0.02 | 0.12 |
| 188 | 0.02 | 0.1 |
| 189 | 0.02 | 0.12 |
| 190 | 0.02 | 0.11 |
| 191 | 0.09 | 4.19 |
| 192 | 0.02 | 0.19 |
| 193 | 0.01 | 0.1 |
| 194 | 0.02 | 0.04 |
| 195 | 0.11 | 1.29 |
| 196 | 0.05 | 0.64 |
| 197 | 0.02 | 0.77 |
| 198 | 1.04 | 16.16 |
| 199 | 0.08 | 3.08 |
| 200 | 0.02 | 0.04 |
| 201 | 0.02 | 0.06 |
| 202 | 0.03 | 0.21 |
| 203 | 0.04 | 0.27 |
| 204 | 0.02 | 0.12 |
| 205 | 0.05 | 0.06 |
| 206 | 0.02 | 0.05 |
| 207 | 0.02 | 0.03 |
| 208 | 0.02 | 0.04 |
| 209 | 0.02 | 0.06 |
| 210 | 5.96 | 24.15 |
| 211 | 3.56 | 49.02 |
| 212 | 28.08 | >50 |
| 213 | 0.08 | 2.29 |
| 214 | 0.03 | 0.14 |
| 215 | 0.03 | 0.48 |
| 216 | 0.02 | 0.18 |
| 217 | 0.03 | 1.01 |
| 218 | 0.02 | 1.13 |
| 219 | 0.04 | 0.26 |
| 220 | 0.02 | 0.44 |
| 221 | 0.09 | 0.29 |
| 222 | 0.02 | 0.09 |
| 223 | 0.02 | 0.09 |
| 224 | 0.14 | 7.92 |
| 225 | 0.24 | 0.98 |
| 226 | 0.02 | 0.2 |
| 227 | 0.02 | 0.63 |
| 228 | 0.04 | 0.22 |
| 229 | 0.05 | 1.56 |
| 230 | 0.33 | 1.04 |
| 231 | 0.01 | 0.19 |
| 232 | 0.01 | 0.19 |
| 233 | 0.02 | 0.28 |
| 234 | 0.03 | 0.49 |
| 235 | 0.02 | 0.11 |
| 236 | 0.09 | 0.32 |
| 237 | 0.03 | 1.55 |
| 238 | 0.04 | 0.9 |
| 239 | 0.12 | 0.64 |
| 240 | 0.04 | 3.14 |
| 241 | 0.08 | 5.84 |
| 242 | 0.03 | 0.61 |
| 243 | 0.11 | 7.11 |
| 244 | 0.16 | 0.58 |
| 245 | 0.1 | 2.35 |
| 246 | 0.02 | 0.15 |
| 247 | 0.03 | 0.18 |
| 248 | 0.03 | 0.39 |
| 249 | 0.02 | 0.75 |
| 250 | 0.12 | 1.22 |
| 251 | 0.05 | 1.81 |
| 252 | 0.28 | 10.78 |
| 253 | 0.08 | 0.54 |
| 254 | 0.58 | 2.64 |

-continued

| Example | IC50 h-fabp4-ecoli-r μM | IC50 h-fabp5-ecoli-r μM |
|---|---|---|
| 255 | 0.1 | 2.92 |
| 256 | 0.08 | 2.51 |
| 257 | 0.04 | 1.59 |
| 258 | 0.02 | 0.47 |
| 259 | 0.02 | 2.66 |
| 260 | 0.02 | 1.36 |
| 261 | 0.04 | 0.49 |
| 262 | 0.01 | 1.88 |
| 263 | 0.05 | 11.91 |
| 264 | 0.7 | >50 |
| 265 | 0.02 | 0.49 |
| 266 | 0.03 | 2.68 |
| 267 | 3.72 | >50 |
| 268 | 0.02 | 0.14 |
| 269 | 0.12 | 1.65 |
| 270 | 0.77 | 12.24 |
| 271 | 3.66 | 14.62 |
| 272 | 6.6 | 32 |
| 273 | 0.02 | 1.57 |
| 274 | 0.17 | 1.4 |
| 275 | 0.49 | 1.31 |
| 276 | 0.02 | 0.1 |
| 277 | 0.2 | 4.04 |
| 278 | 0.04 | 1.46 |
| 279 | 0.02 | 0.29 |
| 280 | 0.02 | 0.03 |
| 281 | 0.02 | 0.05 |
| 282 | 0.03 | 0.07 |
| 283 | 0.01 | 0.27 |
| 284 | 0.03 | 0.72 |
| 285 | 0.02 | 1 |
| 286 | 2.75 | 12.4 |
| 287 | 0.01 | 0.18 |
| 288 | 0.02 | 0.08 |
| 289 | 0.24 | 1.31 |
| 290 | 0.02 | 0.22 |
| 291 | 0.02 | 0.61 |
| 292 | 0.03 | 1.04 |
| 293 | 0.02 | 0.16 |
| 294 | 0.02 | 0.59 |
| 295 | 2.63 | 5.53 |
| 296 | 3.23 | 8.29 |
| 297 | 0.03 | 0.54 |
| 298 | 0.02 | 1.22 |
| 299 | 0.13 | 1.04 |
| 300 | 0.02 | 0.2 |
| 301 | 0.02 | 0.4 |
| 302 | 0.03 | 0.73 |
| 303 | 0.1 | 1.31 |
| 304 | 0.04 | 0.74 |
| 305 | 0.05 | 0.51 |
| 306 | 6.61 | 8.77 |
| 307 | 0.14 | 2.89 |
| 308 | 0.1 | 1.18 |
| 309 | 0.1 | 2.12 |
| 310 | 0.08 | 0.64 |
| 311 | 0.15 | 0.83 |
| 312 | 0.07 | 0.29 |
| 313 | 0.03 | 1.32 |
| 314 | 0.02 | 0.46 |
| 315 | 0.02 | 0.39 |
| 316 | 0.02 | 0.76 |
| 317 | 0.1 | 0.51 |
| 318 | 0.03 | 0.24 |
| 319 | 0.03 | 0.18 |
| 320 | 0.03 | 0.65 |
| 321 | 0.01 | 0.07 |
| 322 | 0.85 | 1.06 |
| 323 | 0.02 | 0.14 |
| 324 | 1.61 | 3.9 |
| 325 | 0.14 | 4.91 |
| 326 | 0.02 | 0.02 |
| 327 | 0.22 | 2.47 |
| 328 | 0.02 | 1.36 |

Compounds of formula (I) and their pharmaceutically acceptable salts or esters thereof as described herein have $IC_{50}$ (FABP4 inhibition) values between 0.000001 μM and 1000 μM, particular compounds have $IC_{50}$ values between 0.000005 μM and 500 μM, further particular compounds have $IC_{50}$ values between 0.00005 μM and 5 μM.

Compounds of formula (I) and their pharmaceutically acceptable salts or esters thereof as described herein have $IC_{50}$ (FABP5 inhibition) values between 0.000001 μM and 1000 μM, particular compounds have $IC_{50}$ values between 0.000005 μM and 500 μM, further particular compounds have $IC_{50}$ values between 0.00005 μM and 50 μM.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

In accordance with the invention, the compounds of formula (I) or their pharmaceutically acceptable salts and esters can be used for the treatment or prophylaxis of type 2 diabetes related microvascular complications (such as, but not limited to diabetic retinopathy, diabetic neuropathy and diabetic nephropathy), coronary artery disease, obesity and underlying inflammatory diseases, chronic inflammatory and autoimmune/inflammatory diseases The invention is illustrated hereinafter by Examples, which have no limiting character.

In case the preparative examples are obtained as a mixture of enantiomers, the pure enantiomers can be separated by methods described herein or by methods known to the person skilled in the art, such as e.g. chiral chromatography or crystallization.

EXAMPLES

All examples and intermediates were prepared under argon atmosphere if not specified otherwise.

General Method A

A mixture of the ester (Intermediate E) (0.129 mmol, 1 eq) and lithium iodide (10 eq) in pyridine (3 ml) is heated to 135° C. for 1-4 days. The pyridine is then removed, the remaining residue is diluted with water and the pH is adjusted to 2-3 by addition of 0.1N HCl. The mixture is extracted with ethyl acetate and the combined extracts are washed with water (acidified to pH 2-3 with 0.1N HCl) and brine, dried ($Na_2SO_4$) and evaporated. The remaining residue is purified by column chromatography.

General Method B

To a solution of the ester (Intermediate E) (0.1 mmol, 1 eq) in DMSO (3 ml) and water (0.1 ml) is added NaOH (2 eq) and the mixture is heated to 100° C. in a sealed tube for 1-4 days. If necessary, additional NaOH (1 eq) and water (0.15 ml) is added during this time. The reaction mixture is then diluted with water and the pH is adjusted to 2-3 by addition of 0.1N HCl. The mixture is extracted with ethyl acetate and the combined extracts are washed with water (acidified to pH 2-3 with 0.1N HCl), dried ($Na_2SO_4$) and evaporated. The remaining residue is purified by column chromatography.

General Method C

A solution of the nitrile (Intermediate N) (0.336 mmol, 1 eq) and azidotrimethylstannane (3 eq) in xylene (3.5 ml) is heated to 120° C. for 1-7 days. The precipitate that forms is filtered off, washed with hot toluene and suspended in a mixture of ethyl acetate and 0.1N HCl. The suspension is stirred vigorously at room temperature until all solids are dissolved. The layers are separated and the aqueous layer is extracted with ethyl acetate. The combined organic layers are washed with water and brine (both acidified to pH 1 with HCl), dried ($Na_2SO_4$) and evaporated. The remaining residue is purified by column chromatography.

If no precipitate forms during the heating period, the reaction mixture is cooled to room temperature and ethyl acetate and 0.1N HCl are added. The mixture is stirred for 1.5 h, the layers are separated and the aqueous layer is extracted with ethyl acetate. The combined organic layers are washed with water and brine (both acidified to pH 1 with HCl), dried ($Na_2SO_4$) and evaporated. The remaining residue is purified by column chromatography.

General Method D

A mixture of the nitrile (Intermediate N) (2.5 mmol, 1 eq), sodium azide (2.2 eq) and zinc chloride (0.5 eq) in DMF (5 ml) is refluxed for 3 days. After evaporation of the solvent the residue is stirred with EtOAc/water. The precipitate is filtered, stirred with 1N HCl/water and filtered. The obtained solid is triturated with ethanol and purified by column chromatography.

| Ex. | Name | Structure | MS | Method | Starting Material |
|---|---|---|---|---|---|
| 1 | 2-Isopropyl-6,8-dimethyl-4-phenyl-5,6,7,8-tetrahydro-1,8-naphthyridine-3-carboxylic acid | 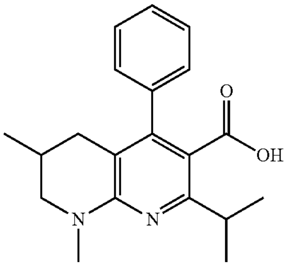 [SMILES: CC1Cc2c(nc(C(C)C)c(C(=O)O)c2-c2ccccc2)N(C)C1] | ESP $[M + H]^+$: 325.3 | A | E1 |
| 2 | 8-Acetyl-2-isopropyl-6-methyl-4-phenyl-5,6,7,8-tetrahydro-1,8-naphthyridine-3-carboxylic acid | 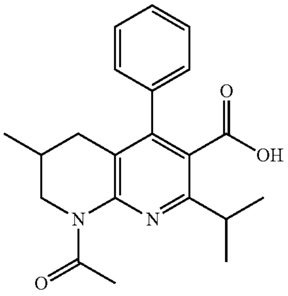 [SMILES: CC(=O)N1CC(C)Cc2c1nc(C(C)C)c(C(=O)O)c2-c1ccccc1] | ESP $[M + H]^+$: 353.3 | A | E2 |
| 3 | 8-Ethyl-2-isopropyl-6-methyl-4-phenyl-5,6,7,8-tetrahydro-1,8-naphthyridine-3-carboxylic acid | 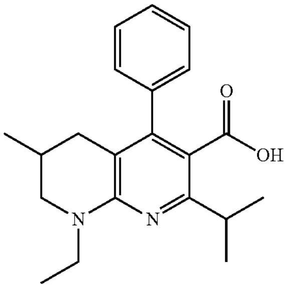 [SMILES: CCN1CC(C)Cc2c1nc(C(C)C)c(C(=O)O)c2-c1ccccc1] | ESP $[M + H]^+$: 339.3 | A | E3 |
| 4 | 4-(3-Chlorophenyl)-2-cyclohexyl-8-ethyl-5,6,7,8-tetrahydro-1,8-naphthyridine-3-carboxylic acid | 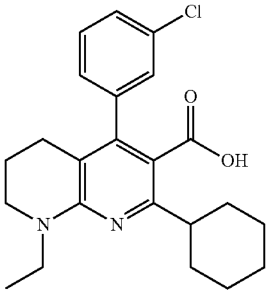 [SMILES: CCN1CCCc2c1nc(C1CCCCC1)c(C(=O)O)c2-c1cccc(Cl)c1] | ESP $[M + H]^+$: 399.1 | A | E4 |
| 5 | 2-Cyclohexyl-8-ethyl-4-phenyl-5,6,7,8-tetrahydro-1,8-naphthyridine-3-carboxylic acid | 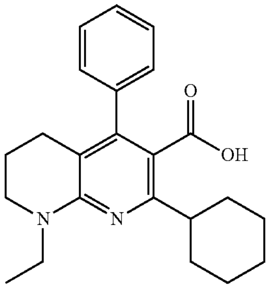 [SMILES: CCN1CCCc2c1nc(C1CCCCC1)c(C(=O)O)c2-c1ccccc1] | ESP $[M + H]^+$: 365.2 | B | E5 |

-continued

| Ex. | Name | Structure | MS | Method | Starting Material |
|---|---|---|---|---|---|
| 6 | 2-Cyclopentyl-8-ethyl-4-phenyl-5,6,7,8-tetrahydro-1,8-naphthyridine-3-carboxylic acid | 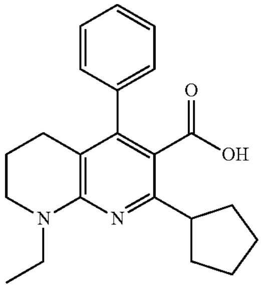 [SMILES: CCN1CCCc2c1nc(C1CCCC1)c(C(=O)O)c2-c1ccccc1] | ESP [M + H]$^+$: 351.4 | A | E6 |
| 7 | 2-Cyclopentyl-8-ethyl-6-methyl-4-phenyl-5,6,7,8-tetrahydro-1,8-naphthyridine-3-carboxylic acid | 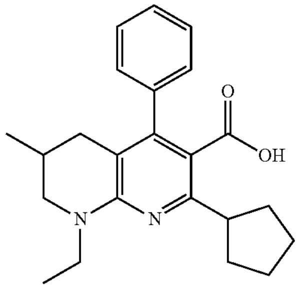 [SMILES: CCN1CC(C)Cc2c1nc(C1CCCC1)c(C(=O)O)c2-c1ccccc1] | ESP [M + H]$^+$: 365.5 | A | E7 |
| 8 | 2-Cyclopentyl-6,8-dimethyl-4-phenyl-5,6,7,8-tetrahydro-1,8-naphthyridine-3-carboxylic acid | 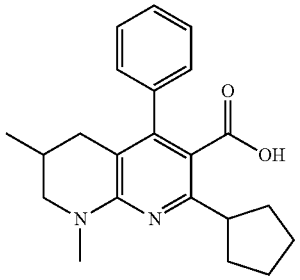 [SMILES: CC1Cc2c(nc(C3CCCC3)c(C(=O)O)c2-c2ccccc2)N(C)C1] | ESP [M + H]$^+$: 351.4 | A | E8 |
| 9 | 2-Isopropyl-6-methyl-4-phenyl-5,6,7,8-tetrahydroquinoline-3-carboxylic acid | 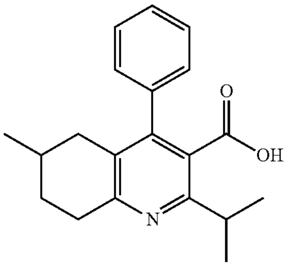 [SMILES: CC1CCc2nc(C(C)C)c(C(=O)O)c(-c3ccccc3)c2C1] | ESP [M + H]$^+$: 310.3 | A | E9 |
| 10 | 6-Ethyl-2-isopropyl-4-phenyl-5,6,7,8-tetrahydroquinoline-3-carboxylic acid | 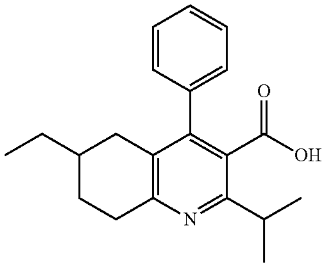 [SMILES: CCC1CCc2nc(C(C)C)c(C(=O)O)c(-c3ccccc3)c2C1] | ESP [M + H]$^+$: 324.2 | A | E10 |

-continued

| Ex. | Name | Structure | MS | Method | Starting Material |
|---|---|---|---|---|---|
| 11 | 2-Isopropyl-6,6-dimethyl-4-phenyl-5,6,7,8-tetrahydro-quinoline-3-carboxylic acid | 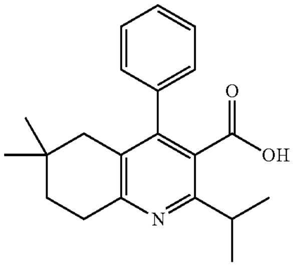 [SMILES: CC(C)c1nc2c(c(-c3ccccc3)c1C(=O)O)CC(C)(C)CC2] | ESN [M − H]$^-$: 322.3 | A | E11 |
| 14 | 4-Phenyl-2-(piperidin-1-yl)-6,7,8,9-tetrahydro-5H-cyclohepta[b]pyridine-3-carboxylic acid | 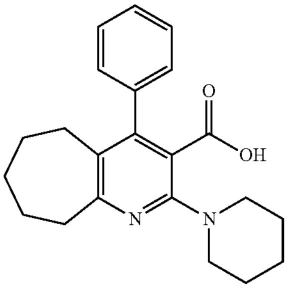 [SMILES: O=C(O)c1c(N2CCCCC2)nc2c(c1-c1ccccc1)CCCCC2] | ESN [M − H]$^-$: 349.4 | A | E14 |
| 15 | 2-(2-Methylpyrrolidin-1-yl)-4-phenyl-6,7,8,9-tetrahydro-5H-cyclohepta[b]pyridine-3-carboxylic acid | 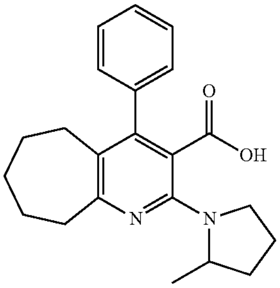 [SMILES: CC1CCCN1c1nc2c(c(-c3ccccc3)c1C(=O)O)CCCCC2] | ESN [M − H]$^-$: 349.4 | A | E15 |
| 16 | 6-Methyl-4-phenyl-2-(piperidin-1-yl)-5,6,7,8-tetrahydroquinoline-3-carboxylic acid | 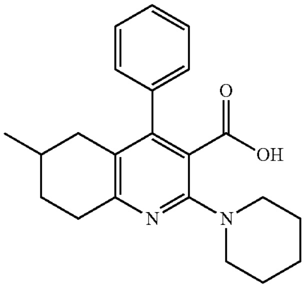 [SMILES: CC1CCc2nc(N3CCCCC3)c(C(=O)O)c(-c3ccccc3)c2C1] | ESN [M − H]$^-$: 349.4 | A | E16 |
| 17 | 2-(Diethylamino)-4-phenyl-6,7,8,9-tetrahydro-5H-cyclohepta[b]pyridine-3-carboxylic acid | 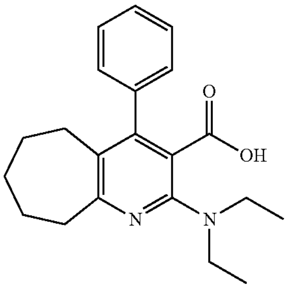 [SMILES: CCN(CC)c1nc2c(c(-c3ccccc3)c1C(=O)O)CCCCC2] | ESN [M − H]$^-$: 337.5 | A | E17 |

-continued

| Ex. | Name | Structure | MS | Method | Starting Material |
|---|---|---|---|---|---|
| 18 | 6-Methyl-2-(2-methylpyrrolidin-1-yl)-4-phenyl-5,6,7,8-tetrahydroquinoline-3-carboxylic acid | 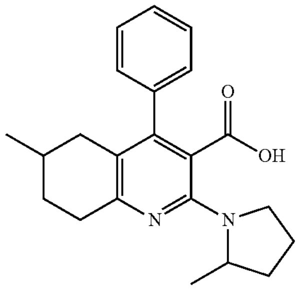 [SMILES: CC1CCc2nc(N3CCCC3C)c(C(=O)O)c(-c3ccccc3)c2C1] | ESN $[M-H]^-$: 349.4 | A | E18 |
| 19 | 2-(Diethylamino)-6-methyl-4-phenyl-5,6,7,8-tetrahydroquinoline-3-carboxylic acid | 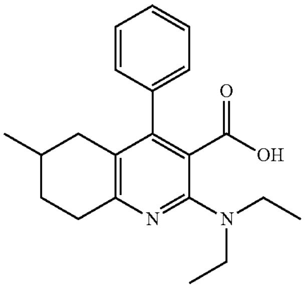 [SMILES: CCN(CC)c1nc2c(c(-c3ccccc3)c1C(=O)O)CC(C)CC2] | ESN $[M-H]^-$: 337.5 | A | E19 |
| 21 | 4-Phenyl-2-(piperidin-1-yl)-6,7-dihydro-5H-cyclopenta[b]pyridine-3-carboxylic acid | 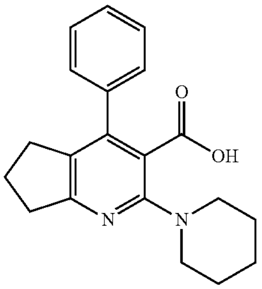 [SMILES: O=C(O)c1c(N2CCCCC2)nc2c(c1-c1ccccc1)CCC2] | ESN $[M-H]^-$: 321.3 | A | E21 |
| 22 | 2-(Diethylamino)-4-phenyl-6,7-dihydro-5H-cyclopenta[b]pyridine-3-carboxylic acid | 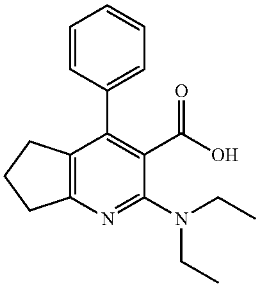 [SMILES: CCN(CC)c1nc2c(c(-c3ccccc3)c1C(=O)O)CCC2] | ESN $[M-H]^-$: 309.4 | A | E22 |
| 25 | 6-Methyl-4-phenyl-2-(piperidin-1-yl)-3-(2H-tetrazol-5-yl)-5,6,7,8-tetrahydroquinoline | 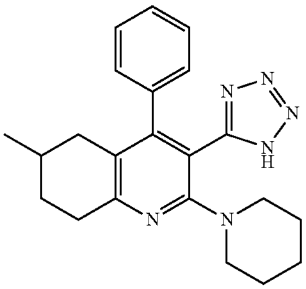 [SMILES: CC1CCc2nc(N3CCCCC3)c(-c3nnn[nH]3)c(-c3ccccc3)c2C1] | ESP $[M+H]^+$: 375.2 | C | N25 |

-continued

| Ex. | Name | Structure | MS | Method | Starting Material |
|---|---|---|---|---|---|
| 26 | N,N-Diethyl-6-methyl-4-phenyl-3-(2H-tetrazol 5-yl)-5,6,7,8-tetrahydroquinolin-2-amine | 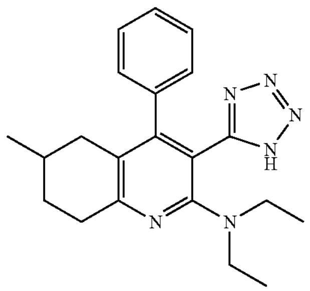 [SMILES: CCN(CC)c1nc2c(c(-c3ccccc3)c1-c1nnn[nH]1)CC(C)CC2] | ESP $[M + H]^+$: 363.4 | C | N26 |
| 27 | 4-Phenyl-2-(piperidin-1-yl)-3-(2H-tetrazol-5-yl) 6-(trifluoromethyl)-5,6,7,8-tetrahydroquinoline | 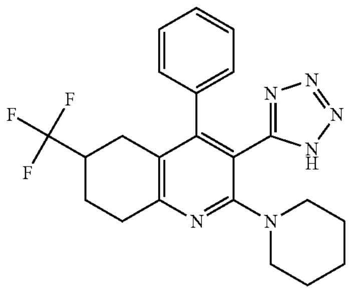 [SMILES: FC(F)(F)C1CCc2nc(N3CCCCC3)c(-c3nnn[nH]3)c(-c3ccccc3)c2C1] | ESP $[M + H]^+$: 429.5 | C | N27 |
| 28 | N,N-Diethyl-4-phenyl-3-(2H-tetrazol-5-yl)-6-(trifluoromethyl)-5,6,7,8-tetrahydroquinolin-2-amine | 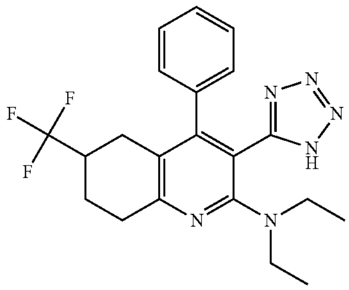 [SMILES: CCN(CC)c1nc2c(c(-c3ccccc3)c1-c1nnn[nH]1)CC(C(F)(F)F)CC2] | ESP $[M + H]^+$: 417.5 | C | N28 |
| 29 | 6-Methyl-4-(1-methyl-1H-pyrazol-5-yl)-2-(piperidin-1-yl)-3-(2H-tetrazol-5-yl)-5,6,7,8-tetrahydroquinoline | 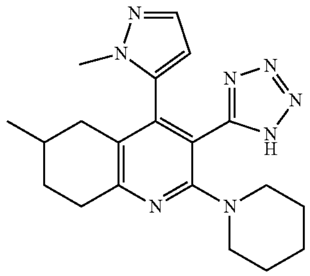 | ESN $[M - H]^-$: 377.5 | C | N29 |
| 30 | 4-Phenyl-2-(piperidin-1-yl)-3-(2H-tetrazol-5-yl)-6,7,8,9-tetrahydro-5H-cyclohepta[b]pyridine | 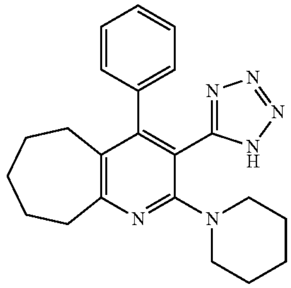 [SMILES: c1ccc(-c2c3c(nc(N4CCCCC4)c2-c2nnn[nH]2)CCCCC3)cc1] | ESN $[M - H]^-$: 373.4 | C | N30 |

-continued

| Ex. | Name | Structure | MS | Method | Starting Material |
|---|---|---|---|---|---|
| 31 | N,N-Diethyl-4-phenyl-3-(2H-tetrazol-5-yl)-6,7,8,9-tetrahydro-5H-cyclohepta[b]pyridin-2-amine | 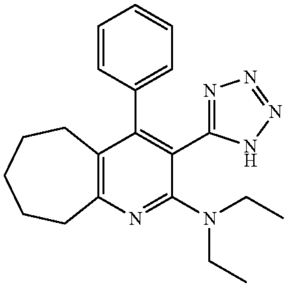 [SMILES: CCN(CC)c1nc2c(c(-c3ccccc3)c1-c1nnn[nH]1)CCCCC2] | ESN [M − H]⁻: 361.1 | C | N31 |
| 32 | 4-(3-Chlorophenyl)-2-(piperidin-1-yl)-3-(1H-tetrazol-5-yl)-6,7,8,9-tetrahydro-5H-cyclohepta[b]pyridine | 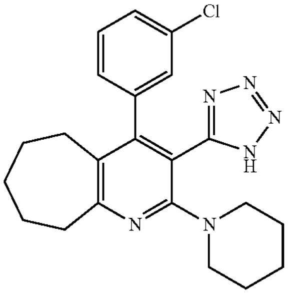 [SMILES: Clc1cccc(-c2c3c(nc(N4CCCCC4)c2-c2nnn[nH]2)CCCCC3)c1] | ESN [M − H]⁻: 407.6 | C | N32 |
| 33 | 4-(3-Chlorophenyl)-N,N-diethyl-3-(1H-tetrazol-5-yl)-6,7,8,9-tetrahydro-5H-cyclohepta[b]pyridin-2-amine | 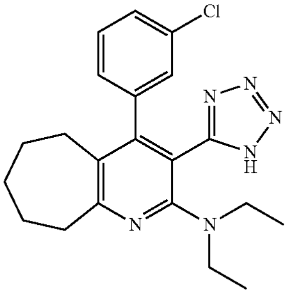 [SMILES: CCN(CC)c1nc2c(c(-c3cccc(Cl)c3)c1-c1nnn[nH]1)CCCCC2] | ESN [M − H]⁻: 395.4 | C | N33 |
| 34 | 4-(1-Methyl-1H-pyrazol-5-yl)-2-(piperidin-1-yl)-3-(1H-tetrazol-5-yl)-6,7,8,9-tetrahydro-5H-cyclohepta[b]pyridine | 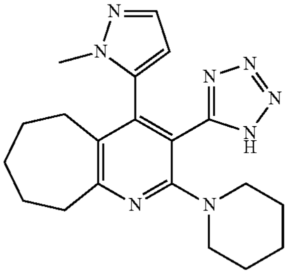 [SMILES: Cn1nccc1-c1c2c(nc(N3CCCCC3)c1-c1nnn[nH]1)CCCCC2] | ESN [M − H]⁻: 377.2 | C | N34 |
| 35 | 4-(4-Fluorophenyl)-6-methyl-2-(piperidin-1-yl)-3-(1H-tetrazol-5-yl)-5,6,7,8-tetrahydroquinoline | 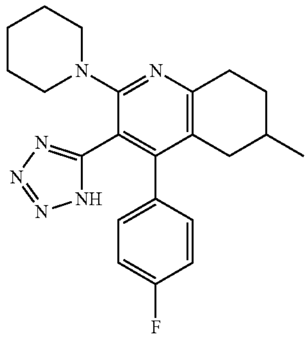 [SMILES: CC1CCc2nc(N3CCCCC3)c(-c3nnn[nH]3)c(-c3ccc(F)cc3)c2C1] | ESN [M − H]⁻: 391.5 | C | N35 |

-continued

| Ex. | Name | Structure | MS | Method | Starting Material |
|---|---|---|---|---|---|
| 36 | 4-(4-Fluorophenyl)-2-(piperidin-1-yl)-3-(1H-tetrazol-5-yl)-7,8-dihydro-5H-pyrano[4,3-b]pyridine | 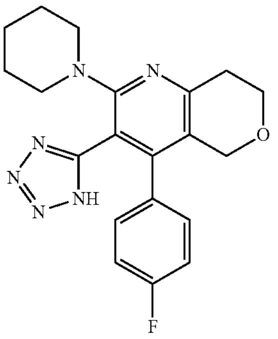 [SMILES: Fc1ccc(-c2c3c(nc(N4CCCCC4)c2-c2nnn[nH]2)CCOC3)cc1] | ESN [M − H]$^-$: 379.5 | C | N36 |
| 38 | 4-(5-Chlorothiophen-2-yl)-N,N-diethyl-3-(1H-tetrazol-5-yl)-6,7,8,9-tetrahydro-5H-cyclohepta[b]pyridin-2-amine | 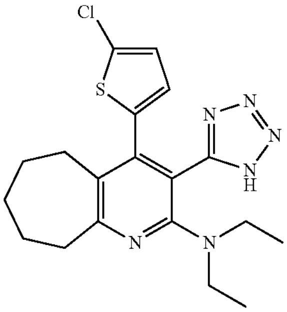 [SMILES: CCN(CC)c1nc2c(c(-c3ccc(Cl)s3)c1-c1nnn[nH]1)CCCCC2] | ESP [M + H]$^+$: 403.5 | C | N38 |
| 39 | 4-(5-Chlorothiophen-2-yl)-2-(piperidin-1-yl)-3-(1H-tetrazol-5-yl)-6,7,8,9-tetrahydro-5H-cyclohepta[b]pyridine | 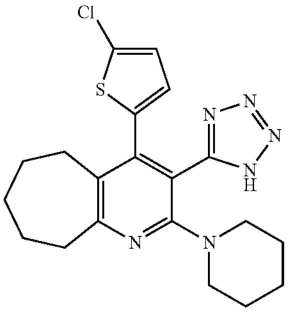 [SMILES: Clc1ccc(-c2c3c(nc(N4CCCCC4)c2-c2nnn[nH]2)CCCCC3)s1] | ESN [M − H]$^-$: 413.5 | C | N39 |
| 40 | N,N-Diethyl-4-(1-methyl-1H-pyrazol-5-yl)-3-(1H-tetrazol-5-yl)-6,7,8,9-tetrahydro-5H-cyclohepta[b]pyridin-2-amine | 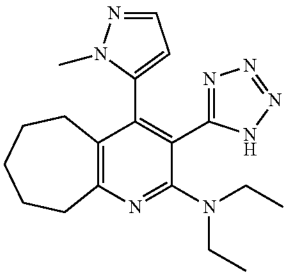 [SMILES: CCN(CC)c1nc2c(c(-c3ccnn3C)c1-c1nnn[nH]1)CCCCC2] | ESN [M − H]$^-$: 365.6 | C | N40 |
| 41 | 5-Methyl-3-(2-(piperidin-1-yl)-3-(1H-tetrazol-5-yl)-6,7,8,9-tetrahydro-5H-cyclohepta[b]pyridin-4-yl)isoxazole | 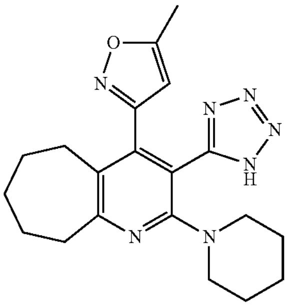 [SMILES: Cc1cc(-c2c3c(nc(N4CCCCC4)c2-c2nnn[nH]2)CCCCC3)no1] | ESP [M + H]$^+$: 380.5 | C | N41 |

-continued

| Ex. | Name | Structure | MS | Method | Starting Material |
|---|---|---|---|---|---|
| 42 | N,N-Diethyl-4-(5-methylisoxazol-3-yl)-3-(1H-tetrazol-5-yl)-6,7,8,9-tetrahydro-5H-cyclohepta[b]pyridin-2-amine | 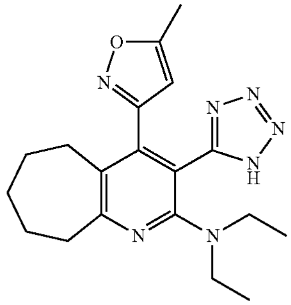 [SMILES: CCN(CC)c1nc2c(c(-c3cc(C)on3)c1-c1nnn[nH]1)CCCCC2] | ESP [M + H]$^+$: 368.5 | C | N42 |
| 44 | 2-(Piperidin-1-yl)-4-(pyridin-4-yl)-3-(1H-tetrazol-5-yl)-6,7,8,9-tetrahydro-5H-cyclohepta[b]pyridine | 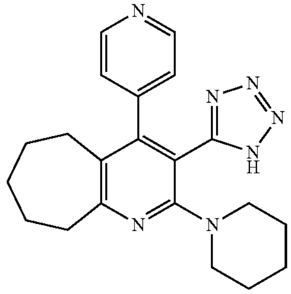 [SMILES: c1cc(-c2c3c(nc(N4CCCCC4)c2-c2nnn[nH]2)CCCCC3)ccn1] | ESP [M + H]$^+$: 376.5 | C | N44 |
| 45 | N,N-Diethyl-4-(pyridin-4-yl)-3-(1H-tetrazol-5-yl)-6,7,8,9-tetrahydro-5H-cyclohepta[b]pyridin-2-amine | 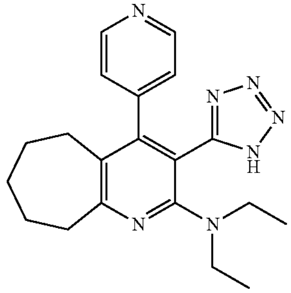 [SMILES: CCN(CC)c1nc2c(c(-c3ccncc3)c1-c1nnn[nH]1)CCCCC2] | ESP [M + H]$^+$: 364.6 | C | N45 |
| 46 | 4-(5-Methylfuran-2-yl)-2-(piperidin-1-yl)-3-(1H-tetrazol-5-yl)-6,7,8,9-tetrahydro-5H-cyclohepta[b]pyridine | 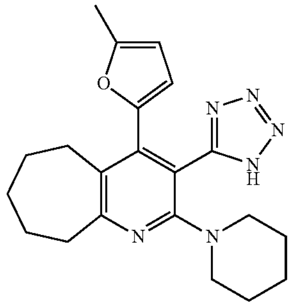 [SMILES: Cc1ccc(-c2c3c(nc(N4CCCCC4)c2-c2nnn[nH]2)CCCCC3)o1] | ESP [M + H]$^+$: 379.4 | C | N46 |
| 47 | N,N-Diethyl-4-(5-methylfuran-2-yl)-3-(1H-tetrazol-5-yl)-6,7,8,9-tetrahydro-5H-cyclohepta[b]pyridin-2-amine | 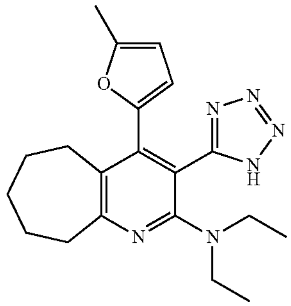 [SMILES: CCN(CC)c1nc2c(c(-c3ccc(C)o3)c1-c1nnn[nH]1)CCCCC2] | ESP [M + H]$^+$: 367.5 | C | N47 |

-continued

| Ex. | Name | Structure | MS | Method | Starting Material |
|---|---|---|---|---|---|
| 48 | 4-(1,5-Dimethyl-1H-pyrazol-4-yl)-2-(piperidin-1-yl)-3-(1H-tetrazol-5-yl)-6,7,8,9-tetrahydro-5H-cyclohepta[b]pyridine | 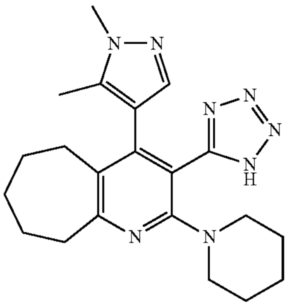 [SMILES: Cc1c(-c2c3c(nc(N4CCCCC4)c2-c2nnn[nH]2)CCCCC3)cnn1C] | ESP $[M + H]^+$: 393.6 | C | N48 |
| 49 | 4-(1,5-Dimethyl-1H-pyrazol-4-yl)-N,N-diethyl-3-(1H-tetrazol-5-yl)-6,7,8,9-tetrahydro-5H-cyclohepta[b]pyridin-2-amine | 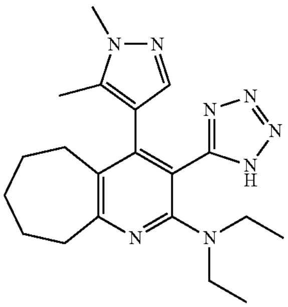 [SMILES: CCN(CC)c1nc2c(c(-c3cnn(C)c3C)c1-c1nnn[nH]1)CCCCC2] | ESP $[M + H]^+$: 381.5 | C | N49 |
| 50 | 4-(5-Chlorothiophen-2-yl)-2-(3-fluoropiperidin-1-yl)-3-(1H-tetrazol-5-yl)-6,7,8,9-tetrahydro-5H-cyclohepta[b]pyridine | 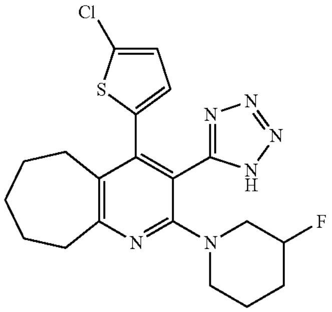 [SMILES: FC1CCCN(c2nc3c(c(-c4ccc(Cl)s4)c2-c2nnn[nH]2)CCCCC3)C1] | ESP $[M + H]^+$: 433.4 | C | N50 |
| 51 | 4-(5-Chlorothiophen-2-yl)-2-(3,3-difluoropiperidin-1-yl)-3-(1H-tetrazol-5-yl)-6,7,8,9-tetrahydro-5H-cyclohepta[b]pyridine | 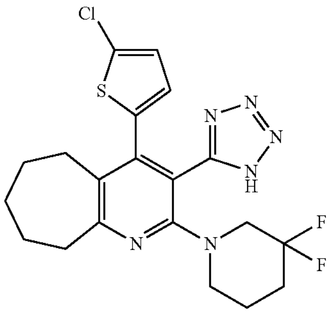 [SMILES: FC1(F)CCCN(c2nc3c(c(-c4ccc(Cl)s4)c2-c2nnn[nH]2)CCCCC3)C1] | ESP $[M + H]^+$: 451.4 | C | N51 |

-continued

| Ex. | Name | Structure | MS | Method | Starting Material |
|---|---|---|---|---|---|
| 52 | 4-(5-Chlorothiophen-2-yl)-2-(4,4-difluoropiperidin-1-yl)-3-(1H-tetrazol-5-yl)-6,7,8,9-tetrahydro-5H-cyclohepta[b]pyridine | 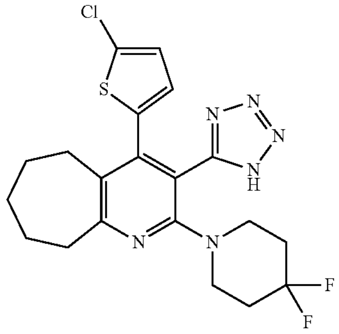 [SMILES: FC1(F)CCN(c2nc3c(c(-c4ccc(Cl)s4)c2-c2nnn[nH]2)CCCCC3)CC1] | ESP $[M + H]^+$: 451.4 | C | N52 |
| 53 | 4-(5-Chlorothiophen-2-yl)-2-(4-fluoropiperidin-1-yl)-3-(1H-tetrazol-5-yl)-6,7,8,9-tetrahydro-5H-cyclohepta[b]pyridine | 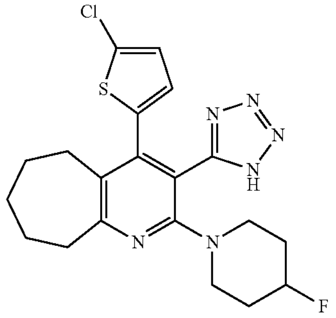 [SMILES: FC1CCN(c2nc3c(c(-c4ccc(Cl)s4)c2-c2nnn[nH]2)CCCCC3)CC1] | ESP $[M + H]^+$: 433.4 | C | N53 |
| 54 | 4-(5-Chlorothiophen-2-yl)-3-(1H-tetrazol-5-yl)-2-(4-(trifluoromethyl) piperidin-1-yl)-6,7,8,9-tetrahydro-5H-cyclohepta[b]pyridine | 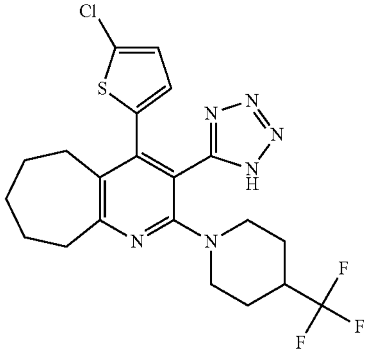 [SMILES: FC(F)(F)C1CCN(c2nc3c(c(-c4ccc(Cl)s4)c2-c2nnn[nH]2)CCCCC3)CC1] | ESP $[M + H]^+$: 483.4 | C | N54 |
| 55 | 4-(5-Chlorothiophen-2-yl)-2-(3,3-difluoroazetidin-1-yl)-3-(1H-tetrazol-5-yl)-6,7,8,9-tetrahydro-5H-cyclohepta[b]pyridine | 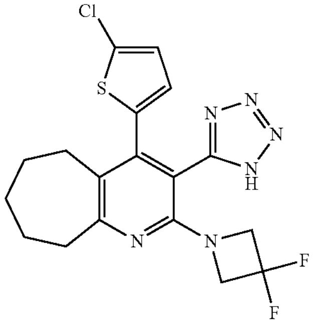 [SMILES: FC1(F)CN(c2nc3c(c(-c4ccc(Cl)s4)c2-c2nnn[nH]2)CCCCC3)C1] | ESP $[M + H]^+$: 423.5 | C | N55 |

-continued

| Ex. | Name | Structure | MS | Method | Starting Material |
|---|---|---|---|---|---|
| 56 | N,N-Diethyl-4-(4-methylthiazol-5-yl)-3-(1H-tetrazol-5-yl)-6,7,8,9-tetrahydro-5H-cyclohepta[b]pyridin-2-amine | 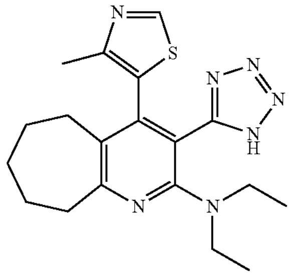 [SMILES: CCN(CC)c1nc2c(c(-c3scnc3C)c1-c1nnn[nH]1)CCCCC2] | ESP [M + H]$^+$: 384.4 | C | N56 |
| 57 | 4-Methyl-5-(2-(piperidin-1-yl)-3-(1H-tetrazol-5-yl)-6,7,8,9-tetrahydro-5H-cyclohepta[b]pyridin-4-yl)thiazole | 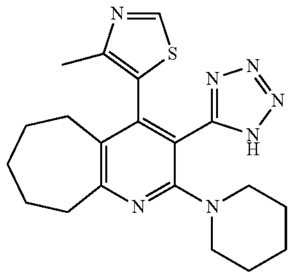 [SMILES: Cc1ncsc1-c1c2c(nc(N3CCCCC3)c1-c1nnn[nH]1)CCCCC2] | ESP [M + H]$^+$: 396.5 | C | N57 |
| 58 | N,N-Diethyl-4-(1-methyl-1H-pyrazol-5-yl)-3-(1H-tetrazol-5-yl)-5,6,7,8,9,10-hexahydrocycloocta[b] pyridin-2-amine | 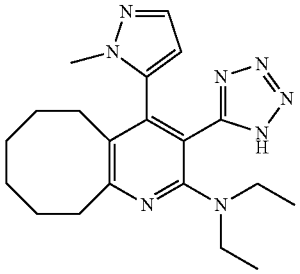 [SMILES: CCN(CC)c1nc2c(c(-c3ccnn3C)c1-c1nnn[nH]1)CCCCCC2] | ESP [M + H]$^+$: 381.5 | C | N58 |
| 59 | 4-(5-Chlorothiophen-2-yl)-2-(3,3-difluoropyrrolidin-1-yl)-3-(1H-tetrazol-5-yl)-6,7,8,9-tetrahydro-5H-cyclohepta[b]pyridine | 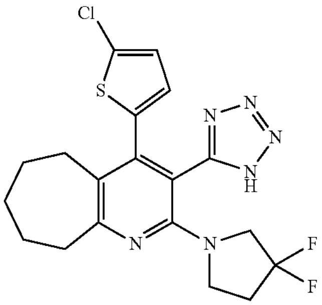 [SMILES: FC1(F)CCN(c2nc3c(c(-c4ccc(Cl)s4)c2-c2nnn[nH]2)CCCCC3)C1] | ESP [M + H]$^+$: 437.4 | C | N59 |
| 60 | 4-(1-Methyl-1H-pyrazol-5-yl)-2-(piperidin-1-yl)-3-(1H-tetrazol-5-yl)-5,6,7,8,9,10-hexahydrocycloocta[b] pyridine | 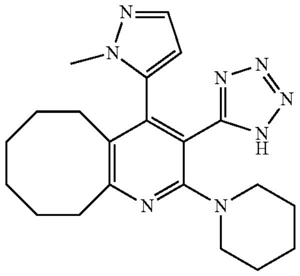 [SMILES: Cn1nccc1-c1c2c(nc(N3CCCCC3)c1-c1nnn[nH]1)CCCCCC2] | ESP [M + H]$^+$: 393.5 | C | N60 |

-continued

| Ex. | Name | Structure | MS | Method | Starting Material |
|---|---|---|---|---|---|
| 61 | Diethyl-[4-pyrimidin-5-yl-3-(1H-tetrazol-5-yl)-6,7,8,9-tetrahydro-5H-cyclohepta[b]pyridin-2-yl]-amine | 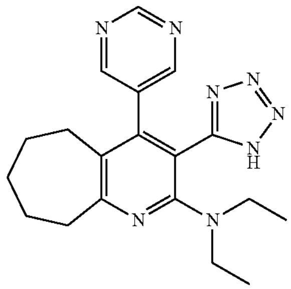 [SMILES: CCN(CC)c1nc2c(c(-c3cncnc3)c1-c1nnn[nH]1)CCCCC2] | ESP $[M + H]^+$: 365.4 | C | N61 |
| 62 | N,N-Diethyl-4-(3-fluoropyridin-4-yl)-3-(1H-tetrazol-5-yl)-6,7,8,9-tetrahydro-5H-cyclohepta[b]pyridin-2-amine | 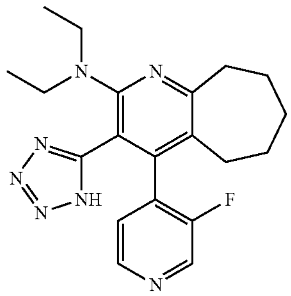 [SMILES: CCN(CC)c1nc2c(c(-c3ccncc3F)c1-c1nnn[nH]1)CCCCC2] | ESP $[M + H]^+$: 382.5 | C | N62 |
| 63 | N,N-Diethyl-4-(2-methoxypyridin-4-yl)-3-(1H-tetrazol-5-yl)-6,7,8,9-tetrahydro-5H-cyclohepta[b]pyridin-2-amine | 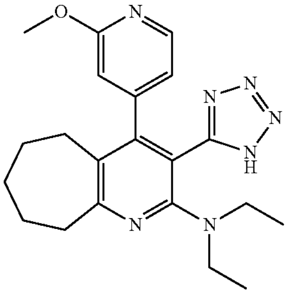 [SMILES: CCN(CC)c1nc2c(c(-c3ccnc(OC)c3)c1-c1nnn[nH]1)CCCCC2] | ESP $[M + H]^+$: 394.5 | C | N63 |
| 64 | 4-Phenyl-3-(1H-tetrazol-5-yl)-6,7,8,9-tetrahydro-5H-cyclohepta[b]pyridin-2-amine | 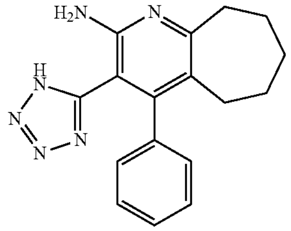 [SMILES: Nc1nc2c(c(-c3ccccc3)c1-c1nnn[nH]1)CCCCC2] | ESP $[M + H]^+$: 307.5 | D | N64 |
| 65 | 2-Propyl-4-(pyridin-4-yl)-3-(1H-tetrazol-5-yl)-6,7,8,9-tetrahydro-5H-cyclohepta[b]pyridine | 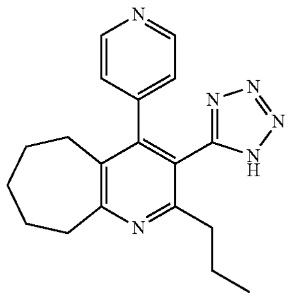 [SMILES: CCCc1nc2c(c(-c3ccncc3)c1-c1nnn[nH]1)CCCCC2] | ESP $[M + H]^+$: 335.5 | C | N65 |

-continued

| Ex. | Name | Structure | MS | Method | Starting Material |
|---|---|---|---|---|---|
| 66 | 4-(1-Methyl-1H-pyrazol-5-yl)-2-(pentan-3-yl)-3-(1H-tetrazol-5-yl)-6,7,8,9-tetrahydro-5H-cyclohepta[b]pyridine | 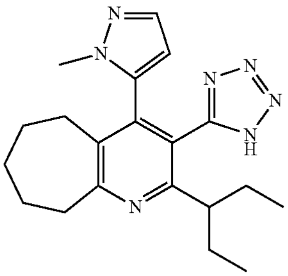 [SMILES: CCC(CC)c1nc2c(c(-c3ccnn3C)c1-c1nnn[nH]1)CCCCC2] | ESP [M + H]$^+$: 366.5 | C | N66 |
| 67 | 4-(3-Chlorophenyl)-2-cyclobutyl-3-(1H-tetrazol-5-yl)-6,7,8,9-tetrahydro-5H-cyclohepta[b]pyridine | 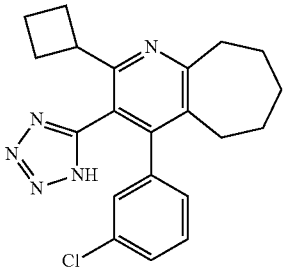 [SMILES: Clc1cccc(-c2c3c(nc(C4CCC4)c2-c2nnn[nH]2)CCCCC3)c1] | ESP [M + H]$^+$: 380.5 | C | N67 |
| 68 | 2-Cyclohexyl-4-pyridin-4-yl-3-(1H-tetrazol-5-yl)-6,7,8,9-tetrahydro-5H-cyclohepta[b]pyridine | 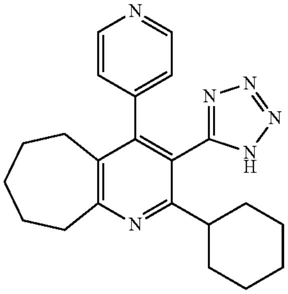 | ESP [M + H]$^+$: 375.5 | C | N68 |
| 69 | 4-(3-Chloro-phenyl)-2-cyclopentyl-3-(1H-tetrazol-5-yl)-6,7,8,9-tetrahydro-5H-cyclohepta[b]pyridine | 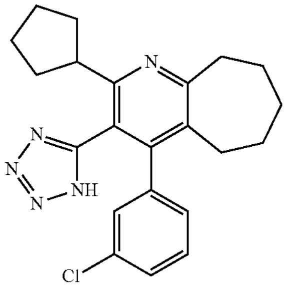 [SMILES: Clc1cccc(-c2c3c(nc(C4CCCC4)c2-c2nnn[nH]2)CCCCC3)c1] | ESP [M + H]$^+$: 394.4 | C | N69 |
| 70 | 2-Cyclohexyl-4-(2-methylpyridin-4-yl)-3-(1H-tetrazol-5-yl)-6,7,8,9-tetrahydro-5H-cyclohepta[b]pyridine | 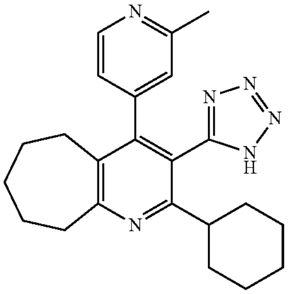 [SMILES: Cc1cc(-c2c3c(nc(C4CCCCC4)c2-c2nnn[nH]2)CCCCC3)ccn1] | ESP [M + H]$^+$: 389.5 | C | N70 |

-continued

| Ex. | Name | Structure | MS | Method | Starting Material |
|---|---|---|---|---|---|
| 71 | 5-(2-Cyclohexyl-3-(1H-tetrazol-5-yl)-6,7,8,9-tetrahydro-5H-cyclohepta[b]pyridin-4-yl)pyridin-2(1H)-one | 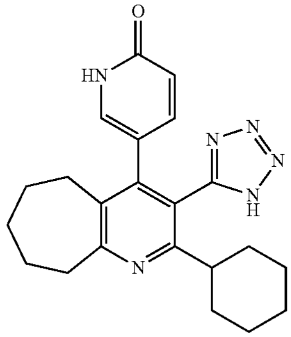 [SMILES: O=c1ccc(-c2c3c(nc(C4CCCCC4)c2-c2nnn[nH]2)CCCCC3)c[nH]1] | ESP [M + H]$^+$: 391.5 | C | N71 |
| 72 | 5-(2-Cyclohexyl-3-(1H-tetrazol-5-yl)-6,7,8,9-tetrahydro-5H-cyclohepta[b]pyridin-4-yl)-1-ethylpyridin-2(1H)-one | 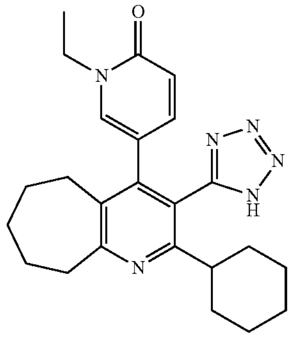 [SMILES: CCn1cc(-c2c3c(nc(C4CCCCC4)c2-c2nnn[nH]2)CCCCC3)ccc1=O] | ESP [M + H]$^+$: 419.5 | C | N72 |
| 73 | 5-(2-Cyclohexyl-3-(1H-tetrazol-5-yl)-6,7,8,9-tetrahydro-5H-cyclohepta[b]pyridin-4-yl)-1-methylpyridin-2(1H)-one | 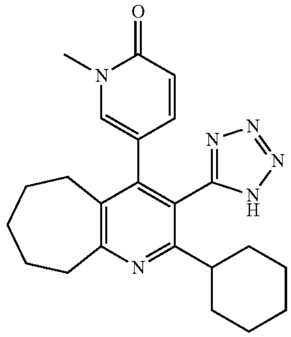 [SMILES: Cn1cc(-c2c3c(nc(C4CCCCC4)c2-c2nnn[nH]2)CCCCC3)ccc1=O] | ESP [M + H]$^+$: 405.5 | C | N73 |
| 74 | 2-Cyclohexyl-4-(1-methyl-1H-pyrazol-5-yl)-3-(1H-tetrazol-5-yl)-6,7,8,9-tetrahydro-5H-cyclohepta[b]pyridine | 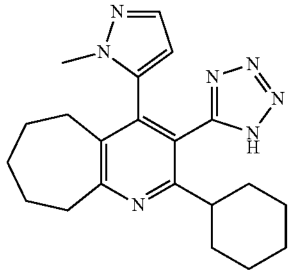 [SMILES: Cn1nccc1-c1c2c(nc(C3CCCCC3)c1-c1nnn[nH]1)CCCCC2] | ESP [M + H]$^+$: 378.5 | C | N74 |
| 75 | 2-Cyclopentyl-4-(pyridin-4-yl)-3-(1H-tetrazol-5-yl)-6,7,8,9-tetrahydro-5H-cyclohepta[b]pyridine | 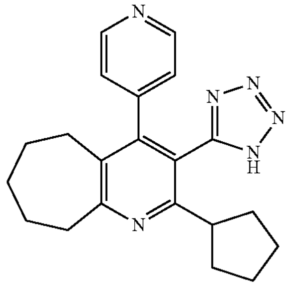 [SMILES: c1cc(-c2c3c(nc(C4CCCC4)c2-c2nnn[nH]2)CCCCC3)ccn1] | ESP [M + H]$^+$: 361.5 | C | N75 |

-continued

| Ex. | Name | Structure | MS | Method | Starting Material |
|---|---|---|---|---|---|
| 76 | 2-Cyclopentyl-4-(1-methyl-1H-pyrazol-5-yl)-3-(1H-tetrazol-5-yl)-6,7,8,9-tetrahydro-5H-cyclohepta[b]pyridine | 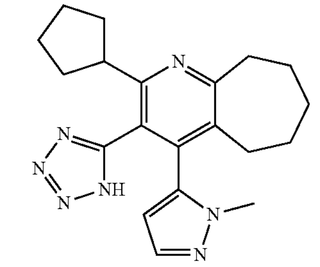 [SMILES: Cn1nccc1-c1c2c(nc(C3CCCC3)c1-c1nnn[nH]1)CCCCC2] | ESP $[M+H]^+$: 364.5 | C | N76 |
| 77 | 1-(4-(3-Chlorophenyl)-2-cyclobutyl-3-(1H-tetrazol-5-yl)-7,8-dihydro-1,6-naphthyridin-6(5H)-yl)ethanone | 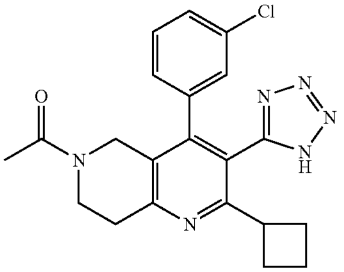 [SMILES: CC(=O)N1CCc2nc(C3CCC3)c(-c3nnn[nH]3)c(-c3cccc(Cl)c3)c2C1] | ESP $[M+H]^+$: 409.4 | C | N77 |
| 78 | 2-Cyclopentyl-4-(6-methoxypyridin-2-yl)-3-(1H-tetrazol-5-yl)-6,7,8,9-tetrahydro-5H-cyclohepta[b]pyridine | 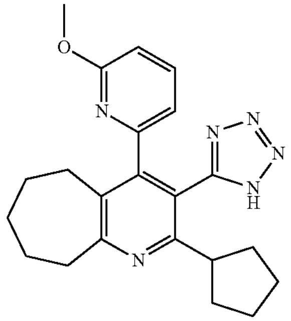 [SMILES: COc1cccc(-c2c3c(nc(C4CCCC4)c2-c2nnn[nH]2)CCCCC3)n1] | ESP $[M+H]^+$: 391.5 | C | N78 |
| 79 | 4-Phenyl-2-(tetrahydro-2H-pyran-2-yl)-3-(1H-tetrazol-5-yl)-6,7,8,9-tetrahydro-5H-cyclohepta[b]pyridine | 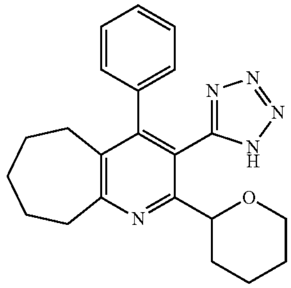 [SMILES: c1ccc(-c2c3c(nc(C4CCCCO4)c2-c2nnn[nH]2)CCCCC3)cc1] | ESP $[M+H]^+$: 376.5 | C | N79 |
| 80 | 2-Cyclopentyl-4-(2-methylpyridin-4-yl)-3-(1H-tetrazol-5-yl)-6,7,8,9-tetrahydro-5H-cyclohepta[b]pyridine | 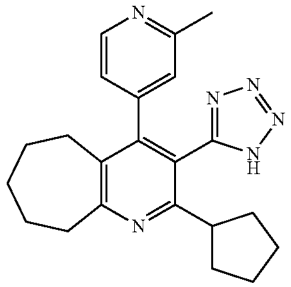 [SMILES: Cc1cc(-c2c3c(nc(C4CCCC4)c2-c2nnn[nH]2)CCCCC3)ccn1] | ESP $[M+H]^+$: 375.5 | C | N80 |

-continued

| Ex. | Name | Structure | MS | Method | Starting Material |
|---|---|---|---|---|---|
| 81 | 4-Phenyl-2-(tetrahydrofuran-3-yl)-3-(1H-tetrazol-5-yl)-6,7,8,9-tetrahydro-5H-cyclohepta[b)pyridine | 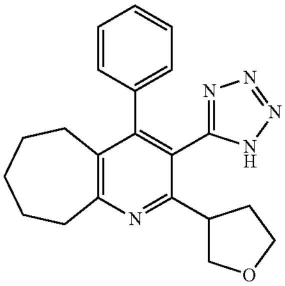 [SMILES: c1ccc(-c2c3c(nc(C4CCOC4)c2-c2nnn[nH]2)CCCCC3)cc1] | ESP $[M + H]^+$: 362.5 | C | N81 |
| 82 | 2-Cyclopentyl-4-(2-methoxypyridin-4-yl)-3-(1H-tetrazol-5-yl)-6,7,8,9-tetrahydro-5H-cyclohepta[b]pyridine | 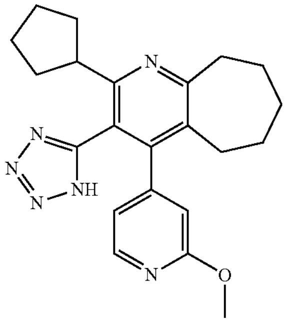 [SMILES: COc1cc(-c2c3c(nc(C4CCCC4)c2-c2nnn[nH]2)CCCCC3)ccn1] | ESP $[M + H]^+$: 391.5 | C | N82 |
| 83 | 2-Cyclohexyl-4-phenyl-3-(1H-tetrazol-5-yl)-6,7,8,9-tetrahydro-5H-cyclohepta[b]pyridine | 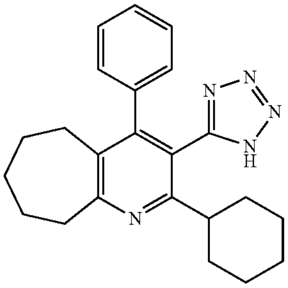 [SMILES: c1ccc(-c2c3c(nc(C4CCCCC4)c2-c2nnn[nH]2)CCCCC3)cc1] | ESP $[M + H]^+$: 374.6 | C | N83 |
| 84 | 2-Cyclopentyl-4-phenyl-3-(1H-tetrazol-5-yl)-6,7,8,9-tetrahydro-5H-cyclohepta[b]pyridine | 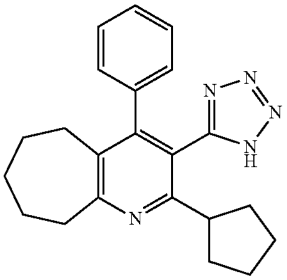 | ESP $[M + H]^+$: 360.6 | C | N84 |
| 85 | 4-Phenyl-2-(tetrahydrofuran-2-yl)-3-(1H-tetrazol-5-yl)-6,7,8,9-tetrahydro-5H-cyclohepta[b]pyridine | 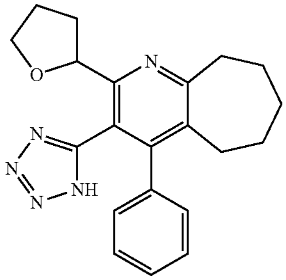 [SMILES: c1ccc(-c2c3c(nc(C4CCCO4)c2-c2nnn[nH]2)CCCCC3)cc1] | ESP $[M + H]^+$: 362.5 | C | N85 |

-continued

| Ex. | Name | Structure | MS | Method | Starting Material |
|---|---|---|---|---|---|
| 86 | 2-Cyclohexyl-4-(3-fluoropyridin-4-yl)-3-(1H-tetrazol-5-yl)-6,7,8,9-tetrahydro-5H-cyclohepta[b]pyridine | 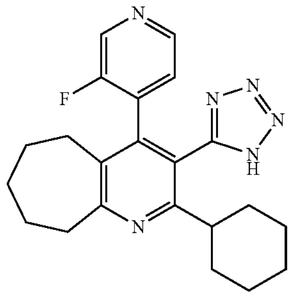 [SMILES: Fc1cnccc1-c1c2c(nc(C3CCCCC3)c1-c1nnn[nH]1)CCCCC2] | ESP [M + H]$^+$: 393.5 | C | N86 |
| 87 | 2-Cyclopentyl-4-(3-fluoropyridin-4-yl)-3-(1H-tetrazol-5-yl)-6,7,8,9-tetrahydro-5H-cyclohepta[b]pyridine | 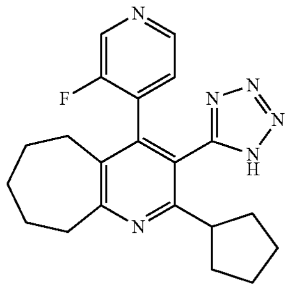 [SMILES: Fc1cnccc1-c1c2c(nc(C3CCCC3)c1-c1nnn[nH]1)CCCCC2] | ESP [M + H]$^+$: 379.5 | C | N87 |
| 88 | 4-Phenyl-2-(tetrahydro-2H-pyran-4-yl)-3-(1H-tetrazol-5-yl)-6,7,8,9-tetrahydro-5H-cyclohepta[b]pyridine | 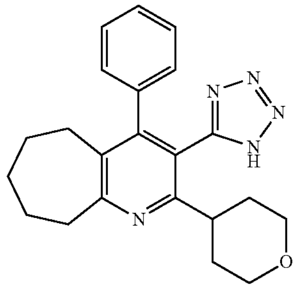 [SMILES: c1ccc(-c2c3c(nc(C4CCOCC4)c2-c2nnn[nH]2)CCCCC3)cc1] | ESP [M + H]$^+$: 376.5 | C | N88 |
| 89 | 2-Cyclohexyl-4-(2-methylpyrimidin-4-yl)-3-(1H-tetrazol-5-yl)-6,7,8,9-tetrahydro-5H-cyclohepta[b]pyridine | 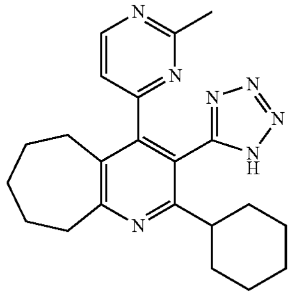 [SMILES: Cc1nccc(-c2c3c(nc(C4CCCCC4)c2-c2nnn[nH]2)CCCCC3)n1] | ESP [M + H]$^+$: 390.5 | C | N89 |
| 90 | 5-(2-Cyclobutyl-3-(1H-tetrazol-5-yl)-6,7,8,9-tetrahydro-5H-cyclohepta[b]pyridin-4-yl)-1-methylpyridin-2(1H)-one | 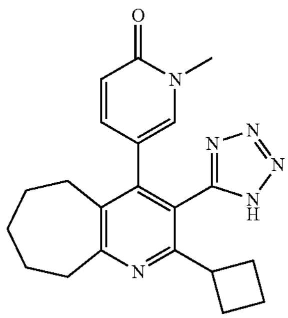 [SMILES: Cn1cc(-c2c3c(nc(C4CCC4)c2-c2nnn[nH]2)CCCCC3)ccc1=O] | ESP [M + H]$^+$: 377.5 | C | N90 |

-continued

| Ex. | Name | Structure | MS | Method | Starting Material |
|---|---|---|---|---|---|
| 91 | 2-Cyclohexyl-4-(pyrimidin-4-yl)-3-(1H-tetrazol-5-yl)-6,7,8,9-tetrahydro-5H-cyclohepta[b]pyridine | 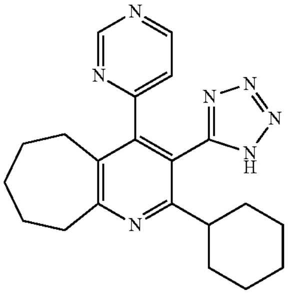 [SMILES: c1cc(-c2c3c(nc(C4CCCCC4)c2-c2nnn[nH]2)CCCCC3)ncn1] | ESP [M + H]$^+$: 376.5 | C | N91 |
| 92 | 2-Cyclopentyl-4-(pyrimidin-4-yl)-3-(1H-tetrazol-5-yl)-6,7,8,9-tetrahydro-5H-cyclohepta[b]pyridine | 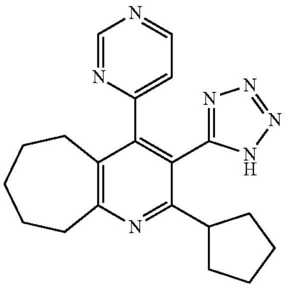 [SMILES: c1cc(-c2c3c(nc(C4CCCC4)c2-c2nnn[nH]2)CCCCC3)ncn1] | ESP [M + H]$^+$: 362.5 | C | N92 |
| 93 | 2-Cyclopentyl-4-(2-methylpyrimidin-4-yl)-3-(1H-tetrazol-5-yl)-6,7,8,9-tetrahydro-5H-cyclohepta[b]pyridine | 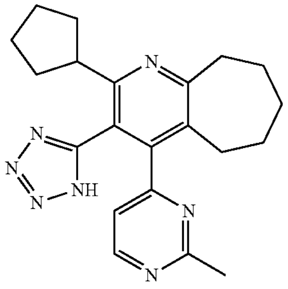 [SMILES: Cc1nccc(-c2c3c(nc(C4CCCC4)c2-c2nnn[nH]2)CCCCC3)n1] | ESP [M + H]$^+$: 376.5 | C | N93 |
| 94 | 2-(1-(Methoxymethyl)cyclopentyl)-4-(2-methylpyridin-4-yl)-3-(1H-tetrazol-5-yl)-6,7,8,9-tetrahydro-5H-cyclohepta[b]pyridine | 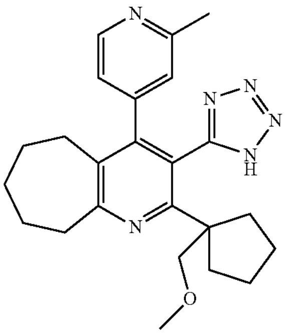 [SMILES: COCC1(c2nc3c(c(-c4ccnc(C)c4)c2-c2nnn[nH]2)CCCCC3)CCCC1] | ESP [M + H]$^+$: 419.5 | C | N94 |
| 95 | 2-Cyclopentyl-4-(pyridazin-4-yl)-3-(1H-tetrazol-5-yl)-6,7,8,9-tetrahydro-5H-cyclohepta[b]pyridine | 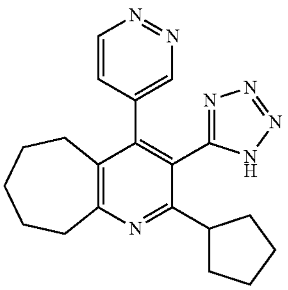 [SMILES: c1cc(-c2c3c(nc(C4CCCC4)c2-c2nnn[nH]2)CCCCC3)cnn1] | ESP [M + H]$^+$: 362.5 | C | N95 |

-continued

| Ex. | Name | Structure | MS | Method | Starting Material |
|---|---|---|---|---|---|
| 96 | 2-Cyclopentyl-4-(6-methylpyridin-2-yl)-3-(1H-tetrazol-5-yl)-6,7,8,9-tetrahydro-5H-cyclohepta[b]pyridine | 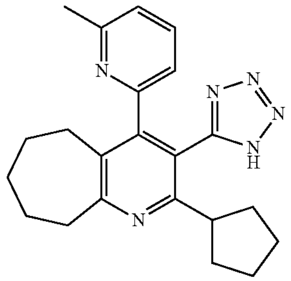 [SMILES: Cc1cccc(-c2c3c(nc(C4CCCC4)c2-c2nnn[nH]2)CCCCC3)n1] | ESP $[M + H]^+$: 375.5 | C | N96 |
| 97 | 2-Cyclopentyl-4-(pyridin-2-yl)-3-(1H-tetrazol-5-yl)-6,7,8,9-tetrahydro-5H-cyclohepta[b]pyridine | 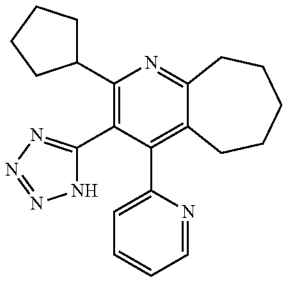 [SMILES: c1ccc(-c2c3c(nc(C4CCCC4)c2-c2nnn[nH]2)CCCCC3)nc1] | ESP $[M + H]^+$: 361.5 | C | N97 |
| 98 | 2-Isopropyl-4-(2-isopropylpyridin-4-yl)-3-(1H-tetrazol-5-yl)-6,7,8,9-tetrahydro-5H-cyclohepta[b]pyridine | 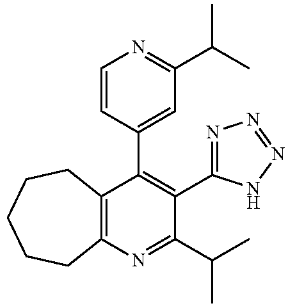 [SMILES: CC(C)c1cc(-c2c3c(nc(C(C)C)c2-c2nnn[nH]2)CCCCC3)ccn1] | ESP $[M + H]^+$: 377.5 | C | N98 |
| 99 | 2-Cyclopentyl-4-(pyrimidin-2-yl)-3-(1H-tetrazol-5-yl)-6,7,8,9-tetrahydro-5H-cyclohepta[b]pyridine | 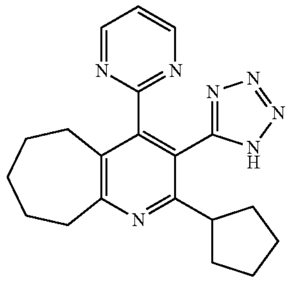 [SMILES: c1cnc(-c2c3c(nc(C4CCCC4)c2-c2nnn[nH]2)CCCCC3)nc1] | ESP $[M + H]^+$: 362.6 | C | N99 |
| 100 | 2-(2-(2-Cyclopentyl-3-(1H-tetrazol-5-yl)-6,7,8,9-tetrahydro-5H-cyclohepta[b]pyridin-4-yl)phenoxy)ethanol | 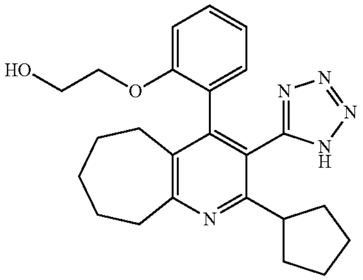 [SMILES: OCCOc1ccccc1-c1c2c(nc(C3CCCC3)c1-c1nnn[nH]1)CCCCC2] | ESP $[M + H]^+$: 420.6 | C | N100 |

-continued

| Ex. | Name | Structure | MS | Method | Starting Material |
|---|---|---|---|---|---|
| 101 | 2-Cyclopentyl-4-(2-isopropylpyrimidin-4-yl)-3-(1H-tetrazol-5-yl)-6,7,8,9-tetrahydro-5H-cyclohepta[b]pyridine | 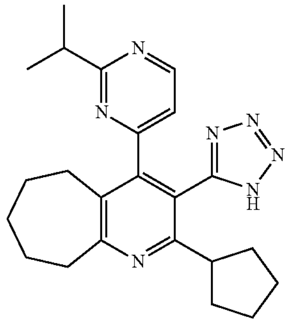 [SMILES: CC(C)c1nccc(-c2c3c(nc(C4CCCC4)c2-c2nnn[nH]2)CCCCC3)n1] | ESP [M + H]$^+$: 404.6 | C | N101 |
| 102 | 2-Isopropyl-4-(2-isopropylpyrimidin-4-yl)-3-(1H-tetrazol-5-yl)-6,7,8,9-tetrahydro-5H-cyclohepta[b]pyridine | 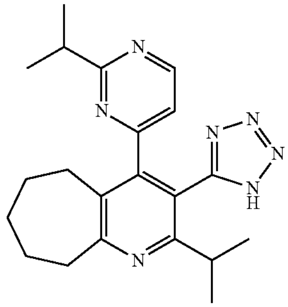 [SMILES: CC(C)c1nccc(-c2c3c(nc(C(C)C)c2-c2nnn[nH]2)CCCCC3)n1] | ESP [M + H]$^+$: 378.6 | C | N102 |
| 103 | 4-(2-Chloropyridin-4-yl)-2-cyclopentyl-3-(1H-tetrazol-5-yl)-6,7,8,9-tetrahydro-5H-cyclohepta[b]pyridine | 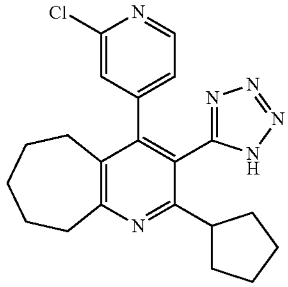 [SMILES: Clc1cc(-c2c3c(nc(C4CCCC4)c2-c2nnn[nH]2)CCCCC3)ccn1] | ESP [M + H]$^+$: 395.5 | C | N103 |
| 104 | 2-(1-(Methoxymethyl) cyclopentyl)-4-(2-methoxypyridin-4-yl)-3-(1H-tetrazol-5-yl)-6,7,8,9-tetrahydro-5H-cyclohepta[b]pyridine | 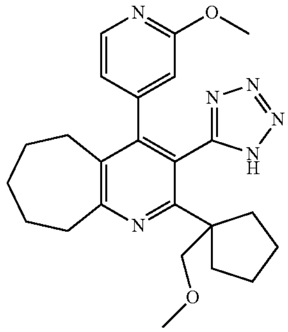 [SMILES: COCC1(c2nc3c(c(-c4ccnc(OC)c4)c2-c2nnn[nH]2)CCCCC3)CCCC1] | ESP [M + H]$^+$: 435.5 | C | N104 |

-continued

| Ex. | Name | Structure | MS | Method | Starting Material |
|---|---|---|---|---|---|
| 105 | 4-(2-Isopropylpyridin-4-yl)-2-(pentan-3-yl)-3-(1H-tetrazol-5-yl)-6,7,8,9-tetrahydro-5H-cyclohepta[b]pyridine | 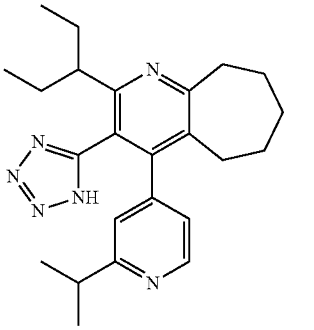 [SMILES: CCC(CC)c1nc2c(c(-c3ccnc(C(C)C)c3)c1-c1nnn[nH]1)CCCCC2] | ESP $[M + H]^+$: 405.6 | C | N105 |
| 106 | 4-(1-Methyl-1H-pyrazol-5-yl)-2-(pentan-3-yl)-3-(2H-tetrazol-5-yl)-6-(trifluoromethyl)-5,6,7,8-tetrahydroquinoline | 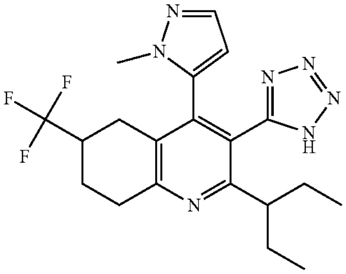 [SMILES: CCC(CC)c1nc2c(c(-c3ccnn3C)c1-c1nnn[nH]1)CC(C(F)(F)F)CC2] | ESP $[M + H]^+$: 420.5 | C | N106 |
| 107 | 2-Cyclohexyl-4-(2-methylpyridin-4-yl)-3-(2H-tetrazol-5-yl)-6-(trifluoromethyl)-5,6,7,8-tetrahydroquinoline | 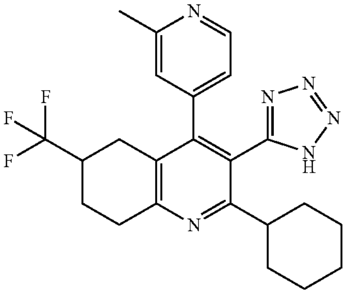 [SMILES: Cc1cc(-c2c3c(nc(C4CCCCC4)c2-c2nnn[nH]2)CCC(C(F)(F)F)C3)ccn1] | ESP $[M + H]^+$: 443.5 | C | N107 |
| 108 | 2-Cyclohexyl-4-(1-methyl-1H-pyrazol-5-yl)-3-(2H-tetrazol-5-yl)-6-(trifluoromethyl)-5,6,7,8-tetrahydroquinoline | 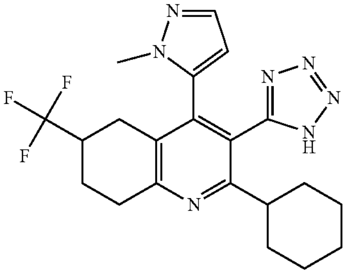 [SMILES: Cn1nccc1-c1c2c(nc(C3CCCCC3)c1-c1nnn[nH]1)CCC(C(F)(F)F)C2] | ESP $[M + H]^+$: 432.5 | C | N108 |
| 109 | 2-Cyclohexyl-6-methyl-4-(1-methyl-1H-pyrazol-5-yl)-3-(2H-tetrazol-5-yl)-5,6,7,8-tctrahydroquinoline | 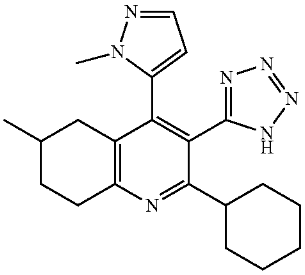 [SMILES: CC1CCc2nc(C3CCCCC3)c(-c3nnn[nH]3)c(-c3ccnn3C)c2C1] | ESP $[M + H]^+$: 378.5 | C | N109 |

-continued

| Ex. | Name | Structure | MS | Method | Starting Material |
|---|---|---|---|---|---|
| 110 | 2-Cyclohexyl-6-methyl-4-(2-methylpyridin-4-yl)-3-(2H-tetrazol-5-yl)-5,6,7,8-tetrahydroquinoline | 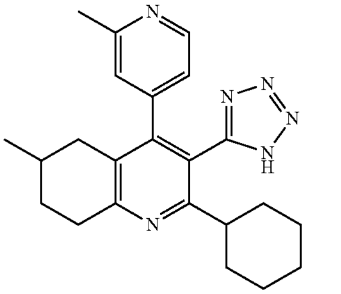 [SMILES: Cc1cc(-c2c3c(nc(C4CCCCC4)c2-c2nnn[nH]2)CCC(C)C3)ccn1] | ESP [M + H]$^+$: 389.5 | C | N110 |
| 111 | 2-Cyclopentyl-4-(1-methyl-1H-pyrazol-5-yl)-3-(2H-tetrazol-5-yl)-6-(trifluoromethyl)-5,6,7,8-tetrahydroquinoline | 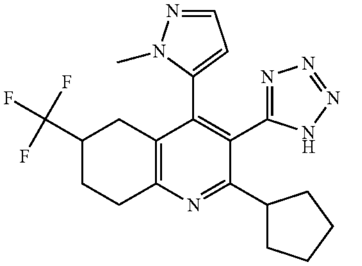 [SMILES: Cn1nccc1-c1c2c(nc(C3CCCC3)c1-c1nnn[nH]1)CCC(C(F)(F)F)C2] | ESP [M + H]$^+$: 418.5 | C | N111 |
| 112 | 2-Cyclopentyl-6,6-difluoro-4-phenyl-3-(2H-tetrazol-5-yl)-5,6,7,8-tetrahydroquinoline | 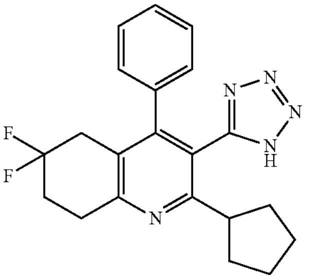 [SMILES: FC1(F)CCc2nc(C3CCCC3)c(-c3nnn[nH]3)c(-c3ccccc3)c2C1] | ESP [M + H]$^+$: 382.4 | C | N112 |
| 113 | 2-Cyclopentyl-6-methyl-4-(2-methylpyridin-4-yl)-3-(2H-tetrazol-5-yl)-5,6,7,8-tetrahydroquinoline | 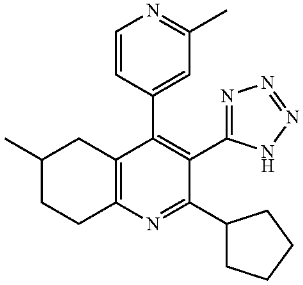 [SMILES: Cc1cc(-c2c3c(nc(C4CCCC4)c2-c2nnn[nH]2)CCC(C)C3)ccn1] | ESP [M + H]$^+$: 375.5 | C | N113 |
| 114 | 4-(2-Cyclohexyl-6-methyl-3-(2H-tetrazol-5-yl)-5,6,7,8-tetrahydroquinolin-4-yl)-3,5-dimethylisoxazole | 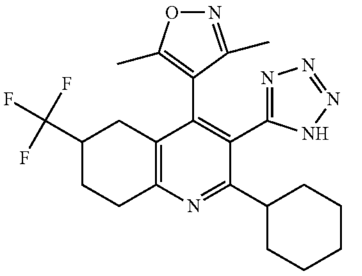 [SMILES: Cc1noc(C)c1-c1c2c(nc(C3CCCCC3)c1-c1nnn[nH]1)CCC(C(F)(F)F)C2] | ESP [M + H]$^+$: 447.6 | C | N114 |

-continued

| Ex. | Name | Structure | MS | Method | Starting Material |
|---|---|---|---|---|---|
| 115 | 4-(2-Cyclohexyl-6-methyl-3-(2H-tetrazol-5-yl)-5,6,7,8-tetrahydroquinolin-4-yl)-3,5-dimethylisoxazole | 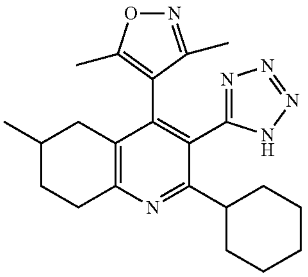 [SMILES: Cc1noc(C)c1-c1c2c(nc(C3CCCCC3)c1-c1nnn[nH]1)CCC(C)C2] | ESP [M + H]$^+$: 393.5 | C | N115 |
| 116 | 2-Cyclopentyl-4-(2-methylpyridin-4-yl)-3-(2H-tetrazol-5-yl)-6-(trifluoromethyl)-5,6,7,8-tetrahydroquinoline | 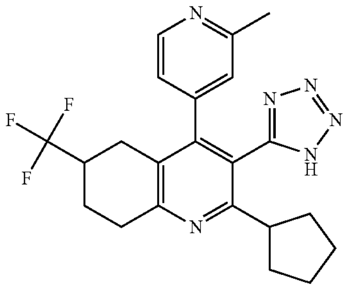 [SMILES: Cc1cc(-c2c3c(nc(C4CCCC4)c2-c2nnn[nH]2)CCC(C(F)(F)F)C3)ccn1] | ESP [M + H]$^+$: 429.5 | C | N116 |
| 117 | 2-Cyclopentyl-4-phenyl-3-(2H-tetrazol-5-yl)-6-(2,2,2-trifluoroethyl)-5,6,7,8-tetrahydro-1,6-naphthyridine | 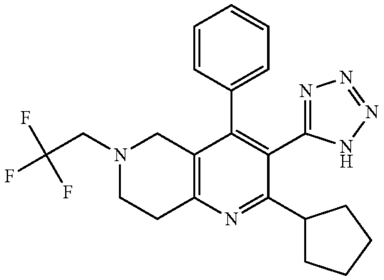 [SMILES: FC(F)(F)CN1CCc2nc(C3CCCC3)c(-c3nnn[nH]3)c(-c3ccccc3)c2C1] | ESP [M + H]$^+$: 429.4 | C | N117 |
| 118 | 2-Cyclopentyl-6,6-dimethyl-4-(2-methylpyridin-4-yl)-3-(2H-tetrazol-5-yl)-5,6,7,8-tetrahydroquinoline | 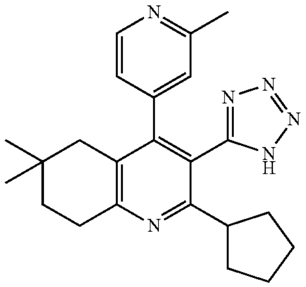 [SMILES: Cc1cc(-c2c3c(nc(C4CCCC4)c2-c2nnn[nH]2)CCC(C)(C)C3)ccn1] | ESP [M + H]$^+$: 389.6 | C | N118 |
| 119 | 2-Cyclopentyl-6-methoxy-4-(2-methylpyridin-4-yl)-3-(2H-tetrazol-5-yl)-5,6,7,8-tetrahydroquinoline | 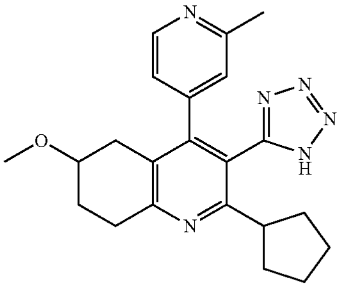 [SMILES: COC1CCc2nc(C3CCCC3)c(-c3nnn[nH]3)c(-c3ccnc(C)c3)c2C1] | ESP [M + H]$^+$: 391.5 | C | N119 |

-continued

| Ex. | Name | Structure | MS | Method | Starting Material |
|---|---|---|---|---|---|
| 120 | 6-Methyl-4-(2-methylpyridin-4-yl)-2-tert-pentyl-3-(2H-tetrazol-5-yl)-5,6,7,8-tetrahydroquinoline | 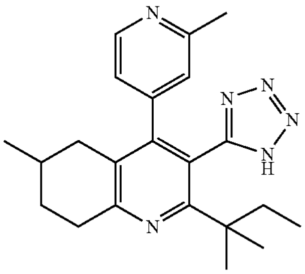 [SMILES: CCC(C)(C)c1nc2c(c(-c3ccnc(C)c3)c1-c1nnn[nH]1)CC(C)CC2] | ESP $[M+H]^+$: 377.6 | C | N120 |
| 121 | 2-Cyclopentyl-4-(2-methylpyridin-4-yl)-3-(2H-tetrazol-5-yl)-5,6,7,8-tetrahydroquinoline | 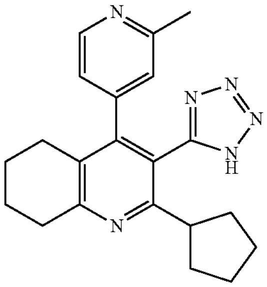 [SMILES: Cc1cc(-c2c3c(nc(C4CCCC4)c2-c2nnn[nH]2)CCCC3)ccn1] | ESP $[M+H]^+$: 361.6 | C | N121 |
| 122 | 2-Cyclohexyl-4-(2-methylpyridin-4-yl)-3-(2H-tetrazol-5-yl)-5,6,7,8-tetrahydroquinoline | 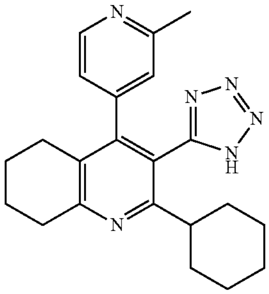 [SMILES: Cc1cc(-c2c3c(nc(C4CCCCC4)c2-c2nnn[nH]2)CCCC3)ccn1] | ESN $[M-H]^-$: 373.4 | C | N122 |
| 123 | 2-(1-Methoxy-2-methylpropan-2-yl)-6-methyl-4-(2-methylpyridin-4-yl)-3-(2H-tetrazol-5-yl)-5,6,7,8-tetrahydroquinoline | 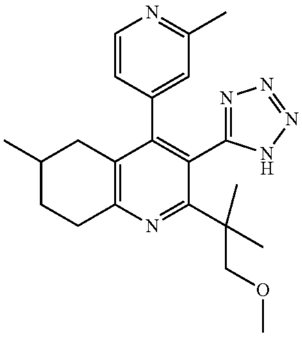 [SMILES: COCC(C)(C)c1nc2c(c(-c3ccnc(C)c3)c1-c1nnn[nH]1)CC(C)CC2] | ESP $[M+H]^+$: 393.6 | C | N123 |
| 124 | 2-Cyclopentyl-4-(2-methylpyridin-4-yl)-3-(2H-tetrazol-5-yl)-6,7-dihydro-5H-cyclopenta[b]pyridine | 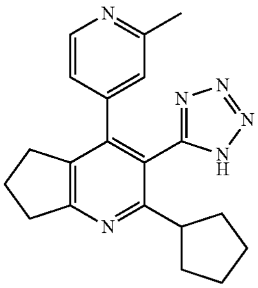 [SMILES: Cc1cc(-c2c3c(nc(C4CCCC4)c2-c2nnn[nH]2)CCC3)ccn1] | ESN [M − H]−: 345.5 | C | N124 |

-continued

| Ex. | Name | Structure | MS | Method | Starting Material |
|---|---|---|---|---|---|
| 125 | 2-Cyclohexyl-4-(2-methylpyridin-4-yl)-3-(2H-tetrazol-5-yl)-6,7-dihydro-5H-cyclopenta[b]pyridine | 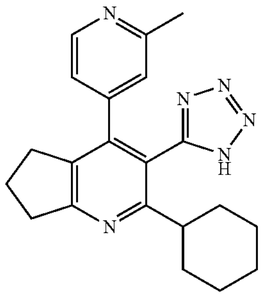 [SMILES: Cc1cc(-c2c3c(nc(C4CCCCC4)c2-c2nnn[nH]2)CCC3)ccn1] | ESP $[M+H]^+$: 361.5 | C | N125 |
| 126 | 2-tert-Butyl-4-phenyl-3-(1H-tetrazol-5-yl)-6,7,8,9-tetrahydro-5H-cyclohepta[b]pyridine | 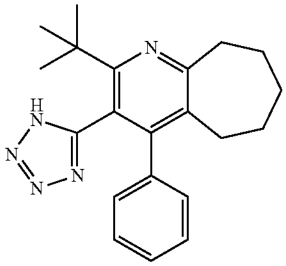 [SMILES: CC(C)(C)c1nc2c(c(-c3ccccc3)c1-c1nnn[nH]1)CCCCC2] | ESP $[M+H]^+$: 348.2 | D | N126 |
| 127 | 2-tert-Butyl-4-(3-fluorophenyl)-3-(1H-tetrazol-5-yl)-6,7,8,9-tetrahydro-5H-cyclohepta[b]pyridine | 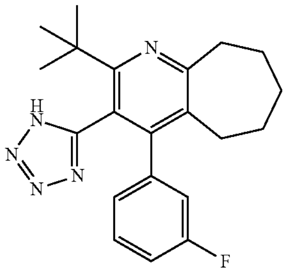 [SMILES: CC(C)(C)c1nc2c(c(-c3cccc(F)c3)c1-c1nnn[nH]1)CCCCC2] | ESP $[M+H]^+$: 366.5 | C | N127 |
| 128 | 2-tert-Butyl-3-(1H-tetrazol-5-yl)-4-(4-(trifluoromethyl)phenyl)-6,7,8,9-tetrahydro-5H-cyclohepta[b]pyridine | 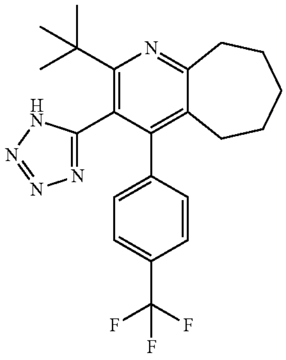 [SMILES: CC(C)(C)c1nc2c(c(-c3ccc(C(F)(F)F)cc3)c1-c1nnn[nH]1)CCCCC2] | ESP $[M+H]^+$: 416.5 | C | N128 |
| 129 | 2-tert-Butyl-3-(1H-tetrazol-5-yl)-4-(3-(trifluoromethyl)phenyl)-6,7,8,9-tetrahydro-5H-cyclohepta[b]pyridine | 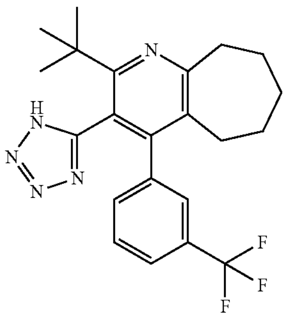 [SMILES: CC(C)(C)c1nc2c(c(-c3cccc(C(F)(F)F)c3)c1-c1nnn[nH]1)CCCCC2] | ESP $[M+H]^+$: 416.4 | C | N129 |

-continued

| Ex. | Name | Structure | MS | Method | Starting Material |
|---|---|---|---|---|---|
| 130 | 2-tert-Butyl-4-(2-methylpyridin-4-yl)-3-(1H-tetrazol-5-yl)-6,7,8,9-tetrahydro-5H-cyclohepta[b]pyridine | 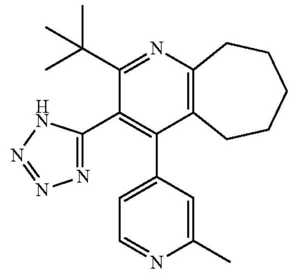 [SMILES: Cc1cc(-c2c3c(nc(C(C)(C)C)c2-c2nnn[nH]2)CCCCC3)ccn1] | ESP $[M + H]^+$: 363.4 | C | N130 |
| 131 | 2-(3,3-Difluorocyclobutyl)-4-phenyl-3-(1H-tetrazol-5-yl)-6,7,8,9-tetrahydro-5H-cyclohepta[b]pyridine | 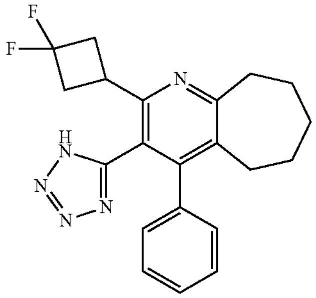 [SMILES: FC1(F)CC(c2nc3c(c(-c4ccccc4)c2-c2nnn[nH]2)CCCCC3)C1] | ESN $[M - H]^-$: 380.2 | C | N131 |
| 132 | 2-tert-Butyl-4-(4-fluoro-phenyl)-3-(1H-tetrazol-5-yl)-6,7,8,9-tetrahydro-5H-cyclohepta[b]pyridine | 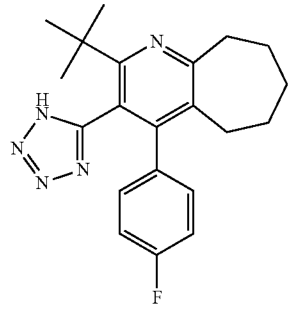 [SMILES: CC(C)(C)c1nc2c(c(-c3ccc(F)cc3)c1-c1nnn[nH]1)CCCCC2] | ESP $[M + H]^+$: 366.5 | C | N132 |
| 133 | 4-(2-tert-Butyl-3-(1H-tetrazol-5-yl)-6,7,8,9-tetrahydro-5H-cyclohepta[b]pyridin-4-yl)oxazole | 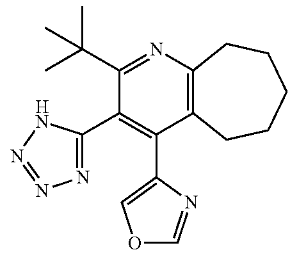 [SMILES: CC(C)(C)c1nc2c(c(-c3cocn3)c1-c1nnn[nH]1)CCCCC2] | ESP $[M + H]^+$: 339.5 | C | N133 |
| 134 | 2-tert-Butyl-4-(1-methyl-1H-pyrazol-3-yl)-3-(1H-tetrazol-5-yl)-6,7,8,9-tetrahydro-5H-cyclohepta[b]pyridine | 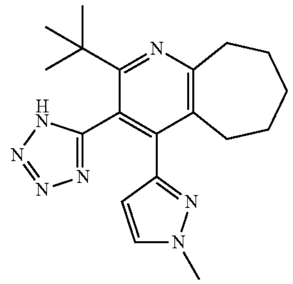 [SMILES: Cn1ccc(-c2c3c(nc(C(C)(C)C)c2-c2nnn[nH]2)CCCCC3)n1] | ESP $[M + H]^+$: 352.5 | C | N134 |

-continued

| Ex. | Name | Structure | MS | Method | Starting Material |
|---|---|---|---|---|---|
| 135 | 2-tert-Butyl-4-(4-methyl-1H-pyrazol-5-yl)-3-(1H-tetrazol-5-yl)-6,7,8,9-tetrahydro-5H-cyclohepta[b]pyridine | 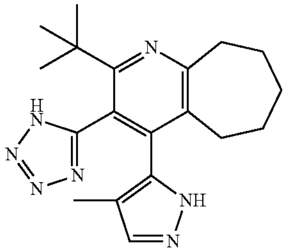 [SMILES: Cc1cn[nH]c1-c1c2c(nc(C(C)(C)C)c1-c1nnn[nH]1)CCCCC2] | ESP [M + H]+: 352.5 | C | N135 |
| 136 | 2-tert-Butyl-4-(3-cyclopropyl-1H-pyrazol-5-yl)-3-(1H-tetrazol-5-yl)-6,7,8,9-tetrahydro-5H-cyclohepta[b]pyridine | 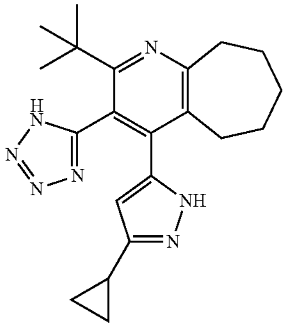 [SMILES: CC(C)(C)c1nc2c(c(-c3cc(C4CC4)n[nH]3)c1-c1nnn[nH]1)CCCCC2] | ESP [M + H]+: 378.6 | C | N136 |
| 137 | 4-(2-tert-Butyl-3-(1H-tetrazol-5-yl)-6,7,8,9-tetrahydro-5H-cyclohepta[b]pyridin-4-yl)-2-methyloxazole | 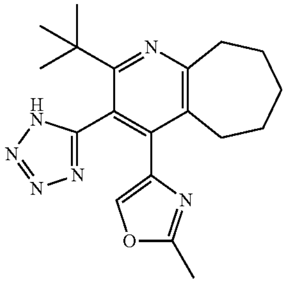 [SMILES: Cc1nc(-c2c3c(nc(C(C)(C)C)c2-c2nnn[nH]2)CCCCC3)co1] | ESP [M + H]+: 353.5 | C | N137 |
| 138 | 2-tert-Butyl-4-(4-chloro-1H-pyrazol-3-yl)-3-(1H-tetrazol-5-yl)-6,7,8,9-tetrahydro-5H-cyclohepta[b]pyridine | 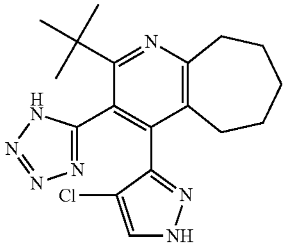 [SMILES: CC(C)(C)c1nc2c(c(-c3n[nH]cc3Cl)c1-c1nnn[nH]1)CCCCC2] | ESN [M − H]−: 370.5 | C | N138 |
| 139 | 2-tert-Butyl-3-(1H-tetrazol-5-yl)-4-(4-(trifluoromethyl)-1H-imidazol-2-yl)-6,7,8,9-tetrahydro-5H-cyclohepta[b]pyridine | 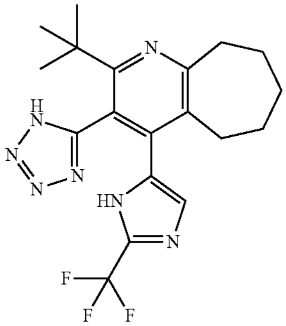 [SMILES: CC(C)(C)c1nc2c(c(-c3cnc(C(F)(F)F)[nH]3)c1-c1nnn[nH]1)CCCCC2] | ESP [M + H]+: 406.2 | C | N139 |

-continued

| Ex. | Name | Structure | MS | Method | Starting Material |
|---|---|---|---|---|---|
| 140 | 2-tert-Butyl-3-(1H-tetrazol-5-yl)-4-(1H-1,2,3-triazol-5-yl)-6,7,8,9-tetrahydro-5H-cyclohepta[b]pyridine | 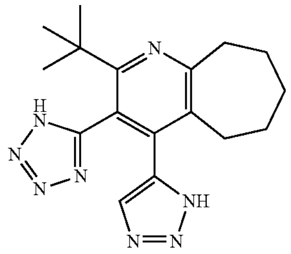 [SMILES: CC(C)(C)c1nc2c(c(-c3cnn[nH]3)c1-c1nnn[nH]1)CCCCC2] | ESP $[M + H]^+$: 339.2 | C | N140 |
| 141 | 2-tert-Butyl-4-(2-butyl-1H-imidazol-4-yl)-3-(1H-tetrazol-5-yl)-6,7,8,9-tetrahydro-5H-cyclohepta[b]pyridine | 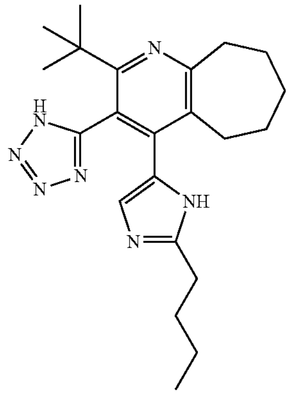 [SMILES: CCCCc1ncc(-c2c3c(nc(C(C)(C)C)c2-c2nnn[nH]2)CCCCC3)[nH]1] | ESP $[M + H]^+$: 394.6 | C | N141 |
| 142 | 2-Furan-2-yl-4-phenyl-3-(1H-tetrazol-5-yl)-6,7,8,9-tetrahydro-5H-cyclohepta[b]pyridine | 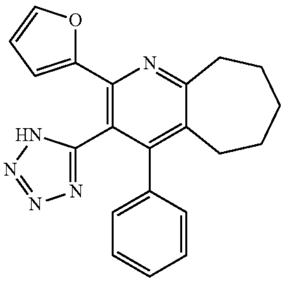 [SMILES: c1ccc(-c2c3c(nc(-c4ccco4)c2-c2nnn[nH]2)CCCCC3)cc1] | ESP $[M + H]^+$: 358.4 | C | N142 |
| 143 | 2-sec-Butyl-4-phenyl-3-(1H-tetrazol-5-yl)-6,7,8,9-tetrahydro-5H-cyclohepta[b]pyridine | 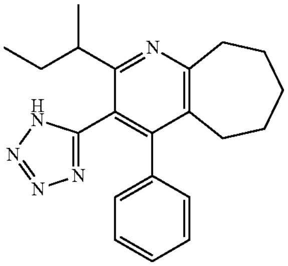 [SMILES: CCC(C)c1nc2c(c(-c3ccccc3)c1-c1nnn[nH]1)CCCCC2] | ESP $[M + H]^+$: 348.5 | C | N143 |
| 144 | 2-(3-Fluorophenyl)-4-phenyl-3-(1H-tetrazol-5-yl)-6,7,8,9-tetrahydro-5H-cyclohepta[b]pyridine | 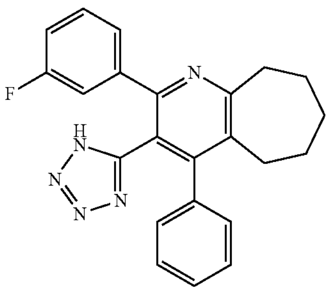 [SMILES: Fc1cccc(-c2nc3c(c(-c4ccccc4)c2-c2nnn[nH]2)CCCCC3)c1] | ESP $[M + H]^+$: 386.5 | C | N144 |

-continued

| Ex. | Name | Structure | MS | Method | Starting Material |
|---|---|---|---|---|---|
| 145 | 2-sec-Butyl-4-(2-methylpyridin-4-yl)-3-(1H-tetrazol-5-yl)-6,7,8,9-tetrahydro-5H-cyclohepta[b]pyridine | 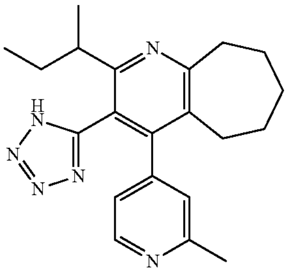 [SMILES: CCC(C)c1nc2c(c(-c3ccnc(C)c3)c1-c1nnn[nH]1)CCCCC2] | ESP $[M + H]^+$: 363.2 | C | N145 |

Example 12

2-Cyclopentyl-4-(6-methoxypyridin-2-yl)-6,7,8,9-tetrahydro-5H-cyclohepta[b]pyridine-3-carboxylic acid

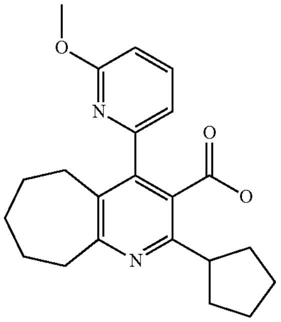 [SMILES: COc1cccc(-c2c3c(nc(C4CCCC4)c2C(=O)O)CCCCC3)n1]

Intermediate N78 (471 mg) and aqueous HCl 37% (2.67 g) were combined with dioxane (20.0 ml) and stirred at 100° C. for 1 h. After cooling to room temperature, the mixture was diluted with water and extracted with EtOAc. The organic layers were dried over $MgSO_4$ and concentrated in vacuo. The crude material was purified by column chromatography (gradient of DCM/MeOH 100:0=>80:20) to give the title compound (47 mg) as a colorless amorphous solid. MS (ESN): m/z=365.4 $[M-H]^-$.

Example 13

2-Cyclopentyl-4-(6-oxo-1,6-dihydropyridin-2-yl)-6,7,8,9-tetrahydro-5H-cyclohepta[b]pyridine-3-carboxylic acid

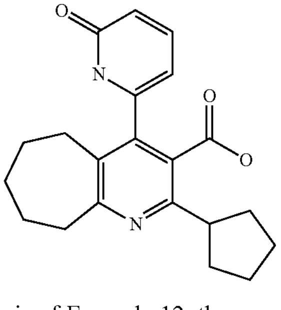

In the synthesis of Example 12, there was also obtained the title compound (114 mg) as a light yellow solid. MS (ESP): m/z=353.4 $[M+H]^+$.

Example 20

4-(3-Chlorophenyl)-6-methyl-2-(pyrrolidin-1-yl)-5,6,7,8-tetrahydroquinoline-3-carboxylic acid

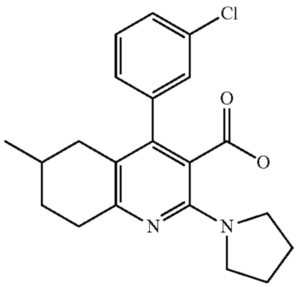 [SMILES: CC1CCc2nc(N3CCCC3)c(C(=O)O)c(-c3cccc(Cl)c3)c2C1]

Step 1: 4-(3-Chlorophenyl)-6-methyl-2-oxo-1,2,5,6,7,8-hexahydroquinoline-3-carboxylic acid

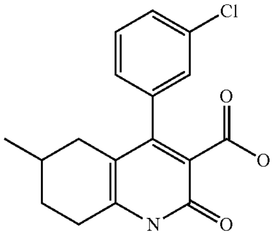 [SMILES: CC1CCc2[nH]c(=O)c(C(=O)O)c(-c3cccc(Cl)c3)c2C1]

A solution of lithium hydroxide (104 mg) in water (4.0 ml) was added at room temperature to a solution of Intermediate P20 (500 mg) in EtOH (9.3 ml) and THF (2.7 ml). After the addition the solution was stirred at 90° C. for 4 h. The organic solvents were removed in vacuo, the residue was diluted with 15 mL of aqueous 1 M NaOH and extracted with dichloromethane. The aqueous layer was acidified with aqueous 1 M HCl to pH1 and extracted with DCM and with EtOAc. The combined organic layers were dried over $MgSO_4$ and concentrated in vacuo to give the title compound (452 mg) as an off-white solid. MS (ESP): m/z=318.1 $[M+H]^+$.

Step 2: 2-Chloro-4-(3-chloro-phenyl)-6-methyl-5,6,7,8-tetrahydro-quinoline-3-carbonyl chloride

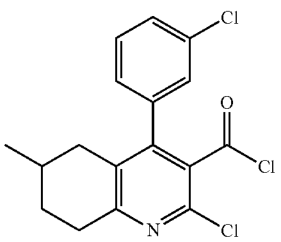 [SMILES: CC1CCc2nc(Cl)c(C(=O)Cl)c(-c3cccc(Cl)c3)c2C1]

A suspension of the product of step 1 (440 mg) in phenylphosphonic dichloride (863 mg) was stirred at 135° C. for 3 h. After cooling to room temperature, the mixture was diluted with water (10 ml) and extracted with DCM. The organic layers were dried over $MgSO_4$ and concentrated in vacuo. The crude material was purified by column chromatography (gradient of DCM/MeOH 100:0=>90:10) to give the title compound (271 mg) as an off-white solid. MS (ESP): m/z=356.0 $[M+H]^+$.

Step 3: 2-Chloro-4-(3-chlorophenyl)-6-methyl-5,6,7,8-tetrahydroquinoline-3-carboxylic acid

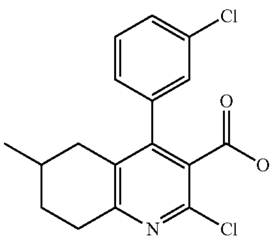 [SMILES: CC1CCc2nc(Cl)c(C(=O)O)c(-c3cccc(Cl)c3)c2C1]

A solution of the product of step 2 (138 mg) in THF (1 ml) and water (1.00 ml) was stirred for 6 days at room temperature, for 5 h at 50° C. and for 11 h at 60° C. The reaction mixture was poured into water (10 ml)/aqueous 1 M NaOH (1 ml) and extracted with diethyl ether.

The aqueous layer was acidified to pH 1 with aqueous 2 M HCl and back-extracted with EtOAc. The organic layers (EtOAc) were combined, dried over $MgSO_4$ and concentrated in vacuo to give the title compound (114 mg) as an off-white solid. MS (ESN): m/z=336.1 $[M-H]^-$.

Step 4: 4-(3-Chlorophenyl)-6-methyl-2-(pyrrolidin-1-yl)-5,6,7,8-tetrahydroquinoline-3-carboxylic acid

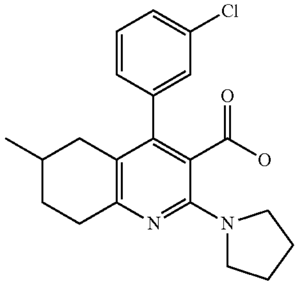 [SMILES: CC1CCc2nc(N3CCCC3)c(C(=O)O)c(-c3cccc(Cl)c3)c2C1]

A suspension of the product of step 3 (50 mg), potassium carbonate (24.7 mg), copper powder (0.56 mg), copper (I) bromide (1.1 mg) and pyrrolidine (18.0 mg) in DMA (0.2 ml) was stirred at 150° C. for 4 h. The reaction mixture was allowed to cool to room temperature overnight. The reaction mixture was poured into EtOAc (10 ml) and water (10 ml) and acidified to pH 3 with saturated aqueous citric acid solution. The mixture was extracted with EtOAc. The organic layers were combined, dried over $MgSO_4$ and concentrated in vacuo. The crude material was purified by preparative TLC (silica gel, 2.0 mm, DCM/MeOH 9:1) to give the title compound (14 mg) as an off-white solid. MS (ESN): m/z=369.1 $[M-H]^-$.

Example 23

4-(3-Chlorophenyl)-6-methyl-2-(piperidin-1-yl)-5,6,7,8-tetrahydroquinoline-3-carboxylic acid

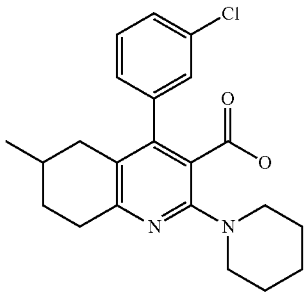 [SMILES: CC1CCc2nc(N3CCCCC3)c(C(=O)O)c(-c3cccc(Cl)c3)c2C1]

In analogy to Example 20, step 4, 2-chloro-4-(3-chlorophenyl)-6-methyl-5,6,7,8-tetrahydroquinoline-3-carboxylic acid (Example 20, step 3) was converted to the title compound by reaction with piperidine in the presence of potassium carbonate, copper powder, copper (I) bromide and DMA. Off-white solid. MS (ESN): m/z=383.4 $[M-H]^-$.

Example 24

5-(6-Methyl-4-phenyl-2-(piperidin-1-yl)-5,6,7,8-tetrahydroquinolin-3-yl)-1,3,4-oxadiazole-2(3H)-thione

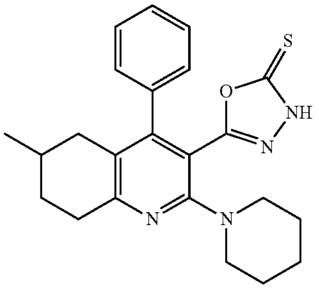 [SMILES: CC1CCc2nc(N3CCCCC3)c(-c3n[nH]c(=S)o3)c(-c3ccccc3)c2C1]

Step 1: 6-Methyl-2-oxo-4-phenyl-1,2,5,6,7,8-hexa-hydro-quinoline-3-carboxylic acid

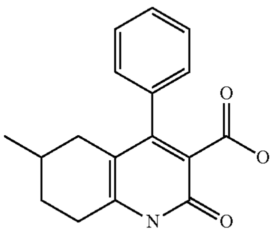 [SMILES: CC1CCc2[nH]c(=O)c(C(=O)O)c(-c3ccccc3)c2C1]

To a solution of intermediate P16 (660 mg, 2.12 mmol) in a solvent mixture of EtOH (6.6 ml), THF (2.64 ml) and water (6.6 ml) was added lithium hydroxide (152 mg, 6.36 mmol) and the reaction mixture was heated to reflux for 2 d. The organic solvents were removed and the pH of the remaining water layer was adjusted to 14. The water layer was washed 3 times with diethyl ether, then acidified to pH1 with 1N HCl and extracted with ethyl acetate. The combined ethyl acetate layers were washed with water and brine, dried ($Na_2SO_4$) and evaporated to obtain the title compound as white solid (550 mg). MS (ESP): m/z=284.2 $[M+H]^+$.

Step 2: N'-(2-Chloro-6-methyl-4-phenyl-5,6,7,8-tetrahydro-quinoline-3-carbonyl)-hydrazinecarboxylic acid 9H-fluoren-9-ylmethyl ester

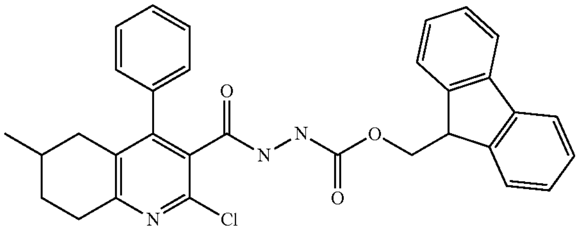 [SMILES: CC1CCc2nc(Cl)c(C(=O)NNC(=O)OCC3c4ccccc4-c4ccccc43)c(-c3ccccc3)c2C1]

A mixture of 6-methyl-2-oxo-4-phenyl-1,2,5,6,7,8-hexa-hydro-quinoline-3-carboxylic acid (170 mg, 600 μmol) and phenylphosphonic dichloride (351 mg, 253 μl, 1.8 mmol) was heated to 135° C. under argon for 6 h. The reaction mixture was then concentrated and the remaining residue was purified by silica column chromatography (50 g silica gel, DCM). The fractions containing the desired 2-chloro-6-methyl-4-phenyl-5,6,7,8-tetrahydro-quinoline-3-carbonyl chloride intermediate were combined, evaporated and dissolved in DCM (4 ml). (9H-Fluoren-9-yl)methyl hydrazinecarboxylate (183 mg, 720 μmol) was added and the reaction mixture was stirred at room temperature for 20 h. Water was added and the mixture was extracted with ethyl acetate. The combined extracts were washed with water and brine, dried ($Na_2SO_4$) and evaporated to obtain the title compound (308 mg) as a white solid. MS (ESP): m/z=538.4 $[M+H]^+$.

Step 3: 2-Chloro-6-methyl-4-phenyl-5,6,7,8-tetra-hydro-quinoline-3-carboxylic acid hydrazide

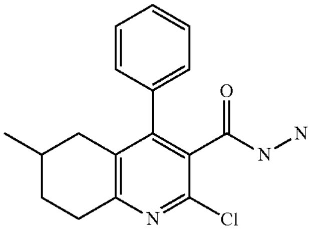 [SMILES: CC1CCc2nc(Cl)c(C(=O)NN)c(-c3ccccc3)c2C1]

To a solution of N'-(2-chloro-6-methyl-4-phenyl-5,6,7,8-tetrahydro-quinoline-3-carbonyl)-hydrazinecarboxylic acid 9H-fluoren-9-ylmethyl ester (170 mg, 253 μmol) in DMF (2.25 ml) was added piperidine (215 mg, 250 μl, 2.53 mmol) and the reaction mixture was stirred at room temperature for 2 h. Water was added and the mixture was extracted with ethyl acetate. The combined extracts were washed with water and brine, dried ($Na_2SO_4$) and evaporated. The remaining residue was purified by silica column chromatography (20 g silica gel, DCM/EtOAc 1:1) to obtain the title compound (71 mg) as a light yellow solid. MS (ESP): m/z=316.2 $[M+H]^+$.

Step 4: 6-Methyl-4-phenyl-2-piperidin-1-yl-5,6,7,8-tetrahydro-quinoline-3-carboxylic acid hydrazide

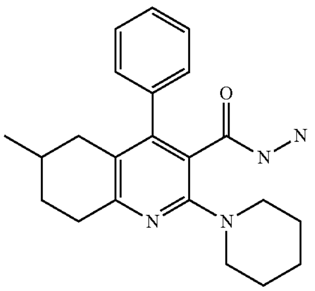 [SMILES: CC1CCc2nc(N3CCCCC3)c(C(=O)NN)c(-c3ccccc3)c2C1]

2-Chloro-6-methyl-4-phenyl-5,6,7,8-tetrahydro-quinoline-3-carboxylic acid hydrazide (70 mg, 222 μmol), piperidine (189 mg, 219 μl, 2.22 mmol) and triethylamine (67.3 mg, 92.7 μl, 665 μmol) were dissolved in DMF (1 ml) and the reaction mixture was heated to 120° C. for 24 h. Water was added and the mixture was extracted with EtOAc. The combined extracts were washed with brine, dried ($Na_2SO_4$) and evaporated. The remaining residue was purified by silica column chromatography (10 g silica gel, DCM/EtOAc 2:1) to obtain the title compound (45 mg) as a white solid. MS (ESP): m/z=365.3 $[M+H]^+$.

Step 5: 5-(6-Methyl-4-phenyl-2-(piperidin-1-yl)-5,6,7,8-tetrahydroquinolin-3-yl)-1,3,4-oxadiazole-2(3H)-thione

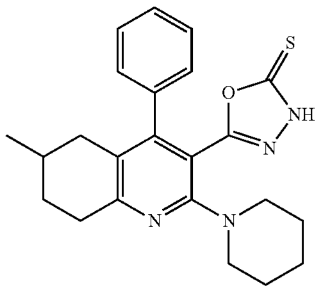 [SMILES: CC1CCc2nc(N3CCCCC3)c(-c3n[nH]c(=S)o3)c(-c3ccccc3)c2C1]

6-Methyl-4-phenyl-2-piperidin-1-yl-5,6,7,8-tetrahydro-quinoline-3-carboxylic acid hydrazide (43 mg, 94.4 μmol) and 1,1'-thiocarbonyldiimidazole (23.5 mg, 132 μmol) were dissolved in THF (1.1 ml). Then triethylamine (15.3 mg, 21.0 μl, 151 μmol) was added and the reaction mixture was stirred at room temperature for 16 h. Water was added and the mixture was extracted with ethyl acetate. The combined extracts were washed with water and brine, dried ($Na_2SO_4$) and evaporated. The remaining residue was purified by silica column chromatography (5 g silica gel, DCM/methanol 95:5). The fractions containing the desired 6-methyl-4-phenyl-2-piperidin-1-yl-5,6,7,8-tetrahydro-quinoline-3-carboxylic acid N'-(imidazole-1-carbothioyl)-hydrazide intermediate were combined, evaporated and dissolved in THF (1.1 ml). Triethylamine (15.3 mg, 21.0 μl, 151 μmol) was added and the reaction mixture was heated in a sealed tube to 50° C. for 4 d. Water was added and the mixture was extracted with ethyl acetate. The combined extracts were washed with brine, dried ($Na_2SO_4$) and evaporated. The remaining residue was purified by silica column chromatography (5 g silica gel, DCM/ethyl acetate 9:1) to obtain the title compound (13 mg) as white solid. MS (ESN): m/z=405.4 $[M-H]^-$.

Examples 37 and 43

4-(1-Methyl-1H-pyrazol-5-yl)-2-(2-methylpyrrolidin-1-yl)-3-(1H-tetrazol-5-yl)-6,7,8,9-tetrahydro-5H-cyclohepta[b]pyridine (diastereomeric racemates)

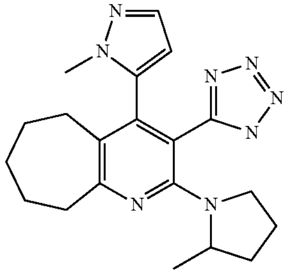 [SMILES: CC1CCCN1c1nc2c(c(-c3ccnn3C)c1-c1nnn[nH]1)CCCCC2]

Using General Method C, Intermediate N37 was converted to the tetrazole. The two diastereomeric racemates (caused by atropisomerism) could be separated by preparative HPLC (reverse phase chromatography, column: Gemini Axia C18 5u 110A 5 micron 100×30 mm, Solvent A: water+0.01% formic acid, Solvent B: acetonitrile, Method: gradient 30% to 95% B).

First-eluting isomer (Example 37): Off-white amorphous solid. MS (ESP): m/z=379.2 $[M+H]^+$.

Second-eluting isomer (Example 43): Colorless amorphous solid. MS (ESP): m/z=379.2 $[M+H]^+$.

Synthesis of Intermediates

Intermediate B79

3-Oxo-3-(tetrahydro-2H-pyran-2-yl)propanenitrile

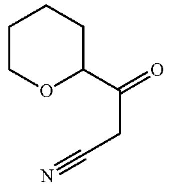 [SMILES: N#CCC(=O)C1CCCCO1]

To a suspension of sodium hydride (55% in mineral oil, 969 mg) in THF (4.79 ml) was added at 70° C. dropwise a solution of methyl tetrahydro-2H-pyran-2-carboxylate (3 g) and acetonitrile (994 mg) in THF (1.96 ml). The mixture was heated to 75° C. and stirred for 2 h. EtOAc was added and acidified with 1 M HCl under stirring (exothermic). The mixture was extracted with EtOAc. The organic layers were dried over $MgSO_4$ and concentrated in vacuo. The crude material was purified by column chromatography (gradient of n-heptane/EtOAc 1:0=>2:3) to give the title compound (2.42 g) as a light brown liquid. MS (ESP): m/z=152.2 $[M+H]^+$.

Intermediate B94

3-(1-(Methoxymethyl)cyclopentyl)-3-oxopropanenitrile

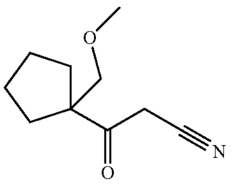

In analogy to the synthesis of Intermediate B79, methyl 1-(methoxymethyl)cyclopentanecarboxylate (CAS#220875-97-8) was converted to the title compound by a reaction with sodium hydride and acetonitrile in THF. Light yellow liquid. MS (ESN): m/z=180.2 $[M-H]^-$.

Intermediates K (Via Knoevenagel Condensation)

General Method E

A solution of the beta-ketoester or beta-ketonitrile or dialkylmalonate (3.5 mmol, 1 eq), the aldehyde (1.1 eq), piperidine (0.15 eq) and acetic acid (0.15 eq) in 2-propanol (10 ml) is stirred at room temperature overnight. Most of the 2-propanol is removed by evaporation. The mixture is diluted with $Na_2S_2O_5$ (20% g/g sol.) and extracted with DCM. The organic layers are washed with $Na_2S_2O_5$ (20% g/g sol.), sat. aqueous $NaHCO_3$ solution and water, dried over $Na_2SO_4$ and evaporated. The products are obtained as cis/trans mixtures and are used in the next step without further purification.

General Method F

A solution of the aldehyde (4.5 mmol, 1 eq), the beta-ketoester or beta-ketonitrile or dialkylmalonate or methyl cyanoacetate (1.1 eq) and piperidine (0.02 eq) in toluene (8.4 ml) is heated to reflux using a Dean-Stark trap for 1-2 h. The reaction mixture is concentrated and the product can be purified by crystallization or chromatography or can be used in the next step without further purification.

General Method G

To a suspension of 2-cyanoacetamide (1.1 eq) in methanol (10 ml) and water (3 ml) are added the aldehyde (40 mmol, 1 eq) and piperidine (0.2 eq). The mixture is stirred for 1-2 h. 1M HCl (9 ml) and water (10 ml) are added. The precipitate is collected by filtration, washed with water and ethyl acetate and dried. The product can be further purified by crystallization or can be used in the next step without further purification.

General Method H

The aldehyde (7.75 mmol, 1 eq), methyl cyanoacetate or a beta-ketonitrile (1 eq) and methanol (5.3 ml) are combined and stirred for 1-4 days. If the product precipitates, it can be collected by filtration. If the product does not precipitate, it can be purified by evaporation of the solvent and either crystallization or chromatography or can be used in the next step without further purification.

General Method I

The aldehyde (4.4 mmol, 1 eq), the beta-ketonitrile (1 eq) and L-proline (0.2 eq) are combined with ethanol or methanol (6.5 ml) and stirred for 1-4 days. If the product precipitates, it can be collected by filtration. If the product does not precipitate, it can be purified by evaporation of the solvent and either crystallization or chromatography or can be used in the next step without further purification.

| Intermediate | Name and Structure | MS | Method | Reagents |
|---|---|---|---|---|
| K4 | Ethyl 3-(3-chlorophenyl)-2-(cyclohexanecarbonyl)acrylate 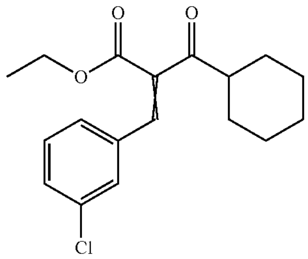 | ESP $[M + H]^+$: 321.1 | E | 3-Chlorobenzaldehyde, 3-cyclohexyl-3-oxo-propionic acid ethyl ester (CAS# 15971-92-3) |
| K5 | 2-Cyclohexanecarbonyl-3-phenyl-acrylic acid ethyl ester 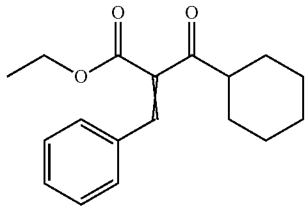 | ESP $[M + H]^+$: 287.0 | E | Benzaldehyde, 3-cyclohexyl-3-oxo-propionic acid ethyl ester (CAS# 15971-92-3) |
| K6 | 2-Cyclopentanecarbonyl-3-phenyl-acrylic acid methyl ester 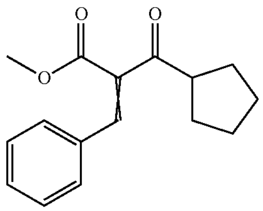 | ESP $[M + H]^+$: 259.1 | E | Benzaldehyde, methyl-3-cyclopentyl-3-oxopropanoate (CAS# 64670-14-0) |
| K20 | Diethyl 2-(3-chlorobenzylidene) malonate 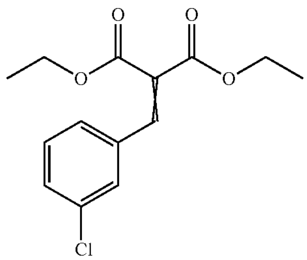 | | E | 3-Chlorobenzaldehyde, diethylmalonate |

-continued

| Intermediate | Name and Structure | MS | Method | Reagents |
|---|---|---|---|---|
| K29 | Methyl 2-cyano-3-(1-methyl-1H-pyrazol-5-yl)acrylate 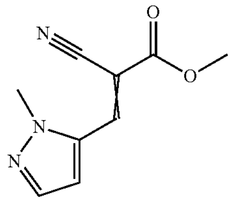 | ESP [M + H]$^+$: 192.3 | F | 1-Methyl-1H-pyrazole-5-carbaldehyde, methyl cyanoacetate |
| K32 | Methyl 3-(3-chlorophenyl)-2-cyanoacrylate 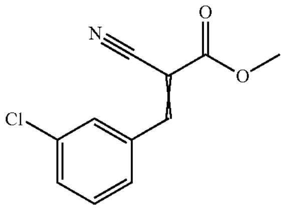 | ESP [M + NH4]$^+$: 238.9 | F | 3-Chlorobenzaldehyde, methyl cyanoacetate |
| K35 | 2-Cyano-3-(4-fluorophenyl) acrylamide 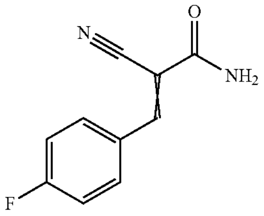 | | G | 4-Fluorobenzaldehyde, 2-cyanoacetamide |
| K38 | Methyl 3-(5-chlorothiophen-2-yl)-2-cyanoacrylate 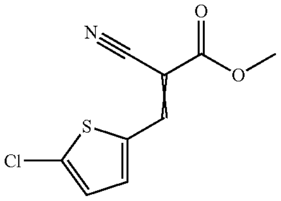 | ESP [M + H]$^+$: 228.3 | F | 5-Chlorothiophene-2-carbaldehyde, methyl cyanoacatate |
| K41 | Methyl 2-cyano-3-(5-methylisoxazol-3-yl)acrylate 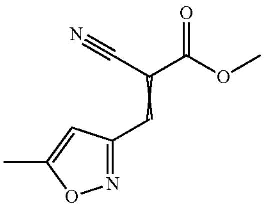 | ESP [M + H]$^+$: 191.3 | F | 5-Methylisoxazole-3-carbaldehyde, methyl cyanoacetate |

-continued

| Intermediate | Name and Structure | MS | Method | Reagents |
|---|---|---|---|---|
| K44 | Methyl-2-cyano-3-(pyridin-4-yl)acrylate 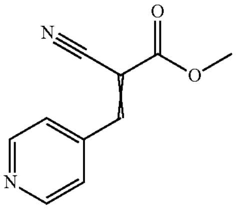 | ESP $[M + H]^+$: 189.1 | F | Isonicotinaldehyde, methyl cyanoacetate |
| K46 | Methyl 2-cyano-3-(5-methylfuran-2-yl)acrylate 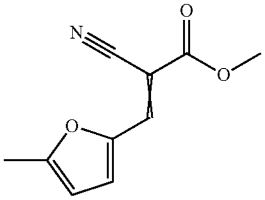 | ESP $[M + H]^+$: 192.3 | F | 5-Methylfuran-2-carbaldehyde, methyl cyanoacetate |
| K48 | Methyl 2-cyano-3-(1,5-dimethyl-1H-pyrazol-4-yl)acrylate 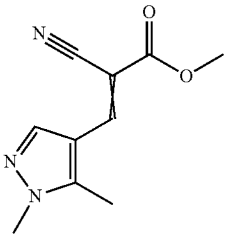 | ESP $[M + H]^+$: 206.4 | F | 1,5-Dimethyl-1H-pyrazole-4-carbaldehyde, methyl cyanoacetate |
| K56 | Methyl 2-cyano-3-(4-methylthiazol-5-yl)acrylate 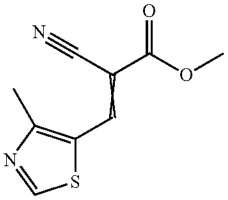 | | F | 4-Methylthiazole-5-carbaldehyde, methyl cyanoacetate |
| K61 | Cyano-3-pyrimidin-5-yl-acrylic acid methyl eter 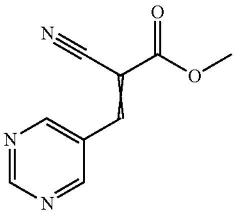 | ESP $[M + H]^+$: 190.3 | F | Pyrimidine-5-carbaldehyde, methyl cyanoacetate |

-continued

| Intermediate | Name and Structure | MS | Method | Reagents |
|---|---|---|---|---|
| K62 | Methyl 2-cyano-3-(3-fluoropyridin-4-yl)acrylate 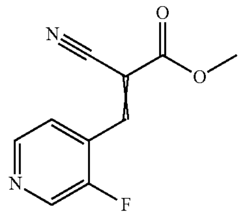 | ESP $[M + H]^+$: 207.3 | H | 3-Fluoroisonicotinaldehyde, methyl cyanoacetate |
| K63 | Methyl 2-cyano-3-(2-methoxypyridin-4-yl)acrylate 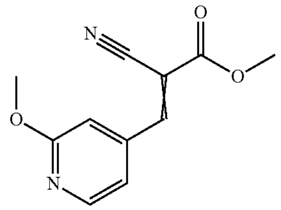 | | H | 2-Methoxyisonicotinaldehyde, methyl cyanoacetate |
| K66 | 4-Ethyl-2-((1-methyl-1H-pyrazol-5-yl)methylene)-3-oxohexanenitrile 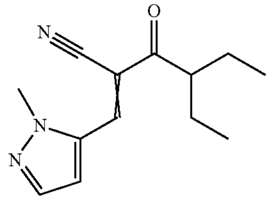 | | F | 1-Methyl-1H-pyrazole-5-carbaldehyde, 4-ethyl-3-oxo-hexanenitrile (CAS# 42124-67-4) |
| K67 | 3-(3-Chloro-phenyl)-2-cyclobutanecarbonyl-acrylonitrile 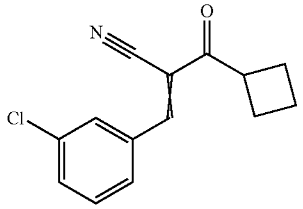 | | F | 3-Chlorobenzaldehyde β-Cyclobutyl-β-oxopropionitrile (CAS# 118431-89-3) |
| K68 | 2-Cyclohexanecarbonyl-3-pyridin-4-yl-acrylonitrile 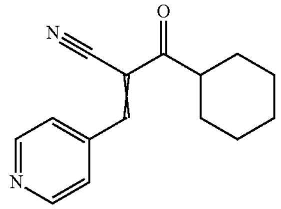 | | F | Isonicotinaldehyde, 3-cyclohexyl-3-oxo-propanenitrile (CAS# 62455-70-3) |

-continued

| Intermediate | Name and Structure | MS | Method | Reagents |
|---|---|---|---|---|
| K69 | 3-(3-Chlorophenyl)-2-(cyclopentanecarbonyl) acrylonitrile 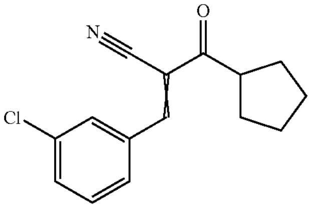 | ESP $[M + H]^+$: 260.3 | F | 3-Chlorobenzaldehyde, 3-cyclopentyl-3-oxopropanenitrile (CAS# 95882-33-0) |
| K70 | 2-Cyclohexanecarbonyl-3-(2-methyl-pyridin-4-yl)-acrylonitrile 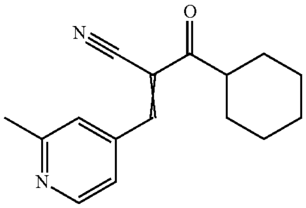 | | I | 2-Methylisonicotinaldehyde, 3-cyclohexyl-3-oxo-propanenitrile (CAS# 62455-70-3) |
| K71 | 2-(Cyclohexanecarbonyl)-3-(6-methoxypyridin-3-yl)acrylonitrile 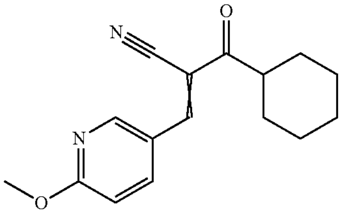 | ESP $[M + H]^+$: 271.4 | F | 6-Methoxynicotinaldehyde, 3-cyclohexyl-3-oxo-propanenitrile (CAS# 62455-70-3) |
| K74 | 2-Cyclohexanecarbonyl-3-(2-methyl-2H-pyrazol-3-yl)-acrylonitrile 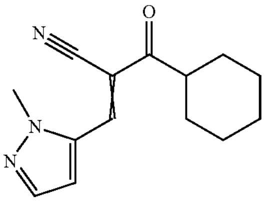 | ESP $[M + H]^+$: 244.4 | F | 1-Methyl-1H-pyrazole-5-carbaldehyde, 3-cyclohexyl-3-oxo-propanenitrile (CAS# 62455-70-3) |
| K75 | 2-Cyclopentanecarbonyl-3-pyridin-4-yl-acrylonitrile 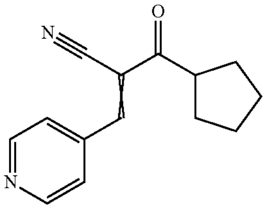 | ESP $[M + H]^+$: 227.4 | H | Isonicotinaldehyde, 3-cyclopentyl-3-oxopropanenitrile (CAS# 95882-33-0) |

-continued

| Intermediate | Name and Structure | MS | Method | Reagents |
|---|---|---|---|---|
| K76 | 2-Cyclopentanecarbonyl-3-(2-methyl-2H-pyrazol-3-yl)-acrylonitrile 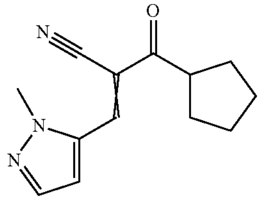 | ESP $[M + H]^+$: 230.4 | F | 1-Methyl-1H-pyrazole-5-carbaldehyde, 3-cyclopentyl-3-oxopropanenitrile (CAS# 95882-33-0) |
| K78 | 2-(Cyclopentanecarbonyl)-3-(6-methoxypyridin-2-yl) acrylonitrile 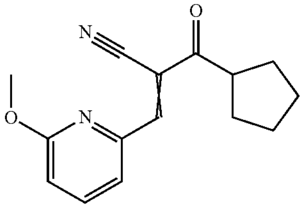 | ESP $[M + H]^+$: 257.4 | F | 6-Methoxypicolinaldehyde, 3-cyclopentyl-3-oxopropanenitrile (CAS# 95882-33-0) |
| K79 | 3-Phenyl-2-(tetrahydro-2H-pyran-2-carbonyl)acrylonitrile 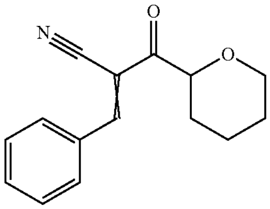 | ESP $[M + H]^+$: 242.3 | F | Benzaldehyde, Intermediate B79 |
| K80 | 2-Cyclopentanecarbonyl-3-(2-methyl-pyridin-4-yl)-acrylonitrile 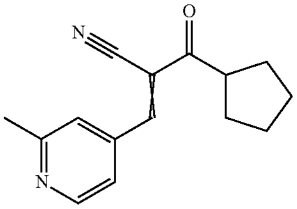 | ESP $[M + H]^+$: 241.4 | I | 2-Methylisonicotinaldehyde, 3-cyclopentyl-3-oxopropanenitrile (CAS# 95882-33-0) |
| K81 | 3-Phenyl-2-(tetrahydrofuran-3-carbonyl)acrylonitrile 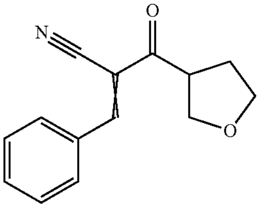 | ESP $[M + H]^+$: 228.4 | F | Benzaldehyde, 3-oxo-3-(tetrahydrofuran-3-yl)propanenitrile (CAS# 1186610-03-6) |

-continued

| Intermediate | Name and Structure | MS | Method | Reagents |
|---|---|---|---|---|
| K82 | 2-Cyclopentanecarbonyl-3-(2-methoxy-pyridin-4-yl)-acrylonitrile 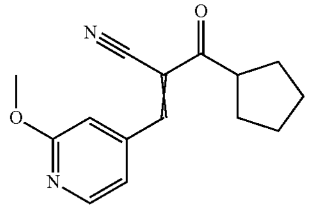 | | H | 2-Methoxyisonicotinaldehyde, 3-cyclopentyl-3-oxopropanenitrile (CAS# 95882-33-0) |
| K83 | 2-(Cyclohexanecarbonyl)-3-phenylacrylonitrile 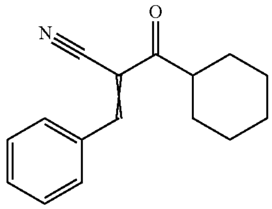 | ESP $[M + H]^+$: 240.3 | F | Benzaldehyde, 3-cyclohexyl-3-oxo-propanenitrile (CAS# 62455-70-3) |
| K84 | 2-(cyclopentanecarbonyl)-3-phenylacrylonitrile 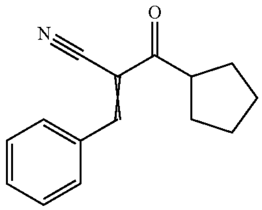 | ESP $[M + H]^+$ 226.1 | F | Benzaldehyde, 3-cyclopentyl-3-oxopropanenitrile (CAS# 95882-33-0) |
| K85 | 3-Phenyl-2-(tetrahydro-furan-2-carbonyl)-acrylonitrile 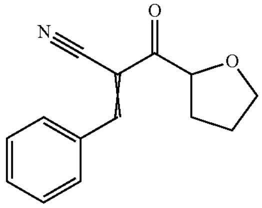 | ESP $[M + H]^+$: 228.3 | H | Benzaldehyde, 3-oxo-3-(tetrahydro-furan-2-yl)-propionitrile (CAS# 1092282-15-9) |
| K86 | 2-Cyclohexanecarbonyl-3-(3-fluoro-pyridin-4-yl)-acrylonitrile 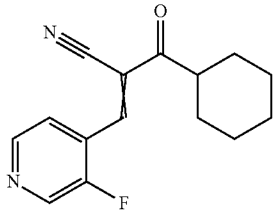 | ESP $[M + H]^+$: 259.4 | H | 3-Fluoroisonicotinaldehyde, 3-cyclohexyl-3-oxo-propanenitrile (CAS# 62455-70-3) |

-continued

| Intermediate | Name and Structure | MS | Method | Reagents |
|---|---|---|---|---|
| K87 | 2-Cyclopentanecarbonyl-3-(3-fluoro-pyridin-4-yl)-acrylonitrile 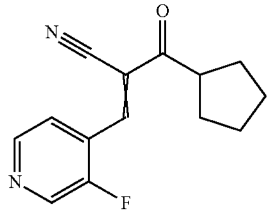 | ESP $[M + H]^+$: 245.4 | H | 3-Fluoroisonicotinaldehyde, 3-cyclopentyl-3-oxopropanenitrile (CAS# 95882-33-0) |
| K88 | 3-Phenyl-2-(tetrahydro-2H-pyran-4-carbonyl)acrylonitrile 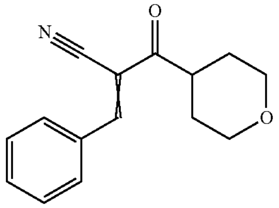 | ESP $[M + H]^+$: 242.4 | I | Benzaldehyde, 3-oxo-3-(tetrahydro-2H-pyran-4-yl)propanenitrile (CAS# 1010798-64-7) |
| K89 | 2-Cyclohexanecarbonyl-3-(2-methyl-pyrimidin-4-yl)-acrylonitrile 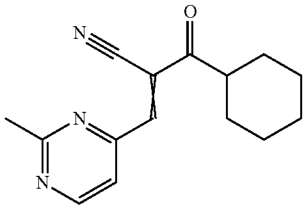 | ESP $[M + H]^+$: 256.4 | H | 2-Methylpyrimidine-4-carbaldehyde, 3-cyclohexyl-3-oxo-propanenitrile (CAS# 62455-70-3) |
| K90 | 2-(Cyclobutanecarbonyl)-3-(6-methoxypyridin-3-yl)acrylonitrile 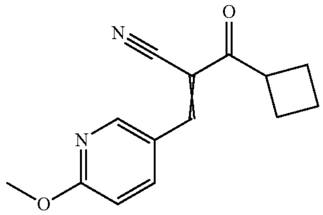 | ESP $[M + H]^+$: 243.4 | I | 6-Methoxynicotinaldehyde, β-Cyclobutyl-β-oxopropionitrile (CAS# 118431-89-3) |
| K91 | 2-Cyclohexanecarbonyl-3-pyrimidin-4-yl-acrylonitrile 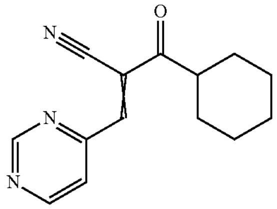 | ESP $[M + H]^+$: 242.4 | H | Pyrimidine-4-carbaldehyde, 3-cyclohexyl-3-oxo-propanenitrile (CAS# 62455-70-3) |

-continued

| Intermediate | Name and Structure | MS | Method | Reagents |
|---|---|---|---|---|
| K92 | 2-Cyclopentanecarbonyl-3-pyrimidin-4-yl-acrylonitrile 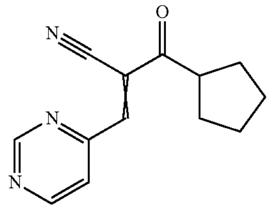 | ESP $[M + H]^+$: 228.4 | H | Pyrimidine-4-carbaldehyde, 3-cyclopentyl-3-oxopropanenitrile (CAS# 95882-33-0) |
| K93 | 2-Cyclopentanecarbonyl-3-(2-methyl-pyrimidin-4-yl)-acrylonitrile 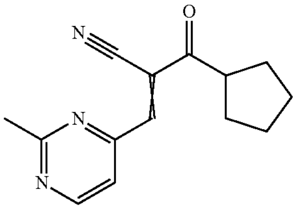 | | H | 2-Methylpyrimidine-4-carbaldehyde, 3-cyclopentyl-3-oxopropanenitrile (CAS# 95882-33-0) |
| K95 | 2-Cyclopentanecarbonyl-3-pyridazin-4-yl-acrylonitrile 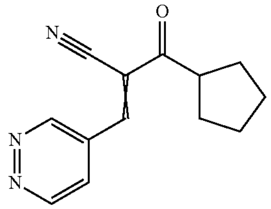 | | H | Pyridazine-4-carbaldehyde, 3-cyclopentyl-3-oxopropanenitrile (CAS# 95882-33-0) |
| K96 | 2-Cyclopentanecarbonyl-3-(6-methyl-pyridin-2-yl)acrylonitrile 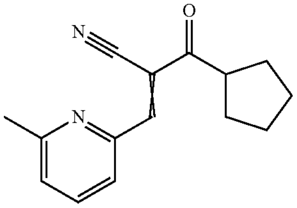 | ESP $[M + H]^+$: 241.4 | H | 6-Methylpicolinaldehyde, 3-cyclopentyl-3-oxopropanenitrile (CAS# 95882-33-0) |

-continued

| Intermediate | Name and Structure | MS | Method | Reagents |
|---|---|---|---|---|
| K97 | 2-Cyclopentanecarbonyl-3-pyridin-2-yl-acrylonitrile 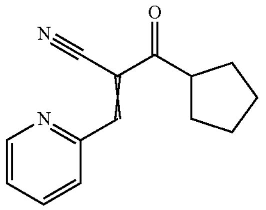 | | H | Picolinaldehyde, 3-cyclopentyl-3-oxopropanenitrile (CAS# 95882-33-0) |
| K99 | 2-Cyclopentanecarbonyl-3-pyrimidin-2-yl-acrylonitrile 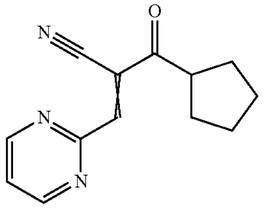 | ESP $[M+H]^+$: 228.4 | I | Pyrimidine-2-carbaldehyde, 3-cyclopentyl-3-oxopropanenitrile (CAS# 95882-33-0) |
| K114 | 2-(Cyclohexanecarbonyl)-3-(3,5-dimethylisoxazol-4-yl)acrylonitrile 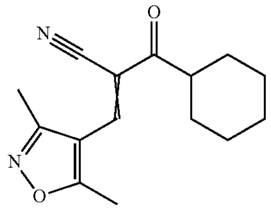 | ESN $[M-H]^-$: 257.4 | F | 3,5-Dimethylisoxazole-4-carbaldehyde, 3-cyclohexyl-3-oxo-propanenitrile (CAS# 62455-70-3) |

Intermediate L

5-Methyl-2-oxo-piperidine-1-carboxylic acid tert-butyl ester

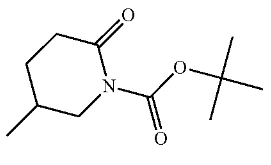

Triethylamine (447 mg, 616 μl, 4.42 mmol), 4-dimethylaminopyridine (54.0 mg, 0.442 mmol) and di-tert-butyldicarbonate (1.45 g, 6.63 mmol) were added to a solution of 5-methylpiperidin-2-one (CAS#3298-16-6) (500 mg, 4.42 mmol) in dry DCM (10 ml) at room temperature and the solution was stirred for 5 h. All volatiles were removed and the remaining oil was purified by silica column chromatography (50 g silica gel, n-hexane/diethyl ether 1:3) to obtain the title compound (717 mg) as yellow oil. MS (ESP): m/z=214.2 $[M+H]^+$.

General Method M

Lithium bis(trimethylsilyl)amide (1M solution in THF, 1.1 eq) is added to a solution of N-protected lactam (1 eq) in THF (1 ml/mmol) at −30° C. and the mixture is stirred for 25 minutes. The mixture is then transferred into a precooled (−20° C.) solution of Knoevenagel condensation products of beta-keto esters and aldehydes (1 eq) in dry THF (1.5 ml/mmol) and the reaction mixture is stirred at −20° C. for 1.5 h. Then saturated $NH_4Cl$ solution is added and the mixture is extracted with ethyl acetate. The combined extracts are dried ($Na_2SO_4$) and evaporated. The remaining residue is dissolved in 1,2-dichloroethane (4 ml/mmol), phosphorus pentachloride (1.2 eq) is added and the reaction mixture is heated to 65° C. for 2.5 h. After cooling to 0° C., ammonia in methanol (2M solution, 6 eq) is added and the precipitating solid is filtered off. The filtrate is concentrated, methanol (5 ml/mmol) and ammonium acetate (4 eq) are added and the mixture is heated to 60° C. for 4 h. Then copper (I) acetate (1.05 eq) is added and the reaction mixture is heated to reflux overnight, cooled to room temperature and filtered. The filtrate is concentrated, $Na_2CO_3$ solution (pH 10) is added and the mixture is extracted with ethyl acetate. The combined extracts are washed with $Na_2CO_3$ solution (pH 10), dried ($Na_2SO_4$) and evaporated and the remaining residue is purified by column chromatography.

| Intermediate | Name and Structure | MS | Method | Reagents |
|---|---|---|---|---|
| AP1 | Methyl 2-isopropyl-6-methyl-4-phenyl-5,6,7,8-tetrahydro-1,8-naphthyridine-3-carboxylate 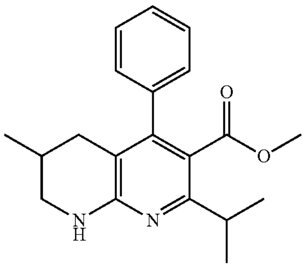 | ESP [M + H]$^+$: 325.3 | M | Methyl 3-methyl-3-oxo-2-(phenylmethylene)pentanoate (CAS# 912998-81-3), intermediate L |
| AP4 | Ethyl 4-(3-chlorophenyl)-2-cyclohexyl-5,6,7,8-tetrahydro-1,8-naphthyridine-3-carboxylate 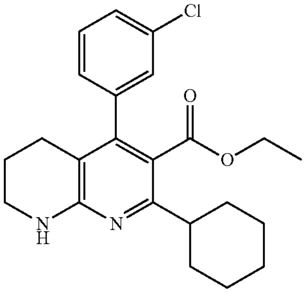 | ESP [M + H]$^+$: 399.1 | M | Intermediate K4, 2-oxopiperidine-1-carboxylic acid tert-butyl ester (CAS# 85908-96-9) |
| AP5 | Ethyl 2-cyclohexyl-4-phenyl-5,6,7,8-tetrahydro-1,8-naphthyridine-3-carboxylate 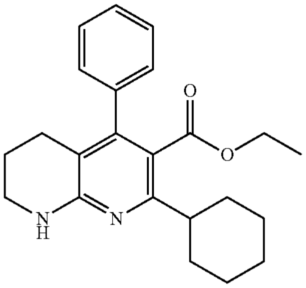 | ESP [M + H]$^+$: 365.2 | M | Intermediate K5, 2-oxopiperidine-1-carboxylic acid tert-butyl ester (CAS# 85908-96-9) |
| AP6 | Methyl 2-cyclopentyl-4-phenyl-5,6,7,8-tetrahydro-1,8-naphthyridine-3-carboxylate 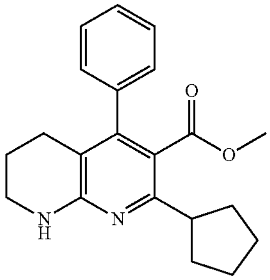 | ESP [M + H]$^+$: 337.3 | M | Intermediate K6, 2-oxopiperidine-1-carboxylic acid tert-butyl ester (CAS# 85908-96-9) |

-continued

| Intermediate | Name and Structure | MS | Method | Reagents |
|---|---|---|---|---|
| AP7 | Methyl 2-cyclopentyl-6-methyl-4-phenyl-5,6,7,8-tetrahydro-1,8-naphthyridine-3-carboxylate 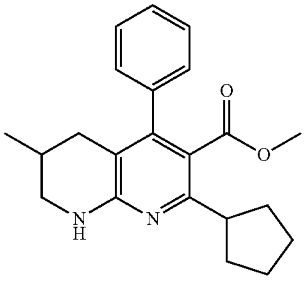 | ESP $[M + H]^+$: 351.5 | M | Intermediate K6, Intermediate L |

General Method N

To a solution of intermediate (AP) (1 eq) in dry DMF (7 ml/mmol) is added carefully sodium hydride (55% in mineral oil, 1.1 eq) at 0° C. and the resulting mixture is stirred for 45 minutes. Then a solution of an alkyl iodide (1.1 eq) in dry DMF (6 ml/mmol) is added, the mixture is allowed to warm to room temperature and is stirred overnight. The reaction mixture is then carefully diluted with water and the pH adjusted to 10 by addition of saturated $Na_2CO_3$ solution. The mixture is extracted with ethyl acetate and the combined organic layers are washed with $Na_2CO_3$ solution (pH 10), dried ($Na_2SO_4$) and evaporated. The remaining residue is purified by silica column chromatography.

General Method O

A mixture of intermediate (AP) (1 eq), triethylamine (3 eq) and a carboxylic acid anhydride (2 eq) in dry DCM (9 ml/mmol) is stirred in a sealed tube at 50° C. for 2 d. The solvent is removed and the remaining residue is purified by silica column chromatography.

General Method P

A solution of a cyclic ketone (0.85 eq) in THF (0.3 ml/mmol) is added dropwise to a solution of NaHMDS (1M solution in THF, 1 eq) in THF (0.5 ml/mmol) at −78° C. The mixture is allowed to warm to 0° C. and is maintained at this temperature for 15 minutes before it is cooled again to −78° C. A pre-cooled solution of Knoevenagel condensation products of beta-keto esters and aldehydes (1 eq) in THF (0.5 ml/mmol) is added quickly and the reaction mixture is stirred at −78° C. for 4 h. Then a solution of acetic acid (4.3 eq) in THF (0.1 ml/mmol) is added, the mixture is warmed to room temperature, diluted with water and extracted with ethyl acetate. The combined extracts are washed with water and brine, dried ($Na_2SO_4$) and evaporated. The remaining residue is dissolved in ethanol (2.5 ml/mmol), ammonium acetate (12.5 eq) and p-toluenesulfonic acid monohydrate (0.05 eq) are added and the mixture is heated to reflux for 1.5 d. The reaction mixture is then concentrated and DCM is added. The white precipitate is filtered off and the filtrate is evaporated. The remaining residue is dissolved in DCM (2.5 ml/mmol), 2,3-dichloro-5,6-dicyano-1,4-benzoquinone (0.95 eq) is added at room temperature and the reaction mixture is stirred for 2 to 2.5 h. Then saturated $NaHCO_3$ solution is added and the mixture is extracted with DCM. The combined organic layers are washed with saturated $NaHCO_3$ solution twice, dried ($Na_2SO_4$) and evaporated. The remaining residue is purified by silica column chromatography.

| Intermediate | Name and Structure | MS | Method | Reagents |
|---|---|---|---|---|
| E1 | Methyl 2-isopropyl-6,8-dimethyl-4-phenyl-5,6,7,8-tetrahydro-1,8-naphthyridine-3-carboxylate 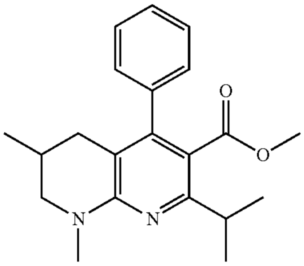 | ESP $[M + H]^+$: 339.3 | N | Intermediate AP1, methyl iodide |

-continued

| Intermediate | Name and Structure | MS | Method | Reagents |
| --- | --- | --- | --- | --- |
| E2 | Methyl 8-acetyl-2-isopropyl-6-methyl-4-phenyl-5,6,7,8-tetrahydro-1,8-naphthyridine-3-carboxylate 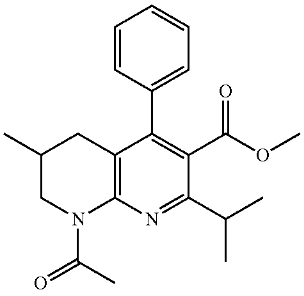 | ESP $[M + H]^+$: 367.1 | O | Intermediate AP1, acetic anhydride |
| E3 | Methyl 8-ethyl-2-isopropyl-6-methyl-4-phenyl-5,6,7,8-tetrahydro-1,8-naphthyridine-3-carboxylate 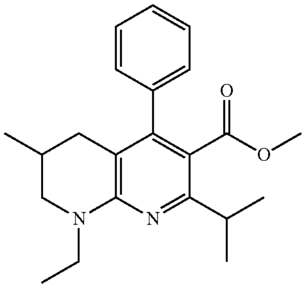 | ESP $[M + H]^+$: 353.3 | N | Intermediate AP1, ethyl iodide |
| E4 | Ethyl 4-(3-chlorophenyl)-2-cyclohexyl-8-ethyl-5,6,7,8-tetrahydro-1,8-naphthyridine-3-carboxylate 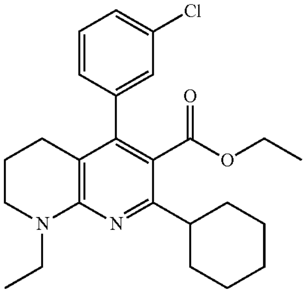 | ESP $[M + H]^+$: 427.5 | N | Intermediate AP4, ethyl iodide |
| E5 | Ethyl 2-cyclohexyl-8-ethyl-4-phenyl-5,6,7,8-tetrahydro-1,8-naphthyridine-3-carboxylate 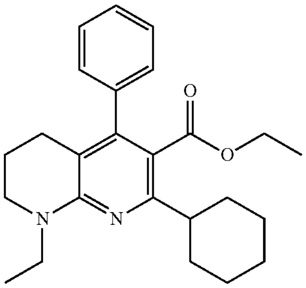 | ESP $[M + H]^+$: 393.2 | N | Intermediate AP5, ethyl iodide |

-continued

| Intermediate | Name and Structure | MS | Method | Reagents |
|---|---|---|---|---|
| E6 | Methyl 2-cyclopentyl-8-ethyl-4-phenyl-5,6,7,8-tetrahydro-1,8-naphthyridine-3-carboxylate 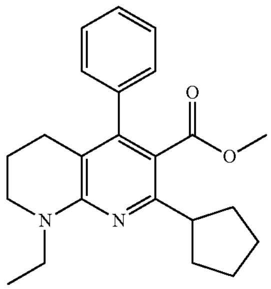 | ESP $[M + H]^+$: 365.2 | N | Intermediate AP6, ethyl iodide |
| E7 | Methyl 2-cyclopentyl-8-ethyl-6-methyl-4-phenyl-5,6,7,8-tetrahydro-1,8-naphthyridine-3-carboxylate 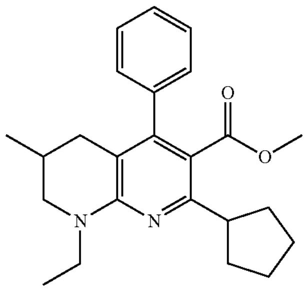 | ESP $[M + H]^+$: 379.5 | N | Intermediate AP7, ethyl iodide |
| E8 | Methyl 2-cyclopentyl-6,8-dimethyl-4-phenyl-5,6,7,8-tetrahydro-1,8-naphthyridine-3-carboxylate 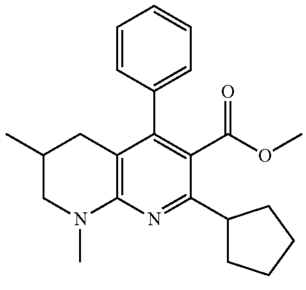 | ESP $[M + H]^+$: 365.5 | N | Intermediate AP7, methyl iodide |
| E9 | Methyl 2-isopropyl-6-methyl-4-phenyl-5,6,7,8-tetrahydroquinoline-3-carboxylate 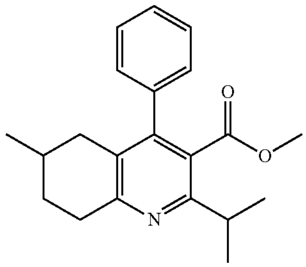 | ESP $[M + H]^+$: 324.2 | P | Methyl 4-methyl-3-oxo-2-(phenylmethylene)pentanoate (CAS# 912998-81-3), 4-methyl-cyclohexanone |

-continued

| Intermediate | Name and Structure | MS | Method | Reagents |
|---|---|---|---|---|
| E10 | Methyl 6-ethyl-2-isopropyl-4-phenyl-5,6,7,8-tetrahydroquinoline-3-carboxylate 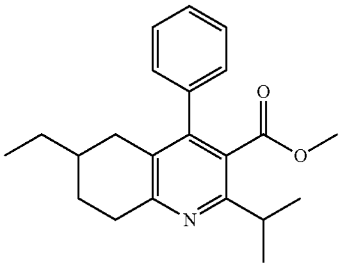 | ESP $[M + H]^+$: 338.3 | P | Methyl 4-methyl-3-oxo-2-(phenylmethylene) pentanoate (CAS# 912998-81-3), 4-ethyl-cyclohexanone |
| E11 | 2-Isopropyl-6,6-dimethyl-4-phenyl-5,6,7,8-tetrahydro-quinoline-3-carboxylic acid methyl ester 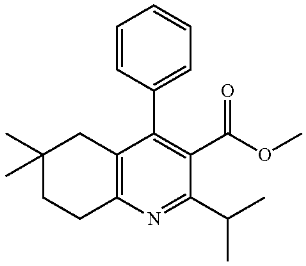 | ESP $[M + H]^+$: 338.2 | P | Methyl 4-methyl-3-oxo-2-(phenylmethylene) pentanoate (CAS# 912998-81-3), 4,4-dimethyl-cyclohexanone |

Intermediates P

General Method Q

Step 1: A solution of the ketone (4.46 mmol, 0.85 eq) in THF (3 ml) is added dropwise at −78° C. to a solution of LiHMDS (1M in THF, 5.24 mmol, 1 eq) in THF (3 ml). The solution is stirred for 1 h at −78° C. A pre-cooled solution of the Knoevenagel adduct (Intermediate K, 5.24 mmol, 1 eq) in THF (3 ml) is added quickly via a double-tip needle at a temperature below −67° C. The solution is stirred at −78° C. for 5 h and then quenched by adding a solution of acetic acid (4.3 eq) in THF (1.5 ml). The mixture is allowed to warm to room temperature, diluted with water and extracted with ethyl acetate. The organic layers are combined, washed with water and brine, dried over $MgSO_4$ and concentrated in vacuo. The product can be purified by flash chromatography.

Step 2: The product of step 1 (1.21 mmol) is combined with ammonium acetate (10 eq) and heated to 120° C. under air for 4-10 h while stirring. After cooling to room temperature, the mixture is extracted with ethyl acetate. The organic layers are combined, washed with water and brine, dried over $MgSO_4$ and concentrated in vacuo.

Step 3: The product of step 2 (1.18 mmol) is combined with $FeCl_3$ (3 eq) and propionic acid (5.5 ml) and heated to reflux for 1 h. The mixture is allowed to cool to room temperature, diluted with 1 M HCl and extracted with DCM. The organic layers are combined, washed with saturated aqueous $NaHCO_3$ solution and brine, dried over $MgSO_4$ and concentrated in vacuo. The product can be purified by flash chromatography to give the pyridone (Intermediate P).

General Method R

A mixture of the ketone (1 eq), the Knoevenagel adduct (Intermediate K, 1 to 2 eq, see table) and ammonium acetate (10 eq) is stirred at 170° C. under air for 5-10 h. After cooling to room temperature, the mixture is diluted with water and extracted with ethyl acetate. The organic layers are combined, washed with water and brine, dried over $MgSO_4$ and concentrated in vacuo. The product can be purified by flash chromatography or crystallization.

| Inter-mediate | Name and Structure | MS | Method | Reagents |
|---|---|---|---|---|
| P14 | Ethyl 2-oxo-4-phenyl-2,5,6,7,8,9-hexahydro-1H-cyclohepta[b]pyridine-3-carboxylate 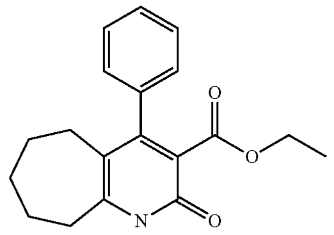 [SMILES: CCOC(=O)c1c(-c2ccccc2)c2c([nH]c1=O)CCCCC2] | ESP $[M + H]^+$: 312.1 | Q | Benzylidene malonic acid diethyl ester (CAS# 5292-53-5), cycloheptanone |
| P16 | Ethyl 6-methyl-2-oxo-4-phenyl-1,2,5,6,7,8-hexahydroquinoline-3-carboxylate 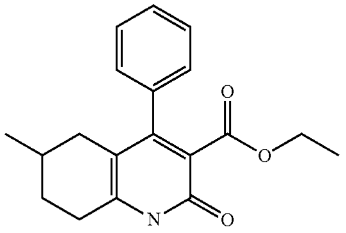 [SMILES: CCOC(=O)c1c(-c2ccccc2)c2c([nH]c1=O)CCC(C)C2] | ESP $[M + H]^+$: 312.3 | Q | Benzylidene malonic acid diethyl ester (CAS# 5292-53-5), 4-methylcyclohexanone |
| P20 | Ethyl 4-(3-chlorophenyl)-6-methyl-2-oxo-1,2,5,6,7,8-hexahydroquinoline-3-carboxylate 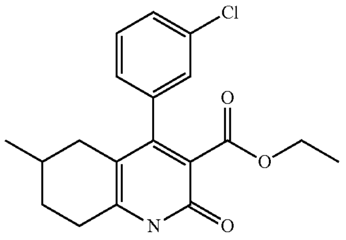 [SMILES: CCOC(=O)c1c(-c2cccc(Cl)c2)c2c([nH]c1=O)CCC(C)C2] | ESN $[M - H]^-$: 344.0 | Q | Intermediate K20, 4-methylcyclohexanone |
| P21 | Ethyl 2-oxo-4-phenyl-2,5,6,7-tetrahydro-1H-cyclopenta[b]pyridine-3-carboxylate 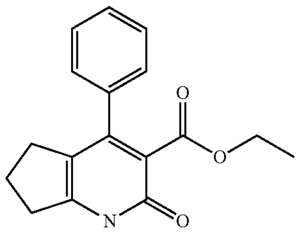 [SMILES: CCOC(=O)c1c(-c2ccccc2)c2c([nH]c1=O)CCC2] | ESN $[M - H]^-$: 282.0 | Q | Benzylidene malonic acid diethyl ester (CAS# 5292-53-5), cyclopentanone |

-continued

| Inter-mediate | Name and Structure | MS | Method | Reagents |
|---|---|---|---|---|
| P25 | 6-Methyl-2-oxo-4-phenyl-1,2,5,6,7,8-hexahydroquinoline-3-carbonitrile 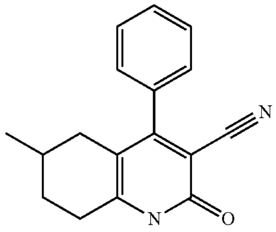 [SMILES: CC1CCc2[nH]c(=O)c(C#N)c(-c3ccccc3)c2C1] | ESN [M − H]⁻: 262.9 | R | 2-Cyano-3-phenylpropenoic acid ethyl ester (CAS# 2025-40-3, 2 eq), 4-methylcyclohexanone |
| P27 | 2-Oxo-4-phenyl-6-(trifluoromethyl)-1,2,5,6,7,8-hexahydroquinoline-3-carbonitrile 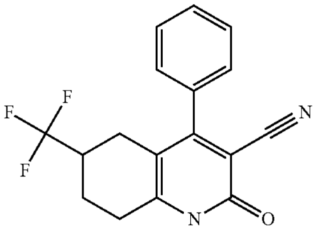 [SMILES: N#Cc1c(-c2ccccc2)c2c([nH]c1=O)CCC(C(F)(F)F)C2] | ESP [M + H]⁺: 319.3 | R | 2-Cyano-3-phenylpropenoic acid ethyl ester (CAS# 2025-40-3, 2 eq), 4-(trifluoromethyl)-cyclohexanone |
| P29 | 6-Methyl-4-(1-methyl-1H-pyrazol-5-yl)-2-oxo-1,2,5,6,7,8-hexahydroquinoline-3-carbonitrile 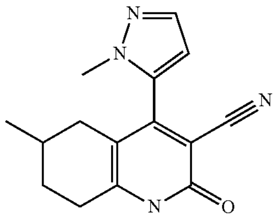 [SMILES: CC1CCc2[nH]c(=O)c(C#N)c(-c3ccnn3C)c2C1] | ESP [M + H]⁺: 269.0 | R | Intermediate K29 (1.2 eq), 4-methylcyclohexanone |
| P30 | 2-Oxo-4-phenyl-2,5,6,7,8,9-hexahydro-1H-cyclohepta[b]pyridine-3-carbonitrile 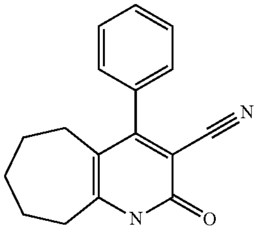 [SMILES: N#Cc1c(-c2ccccc2)c2c([nH]c1=O)CCCCC2] | ESP [M + H]⁺: 265.0 | R | 2-Cyano-3-phenylpropenoic acid ethyl ester (CAS# 2025-40-3, 1.2 eq), cycloheptanone |

-continued

| Inter-mediate | Name and Structure | MS | Method | Reagents |
|---|---|---|---|---|
| P32 | 4-(3-Chloro-phenyl)-2-oxo-2,5,6,7,8,9-hexahydro-1H-cyclohepta[b]pyridine-3-carbonitrile 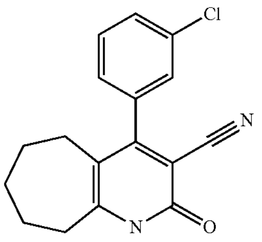 [SMILES: N#Cc1c(-c2cccc(Cl)c2)c2c([nH]c1=O)CCCCC2] | ESP [M + H]$^+$: 299.4 | R | Intermediate K32 (1.2 eq), cycloheptanone |
| P34 | 4-(1-Methyl-1H-pyrazol-5-yl)-2-oxo-2,5,6,7,8,9-hexahydro-1H-cyclohepta[b]pyridine-3-carbonitrile 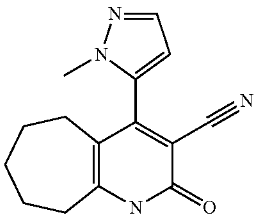 [SMILES: Cn1nccc1-c1c2c([nH]c(=O)c1C#N)CCCCC2] | ESP [M + H]$^+$: 269.2 | R | Intermediate K29 (1.2 eq), cycloheptanone |
| P38 | 4-(5-Chlorothiophen-2-yl)-2-oxo-2,5,6,7,8,9-hexahydro-1H-cyclohepta[b]pyridine-3-carbonitrile 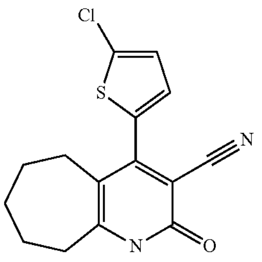 [SMILES: N#Cc1c(-c2ccc(Cl)s2)c2c([nH]c1=O)CCCCC2] | ESP [M + H]$^+$: 305.1 | R | Intermediate K38 (1.2 eq), cycloheptanone |
| P41 | 4-(5-Methyl-isoxazol-3-yl)-2-oxo-2,5,6,7,8,9-hexahydro-1H-cyclohepta[b]pyridine-3-carbonitrile 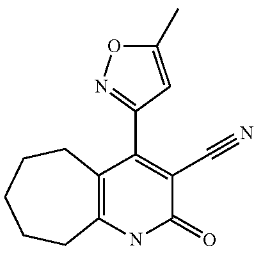 [SMILES: Cc1cc(-c2c3c([nH]c(=O)c2C#N)CCCCC3)no1] | ESP [M + H]$^+$: 270.3 | R | Intermediate K41 (1.2 eq), cycloheptanone |

-continued

| Inter-mediate | Name and Structure | MS | Method | Reagents |
|---|---|---|---|---|
| P44 | 2-Oxo-4-(pyridin-4-yl)-2,5,6,7,8,9-hexahydro-1H-cyclohepta[b]pyridine-3-carbonitrile 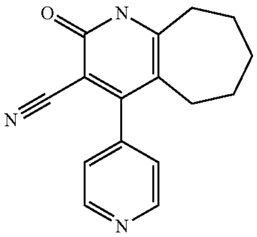 [SMILES: N#Cc1c(-c2ccncc2)c2c([nH]c1=O)CCCCC2] | ESP [M + H]$^+$: 266.1 | R | Intermediate K44 (1.2 eq), cycloheptanone |
| P46 | 4-(5-Methylfuran-2-yl)-2-oxo-2,5,6,7,8,9-hexahydro-1H-cyclohepta[b]pyridine-3-carbonitrile 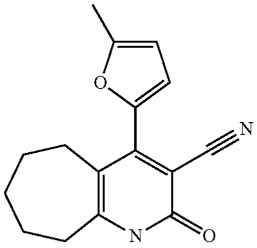 [SMILES: Cc1ccc(-c2c3c([nH]c(=O)c2C#N)CCCCC3)o1] | ESP [M + H]+: 269.3 | R | Intermediate K46 (1.2 eq), cycloheptanone |
| P48 | 4-(1,5-Dimethyl-1H-pyrazol-4-yl)-2-oxo-2,5,6,7,8,9-hexahydro-1H-cyclohepta[b]pyridine-3-carbonitrile 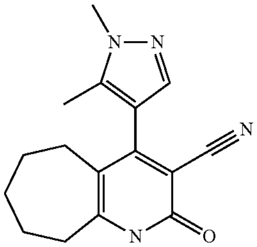 [SMILES: Cc1c(-c2c3c([nH]c(=O)c2C#N)CCCCC3)cnn1C] | ESP [M + H]$^+$: 283.4 | R | Intermediate K48 (1.2 eq), cycloheptanone |
| P56 | 4-(4-Methylthiazol-5-yl)-2-oxo-2,5,6,7,8,9-hexahydro-1H-cyclohepta[b]pyridine-3-carbonitrile 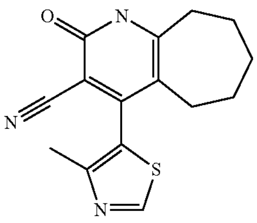 [SMILES: Cc1ncsc1-c1c2c([nH]c(=O)c1C#N)CCCCC2] | ESP [M + H]$^+$: 286.3 | R | Intermediate K56 (1.2 eq), cycloheptanone |

-continued

| Inter-mediate | Name and Structure | MS | Method | Reagents |
|---|---|---|---|---|
| P58 | 4-(2-Methyl-2H-pyrazol-3-yl)-2-oxo-1,2,5,6,7,8,9,10-octahydro-cycloocta[b]pyridine-3-carbonitrile 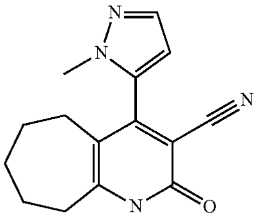 | ESP $[M + H]^+$: 283.4 | R | Intermediate K29 (1.2 eq), cyclooctanone |
| P61 | 2-Oxo-4-pyrimidin-5-yl-2,5,6,7,8,9-hexahydro-1H-cyclohepta[b]pyridine-3-carbonitrile 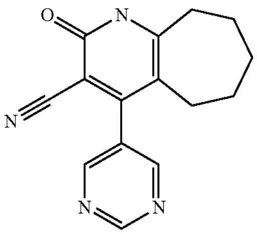 [SMILES: N#Cc1c(-c2cncnc2)c2c([nH]c1=O)CCCCC2] | ESP $[M + H]^+$: 267.4 | R | Intermediate K61 (1.2 eq), cycloheptanone |
| P62 | 4-(3-Fluoropyridin-4-yl)-2-oxo-2,5,6,7,8,9-hexahydro-1H-cyclohepta[b]pyridine-3-carbonitrile 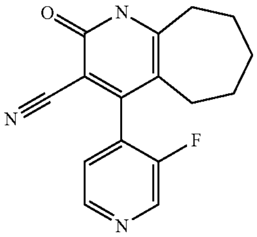 [SMILES: N#Cc1c(-c2ccncc2F)c2c([nH]c1=O)CCCCC2] | ESP $[M + H]^+$: 284.3 | R | Intermediate K62 (1.2 eq), cycloheptanone |
| P63 | 4-(2-Methoxy-pyridin-4-yl)-2-oxo-2,5,6,7,8,9-hexahydro-1H-cyclohepta[b]pyridine-3-carbonitrile 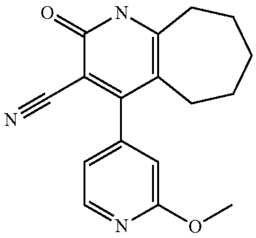 [SMILES: COc1cc(-c2c3c([nH]c(=O)c2C#N)CCCCC3)ccn1] | ESP $[M + H]^+$: 296.4 | R | Intermediate K63 (1.2 eq), cycloheptanone |

Intermediate P35

4-(4-Fluoro-phenyl)-6-methyl-2-oxo-1,2,5,6,7,8-hexahydro-quinoline-3-carbonitrile

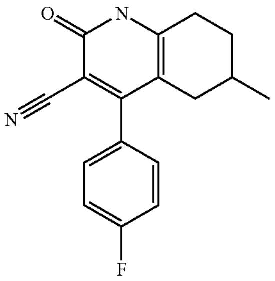 [SMILES: CC1CCc2[nH]c(=O)c(C#N)c(-c3ccc(F)cc3)c2C1]

To a solution of 2-cyano-3-(4-fluorophenyl)acrylamide (Intermediate K35, 2 g) in DMSO (21.0 ml) were added 4-methylcyclohexanone (1.18 g) and potassium tert-butoxide (1.18 g) at room temperature under air with exclusion of moisture. After stirring for 30 min, MS indicated formation of the Michael adduct. Potassium tert-butoxide (3.54 g) was added and stirring was continued at room temperature for 3 h. Water (80 ml) was added and the mixture was cooled in an ice bath. Slowly the mixture was acidified with 25% HCl. The precipitate was collected by filtration, washed with water and dried. The crude material was purified by flash chromatography ($SiO_2$, 0% to 100% EtOAc in n-heptane) to afford the title compound (1.02 g), sufficiently pure to be used in the next step without further purification as an off-white solid. MS (ESP): m/z=283.3 $[M+H]^+$.

Intermediate P36

4-(4-Fluoro-phenyl)-2-oxo-1,5,7,8-tetrahydro-2H-pyrano[4,3-b]pyridine-3-carbonitrile

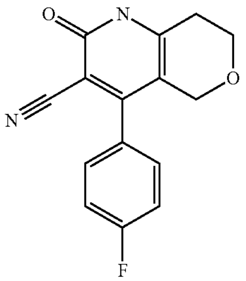 [SMILES: N#Cc1c(-c2ccc(F)cc2)c2c([nH]c1=O)CCOC2]

In analogy to the synthesis of Intermediate P35, the title compound was synthesized starting from 2-cyano-3-(4-fluorophenyl)acrylamide (Intermediate K35) and dihydro-2H-pyran-4(3H)-one. MS (ESP): m/z=271.0 $[M+H]^+$.

Intermediates E/N

General Method S

Step 1: A solution of the pyridone (Intermediate P, 0.51 mmol, 1 eq) in dry DMA (2.73 ml) is added dropwise to a suspension of sodium hydride (55% in mineral oil, 1.3 eq) in dry DMA (0.91 ml). The mixture is stirred for 45 min. A solution of N-phenylbis(trifluoromethanesulfonimide) (1.3 eq) in DMA (2.73 ml) is added dropwise, then the reaction is stirred at room temperature overnight. The reaction is quenched with saturated aqueous $NH_4Cl$ solution and extracted with ethyl acetate. The organic layers are combined, washed with water and brine, dried over $MgSO_4$ and concentrated in vacuo. The product can be purified by flash chromatography.

Step 2: A suspension of the triflate obtained in step 1 (0.31 mmol, 1 eq), a primary or secondary amine (4 eq) and potassium carbonate (2 eq) in THF (4.7 ml) is heated to 70° C. for 1-10 h. After cooling to room temperature, the mixture is diluted with water and extracted with ethyl acetate. The organic layers are combined, washed with water and brine, dried over $MgSO_4$ and concentrated in vacuo. The product can be purified by flash chromatography.

General Method T

Step 1: A mixture of the pyridone (Intermediate P, 3.0 mmol, 1 eq) and phosphorus oxychloride (30 eq) is stirred at reflux for 2-20 h. After cooling to room temperature the mixture is slowly and carefully diluted with water, neutralized with 2 M aqueous NaOH and extracted with DCM. The organic layers are combined, washed with water and brine, dried over $MgSO_4$ and concentrated in vacuo. The product can be purified by flash chromatography.

Step 2: A solution of the 2-chloropyridine obtained in step 1 (0.35 mmol, 1 eq), a primary or secondary amine (2 eq) and triethylamine (3 eq) in DMF (1.5 ml) is heated to 120° C. for 1-20 h. If the reaction does not reach completion, more of the primary or secondary amine and triethylamine can be added. After cooling to room temperature, the mixture is diluted with water and extracted with ethyl acetate. The organic layers are combined, washed with water and brine, dried over $MgSO_4$ and concentrated in vacuo. The product can be purified by flash chromatography.

| Intermediate | Name and Structure | MS | Method | Reagents |
|---|---|---|---|---|
| E14 | Ethyl 4-phenyl-2-(piperidin-1-yl)-6,7,8,9-tetrahydro-5H-cyclohepta[b]pyridine-3-carboxylate 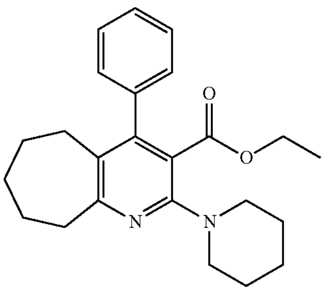 | ESP $[M + H]^+$: 379.5 | S | Intermediate P14, piperidine |

-continued

| Intermediate | Name and Structure | MS | Method | Reagents |
|---|---|---|---|---|
| E15 | Ethyl 2-(2-methylpyrrolidin-1-yl)-4-phenyl-6,7,8,9-tetrahydro-5H-cyclohepta[b]pyridine-3-carboxylate 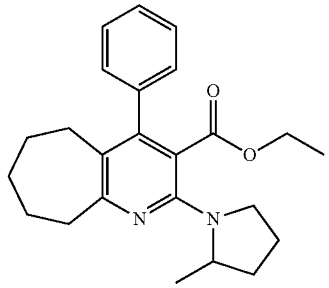 | ESP $[M + H]^+$: 379.5 | S | Intermediate P14, 2-methylpyrrolidine |
| E16 | Ethyl 6-methyl-4-phenyl-2-(piperidin-1-yl)-5,6,7,8-tetrahydroquinoline-3-carboxylate 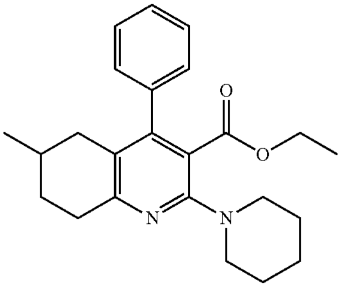 | ESP $[M + H]^+$: 379.5 | S | Intermediate P16, piperidine |
| E17 | Ethyl 2-(diethylamino)-4-phenyl-6,7,8,9-tetrahydro-5H-cyclohepta[b]pyridine-3-carboxylate 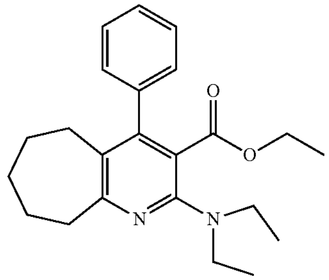 | ESP $[M + H]^+$: 367.3 | S | Intermediate P14, diethylamine |
| E18 | Ethyl 6-methyl-2-(2-methylpyrrolidin-1-yl)-4-phenyl-5,6,7,8-tetrahydroquinoline-3-carboxylate 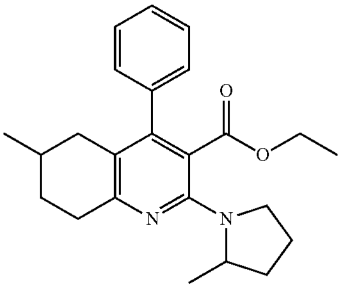 | ESP $[M + H]^+$: 379.4 | S | Intermediate P16, 2-methylpyrrolidine |

-continued

| Intermediate | Name and Structure | MS | Method | Reagents |
|---|---|---|---|---|
| E19 | Ethyl 2-(diethylamino)-6-methyl-4-phenyl-5,6,7,8-tetrahydroquinoline-3-carboxylate 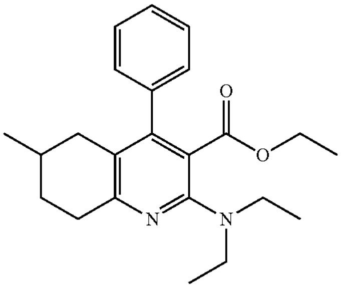 | ESP $[M + H]^+$: 367.1 | S | Intermediate P16, diethylamine |
| E21 | Ethyl 4-phenyl-2-(piperidin-1-yl)-6,7-dihydro-5H-cyclopenta[b] pyridine-3-carboxylate 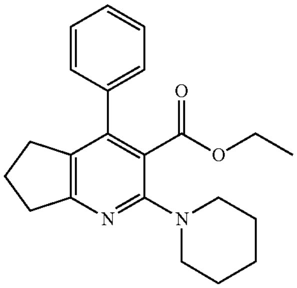 | ESP $[M + H]^+$: 351.3 | S | Intermediate P21, piperidine |
| E22 | Ethyl 2-(diethylamino)-4-phenyl-6,7-dihydro-5H-cyclopenta[b]pyridine-3-carboxylate 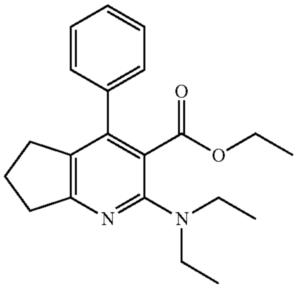 | ESP $[M + H]^+$: 339.4 | S | Intermediate P21, diethylamine |
| N25 | 6-Methyl-4-phenyl-2-(piperidin-1-yl)-5,6,7,8-tetrahydroquinoline-3-carbonitrile 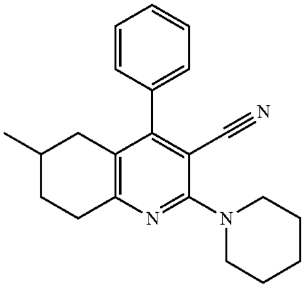 | ESP $[M + H]^+$: 332.2 | T | Intermediate P25, piperidine |

-continued

| Intermediate | Name and Structure | MS | Method | Reagents |
|---|---|---|---|---|
| N26 | 2-(Diethylamino)-6-methyl-4-phenyl-5,6,7,8-tetrahydroquinoline-3-carbonitrile 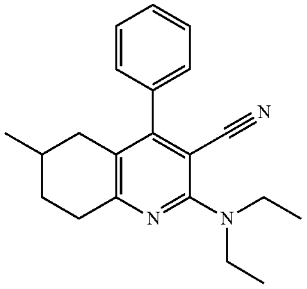 | ESP $[M + H]^+$: 320.3 | T | Intermediate P25, diethylamine |
| N27 | 4-Phenyl-2-(piperidin-1-yl)-6-(trifluoromethyl)-5,6,7,8-tetrahydroquinoline-3-carbonitrile 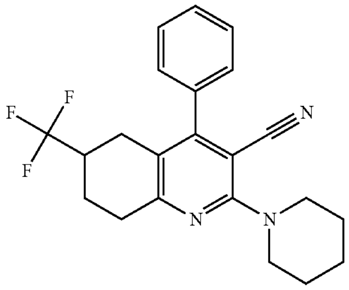 | ESP $[M + H]^+$: 386.5 | S | Intermediate P27, piperidine |
| N28 | 2-(Diethylamino)-4-phenyl-6-(trifluoromethyl)-5,6,7,8-tetrahydroquinoline-3-carbonitrile 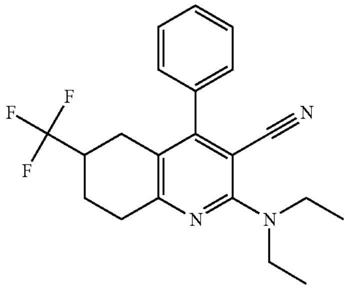 | ESP $[M + H]^+$: 374.6 | S | Intermediate P27, diethylamine |
| N29 | 6-Methyl-4-(1-methyl-1H-pyrazol-5-yl)-2-(piperidin-1-yl)-5,6,7,8-tetrahydroquinoline-3-carbonitrile 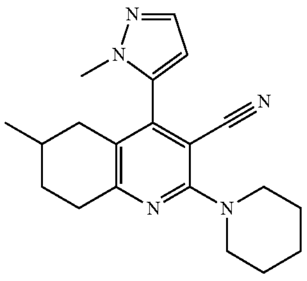 | ESP $[M + H]^+$: 336.4 | S | Intermediate P29, piperidine |

-continued

| Intermediate | Name and Structure | MS | Method | Reagents |
|---|---|---|---|---|
| N30 | 4-Phenyl-2-(piperidin-1-yl)-6,7,8,9-tetrahydro-5H-cyclohepta[b]pyridine-3-carbonitrile 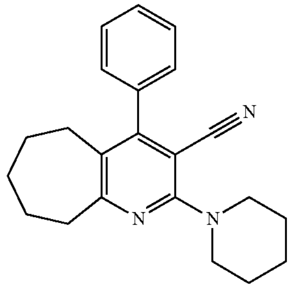 | ESP $[M + H]^+$: 332.3 | S | Intermediate P30, piperidine |
| N31 | 2-(Diethylamino)-4-phenyl-6,7,8,9-tetrahydro-5H-cyclohepta[b]pyridine-3-carbonitrile 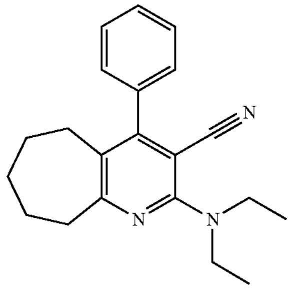 | ESP $[M + H]^+$: 320.1 | S | Intermediate P30, diethylamine |
| N32 | 4-(3-Chlorophenyl)-2-(piperidin-1-yl)-6,7,8,9-tetrahydro-5H-cyclohepta[b]pyridine-3-carbonitrile 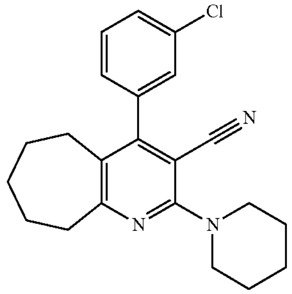 | ESP $[M + H]^+$: 366.1 | S | Intermediate P32, piperidine |
| N33 | 4-(3-Chlorophenyl)-2-(diethylamino)-6,7,8,9-tetrahydro-5H-cyclohepta[b]pyridine-3-carbonitrile 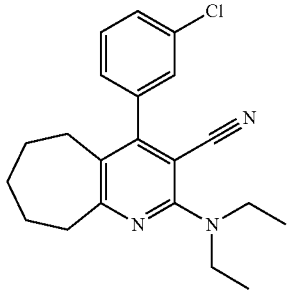 | ESP $[M + H]^+$: 354.3 | S | Intermediate P32, diethylamine |

-continued

| Intermediate | Name and Structure | MS | Method | Reagents |
|---|---|---|---|---|
| N34 | 4-(1-Methyl-1H-pyrazol-5-yl)-2-(piperidin-1-yl)-6,7,8,9-tetrahydro-5H-cyclohepta[b]pyridine-3-carbonitrile 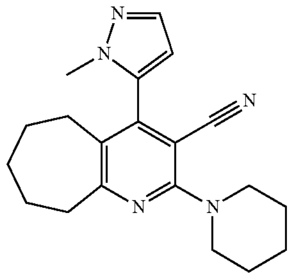 | ESP $[M + H]^+$: 336.2 | S | Intermediate P34, piperidine |
| N35 | 4-(4-Fluorophenyl)-6-methyl-2-(piperidin-1-yl)-5,6,7,8-tetrahydroquinoline-3-carbonitrile 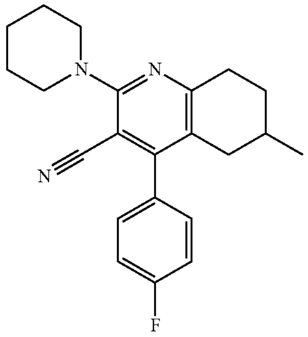 | ESP $[M + H]^+$: 350.3 | T | Intermediate P35, piperidine |
| N36 | 4-(4-Fluorophenyl)-2-(piperidin-1-yl)-7,8-dihydro-5H-pyrano[4,3-b]pyridine-3-carbonitrile 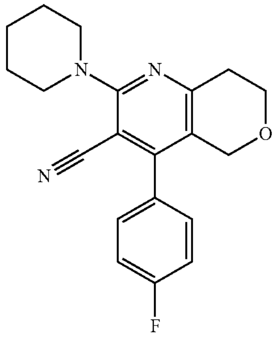 | ESP $[M + H]^+$: 338.4 | T | Intermediate P36, piperidine |
| N37 | 4-(1-Methyl-1H-pyrazol-5-yl)-2-(2-methylpyrrolidin-1-yl)-6,7,8,9-tetrahydro-5H-cyclohepta[b]pyridine-3-carbonitrile 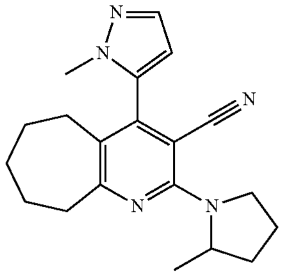 | ESP $[M + H]^+$: 336.2 | S | Intermediate P34, 2-methylpyrrolidine |

-continued

| Intermediate | Name and Structure | MS | Method | Reagents |
|---|---|---|---|---|
| N38 | 4-(5-Chlorothiophen-2-yl)-2-(diethylamino)-6,7,8,9-tetrahydro-5H-cyclohepta[b]pyridine-3-carbonitrile<br>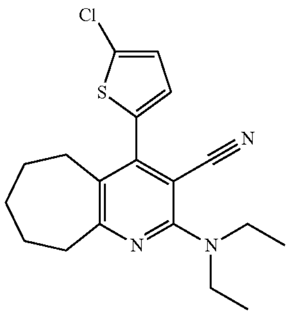 | ESP $[M + H]^+$: 360.2 | S | Intermediate P38, diethylamine |
| N39 | 4-(5-Chlorothiophen-2-yl)-2-(piperidin-1-yl)-6,7,8,9-tetrahydro-5H-cyclohepta[b]pyridine-3-carbonitrile<br>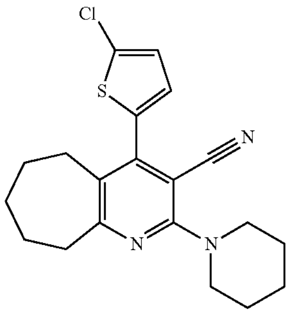 | ESP $[M + H]^+$: 372.2 | S | Intermediate P38, piperidine |
| N40 | 2-(Diethylamino)-4-(1-methyl-1H-pyrazol-5-yl)-6,7,8,9-tetrahydro-5H-cyclohepta[b]pyridine-3-carbonitrile<br>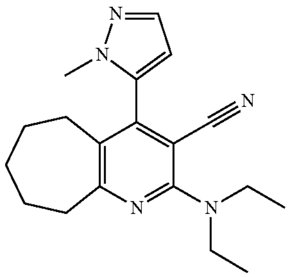 | ESP $[M + H]^+$: 324.4 | S | Intermediate P34, diethylamine |
| N41 | 4-(5-Methylisoxazol-3-yl)-2-(piperidin-1-yl)-6,7,8,9-tetrahydro-5H-cyclohepta[b]pyridine-3-carbonitrile<br>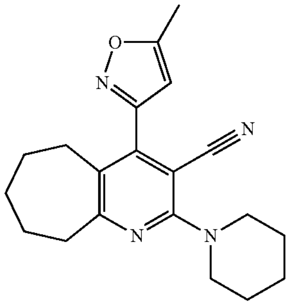 | ESP $[M + H]^+$: 337.5 | S | Intermediate P41, piperidine |

-continued

| Intermediate | Name and Structure | MS | Method | Reagents |
|---|---|---|---|---|
| N42 | 2-(Diethylamino)-4-(5-methylisoxazol-3-yl)-6,7,8,9-tetrahydro-5H-cyclohepta[b]pyridine-3-carbonitrile 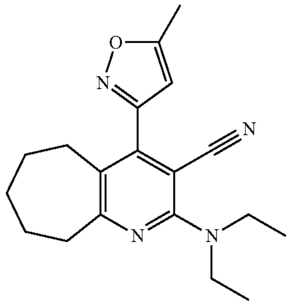 | ESP $[M + H]^+$: 325.5 | S | Intermediate P41, diethylamine |
| N44 | 2-(Piperidin-1-yl)-4-(pyridin-4-yl)-6,7,8,9-tetrahydro-5H-cyclohepta[b]pyridine-3-carbonitrile 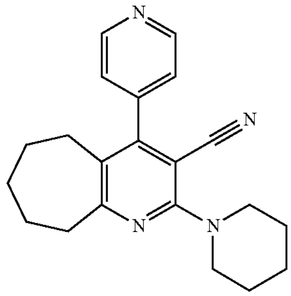 | ESP $[M + H]^+$: 333.4 | S | Intermediate P44, piperidine |
| N45 | 2-(Diethylamino)-4-(pyridin-4-yl)-6,7,8,9-tetrahydro-5H-cyclohepta[b]pyridine-3-carbonitrile 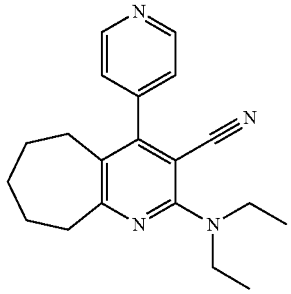 | ESP $[M + H]^+$: 321.3 | S | Intermediate P44, diethylamine |
| N46 | 4-(5-Methylfuran-2-yl)-2-(piperidin-1-yl)-6,7,8,9-tetrahydro-5H-cyclohepta[b]pyridine-3-carbonitrile 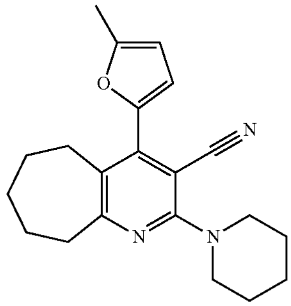 | ESP $[M + H]^+$: 336.5 | S | Intermediate P46, piperidine |

-continued

| Intermediate | Name and Structure | MS | Method | Reagents |
|---|---|---|---|---|
| N47 | 2-(Diethylamino)-4-(5-methylfuran-2-yl)-6,7,8,9-tetrahydro-5H-cyclohepta[b]pyridine-3-carbonitrile 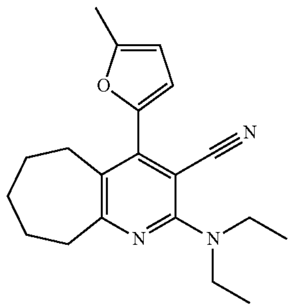 | ESP $[M + H]^+$: 324.5 | S | Intermediate P46, diethylamine |
| N48 | 4-(1,5-Dimethyl-1H-pyrazol-4-yl)-2-(piperidin-1-yl)-6,7,8,9-tetrahydro-5H-cyclohepta[b]pyridine-3-carbonitrile 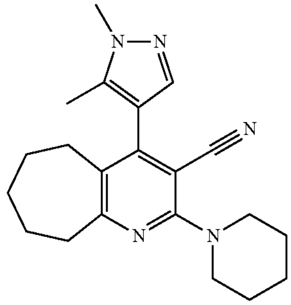 | ESP $[M + H]^+$: 350.5 | S | Intermediate P48, piperidine |
| N49 | 2-(Diethylamino)-4-(1,5-dimethyl-1H-pyrazol-4-yl)-6,7,8,9-tetrahydro-5H-cyclohepta[b]pyridine-3-carbonitrile 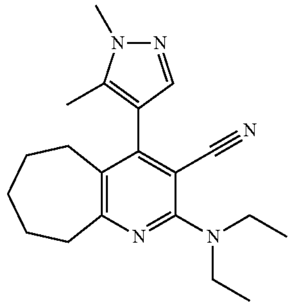 | ESP $[M + H]^+$: 338.5 | S | Intermediate P48, diethylamine |
| N50 | 4-(5-Chloro-thiophen-2-yl)-2-(3-fluoro-piperidin-1-yl)-6,7,8,9-tetrahydro-5H-cyclohepta[b]pyridine-3-carbonitrile 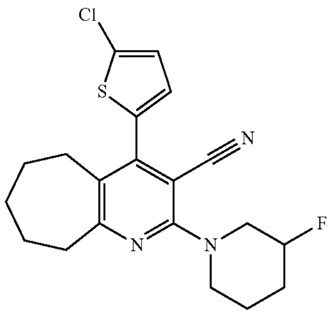 | ESP $[M + H]^+$: 390.4 | S | Intermediate P38, 3-fluoropiperidine |

-continued

| Intermediate | Name and Structure | MS | Method | Reagents |
|---|---|---|---|---|
| N51 | 4-(5-Chloro-thiophen-2-yl)-2-(3,3-difluoro-piperidin-1-yl)-6,7,8,9-tetrahydro-5H-cyclohepta[b]pyridine-3-carbonitrile 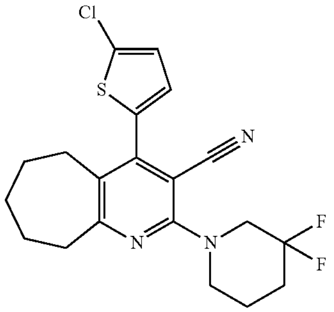 | ESP $[M + H]^+$: 408.4 | S | Intermediate P38, 3,3-difluoropiperidine |
| N52 | 4-(5-Chlorothiophen-2-yl)-2-(4,4-difluoropiperidin-1-yl)-6,7,8,9-cyclohepta[b]pyridine-3-carbonitrile 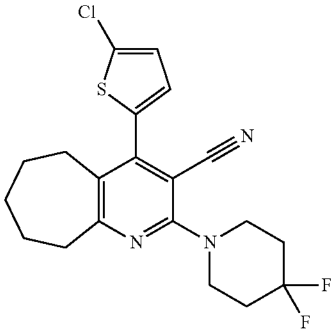 | | S | Intermediate P38, 4,4-difluoropiperidine |
| N53 | 4-(5-Chlorothiophen-2-yl)-2-(4-fluoropiperidin-1-yl)-6,7,8,9-tetrahydro-5H-cyclohepta[b]pyridine-3-carbonitrile 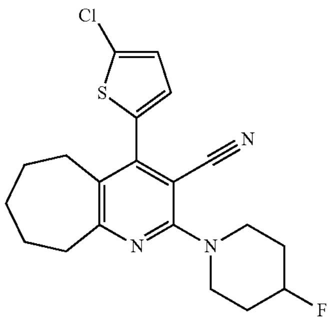 | ESP $[M + H]^+$: 390.3 | S | Intermediate P38, 4-fluoropiperidine |

-continued

| Intermediate | Name and Structure | MS | Method | Reagents |
|---|---|---|---|---|
| N54 | 4-(5-Chloro-thiophen-2-yl)-2-(4-trifluoromethyl-piperidin-1-yl)-6,7,8,9-tetrahydro-5H-cyclohepta[b]pyridine-3-carbonitrile 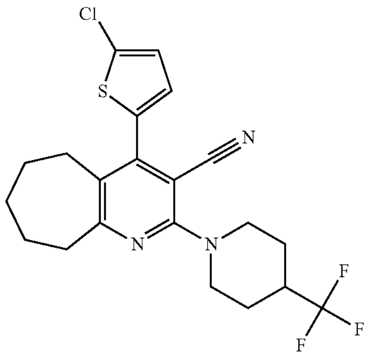 | | S | Intermediate P38, 4-(trifluoromethyl) piperidine |
| N55 | 4-(5-Chlorothiophen-2-yl)-2-(3,3-difluoroazetidin-1-yl)-6,7,8,9-tetrahydro-5H-cyclohepta[b]pyridine-3-carbonitrile 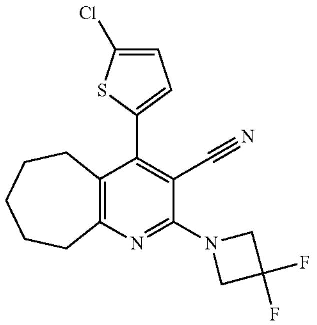 | ESP [M + H]$^+$: 380.3 | S | Intermediate P38, 3,3-difluoroazetidine |
| N56 | 2-(Diethylamino)-4-(4-methylthiazol-5-yl)-6,7,8,9-tetrahydro-5H-cyclohepta[b]pyridine-3-carbonitrile 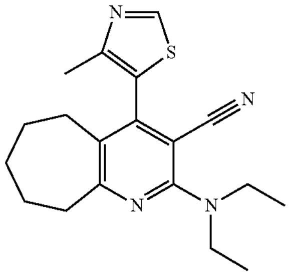 | ESP [M + H]$^+$: 341.4 | S | Intermediate P56, diethylamine |

-continued

| Intermediate | Name and Structure | MS | Method | Reagents |
|---|---|---|---|---|
| N57 | 4-(4-Methylthiazol-5-yl)-2-(piperidin-1-yl)-6,7,8,9-tetrahydro-5H-cyclohepta[b]pyridine-3-carbonitrile 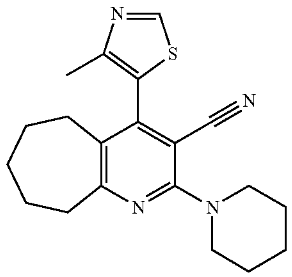 | ESP $[M + H]^+$: 353.4 | S | Intermediate P56, piperidine |
| N58 | 2-(Diethylamino)-4-(1-methyl-1H-pyrazol-5-yl)-5,6,7,8,9,10-hexahydrocycloocta[b] pyridine-3-carbonitrile 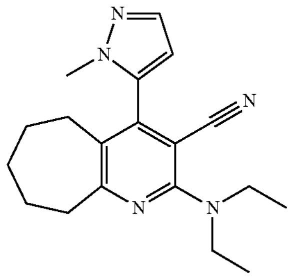 | ESP $[M + H]^+$: 338.5 | S | Intermediate P58, diethylamine |
| N59 | 4-(5-Chloro-thiophen-2-yl)-2-(3,3-difluoro-pyrrolidin-1-yl)-6,7,8,9-tetrahydro-5H-cyclohepta[b]pyridine-3-carbonitrile 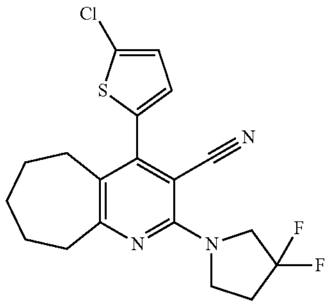 | | S | Intermediate P38, 3,3-difluoropyrrolidine |
| N60 | 4-(1-Methyl-1H-pyrazol-5-yl)-2-(piperidin-1-yl)-5,6,7,8,9,10-hexahydrocycloocta[b]pyridine-3-carbonitrile 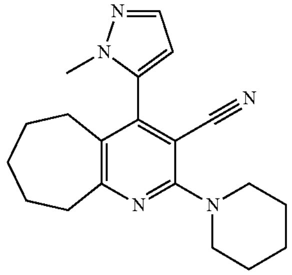 | ESP $[M + H]^+$: 350.5 | S | Intermediate P58, piperidine |

-continued

| Intermediate | Name and Structure | MS | Method | Reagents |
|---|---|---|---|---|
| N61 | 2-(Diethylamino)-4-(pyrimidin-5-yl)-6,7,8,9-tetrahydro-5H-cyclohepta[b]pyridine-3-carbonitrile 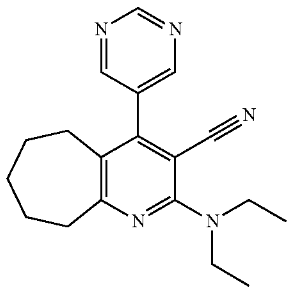 | ESP $[M + H]^+$: 322.4 | S | Intermediate P61, diethylamine |
| N62 | 2-(Diethylamino)-4-(3-fluoropyridin-4-yl)-6,7,8,9-tetrahydro-5H-cyclohepta[b]pyridine-3-carbonitrile 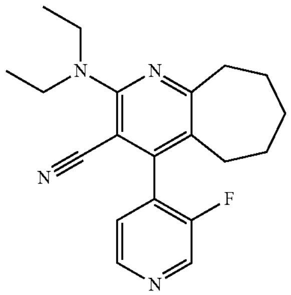 | ESP $[M + H]^+$: 339.4 | S | Intermediate P62, diethylamine |
| N63 | 2-Diethylamino-4-(2-methoxy-pyridin-4-yl)-6,7,8,9-tetrahydro-5H-cyclohepta[b]pyridine-3-carbonitrile 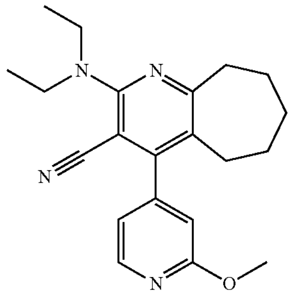 | ESP $[M + H]^+$: 351.5 | S | Intermediate P63, diethylamine |

Intermediate N64

2-Amino-4-phenyl-6,7,8,9-tetrahydro-5H-cyclohepta[b]pyridine-3-carbonitrile

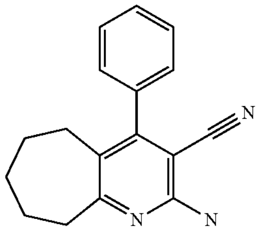 [SMILES: N#Cc1c(N)nc2c(c1-c1ccccc1)CCCCC2]

Prepared according to: Kambe, Satoshi; Saito, Koji; Sakurai, Akio; Midorikawa, Hiroshi *Synthesis* 1980, 5, 366-8.

Intermediate N65

2-Propyl-4-pyridin-4-yl-6,7,8,9-tetrahydro-5H-cyclohepta[b]pyridine-3-carbonitrile

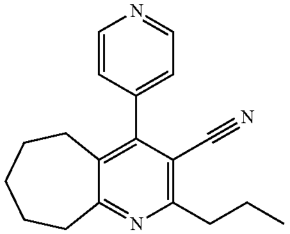 [SMILES: CCCc1nc2c(c(-c3ccncc3)c1C#N)CCCCC2]

Intermediate P44 was converted to 3-cyano-4-(pyridin-4-yl)-6,7,8,9-tetrahydro-5H-cyclohepta[b]pyridin-2-yl trifluoromethanesulfonate using General Method S, step 1. 3-Cyano-4-(pyridin-4-yl)-6,7,8,9-tetrahydro-5H-cyclohepta[b]pyridin-2-yl trifluoromethanesulfonate (1096 mg), n-propylboronic acid (727 mg) and potassium phosphate tribasic (1.79 g) were combined with toluene (34.4 ml), molsieves (4

Å) were added and the mixture was stirred at room temperature for 5 min. (1,3-Diisopropylimidazol-2-ylidene)(3-chloropyridyl)palladium(II) dichloride (PEPPSI) (150 mg) was added and the reaction mixture was heated to 100° C. for 52 h. (1,3-Diisopropylimidazol-2-ylidene)(3-chloropyridyl)palladium(II) dichloride (150 mg) was added and stirring at 100° C. was continued for 24 h. The reaction mixture was filtered with EtOAc and water through glass fiber paper, then it was extracted with EtOAc, the organic phases were washed with water and brine, dried over $MgSO_4$ and concentrated in vacuo. The crude material was purified by flash chromatography (silica gel, 50 g, 5% to 60% EtOAc in n-heptane) to give the title compound (156 mg) as an off-white solid. MS (ESP): m/z=292.4 $[M+H]^+$.

General Method U

The Knoevenagel condensation product (Intermediate K, 1.1 mmol, 1.2 eq), ketone (1 eq) and ammonium acetate (10 eq) is combined and heated to 170° C. for 2.5 h in an open flask. The reaction mixture is cooled to room temperature, diluted with water and extracted 3 times with EtOAc. Combined organic phases are re-extracted with water and brine and dried over $MgSO_4$. Evaporation of the solvent is followed by either crystallization or purification by chromatography or using it as such in the next step without further purification.

General Method V

A suspension of aldehyde (2.8 mmol, 1 eq), ketone (1 eq), ketonitrile (1 eq), ammonium acetate (5 eq) and toluene (9 ml) is refluxed for 50 min. The reaction mixture is cooled to room temperature, diluted with water and extracted 3 times with EtOAc. The combined organic phases are evaporated and the dihydropyridine-intermediate is dissolved in acetone (14 ml). At room temperature a suspension of ceric ammonium nitrate (3.1 g, 2 eq) in water (2 ml) is slowly added and the yellow reaction mixture is stirred for 30 min. After evaporation of the solvents the residue is extracted with water/EtOAc (3×). The combined organic phases are concentrated and purified by crystallization or chromatography.

| Intermediate | Name and Structure | MS | Method | Reagents |
|---|---|---|---|---|
| N66 | 4-(1-Methyl-1H-pyrazol-5-yl)-2-(pentan-3-yl)-6,7,8,9-tetrahydro-5H-cyclohepta[b]pyridine-3-carbonitrile 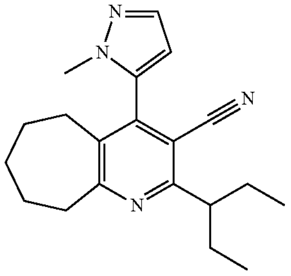 | ESP $[M + H]^+$: 323.2 | U | Intermediate K66, cycloheptanone |

-continued

| Intermediate | Name and Structure | MS | Method | Reagents |
|---|---|---|---|---|
| N67 | 4-(3-Chlorophenyl)-2-cyclobutyl-6,7,8,9-tetrahydro-5H-cyclohepta[b]pyridine-3-carbonitrile 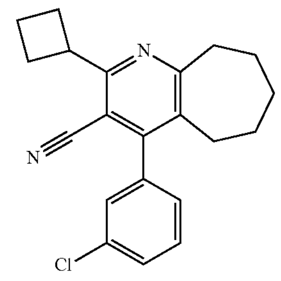 | ESP $[M + H]^+$: 337.1 | U | Intermediate K67, cycloheptanone |
| N68 | 2-Cyclohexyl-4-(pyridin-4-yl)-6,7,8,9-tetrahydro-5H-cyclohepta[b]pyridine-3-carbonitrile 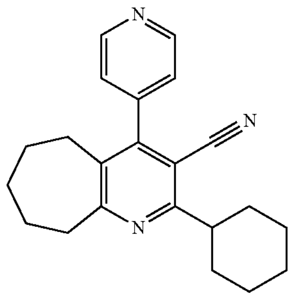 | ESP $[M + H]^+$: 332.5 | U | Intermediate K68, cycloheptanone |
| N69 | 4-(3-Chlorophenyl)-2-cyclopentyl-6,7,8,9-tetrahydro-5H-cyclohepta[b]pyridine-3-carbonitrile 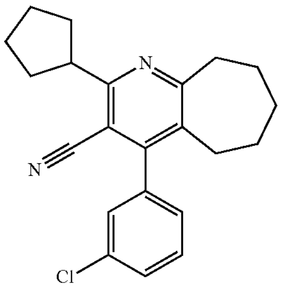 | ESP $[M + H]^+$: 351.4 | U | Intermediate K69, cycloheptanone |
| N70 | 2-Cyclohexyl-4-(2-methylpyridin-4-yl)-6,7,8,9-tetrahydro-5H-cyclohepta[b]pyridine-3-carbonitrile 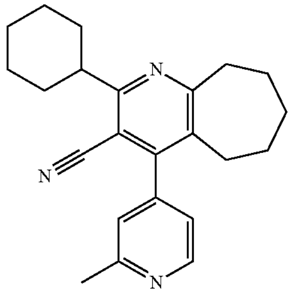 | ESP $[M + H]^+$: 346.5 | U | Intermediate K70, cycloheptanone |

-continued

| Intermediate | Name and Structure | MS | Method | Reagents |
|---|---|---|---|---|
| N74 | 2-Cyclohexyl-4-(1-methyl-1H-pyrazol-5-yl)-6,7,8,9-tetrahydro-5H-cyclohepta[b]pyridine-3-carbonitrile 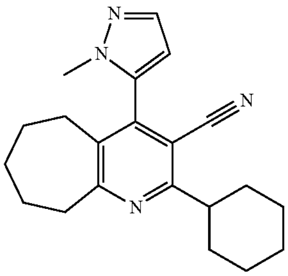 | ESP [M + H]$^+$: 335.5 | U | Intermediate K74, cycloheptanone |
| N75 | 2-Cyclopentyl-4-pyridin-4-yl-6,7,8,9-tetrahydro-5H-cyclohepta[b]pyridine-3-carbonitrile 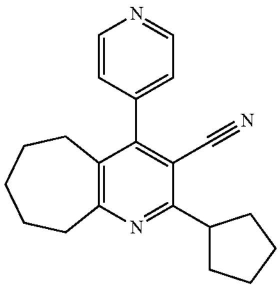 | ESP [M + H]$^+$: 318.4 | U | Intermediate K75, cycloheptanone |
| N76 | 2-Cyclopentyl-4-(1-methyl-1H-pyrazol-5-yl)-6,7,8,9-tetrahydro-5H-cyclohepta[b]pyridine-3-carbonitrile 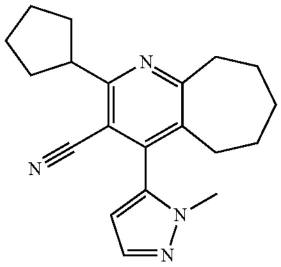 | ESP [M + H]$^+$: 321.4 | U | Intermediate K76, cycloheptanone |
| N77 | 6-Acetyl-4-(3-chlorophenyl)-2-cyclobutyl-5,6,7,8-tetrahydro-[1,6]naphthyridin-3-carbonitrile 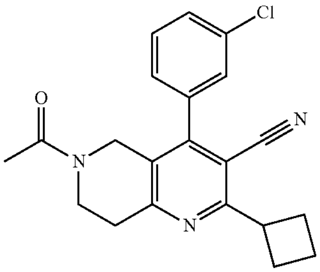 | ESP [M + H]$^+$: 366.4 | U | Intermediate K67, 1-acetylpiperidin-4-one |

-continued

| Intermediate | Name and Structure | MS | Method | Reagents |
|---|---|---|---|---|
| N78 | 2-Cyclopentyl-4-(6-methoxypyridin-2-yl)-6,7,8,9-tetrahydro-5H-cyclohepta[b]pyridine-3-carbonitrile 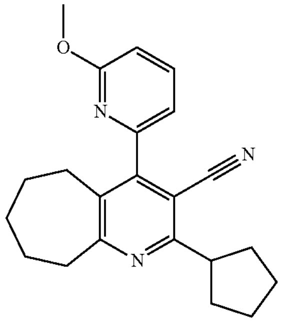 | ESP [M + H]$^+$: 348.5 | U | Intermediate K78, cycloheptanone |
| N79 | 4-Phenyl-2-(tetrahydro-2H-pyran-2-yl)-6,7,8,9-tetrahydro-5H-cyclohepta[b]pyridine-3-carbonitrile 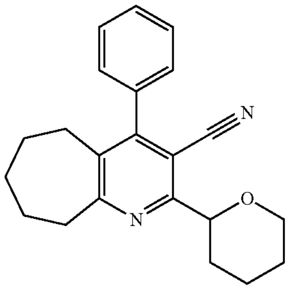 | ESP [M + H]$^+$: 333.4 | U | Intermediate K79, cycloheptanone |
| N80 | 2-Cyclopentyl-4-(2-methylpyridin-4-yl)-6,7,8,9-tetrahydro-5H-cyclohepta[b]pyridine-3-carbonitrile 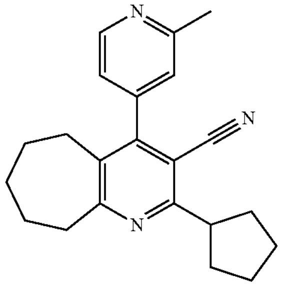 | ESP [M + H]$^+$: 332.5 | U | Intermediate K80, cycloheptanone |
| N81 | 4-Phenyl-2-(tetrahydrofuran-3-yl)-6,7,8,9-tetrahydro-5H-cyclohepta[b]pyridine-3-carbonitrile 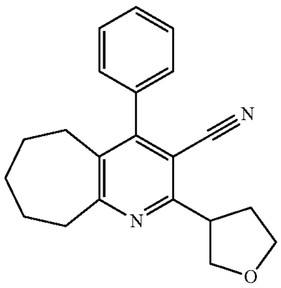 | ESP [M + H]$^+$: 319.4 | U | Intermediate K81, cycloheptanone |

-continued

| Intermediate | Name and Structure | MS | Method | Reagents |
|---|---|---|---|---|
| N82 | 2-Cyclopentyl-4-(2-methoxy-pyridin-4-yl)-6,7,8,9-tetrahydro-5H-cyclohepta[b]pyridine-3-carbonitrile 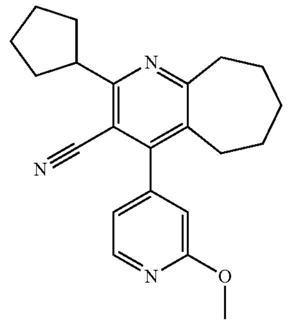 | ESP [M + H]$^+$: 348.5 | U | Intermediate K82, cycloheptanone |
| N83 | 2-Cyclopentyl-4-phenyl-6,7,8,9-tetrahydro-5H-cyclohepta[b]pyridine-3-carbonitrile 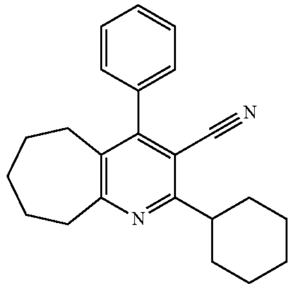 | ESP [M + H]$^+$: 331.5 | U | Intermediate K83, cycloheptanone |
| N84 | 2-Cyclopentyl-4-phenyl-6,7,8,9-tetrahydro-5H-cyclohepta[b]pyridine-3-carbonitrile 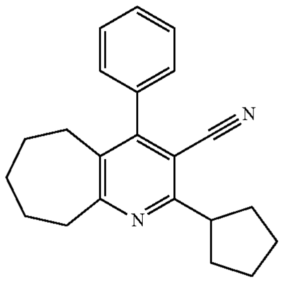 | ESP [M + H]$^+$: 317.4 | U | Intermediate K84, cycloheptanone |
| N85 | 4-Phenyl-2-(tetrahydrofuran-2-yl)-6,7,8,9-tetrahydro-5H-cyclohepta[b]pyridine-3-carbonitrile 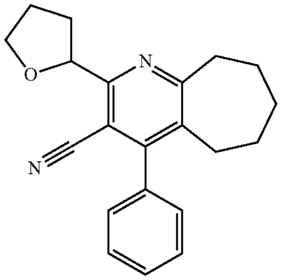 | ESP [M + H]$^+$: 319.4 | U | Intermediate K85, cycloheptanone |

-continued

| Intermediate | Name and Structure | MS | Method | Reagents |
|---|---|---|---|---|
| N86 | 2-Cyclohexyl-4-(3-fluoropyridin-4-yl)-6,7,8,9-tetrahydro-5H-cyclohepta[b]pyridine-3-carbonitrile 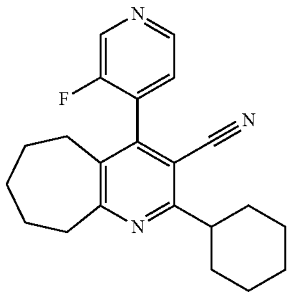 | ESP [M + H]$^+$: 350.5 | U | Intermediate K86, cycloheptanone |
| N87 | 2-Cyclopentyl-4-(3-fluoropyridin-4-yl)-6,7,8,9-tetrahydro-5H-cyclohepta[b]pyridine-3-carbonitrile 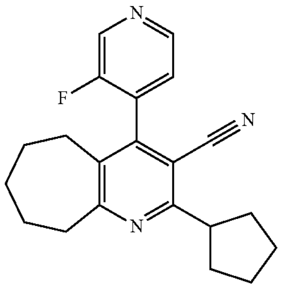 | ESP [M + H]$^+$: 336.5 | U | Intermediate K87, cycloheptanone |
| N88 | 4-Phenyl-2-(tetrahydro-2H-pyran-4-yl)-6,7,8,9-tetrahydro-4H-cyclohepta[b]pyridine-3-carbonitrile 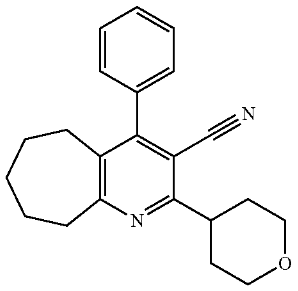 | ESP [M + H]$^+$: 333.5 | U | Intermediate K88, cycloheptanone |
| N89 | 2-Cyclohexyl-4-(2-methylpyrimidin-4-yl)-6,7,8,9-tetrahydro-5H-cyclohepta[b]pyridine-3-carbonitrile 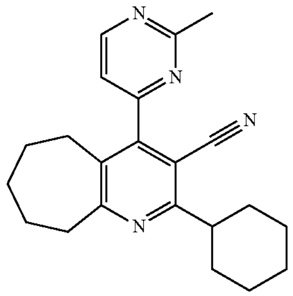 | ESP [M + H]$^+$: 347.5 | U | Intermediate K89, cycloheptanone |

-continued

| Intermediate | Name and Structure | MS | Method | Reagents |
|---|---|---|---|---|
| N91 | 2-Cyclohexyl-4-(pyrimidin-4-yl)-6,7,8,9-tetrahydro-5H-cyclohepta[b]pyridine-3-carbonitrile 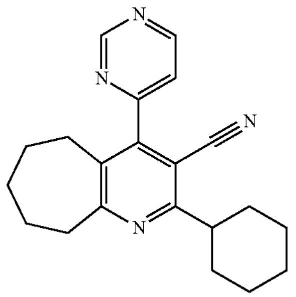 | ESP $[M + H]^+$: 333.5 | U | Intermediate K91, cycloheptanone |
| N92 | 2-Cyclopentyl-4-(pyrimidin-4-yl)-6,7,8,9-tetrahydro-5H-cyclohepta[b]pyridine-3-carbonitrile 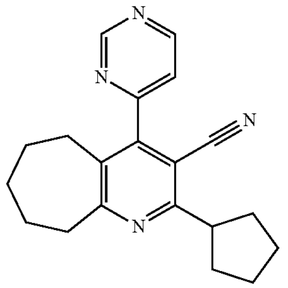 | ESP $[M + H]^+$: 319.5 | U | Intermediate K92, cycloheptanone |
| N93 | 2-Cyclopentyl-4-(2-methylpyrimidin-4-yl)-6,7,8,9-tetrahydro-5H-cyclohepta[b]pyridine-3-carbonitrile 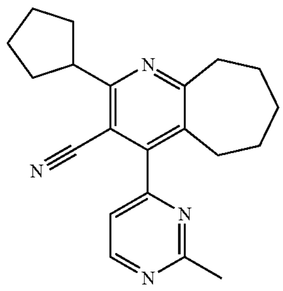 | ESP $[M + H]^+$: 333.5 | U | Intermediate K93, cycloheptanone |
| N94 | 2-(1-(Methoxymethyl)cyclopentyl)-4-(2-methylpyridin-4-yl)-6,7,8,9-tetrahydro-5H-cyclohepta[b]pyridine-3-carbonitrile 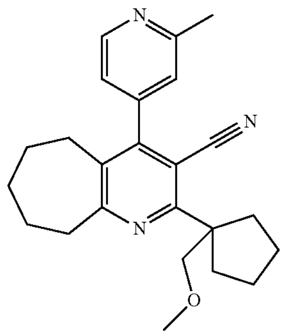 | ESP $[M + H]^+$: 376.5 | V | Intermediate B94, cycloheptanone, 2-methylisonicotinaldehyde |

-continued

| Intermediate | Name and Structure | MS | Method | Reagents |
|---|---|---|---|---|
| N95 | 2-Cyclopentyl-4-(pyridazin-4-yl)-6,7,8,9-tetrahydro-5H-cyclohepta[b]pyridine-3-carbonitrile 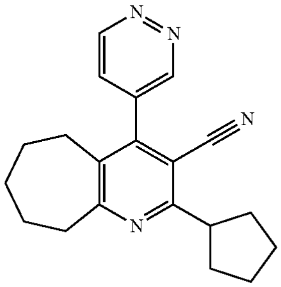 | ESP [M + H]$^+$: 319.5 | U | Intermediate K95, cycloheptanone |
| N96 | 2-Cyclopentyl-4-(6-methylpyridin-2-yl)-6,7,8,9-tetrahydro-5H-cyclohepta[b]pyridine-3-carbonitrile 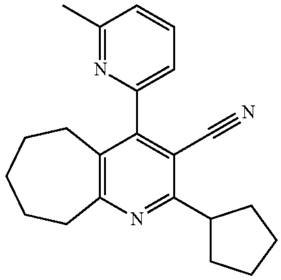 | ESP [M + H]$^+$: 332.5 | U | Intermediate K96, cycloheptanone |
| N97 | 2-Cyclopentyl-4-(pyridin-2-yl)-6,7,8,9-tetrahydro-5H-cyclohepta[b]pyridine-3-carbonitrile 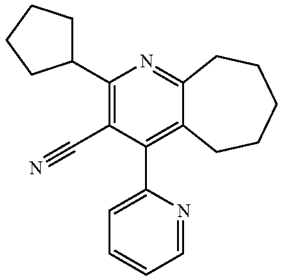 | ESP [M + H]$^+$: 318.5 | U | Intermediate K97, cycloheptanone |
| N98 | 2-Isopropyl-4-(2-isopropylpyridin-4-yl)-6,7,8,9-tetrahydro-5H-cyclohepta[b]pyridine-3-carbonitrile 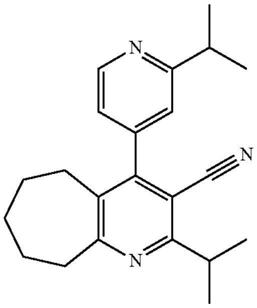 | ESP [M + H]$^+$: 334.5 | V | 4-Methyl-3-oxopentanenitrile (CAS# 29509-06-6), cycloheptanone, 2-isopropyliso-nicotinaldehyde |

-continued

| Intermediate | Name and Structure | MS | Method | Reagents |
|---|---|---|---|---|
| N99 | 2-Cyclopentyl-4-(pyrimidin-2-yl)-6,7,8,9-tetrahydro-5H-cyclohepta[b]pyridine-3-carbonitrile 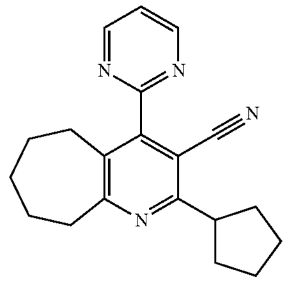 | ESP $[M + H]^+$: | U | Intermediate K99, cycloheptanone |
| N100 | 2-Cyclopentyl-4-(2-(2-hydroxyethoxy)phenyl)-6,7,8,9-tetrahydro-5H-cyclohepta[b]pyridine-3-carbonitrile 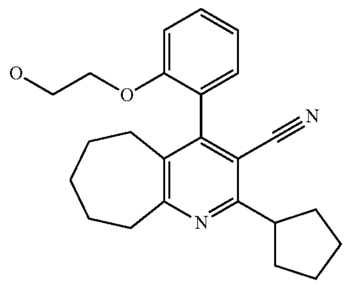 | ESP $[M + H]^+$: 377.5 | V | 3-Cyclopentyl-3-oxopropanenitrile (CAS# 95882-33-0), cycloheptanone, 2-(2-hydroxyethoxy) benzaldehyde |
| N101 | 2-Cyclopentyl-4-(2-isopropylpyrimidin-4-yl)-6,7,8,9-tetrahydro-5H-cyclohepta[b]pyridine-3-carboxamide 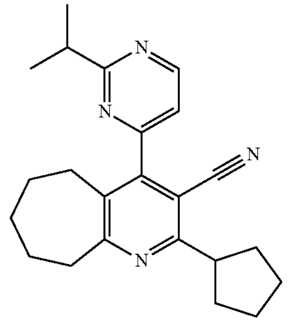 | ESP $[M + H]^+$: 361.6 | V | 3-Cyclopentyl-3-oxopropanenitrile (CAS# 95882-33-0), cycloheptanone, 2-isopropyl-pyrimidine-4-carbaldehyde |
| N102 | 2-Isopropyl-4-(2-isopropylpyrimidin-4-yl)-6,7,8,9-tetrahydro-5H-cyclohepta[b]pyridine-3-carbonitrile 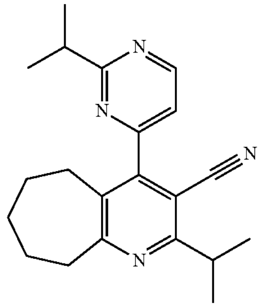 | ESP $[M + H]^+$: 335.5 | V | 4-Methyl-3-oxopentanenitrile (CAS# 29509-06-6), cycloheptanone, 2-isopropyl-pyrimidine-4-carbaldehyde |

-continued

| Intermediate | Name and Structure | MS | Method | Reagents |
|---|---|---|---|---|
| N103 | 4-(2-Chloropyridin-4-yl)-2-cyclopentyl-6,7,8,9-tetrahydro-5H-cyclohepta[b]pyridine-3-carbonitrile 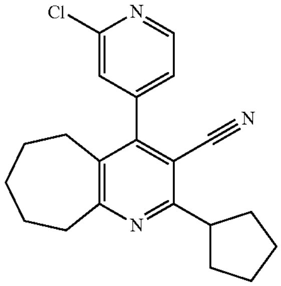 | ESP [M + H]$^+$: 352.5 | V | 3-Cyclopentyl-3-oxopropanenitrile (CAS# 95882-33-0), cycloheptanone, 2-chloropyridine-4-carbaldehyde |
| N104 | 2-(1-(Methoxymethyl)cyclopentyl)-4-(2-methoxypyridin-4-yl)-6,7,8,9-tetrahydro-5H-cyclohepta[b]pyridine-3-carbonitrile 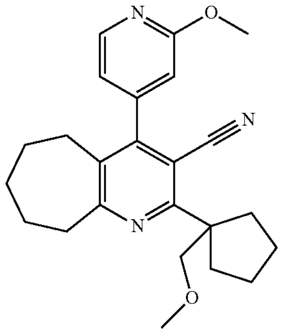 | ESP [M + H]$^+$: 392.5 | V | Intermediate B94, cycloheptanone, 2-methoxypyridine-4-carbaldehyde |
| N105 | 4-(2-Isopropylpyridin-4-yl)-2-(pentan-3-yl)-6,7,8,9-tetrahydro-5H-cyclohepta[b]pyridine-3-carbonitrile 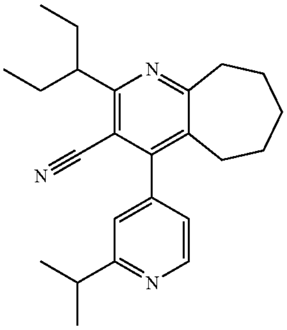 | ESP [M + H]$^+$: 362.6 | V | 4-Ethyl-3-oxo-hexanenitrile (CAS# 42124-67-4), cycloheptanone, 2-isopropylpyridine-4-carbaldehyde |
| N106 | 4-(1-Methyl-1H-pyrazol-5-yl)-2-(pentan-3-yl)-6-(trifluoromethyl)-5,6,7,8-tetrahydroquinoline-3-carbonitrile 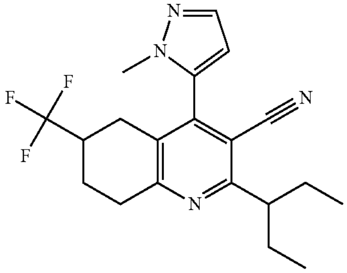 | ESP [M + H]$^+$: 377.2 | U | Intermediate K66, 4-trifluoromethyl-cyclohexanone |

-continued

| Intermediate | Name and Structure | MS | Method | Reagents |
|---|---|---|---|---|
| N107 | 2-Cyclohexyl-4-(2-methylpyridin-4-yl)-6-(trifluoromethyl)-6,7,8,9-tetrahydroquinoline-3-carbonitrile<br>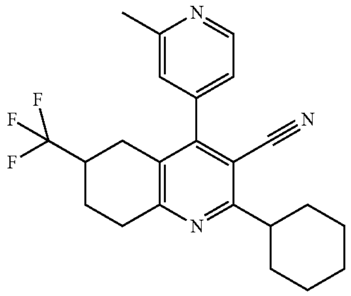 | ESP [M + H]$^+$: 400.5 | U | Intermediate K70, 4-trifluoromethyl-cyclohexanone |
| N108 | 2-Cyclohexyl-4-(1-methyl-1H-pyrazol-5-yl)-6-(trifluoromethyl)-5,6,7,8-tetrahydroquinoline-3-carbonitrile<br>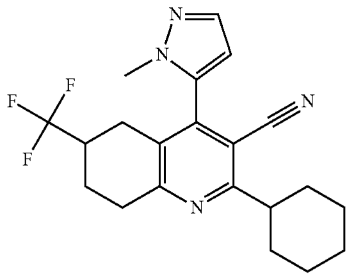 | ESP [M + H]$^+$: 389.4 | U | Intermediate K74, 4-trifluoromethyl-cyclohexanone |
| N109 | 2-Cyclohexyl-6-methyl-4-(1-methyl-1H-pyrazol-5-yl)-5,6,7,8-tetrahydroquinoline-3-carbonitrile<br>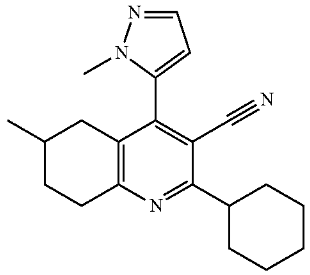 | ESP [M + H]$^+$: 335.5 | U | Intermediate K74, 4-methyl-cyclohexanone |
| N110 | 2-Cyclohexyl-6-methyl-4-(2-methylpyridin-4-yl)-5,6,7,8-tetrahydroquinoline-3-carbonitrile<br>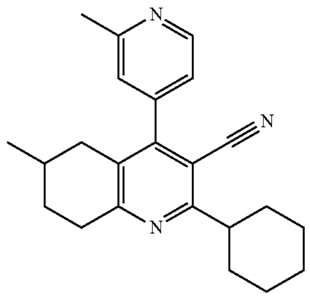 | ESP [M + H]$^+$: 346.5 | U | Intermediate K70, 4-methyl-cyclohexanone |

-continued

| Intermediate | Name and Structure | MS | Method | Reagents |
|---|---|---|---|---|
| N111 | 2-Cyclopentyl-4-(1-methyl-1H-pyrazol-5-yl)-6-(trifluoromethyl)-5,6,7,8-tetrahydroquinoline-3-carbonitrile 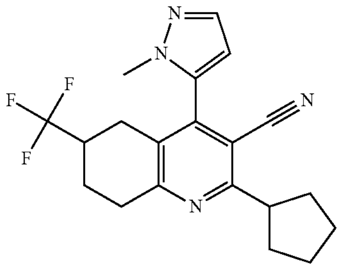 | ESP $[M + H]^+$: 375.4 | U | Intermediate K76, 4-trifluoromethyl-cyclohexanone |
| N112 | 2-Cyclopentyl-6,6-difluoro-4-phenyl-5,6,7,8-tetrahydroquinoline-3-carbonitrile 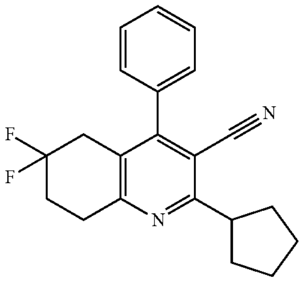 | ESP $[M + H]^+$: 339.4 | U | Intermediate K84, 4,4-difluoro-cyclohexanone |
| N113 | 2-Cyclopentyl-6-methyl-4-(2-methylpyridin-4-yl)-5,6,7,8-tetrahydroquinoline-3-carbonitrile 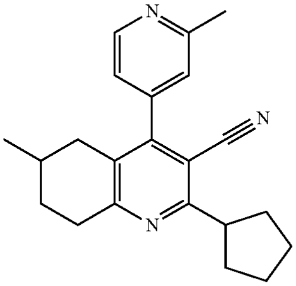 | ESP $[M + H]^+$: 332.5 | U | Intermediate K80, 4-methyl-cyclohexanone |
| N114 | 2-Cyclohexyl-4-(3,5-dimethylisoxazol-4-yl)-6-(trifluoromethyl)-5,6,7,8-tetrahydroquinoline-3-carbonitrile 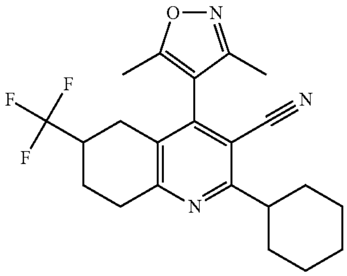 | ESP $[M + H]^+$: 404.5 | U | Intermediate K114, 4-trifluoromethyl-cyclohexanone |

-continued

| Intermediate | Name and Structure | MS | Method | Reagents |
|---|---|---|---|---|
| N115 | 2-Cyclohexyl-4-(3,5-dimethylisoxazol-4-yl)-6-methyl-5,6,7,8-tetrahydroquinoline-3-carbonitrile 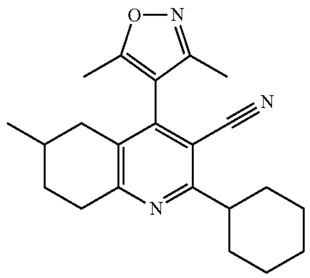 | ESP $[M + H]^+$: 350.5 | U | Intermediate K114, 4-methyl-cyclohexanone |
| N116 | 2-Cyclopentyl-4-(2-methylpyridin-4-yl)-6-(trifluoromethyl)-5,6,7,8-tetrahydroquinoline-3-carbonitrile 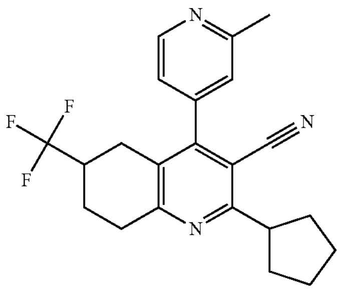 | ESP $[M + H]^+$: 386.6 | U | Intermediate K80, 4-trifluoromethyl-cyclohexanone |
| N117 | 2-Cyclopentyl-4-phenyl-6-(2,2,2-trifluoroethyl)-5,6,7,8-tetrahydro-1,6-naphthyridine-3-carbonitrile 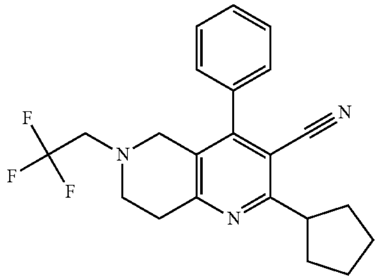 | ESP $[M + H]^+$: 386.5 | U | Intermediate K84, 1-(2,2,2-trifluoroethyl)-piperidin-4-one |
| N118 | 2-Cyclopentyl-6,6-dimethyl-4-(2-methylpyridin-4-yl)-5,6,7,8-tetrahydroquinoline-3-carbonitrile 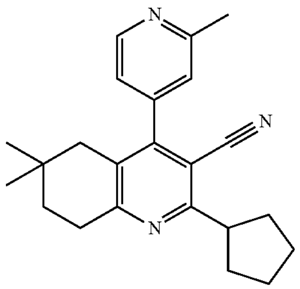 | ESP $[M + H]^+$: 346.5 | V | 3-Cyclopentyl-3-oxopropanenitrile (CAS# 95882-33-0), 4,4-dimethyl-cyclohexanone, 2-methyl-pyridine-4-carbaldehyde |

-continued

| Intermediate | Name and Structure | MS | Method | Reagents |
|---|---|---|---|---|
| N119 | 2-Cyclopentyl-6-methoxy-4-(2-methylpyridin-4-yl)-5,6,7,8-tetrahydroquinoline-3-carbonitrile 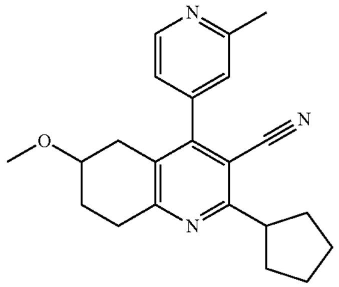 | ESP $[M + H]^+$: 348.5 | V | 3-Cyclopentyl-3-oxopropanenitrile (CAS# 95882-33-0), 4-methoxy-cyclohexanone, 2-methyl-pyridine-4-carbaldehyde |
| N120 | 6-Methyl-4-(2-methylpyridin-4-yl)-2-tert-pentyl-5,6,7,8-tetrahydroquinoline-3-carbonitrile 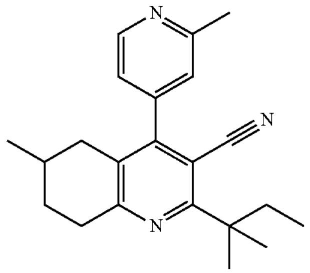 | ESP $[M + H]^+$: 334.5 | V | 4,4-Dimethyl-3-oxohexanenitrile (CAS# 876299-62-6), 4-methyl-cyclohexanone, 2-methyl-pyridine-4-carbaldehyde |
| N121 | 2-Cyclopentyl-4-(2-methylpyridin-4-yl)-5,6,7,8-tetrahydroquinoline-3-carbonitrile 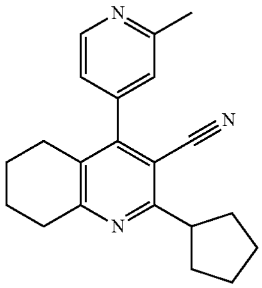 | ESP $[M + H]^+$: 318.5 | V | 3-Cyclopentyl-3-oxopropanenitrile (CAS# 95882-33-0), cyclohexanone, 2-methyl-pyridine-4-carbaldehyde |
| N122 | 2-Cyclohexyl-4-(2-methylpyridin-4-yl)-5,6,7,8-tetrahydroquinoline-3-carbonitrile 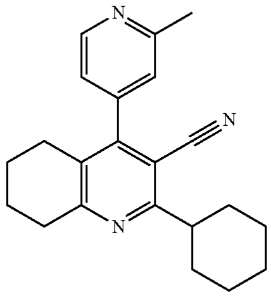 | ESP $[M + H]^+$: 332.6 | V | 3-Cyclohexyl-3-oxo-propanenitrile (CAS# 62455-70-3), cyclohexanone, 2-methyl-pyridine-4-carbaldehyde |

-continued

| Intermediate | Name and Structure | MS | Method | Reagents |
|---|---|---|---|---|
| N123 | 2-(1-Methoxy-2-methylpropan-2-yl)-6-methyl-4-(2-methylpyridin-4-yl)-5,6,7,8-tetrahydroquinoline-3-carbonitrile 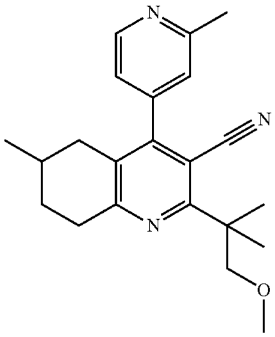 | ESP $[M + H]^+$: 350.6 | V | 5-Methoxy-4,4-dimethyl-3-oxopentanenitrile (CAS# 90087-79-9), 4-methyl-cyclohexanone, 2-methyl-pyridine-4-carbaldehyde |
| N124 | 2-Cyclopentyl-4-(2-methylpyridin-4-yl)-6,7-dihydro-5H-cyclopenta[b]pyridine-3-carbonitrile 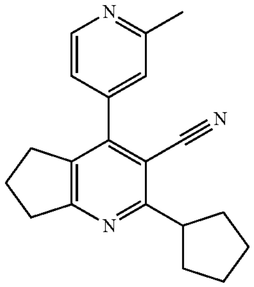 | ESP $[M + H]^+$: 304.6 | V | 3-Cyclopentyl-3-oxopropanenitrile (CAS# 95882-33-0), cyclopentanone, 2-methyl-pyridine-4-carbaldehyde |
| N125 | 2-Cyclohexyl-4-(2-methylpyridin-4-yl)-6,7-dihydro-5H-cyclopenta[b]pyridine-3-carbonitrile 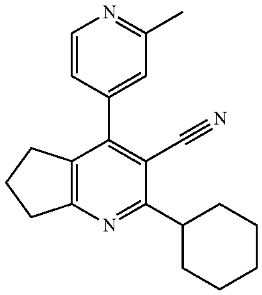 | ESP $[M + H]^+$: 318.1 | V | 3-Cyclohexyl-3-oxo-propanenitrile (CAS# 62455-70-3), cyclopentanone, 2-methyl-pyridin-4-carbaldehyde |
| N126 | 2-tert-Butyl-4-phenyl-6,7,8,9-tetrahydro-5H-cyclohepta[b] pyridine-3-carbonitrile 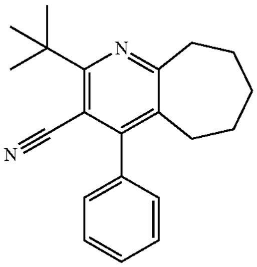 | ESP $[M + H]^+$: 305.4 | V | 4,4-Dimethyl-3-oxo-pentanenitrile (CAS# 5999-7-51-2), cycloheptanone, benzaldehyde |

-continued

| Intermediate | Name and Structure | MS | Method | Reagents |
|---|---|---|---|---|
| N127 | 2-tert-Butyl-4-(3-fluorophenyl)-6,7,8,9-tetrahydro-5H-cyclohepta[b]pyridine-3-carbonitrile 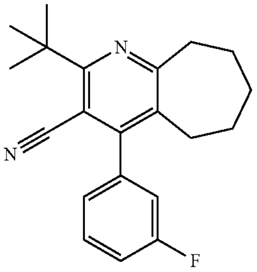 | ESP [M + H]$^+$: 323.5 | V | 4,4-Dimethyl-3-oxo-pentanenitrile (CAS# 59997-51-2), cycloheptanone, 3-fluoro-benzaldehyde |
| N128 | 2-tert-Butyl-4-(4-(trifluoromethyl)phenyl)-6,7,8,9-tetrahydro-5H-cyclohepta[b]pyridine-3-carbonitrile 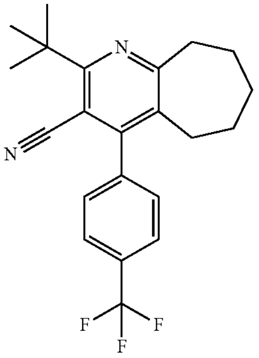 | ESP [M + H]$^+$: 373.5 | V | 4,4-Dimethyl-3-oxo-pentanenitrile (CAS# 59997-51-2), cycloheptanone, 4-trifluoromethyl-benzaldehyde |
| N129 | 2-tert-Butyl-4-(3-(trifluoromethyl)phenyl)-6,7,8,9-tetrahydro-5H-cyclohepta[b]pyridine-3-carbonitrile 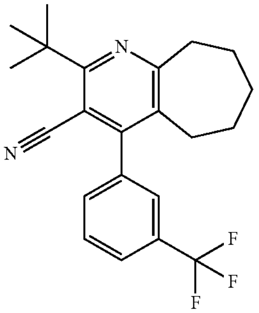 | ESP [M + H]$^+$: 373.5 | V | 4,4-Dimethyl-3-oxo-pentanenitrile (CAS# 59997-51-2), cycloheptanone, 3-trifluoromethyl-benzaldehyde |
| N130 | 2-tert-Butyl-4-(2-methylpyridin-4-yl)-6,7,8,9-tetrahydro-5H-cyclohepta[b]pyridine-3-carbonitrile 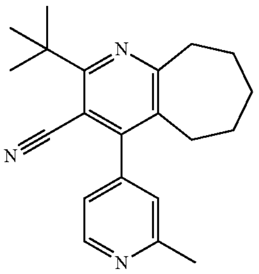 | ESP [M + H]$^+$: 320.5 | V | 4,4-Dimethyl-3-oxo-pentanenitrile (CAS# 59997-51-2), cycloheptanone, 2-methyl-pyridine-4-carbaldehyde |

-continued

| Intermediate | Name and Structure | MS | Method | Reagents |
|---|---|---|---|---|
| N131 | 2-(3,3-Difluorocyclobutyl)-4-phenyl-3-(1H-tetrazol-5-yl)-6,7,8,9-tetrahydro-5H-cyclohepta[b]pyridine 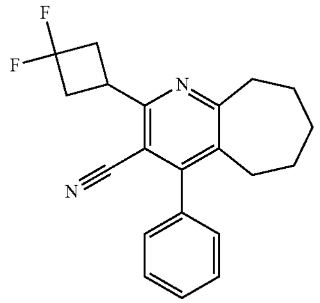 | ESN $[M-H]^-$: 380.1 | V | 3-(3,3-Difluoro-cyclobutyl)-3-oxo-propionitrile (CAS# 1234616-26-2), cycloheptanone, benzaldehyde |
| N132 | 2-tert-Butyl-4-(4-fluoro-phenyl)-6,7,8,9-tetrahydro-5H-cyclohepta[b]pyridine-3-carbonitrile 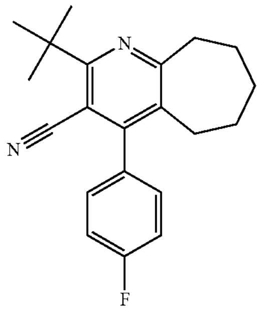 | ESP $[M+H]^+$: 323.4 | V | 4,4-Dimethyl-3-oxo-pentanenitrile (CAS# 59997-51-2), cycloheptanone, 4-fluoro-benzaldehyde |
| N133 | 2-tert-Butyl-4-(oxazol-4-yl)-6,7,8,9-tetrahydro-5H-cyclohepta[b] pyridine-3-carbonitrile 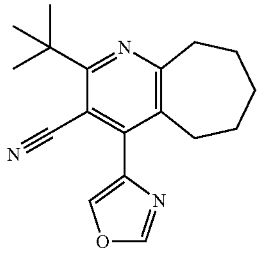 | ESP $[M+H]^+$: 296.4 | V | 4,4-Dimethyl-3-oxo-pentanenitrile (CAS# 59997-51-2), cycloheptanone, oxazole-4-carbaldehyde |
| N134 | 2-tert-Butyl-4-(1-methyl-1H-pyrazol-3-yl)-6,7,8,9-tetrahydro-5H-cyclohepta[b]pyridine-3-carbonitrile 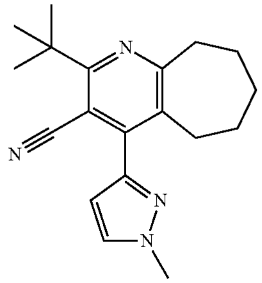 | ESP $[M+H]^+$: 309.5 | V | 4,4-Dimethyl-3-oxo-pentanenitrile (CAS# 59997-51-2), cycloheptanone, 1-methyl-1H-pyrazole-3-carbaldehyde |

-continued

| Intermediate | Name and Structure | MS | Method | Reagents |
|---|---|---|---|---|
| N135 | 2-tert-Butyl-4-(4-methyl-1H-pyrazol-5-yl)-6,7,8,9-tetrahydro-5H-cyclohepta[b]pyridine-3-carbonitrile 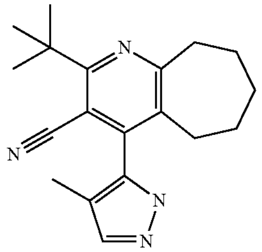 | ESP $[M + H]^+$: 309.4 | V | 4,4-Dimethyl-3-oxo-pentanenitrile (CAS# 59997-51-2), cycloheptanone, 4-methyl-2H-pyrazole-3-carbaldehyde |
| N136 | 2-tert-Butyl-4-(3-cyclopropyl-1H-pyrazol-5-yl)-6,7,8,9-tetrahydro-5H-cyclohepta[b]pyridine-3-carbonitrile 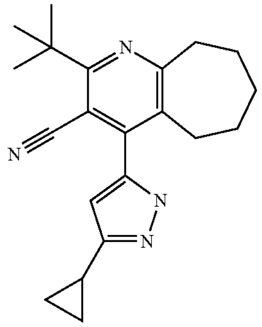 | ESP $[M + H]^+$: 335.5 | V | 4,4-Dimethyl-3-oxo-pentanenitrile (CAS# 59997-51-2), cycloheptanone, 5-cyclopropyl-2H-pyrazole-3-carbaldehyde |
| N137 | 2-tert-Butyl-4-(2-methyloxazol-4-yl)-6,7,8,9-tetrahydro-5H-cyclohepta[b]pyridine-3-carbonitrile 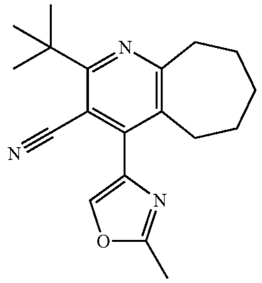 | ESP $[M + H]^+$: 310.4 | V | 4,4-Dimethyl-3-oxo-pentanenitrile (CAS# 59997-51-2), cycloheptanone, 2-methyl-oxazole-4-carbaldehyde |
| N138 | 2-tert-Butyl-4-(4-chloro-1H-pyrazol-3-yl)-6,7,8,9-tetrahydro-5H-cyclohepta[b]pyridine-3-carbonitrile 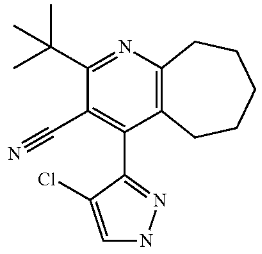 | ESP $[M + H]^+$: 329.4 | V | 4,4-Dimethyl-3-oxo-pentanenitrile (CAS# 59997-51-2), cycloheptanone, 4-chloro-1H-pyrazole-3-carbaldehyde |

-continued

| Intermediate | Name and Structure | MS | Method | Reagents |
|---|---|---|---|---|
| N139 | 2-tert-Butyl-4-(4-(trifluoromethyl)-1H-imidazol-2-yl)-6,7,8,9-tetrahydro-5H-cyclohepta[b]pyridine-3-carbonitrile 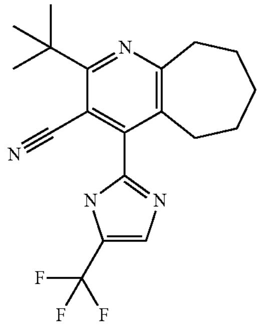 | ESP [M + H]$^+$: 363.5 | V | 4,4-Dimethyl-3-oxo-pentanenitrile (CAS# 59997-51-2), cycloheptanone, 5-trifluoromethyl-1H-imidazole-2-carbaldehyde |
| N140 | 2-tert-Butyl-4-(1H-1,2,3-triazol-5-yl)-6,7,8,9-tetrahydro-5H-cyclohepta[b]pyridine-3-carbonitrile 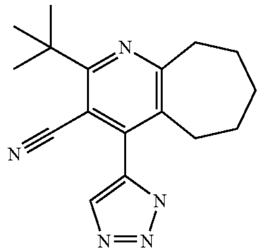 | ESP [M + H]$^+$: 296.4 | V | 4,4-Dimethyl-3-oxo-pentanenitrile (CAS# 59997-51-2), cycloheptanone,3H-[1,2,3]triazole-4-carbaldehyde |
| N141 | 2-tert-Butyl-4-(2-butyl-1H-imidazol-4-yl)-6,7,8,9-tetrahydro-5H-cyclohepta[b]pyridine-3-carbonitrile 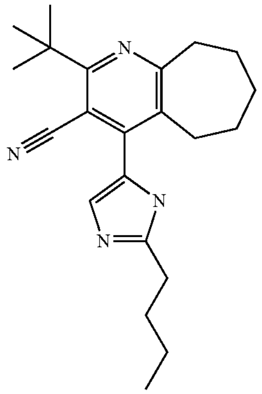 | ESP [M + H]$^+$: 351.5 | V | 4,4-Dimethyl-3-oxo-pentanenitrile (CAS# 59997-51-2), cycloheptanone, 2-butyl-3H-imidazole-4-carbaldehyde |
| N142 | 2-Furan-2-yl-4-phenyl-6,7,8,9-tetrahydro-5H-cyclohepta[b]pyridine-3-carbonitrile 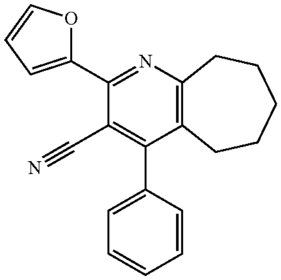 | ESP [M + H]$^+$: 315.4 | V | 2-Furoylacetonitrile (CAS# 31909-58-7), cycloheptanone, benzaldehyde |

-continued

| Intermediate | Name and Structure | MS | Method | Reagents |
|---|---|---|---|---|
| N143 | 2-sec-Butyl-4-phenyl-6,7,8,9-tetrahydro-5H-cyclohepta[b]pyridine-3-carbonitrile 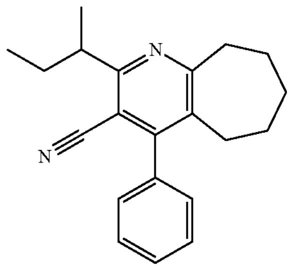 | ESP $[M + H]^+$: 305.5 | V | 4-Methyl-3-oxohexanenitrile (CAS# 42124-66-3), cycloheptanone, benzaldehyde |
| N144 | 2-(3-Fluorophenyl)-4-phenyl-6,7,8,9-tetrahydro-5H-cyclohepta[b]pyridine-3-carbonitrile 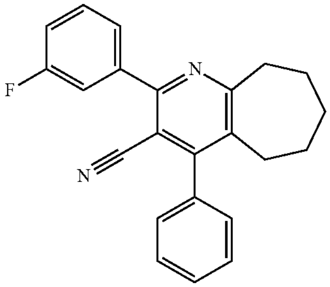 | ESP $[M + H]^+$: 343.4 | V | 3-Fluorobenzoyl-acetonitrile (CAS# 21667-61-8), cycloheptanone, benzaldehyde |
| N145 | 2-sec-Butyl-4-(2-methylpyridin-4-yl)-6,7,8,9-tetrahydro-5H-cyclohepta[b]pyridine-3-carbonitrile 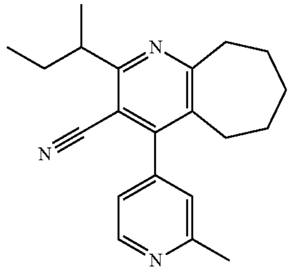 | ESP $[M + H]^+$: 320.5 | V | 4-Methyl-3-oxohexanenitrile (CAS# 42124-66-3), cycloheptanone, 2-methyl-pyridine-4-carbaldehyde |

Intermediate N71

2-Cyclohexyl-4-(6-oxo-1,6-dihydropyridin-3-yl)-6,7,8,9-tetrahydro-5H-cyclohepta[b]pyridine-3-carbonitrile

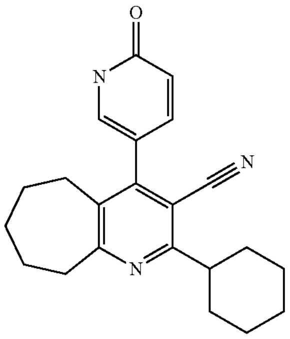 [SMILES: N#Cc1c(C2CCCCC2)nc2c(c1-c1ccc(=O)[nH]c1)CCCCC2]

Using General Method R, Intermediate K71 was reacted with cycloheptanone and ammonium acetate to give 2-cyclohexyl-4-(6-methoxypyridin-3-yl)-6,7,8,9-tetrahydro-5H-cyclohepta[b]pyridine-3-carbonitrile. 2-Cyclohexyl-4-(6-methoxypyridin-3-yl)-6,7,8,9-tetrahydro-5H-cyclohepta[b]pyridine-3-carbonitrile (1.162 g) and aqueous HCl 37% (6.34 g) were combined with dioxane (47.5 ml) and stirred at 100° C. for 1 h. After cooling to room temperature, the mixture was diluted with water and extracted with EtOAc. The organic layers were concentrated in vacuo. The crude material was suspended in a small amount of EtOAc. The product was collected by filtration, washed with EtOAc and dried to give the title compound (1.12 g) as a colorless solid. MS (ESP): m/z=348.5 $[M+H]^+$.

Intermediate N72

2-Cyclohexyl-4-(1-ethyl-6-oxo-1,6-dihydropyridin-3-yl)-6,7,8,9-tetrahydro-5H-cyclohepta[b]pyridine-3-carbonitrile

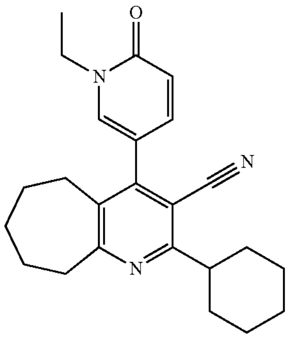 [SMILES: CCn1cc(-c2c(C#N)c(C3CCCCC3)nc3c2CCCCC3)ccc1=O]

A suspension of Intermediate N71 (250 mg), potassium carbonate (109 mg) and ethyl iodide (118 mg) in DMA (4.13 ml) was stirred at room temperature for 3 days. The mixture was diluted with water and extracted with EtOAc. The organic layers were washed with water and brine, dried over $MgSO_4$ and concentrated in vacuo. The crude material was purified by flash chromatography (silica gel, 0% to 10% MeOH in DCM) to give the title compound (184 mg) as colorless foam. MS (ESP): m/z=376.5 $[M+H]^+$.

Intermediate N73

2-Cyclohexyl-4-(1-methyl-6-oxo-1,6-dihydropyridin-3-yl)-6,7,8,9-tetrahydro-5H-cyclohepta[b]pyridine-3-carbonitrile

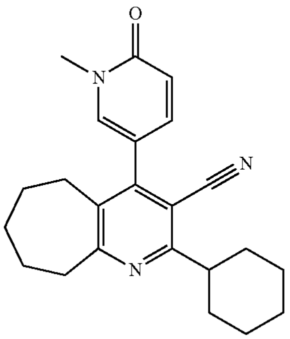 [SMILES: Cn1cc(-c2c(C#N)c(C3CCCCC3)nc3c2CCCCC3)ccc1=O]

In analogy to the synthesis of Intermediate N72, Intermediate N71 was converted to the title compound by reaction with methyl iodide in the presence of potassium carbonate. Colorless foam. MS (ESP): m/z=362.5 $[M+H]^+$.

Intermediate N90

2-Cyclobutyl-4-(1-methyl-6-oxo-1,6-dihydropyridin-3-yl)-6,7,8,9-tetrahydro-5H-cyclohepta[b]pyridine-3-carbonitrile

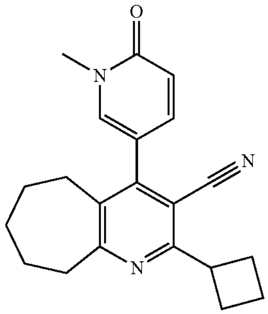 [SMILES: Cn1cc(-c2c(C#N)c(C3CCC3)nc3c2CCCCC3)ccc1=O]

Using General Method R, Intermediate K90 was reacted with cycloheptanone and ammonium acetate to give 2-cyclobutyl-4-(6-methoxypyridin-3-yl)-6,7,8,9-tetrahydro-5H-cyclohepta[b]pyridine-3-carbonitrile. This compound was converted to 2-cyclobutyl-4-(6-oxo-1,6-dihydropyridin-3-yl)-6,7,8,9-tetrahydro-5H-cyclohepta[b]pyridine-3-carbonitrile by reaction with HCl in dioxane in analogy to the synthesis of Intermediate N71. This compound was converted to the title compound by reaction with methyl iodide in the presence of potassium carbonate in analogy to the synthesis of Intermediate N72. Off-white amorphous solid. MS (ESP): m/z=334.3 $[M+H]^+$.

General Method W: Conversion of a Methoxymethyl to a Hydroxymethyl Group

The methoxymethyl compound (1 equivalent) is combined with 48% aqueous HBr (29.0 equivalents) and stirred at 100° C. for 1-3 h. After cooling to room temperature, the product is collected by filtration, washed with water and dried. If desired, the product can be further purified by chromatography. Alternatively, the product can be obtained by extraction using e.g. EtOAc.

General Method Z: Conversion of a Nitrile to a Carboxylic Acid

The nitrile (1 equivalent) and sulfuric acid (50% in water, 24 equivalents) are combined. The reaction mixture is heated to 145° C. (temperature of heating block) and stirred for 3 h. After cooling to room temperature, the mixture is placed in an ice bath and cooled to 5-10° C. A solution of sodium nitrite (1.8 equivalents) in water is slowly added under the surface of the reaction mixture and then heated up to 50° C. The reaction mixture is stirred over night at 50° C., and cooled down to room temperature. Water is added and stirred for 30 min. The reaction mixture is poured into 1 M aqueous NaOH and extracted with diethyl ether. The aqueous layer is acidified to pH 1 with HCl and extracted with EtOAc. The combined organic layers are dried over $MgSO_4$, evaporated and dried. The product can be purified by chromatography.

| Ex. | Name | Structure | MS | Method | Starting Material |
|---|---|---|---|---|---|
| 149 | 4-(2-Chloropyridin-4-yl)-2-(tetrahydrofuran-2-yl)-3-(1H-tetrazol-5-yl)-6,7,8,9-tetrahydro-5H-cyclohepta[b]pyridine | 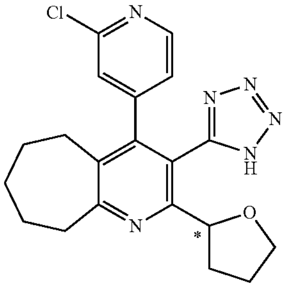 [SMILES: Clc1cc(-c2c3c(nc(C4CCCO4)c2-c2nnn[nH]2)CCCCC3)ccn1] | ESP $[M + H]^+$: 397.6 | C | N149 |
| 150 | 4-(2-Chloropyridin-4-yl)-2-(tetrahydrofuran-2-yl)-3-(1H-tetrazol-5-yl)-6,7,8,9-tetrahydro-5H-cyclohepta[b]pyridine | 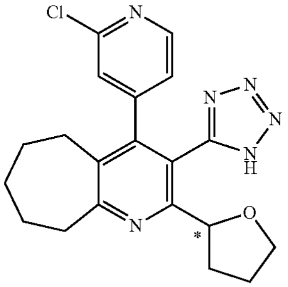 [SMILES: Clc1cc(-c2c3c(nc(C4CCCO4)c2-c2nnn[nH]2)CCCCC3)ccn1] | ESP $[M + H]^+$: 397.6 | C | N150 |
| 151 | 4-Phenyl-2-(tetrahydrofuran-2-yl)-3-(1H-tetrazol-5-yl)-5,6,7,8,9,10-hexahydrocycloocta[b]pyridine | 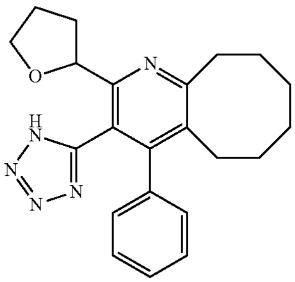 [SMILES: c1ccc(-c2c3c(nc(C4CCCO4)c2-c2nnn[nH]2)CCCCCC3)cc1] | ESP $[M + H]^+$: 376.6 | C | N151 |
| 154 | 2-(2-Methyltetrahydrofuran-2-yl)-4-phenyl-3-(1H-tetrazol-5-yl)-6,7,8,9-tetrahydro-5H-cyclohepta[b]pyridine | 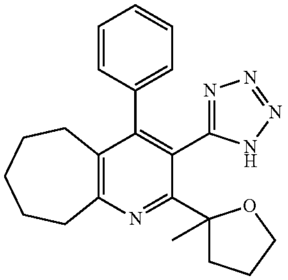 [SMILES: CC1(c2nc3c(c(-c4ccccc4)c2-c2nnn[nH]2)CCCCC3)CCCO1] | ESP $[M + H]^+$: 376.6 | C | N154 |

-continued

| Ex. | Name | Structure | MS | Method | Starting Material |
|---|---|---|---|---|---|
| 157 | 4-(3-Methoxyphenyl)-2-(2-methyltetrahydrofuran-2-yl)-3-(1H-tetrazol-5-yl)-6,7,8,9-tetrahydro-5H-cyclohepta[b]pyridine | 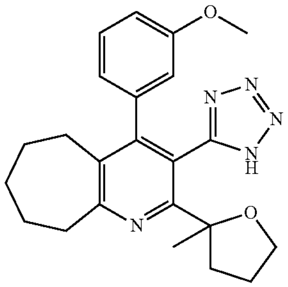 [SMILES: COc1cccc(-c2c3c(nc(C4(C)CCCO4)c2-c2nnn[nH]2)CCCCC3)c1] | ESP [M + H]$^+$: 406.6 | C | N157 |
| 160 | 4-(2-Methylpyridin-4-yl)-2-(2-methyltetrahydrofuran-2-yl)-3-(1H-tetrazol-5-yl)-6,7,8,9-tetrahydro-5H-cyclohepta[b]pyridine | 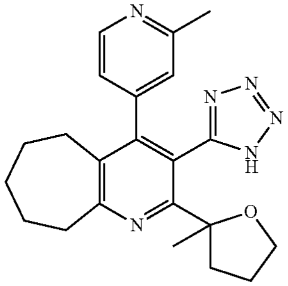 [SMILES: Cc1cc(-c2c3c(nc(C4(C)CCCO4)c2-c2nnn[nH]2)CCCCC3)ccn1] | ESP [M + H]$^+$: 391.6 | C | N160 |
| 161 | 2-[2-Methyloxolan-2-yl]-4-(2-methylpyridin-4-yl)-3-(1H-tetrazol-5-yl)-6,7,8,9-tetrahydro-5H-cyclohepta[b]pyridine | 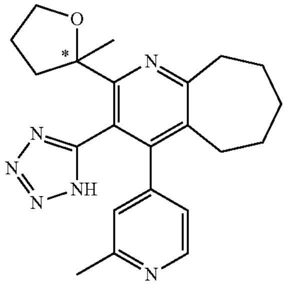 [SMILES: Cc1cc(-c2c3c(nc(C4(C)CCCO4)c2-c2nnn[nH]2)CCCCC3)ccn1] | ESP [M + H]$^+$: 391.5 | C | N161 |
| 162 | 2-[2-Methyloxolan-2-yl]-4-(2-methylpyridin-4-yl)-3-(1H-tetrazol-5-yl)-6,7,8,9-tetrahydro-5H-cyclohepta[b]pyridine | 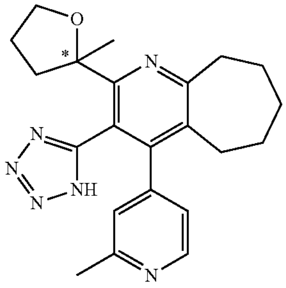 [SMILES: Cc1cc(-c2c3c(nc(C4(C)CCCO4)c2-c2nnn[nH]2)CCCCC3)ccn1] | ESP [M + H]$^+$: 391.5 | C | N162 |
| 163 | 4-(3-Chlorophenyl)-2-(2-methyltetrahydrofuran-2-yl)-3-(1H-tetrazol-5-yl)-6,7,8,9-tetrahydro-5H-cyclohepta[b]pyridine | 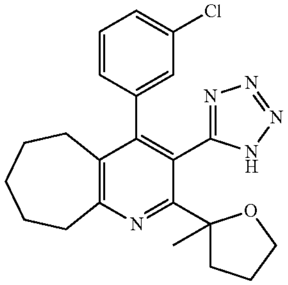 [SMILES: CC1(c2nc3c(c(-c4cccc(Cl)c4)c2-c2nnn[nH]2)CCCCC3)CCCO1] | ESP [M + H]$^+$: 410.5 | C | N163 |

-continued

| Ex. | Name | Structure | MS | Method | Starting Material |
|---|---|---|---|---|---|
| 166 | 2-(1-Methylcyclopentyl)-4-(2-methylpyridin-4-yl)-3-(1H-tetrazol-5-yl)-6,7,8,9-tetrahydro-5H-cyclohepta[b]pyridine | 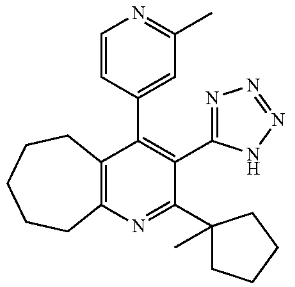 [SMILES: Cc1cc(-c2c3c(nc(C4(C)CCCC4)c2-c2nnn[nH]2)CCCCC3)ccn1] | ESP $[M + H]^+$: 389.6 | C | N166 |
| 167 | 2-(1-Methylcyclopentyl)-4-phenyl-3-(1H-tetrazol-5-yl)-6,7,8,9-tetrahydro-5H-cyclohepta[b]pyridine | 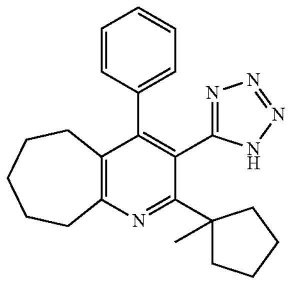 [SMILES: CC1(c2nc3c(c(-c4ccccc4)c2-c2nnn[nH]2)CCCCC3)CCCC1] | ESP $[M + H]^+$: 374.7 | C | N167 |
| 168 | 4-(2-Methoxypyridin-4-yl)-2-(1-methylcyclopentyl)-3-(1H-tetrazol-5-yl)-6,7,8,9-tetrahydro-5H-cyclohepta[b]pyridine | 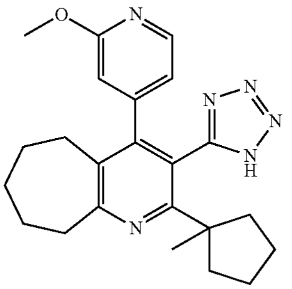 [SMILES: COc1cc(-c2c3c(nc(C4(C)CCCC4)c2-c2nnn[nH]2)CCCCC3)ccn1] | ESP $[M + H]^+$: 405.7 | C | N168 |
| 170 | 4-(3-Chloro-phenyl)-2-(1-methyl-cyclopentyl)-3-(1H-tetrazol-5-yl)-6,7,8,9-tetrahydro-5H-cyclohepta[b]pyridine | 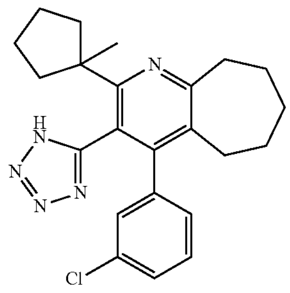 [SMILES: CC1(c2nc3c(c(-c4cccc(Cl)c4)c2-c2nnn[nH]2)CCCCC3)CCCC1] | ESP $[M + H]^+$: 408.5 | C | N170 |
| 171 | 4-(1-Methyl-1H-pyrazol-5-yl)-2-(1-methylcyclohexyl)-3-(1H-tetrazol-5-yl)-6,7,8,9-tetrahydro-5H-cyclohepta[b]pyridine | 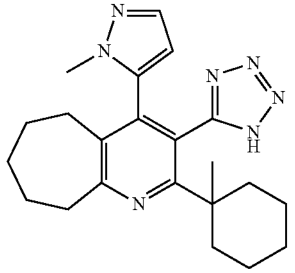 [SMILES: Cn1nccc1-c1c2c(nc(C3(C)CCCCC3)c1-c1nnn[nH]1)CCCCC2] | ESP $[M + H]^+$: 392.6 | C | N171 |

-continued

| Ex. | Name | Structure | MS | Method | Starting Material |
|---|---|---|---|---|---|
| 172 | 2-(1-Methylcyclohexyl)-4-(2-methylpyridin-4-yl)-3-(1H-tetrazol-5-yl)-6,7,8,9-tetrahydro-5H-cyclohepta[b]pyridine | 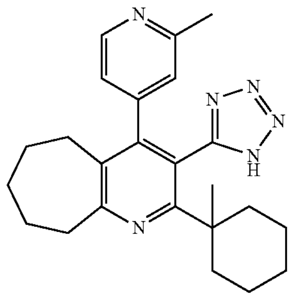 [SMILES: Cc1cc(-c2c3c(nc(C4(C)CCCCC4)c2-c2nnn[nH]2)CCCCC3)ccn1] | ESP [M + H]$^+$: 403.6 | C | N172 |
| 173 | 2-(1-Methoxymethyl-cyclopentyl)-4-(2-methyl-2H-pyrazol-3-yl)-3-(1H-tetrazol-5-yl)-6,7,8,9-tetrahydro-5H-cyclohepta[b]pyridine | 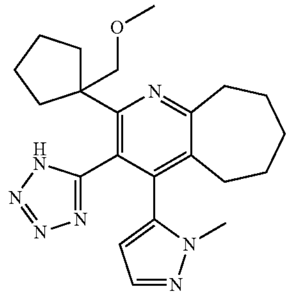 [SMILES: COCC1(c2nc3c(c(-c4ccnn4C)c2-c2nnn[nH]2)CCCCC3)CCCC1] | ESP [M + H]$^+$: 408.6 | C | N173 |
| 174 | 4-(3-Fluoropyridin-4-yl)-2-(1-(methoxymethyl) cyclopentyl)-3-(1H-tetrazol-5-yl)-6,7,8,9-tetrahydro-5H-cyclohepta[b]pyridine | 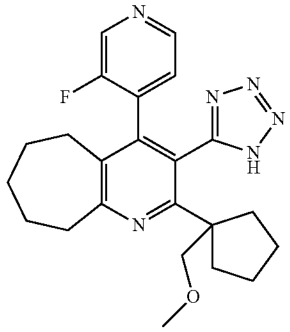 [SMILES: COCC1(c2nc3c(c(-c4ccncc4F)c2-c2nnn[nH]2)CCCCC3)CCCC1] | ESP [M + H]$^+$: 423.5 | C | N174 |
| 175 | 2-(1-(Methoxymethyl) cyclopentyl)-4-(4-methyl-1H-pyrazol-3-yl)-3-(1H-tetrazol-5-yl)-6,7,8,9-tetrahydro-5H-cyclohepta[b]pyridine | 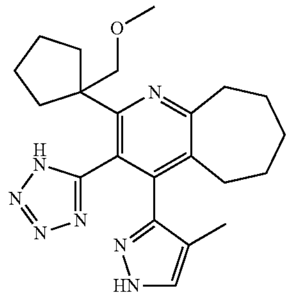 [SMILES: COCC1(c2nc3c(c(-c4n[nH]cc4C)c2-c2nnn[nH]2)CCCCC3)CCCC1] | ESP [M + H]$^+$: 408.6 | C | N175 |
| 176 | 4-(1H-Indol-4-yl)-2-(1-(methoxymethyl) cyclopentyl)-3-(1H-tetrazol-5-yl)-6,7,8,9-tetrahydro-5H-cyclohepta[b]pyridine | 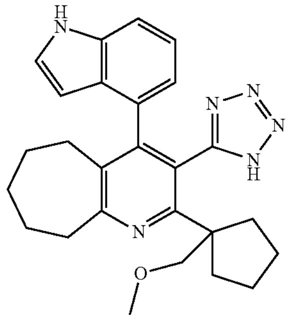 [SMILES: COCC1(c2nc3c(c(-c4cccc5[nH]ccc45)c2-c2nnn[nH]2)CCCCC3)CCCC1] | ESP [M + H]$^+$: 443.7 | C | N176 |

-continued

| Ex. | Name | Structure | MS | Method | Starting Material |
|---|---|---|---|---|---|
| 177 | 4-(2-Chloropyridin-4-yl)-2-(1-(methoxymethyl) cyclopentyl)-3-(1H-tetrazol-5-yl)-6,7,8,9-tetrahydro-5H-cyclohepta[b]pyridine | 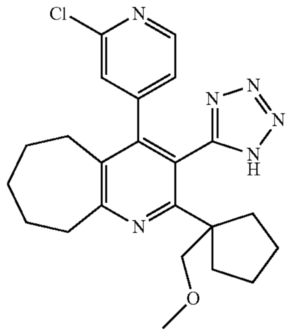 [SMILES: COCC1(c2nc3c(c(-c4ccnc(Cl)c4)c2-c2nnn[nH]2)CCCCC3)CCCC1] | ESP [M + H]$^+$: 439.5 | C | N177 |
| 178 | 4-(2-Ethylpyridin-4-yl)-2-(1-(methoxymethyl) cyclopentyl)-3-(1H-tetrazol-5-yl)-6,7,8,9-tetrahydro-5H-cyclohepta[b]pyridine | 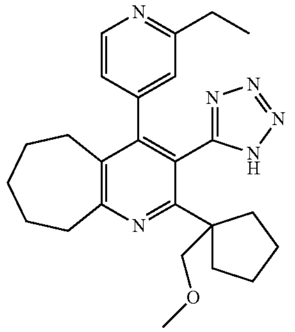 | ESP [M + H]$^+$: 433.6 | C | N178 |
| 179 | 3-(2-(1-(Methoxymethyl) cyclopentyl)-3-(1H-tetrazol-5-yl)-6,7,8,9-tetrahydro-5H-cyclohepta[b]pyridin-4-yl)-2-methylphenol | 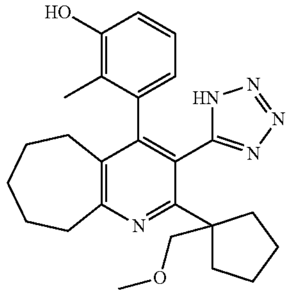 [SMILES: COCC1(c2nc3c(c(-c4cccc(O)c4C)c2-c2nnn[nH]2)CCCCC3)CCCC1] | ESP [M + H]$^+$: 434.7 | C | N179 |
| 180 | 4-(2-(1-(Methoxymethyl) cyclopentyl)-3-(1H-tetrazol-5-yl)-6,7,8,9-tetrahydro-5H-cyclohepta[b]pyridin-4-yl)-2-methyloxazole | 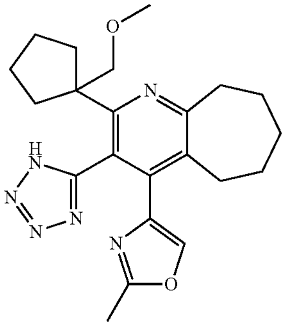 [SMILES: COCC1(c2nc3c(c(-c4coc(C)n4)c2-c2nnn[nH]2)CCCCC3)CCCC1] | ESP [M + H]$^+$: 409.6 | C | N180 |

-continued

| Ex. | Name | Structure | MS | Method | Starting Material |
|---|---|---|---|---|---|
| 181 | 4-(1H-Indazol-4-yl)-2-(1-(methoxymethyl)cyclopentyl)-3-(1H-tetrazol-5-yl)-6,7,8,9-tetrahydro-5H-cyclohepta[b]pyridine | 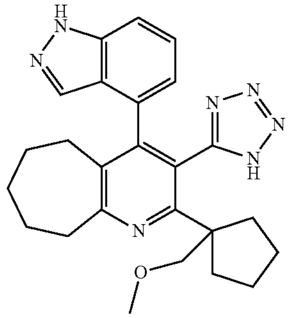 [SMILES: COCC1(c2nc3c(c(-c4cccc5[nH]ncc45)c2-c2nnn[nH]2)CCCCC3)CCCC1] | ESP $[M + H]^+$: 444.7 | C | N181 |
| 182 | 2-(1-(Methoxymethyl)cyclopentyl)-3-(1H-tetrazol-5-yl)-4-(2-(trifluoromethyl)pyridin-4-yl)-6,7,8,9-tetrahydro-5H-cyclohepta[b]pyridine | 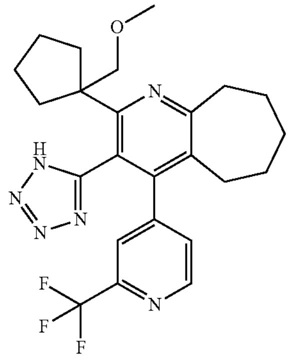 [SMILES: COCC1(c2nc3c(c(-c4ccnc(C(F)(F)F)c4)c2-c2nnn[nH]2)CCCCC3)CCCC1] | ESP $[M + H]^+$: 473.6 | C | N182 |
| 183 | 2-(1-(Methoxymethyl)cyclopentyl)-3-(1H-tetrazol-5-yl)-4-(2-(2,2,2-trifluoroethoxy)pyridin-4-yl)-6,7,8,9-tetrahydro-5H-cyclohepta[b]pyridine | 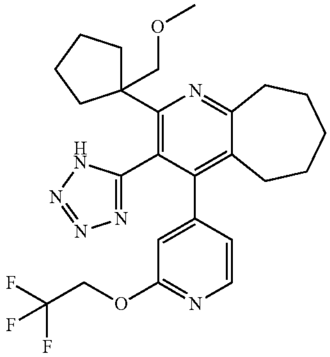 [SMILES: COCC1(c2nc3c(c(-c4ccnc(OCC(F)(F)F)c4)c2-c2nnn[nH]2)CCCCC3)CCCC1] | ESP $[M + H]^+$: 503.6 | C | N183 |
| 184 | 2-(1-(Methoxymethyl)cyclopentyl)-4-phenyl-3-(1H-tetrazol-5-yl)-6,7,8,9-tetrahydro-5H-cyclohepta[b]pyridine | 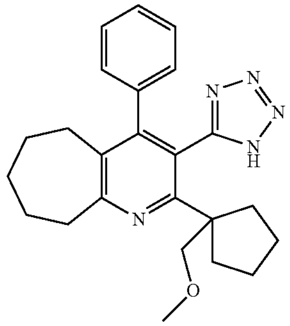 [SMILES: COCC1(c2nc3c(c(-c4ccccc4)c2-c2nnn[nH]2)CCCCC3)CCCC1] | ESP $[M + H]^+$: 404.6 | C | N184 |

-continued

| Ex. | Name | Structure | MS | Method | Starting Material |
|---|---|---|---|---|---|
| 185 | 4-(2-Ethoxypyridin-4-yl)-2-(1-(methoxymethyl) cyclopentyl)-3-(1H-tetrazol-5-yl)-6,7,8,9-tetrahydro-5H-cyclohepta[b]pyridine | 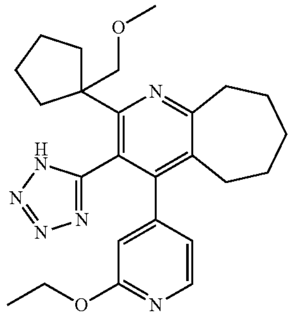 [SMILES: CCOc1cc(-c2c3c(nc(C4(COC)CCCC4)c2-c2nnn[nH]2)CCCCC3)ccn1] | ESP $[M + H]^+$: 449.6 | C | N185 |
| 186 | 4-(4-Fluoro-3-methoxyphenyl)-2-(1-(methoxymethyl) cyclopentyl)-3-(1H-tetrazol-5-yl)-6,7,8,9-tetrahydro-5H-cyclohepta[b]pyridine | 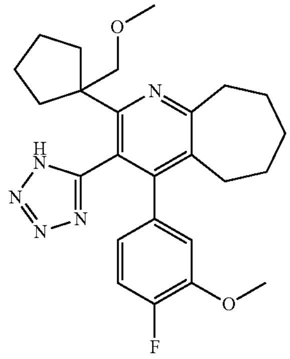 [SMILES: COCC1(c2nc3c(c(-c4ccc(F)c(OC)c4)c2-c2nnn[nH]2)CCCCC3)CCCC1] | ESP $[M + H]^+$: 452.6 | C | N186 |
| 187 | 4-(4-Fluorophenyl)-2-(1-(methoxymethyl) cyclopentyl)-3-(1H-tetrazol-5-yl)-6,7,8,9-tetrahydro-5H-cyclohepta[b]pyridine | 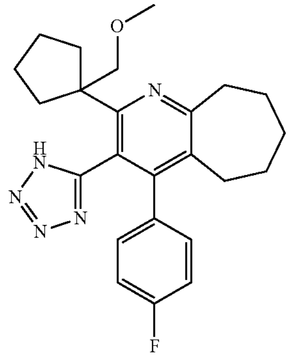 [SMILES: COCC1(c2nc3c(c(-c4ccc(F)cc4)c2-c2nnn[nH]2)CCCCC3)CCCC1] | ESP $[M + H]^+$: 422.6 | C | N187 |
| 188 | 2-(1-Methoxymethyl) cyclopentyl)-4-(3-methoxyphenyl)-3-(1H-tetrazol-5-yl)-6,7,8,9-tetrahydro-5H-cyclohepta[b]pyridine | 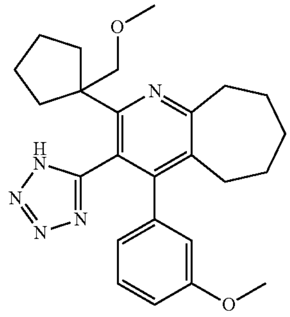 [SMILES: COCC1(c2nc3c(c(-c4cccc(OC)c4)c2-c2nnn[nH]2)CCCCC3)CCCC1] | ESP $[M + H]^+$: 434.6 | C | N188 |

-continued

| Ex. | Name | Structure | MS | Method | Starting Material |
|---|---|---|---|---|---|
| 189 | 4-(2-Fluoro-5-methoxyphenyl)-2-(1-(methoxymethyl)cyclopentyl)-3-(1H-tetrazol-5-yl)-6,7,8,9-tetrahydro-5H-cyclohepta[b]pyridine | 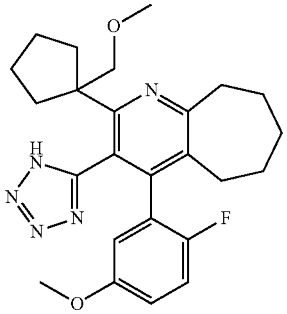 [SMILES: COCC1(c2nc3c(c(-c4cc(OC)ccc4F)c2-c2nnn[nH]2)CCCCC3)CCCC1] | ESP $[M + H]^+$: 452.6 | C | N189 |
| 190 | 4-(3-Chloro-phenyl)-2-(1-methoxymethyl-cyclopentyl)-3-(1H-tetrazol-5-yl)-6,7,8,9-tetrahydro-5H-cyclohepta[b]pyridine | 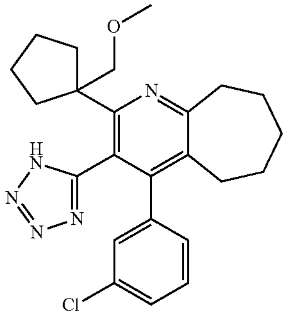 [SMILES: COCC1(c2nc3c(c(-c4cccc(Cl)c4)c2-c2nnn[nH]2)CCCCC3)CCCC1] | ESP $[M + H]^+$: 438.6 | C | N190 |
| 191 | 2-(3-(Methoxymethyl)pentan-3-yl)-4-(1-methyl-1H-pyrazol-5-yl)-3-(1H-tetrazol-5-yl)-6,7,8,9-tetrahydro-5H-cyclohepta[b]pyridine | 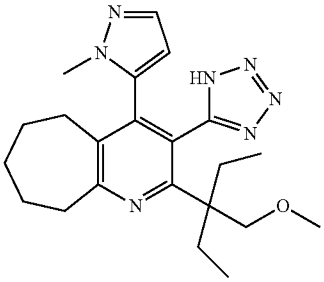 [SMILES: CCC(CC)(COC)c1nc2c(c(-c3ccnn3C)c1-c1nnn[nH]1)CCCCC2] | ESP $[M + H]^+$: 410.7 | C | N191 |
| 192 | 2-(3-(Methoxymethyl)pentan-3-yl)-4-phenyl-3-(1H-tetrazol-5-yl)-6,7,8,9-tetrahydro-5H-cyclohepta[b]pyridine | 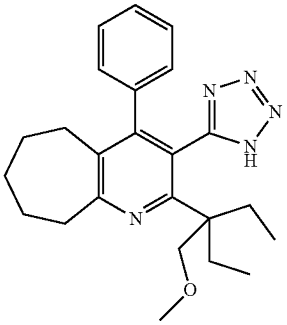 [SMILES: CCC(CC)(COC)c1nc2c(c(-c3ccccc3)c1-c1nnn[nH]1)CCCCC2] | ESP $[M + H]^+$: 406.7 | C | N192 |
| 193 | 2-Cyclopentyl-4-(2-ethylpyridin-4-yl)-3-(1H-tetrazol-5-yl)-6,7,8,9-tetrahydro-5H-cyclohepta[b]pyridine | 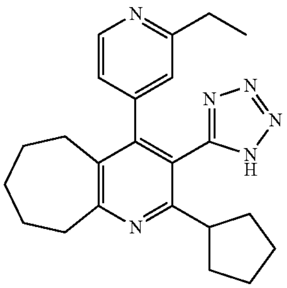 [SMILES: CCc1cc(-c2c3c(nc(C4CCCC4)c2-c2nnn[nH]2)CCCCC3)ccn1] | ESP $[M + H]^+$: 389.6 | C | N193 |

-continued

| Ex. | Name | Structure | MS | Method | Starting Material |
|---|---|---|---|---|---|
| 194 | 4-(2-Cyclopentyl-3-(1H-tetrazol-5-yl)-6,7,8,9-tetrahydro-5H-cyclohepta[b]pyridin-4-yl)-N-methylpyridin-2-amine | 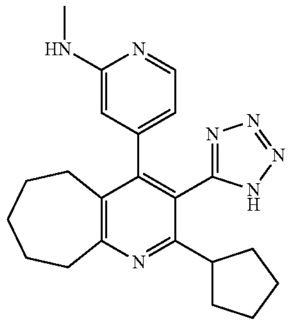 [SMILES: CNc1cc(-c2c3c(nc(C4CCCC4)c2-c2nnn[nH]2)CCCCC3)ccn1] | ESP $[M + H]^+$: 390.7 | C | N194 |
| 195 | 2-Cyclopentyl-3-(1H-tetrazol-5-yl)-4-(2-(trifluoromethyl)pyridin-4-yl)-6,7,8,9-tetrahydro-5H-cyclohepta[b]pyridine | 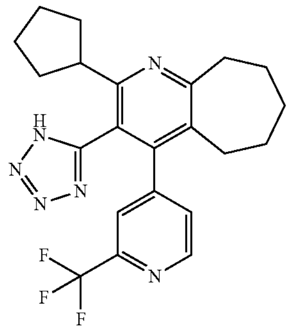 [SMILES: FC(F)(F)c1cc(-c2c3c(nc(C4CCCC4)c2-c2nnn[nH]2)CCCCC3)ccn1] | ESP $[M + H]^+$: 429.5 | C | N195 |
| 196 | 4-(1-Methyl-1H-pyrazol-5-yl)-2-(3-methylpentan-3-yl)-3-(1H-tetrazol-5-yl)-6,7,8,9-tetrahydro-5H-cyclohepta[b]pyridine | 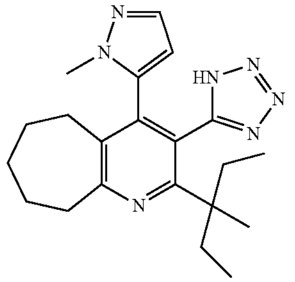 [SMILES: CCC(C)(CC)c1nc2c(c(-c3ccnn3C)c1-c1nnn[nH]1)CCCCC2] | ESP $[M + H]^+$: 380.7 | C | N196 |
| 197 | 4-(2-Ethylpyridin-4-yl)-2-isopropyl-3-(1H-tetrazol-5-yl)-6,7,8,9-tetrahydro-5H-cyclohepta[b]pyridine | 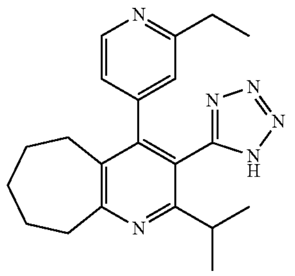 [SMILES: CCc1cc(-c2c3c(nc(C(C)C)c2-c2nnn[nH]2)CCCCC3)ccn1] | ESP $[M + H]^+$: 363.6 | C | N197 |
| 198 | 2-Isopropyl-3-(1H-tetrazol-5-yl)-4-(2-(2,2,2-trifluoroethoxy)pyridin-4-yl)-6,7,8,9-tetrahydro-5H-cyclohepta[b]pyridine | 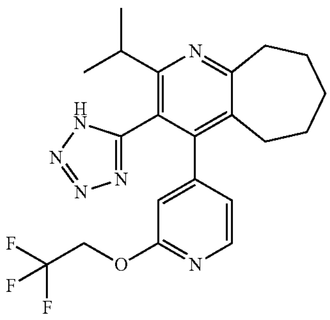 [SMILES: CC(C)c1nc2c(c(-c3ccnc(OCC(F)(F)F)c3)c1-c1nnn[nH]1)CCCCC2] | ESP $[M + H]^+$: 333.6 | C | N198 |

-continued

| Ex. | Name | Structure | MS | Method | Starting Material |
|---|---|---|---|---|---|
| 199 | 4-(2-Ethoxypyridin-4-yl)-2-isopropyl-3-(1H-tetrazol-5-yl)-6,7,8,9-tetrahydro-5H-cyclohepta[b]pyridine | 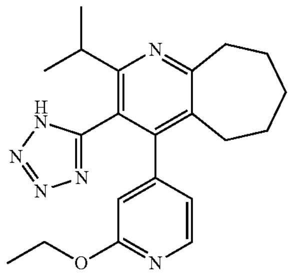 [SMILES: CCOc1cc(-c2c3c(nc(C(C)C)c2-c2nnn[nH]2)CCCCC3)ccn1] | ESP [M + H]$^+$: 379.6 | C | N199 |
| 200 | 2-(1-Methoxycyclopentyl)-4-phenyl-3-(1H-tetrazol-5-yl)-6,7,8,9-tetrahydro-5H-cyclohepta[b]pyridine | 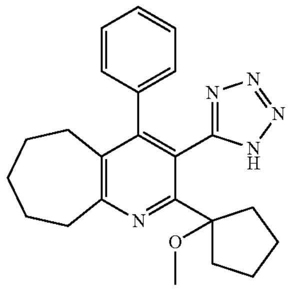 [SMILES: COC1(c2nc3c(c(-c4ccccc4)c2-c2nnn[nH]2)CCCCC3)CCCC1] | ESP [M + H]$^+$: 390.7 | C | N200 |
| 201 | 2-(1-Methoxycyclopentyl)-4-phenyl-3-(1H-tetrazol-5-yl)-5,6,7,8-tetrahydroquinoline | 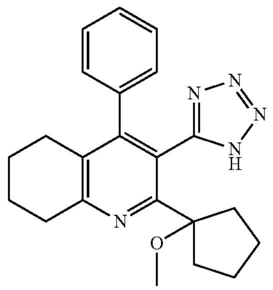 [SMILES: COC1(c2nc3c(c(-c4ccccc4)c2-c2nnn[nH]2)CCCC3)CCCC1] | ESP [M + H]$^+$: 376.7 | C | N201 |
| 202 | 2-(1-Methoxycyclopentyl)-4-(2-methoxypyridin-4-yl)-3-(1H-tetrazol-5-yl)-6,7,8,9-tetrahydro-5H-cyclohepta[b]pyridine | 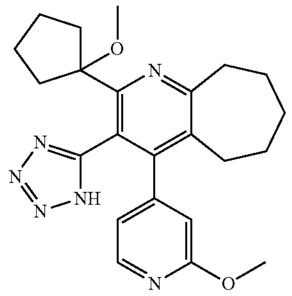 [SMILES: COc1cc(-c2c3c(nc(C4(OC)CCCC4)c2-c2nnn[nH]2)CCCCC3)ccn1] | ESP [M + H]$^+$: 421.6 | C | N202 |
| 203 | 4-(2-Chloropyridin-4-yl)-2-(1-methoxycyclopentyl)-3-(1H-tetrazol-5-yl)-6,7,8,9-tetrahydro-5H-cyclohepta[b]pyridine | 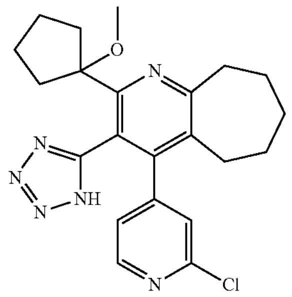 [SMILES: COC1(c2nc3c(c(-c4ccnc(Cl)c4)c2-c2nnn[nH]2)CCCCC3)CCCC1] | ESP [M + H]$^+$: 425.6 | C | N203 |

-continued

| Ex. | Name | Structure | MS | Method | Starting Material |
|---|---|---|---|---|---|
| 204 | 2-(1-Methoxycyclopentyl)-4-(2-methylpyridin-4-yl)-3-(1H-tetrazol-5-yl)-6,7,8,9-tetrahydro-5H-cyclohepta[b]pyridine | 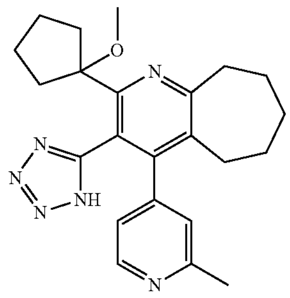 [SMILES: COC1(c2nc3c(c(-c4ccnc(C)c4)c2-c2nnn[nH]2)CCCCC3)CCCC1] | ESP [M + H]$^+$: 405.5 | C | N204 |
| 205 | (1-(4-Phenyl-3-(1H-tetrazol-5-yl)-6,7,8,9-tetrahydro-5H-cyclohepta[b]pyridin-2-yl)cyclopentyl)methanol | 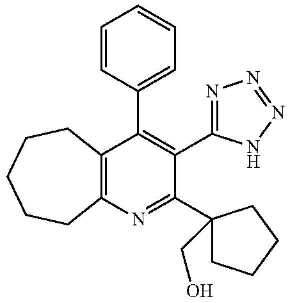 [SMILES: OCC1(c2nc3c(c(-c4ccccc4)c2-c2nnn[nH]2)CCCCC3)CCCC1] | ESP [M + H]$^+$: 390.6 | C | N205 |
| 206 | (1-(4-Phenyl-3-(1H-tetrazol-5-yl)-5,6,7,8-tetrahydroquinolin-2-yl)cyclopentyl)methanol | 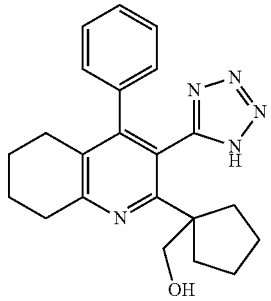 [SMILES: OCC1(c2nc3c(c(-c4ccccc4)c2-c2nnn[nH]2)CCCC3)CCCC1] | ESP [M + H]$^+$: 376.6 | W | Ex. 216 |
| 207 | (1-(4-(2-Methylpyridin-4-yl)-3-(1H-tetrazol-5-yl)-6,7,8,9-tetrahydro-5H-cyclohepta[b]pyridin-2-yl)cyclopentyl)methanol | 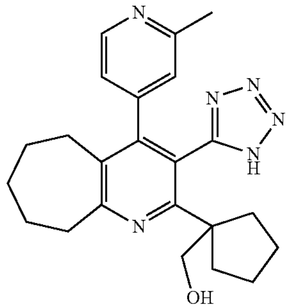 [SMILES: Cc1cc(-c2c3c(nc(C4(CO)CCCC4)c2-c2nnn[nH]2)CCCCC3)ccn1] | ESP [M + H]$^+$: 405.6 | W | Ex. 94 |
| 208 | (1-(4-(3-Chlorophenyl)-3-(1H-tetrazol-5-yl)-6,7,8,9-tetrahydro-5H-cyclohepta[b]pyridin-2-yl)cyclopentyl)methanol | 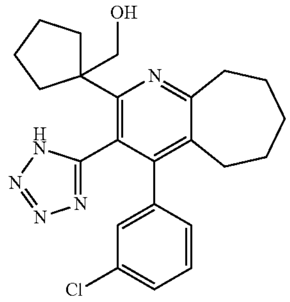 [SMILES: OCC1(c2nc3c(c(-c4cccc(Cl)c4)c2-c2nnn[nH]2)CCCCC3)CCCC1] | ESP [M + H]$^+$: 424.5 | W | Ex. 190 |

-continued

| Ex. | Name | Structure | MS | Method | Starting Material |
|---|---|---|---|---|---|
| 209 | (1-(4-(4-Fluorophenyl)-3-(1H-tetrazol-5-yl)-6,7,8,9-tetrahydro-5H-cyclohepta[b]pyridin-2-yl)cyclopentyl)methanol | 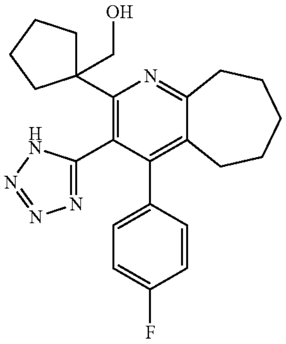 [SMILES: OCC1(c2nc3c(c(-c4ccc(F)cc4)c2-c2nnn[nH]2)CCCCC3)CCCC1] | ESP [M + H]$^+$: 408.6 | W | Ex. 187 |
| 210 | (S)-tert-Butyl 2-(4-phenyl-3-(1H-tetrazol-5-yl)-6,7,8,9-tetrahydro-5H-cyclohepta[b]pyridin-2-yl)pyrrolidine-1-carboxylate | 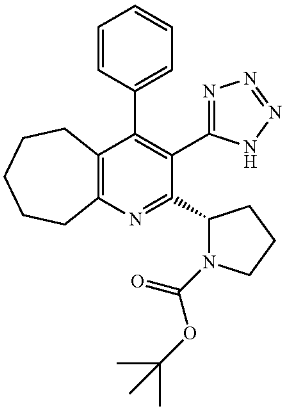 [SMILES: CC(C)(C)OC(=O)N1CCC[C@H]1c1nc2c(c(-c3ccccc3)c1-c1nnn[nH]1)CCCCC2] | ESP [M + H]$^+$: 461.7 | C | N210 |
| 212 | 2-Cyclopentyl-4-phenyl-3-(1H-tetrazol-5-yl)-7,8-dihydro-5H-pyrido[2,3-c]azepin-9(6H)-one | 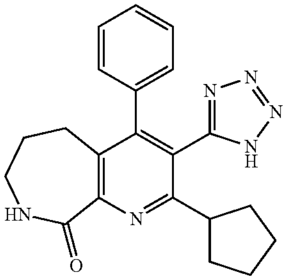 [SMILES: O=C1NCCCc2c1nc(C1CCCC1)c(-c1nnn[nH]1)c2-c1ccccc1] | ESP [M + H]$^+$: 375.6 | C | N212 |
| 213 | 2-(1-Methoxy-2-methylpropan-2-yl)-6,6-dimethyl-4-(1-methyl-1H-pyrazol-5-yl)-3-(2H-tetrazol-5-yl)-5,6,7,8-tetrahydroquinoline | 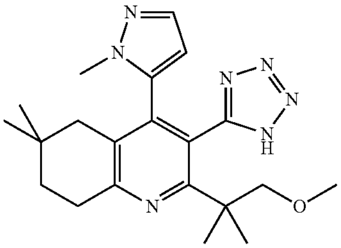 | ESP [M + H]$^+$: 396.6 | C | N213 |
| 214 | 6,6-Dimethyl-4-(1-methyl-1H-pyrazol-5-yl)-2-tert-pentyl-3-(2H-tetrazol-5-yl)-5,6,7,8-tetrahydroquinoline | 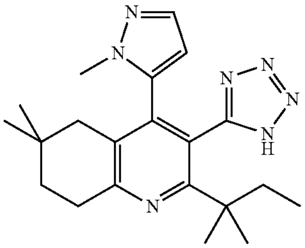 [SMILES: CCC(C)(C)c1nc2c(c(-c3ccnn3C)c1-c1nnn[nH]1)CC(C)(C)CC2] | ESP [M + H]$^+$: 380.6 | C | N214 |

-continued

| Ex. | Name | Structure | MS | Method | Starting Material |
|---|---|---|---|---|---|
| 215 | 2-(1-Methoxy-2-methylpropan-2-yl)-6,6-dimethyl-4-(2-methylpyridin-4-yl)-3-(2H-tetrazol-5-yl)-5,6,7,8-tetrahydroquinoline | 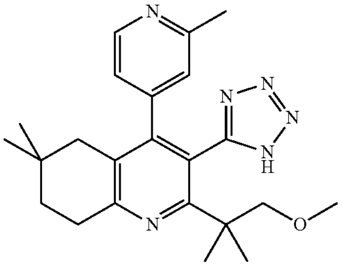 | ESP $[M + H]^+$: 407.6 | C | N215 |
| 216 | 2-(1-(Methoxymethyl (cyclopentyl)-4-phenyl-3-(2H-tetrazol-5-yl)-5,6,7,8-tetrahydroquinoline | 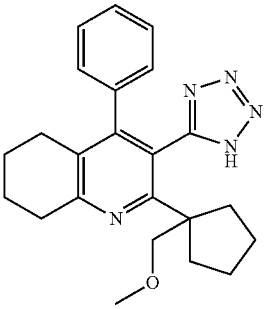 | ESP $[M + H]^+$: 309.6 | C | N216 |
| 217 | 6,6-Difluoro-2-(1-(methoxymethyl) cyclopentyl)-4-phenyl-3-(2H-tetrazol-5-yl)-5,6,7,8-tetrahydroquinoline | 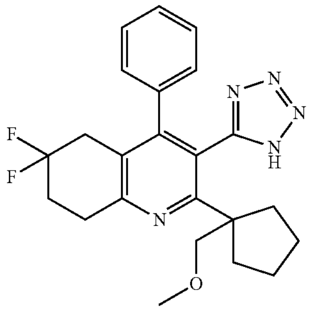 [SMILES: COCC1(c2nc3c(c(-c4ccccc4)c2-c2nnn[nH]2)CC(F)(F)CC3)CCCC1] | ESP $[M + H]^+$: 426.5 | C | N217 |
| 218 | 6,6-Difluoro-2-(1-methoxymethyl-cyclohexyl)-4-phenyl-3-(1H-tetrazol-5-yl)-5,6,7,8-tetrahydro-quinoline | 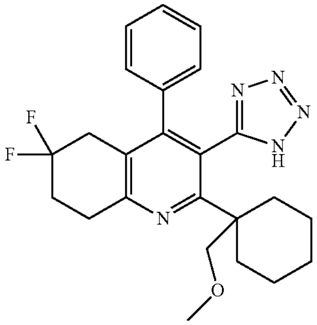 [SMILES: COCC1(c2nc3c(c(-c4ccccc4)c2-c2nnn[nH]2)CC(F)(F)CC3)CCCCC1] | ESP $[M + H]^+$: 440.7 | C | N218 |
| 219 | 6,6-Difluoro-2-(1-(methoxymethyl) cyclopentyl)-4-(2-methylpyridin-4-yl)-3-(2H-tetrazol-5-yl)-5,6,7,8-tetrahydroquinoline | 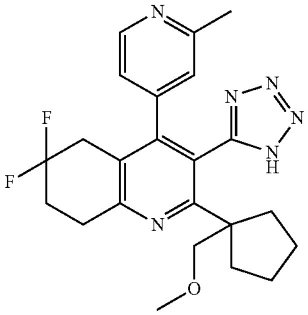 [SMILES: COCC1(c2nc3c(c(-c4ccnc(C)c4)c2-c2nnn[nH]2)CC(F)(F)CC3)CCCC1] | ESP $[M + H]^+$: 441.7 | C | N219 |

-continued

| Ex. | Name | Structure | MS | Method | Starting Material |
|---|---|---|---|---|---|
| 220 | 2-(4-Methyltetrahydro-2H-pyran-4-yl)-4-phenyl-3-(2H-tetrazol-5-yl)-5,6,7,8-tetrahydroquinoline | 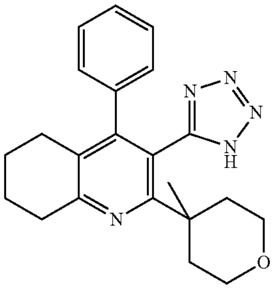 [SMILES: CC1(c2nc3c(c(-c4ccccc4)c2-c2nnn[nH]2)CCCC3)CCOCC1] | ESP [M + H]$^+$: 376.6 | C | N220 |
| 221 | 6,6-Difluoro-2-(4-methyltetrahydro-2H-pyran-4-yl)-4-phenyl-3-(2H-tetrazol-5-yl)-5,6,7,8-tetrahydroquinoline | 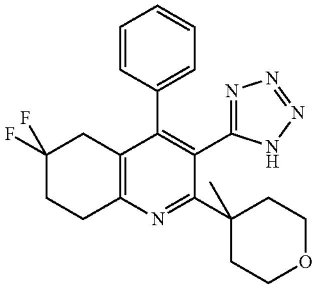 [SMILES: CC1(c2nc3c(c(-c4ccccc4)c2-c2nnn[nH]2)CC(F)(F)CC3)CCOCC1] | ESP [M + H]$^+$: 412.6 | C | N221 |
| 222 | 2-(1-(Methoxymethyl) cyclopentyl)-6-methyl-4-(2-methylpyridin-4-yl)-3-(2H-tetrazol-5-yl)-5,6,7,8-tetrahydroquinoline | 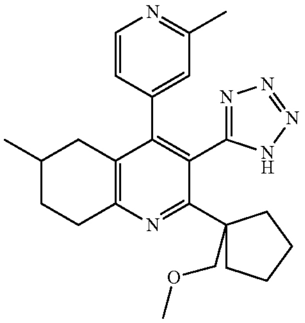 [SMILES: COCC1(c2nc3c(c(-c4ccnc(C)c4)c2-c2nnn[nH]2)CC(C)CC3)CCCC1] | ESP [M + H]$^+$: 419.6 | C | N222 |
| 223 | 2-(1-(Methoxymethyl) cyclohexyl)-4-phenyl-3-(2H-tetrazol-5-yl)-5,6,7,8-tetrahydroquinoline | 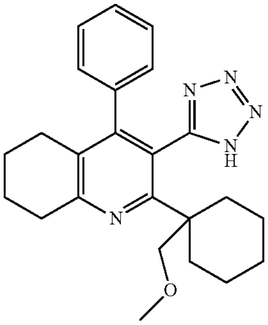 [SMILES: COCC1(c2nc3c(c(-c4ccccc4)c2-c2nnn[nH]2)CCCC3)CCCCC1] | ESP [M + H]$^+$: 404.6 | C | N223 |
| 224 | 6,6-Difluoro-2-(1-(methoxymethyl) cyclopentyl)-4-(1-methyl-1H-pyrazol-5-yl)-3-(2H-tetrazol-5-yl)-5,6,7,8-tetrahydroquinoline | 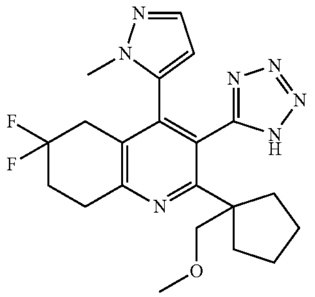 [SMILES: COCC1(c2nc3c(c(-c4ccnn4C)c2-c2nnn[nH]2)CC(F)(F)CC3)CCCC1] | ESP [M + H]$^+$: 430.6 | C | N224 |

-continued

| Ex. | Name | Structure | MS | Method | Starting Material |
|---|---|---|---|---|---|
| 225 | 2-(1-(Methoxymethyl) cyclopentyl)-6,6-dimethyl-4-(1-methyl-1H-pyrazol-5-yl)-3-(2H-tetrazol-5-yl)-5,6,7,8-tetrahydroquinoline | 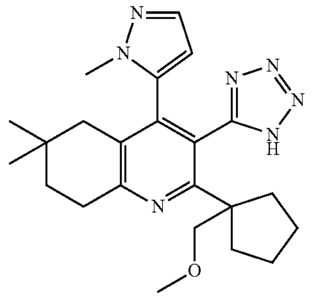 [SMILES: COCC1(c2nc3c(c(-c4ccnn4C)c2-c2nnn[nH]2)CC(C)(C)CC3)CCCC1] | ESP $[M + H]^+$: 422.6 | C | N225 |
| 226 | 2-(2-Methyltetrahydrofuran-2-yl)-4-phenyl-3-(2H-tetrazol-5-yl)-5,6,7,8-tetrahydroquinoline | 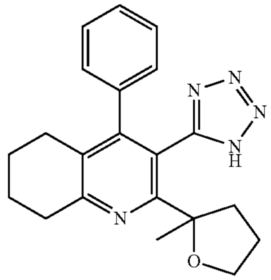 [SMILES: CC1(c2nc3c(c(-c4ccccc4)c2-c2nnn[nH]2)CCCC3)CCCO1] | ESP $[M + H]^+$: 362.6 | C | N226 |
| 227 | 6,6-Difluoro-2-(2-methyltetrahydrofuran-2-yl)-4-phenyl-3-(2H-tetrazol-5-yl)-5,6,7,8-tetrahydroquinoline | 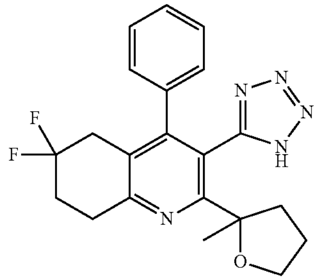 [SMILES: CC1(c2nc3c(c(-c4ccccc4)c2-c2nnn[nH]2)CC(F)(F)CC3)CCCO1] | ESP $[M + H]^+$: 398.6 | C | N227 |
| 228 | 6,6-Dimethyl-2-(2-methyltetrahydrofuran-2-yl)-4-phenyl-3-(2H-tetrazol-5-yl)-5,6,7,8-tetrahydroquinoline | 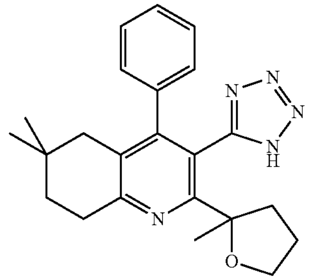 [SMILES: CC1(C)CCc2nc(C3(C)CCCO3)c(-c3nnn[nH]3)c(-c3ccccc3)c2C1] | ESP $[M + H]^+$: 390.7 | C | N228 |
| 229 | 4-(1-Methyl-1H-pyrazol-5-yl)-2-(2-methyltetrahydrofuran-2-yl)-3-(2H-tetrazol-5-yl)-5,6,7,8-tetrahydroquinoline | 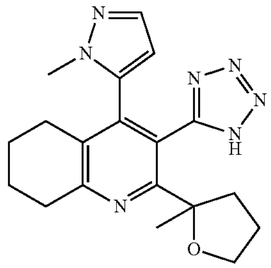 [SMILES: Cn1nccc1-c1c2c(nc(C3(C)CCCO3)c1-c1nnn[nH]1)CCCC2] | ESP $[M + H]^+$: 366.6 | C | N229 |

-continued

| Ex. | Name | Structure | MS | Method | Starting Material |
|---|---|---|---|---|---|
| 230 | 6,6-Dimethyl-4-(1-methyl-1H-pyrazol-5-yl)-2-(2-methyltetrahydrofuran-2-yl)-3-(2H-tetrazol-5-yl)-5,6,7,8-tetrahydroquinoline | 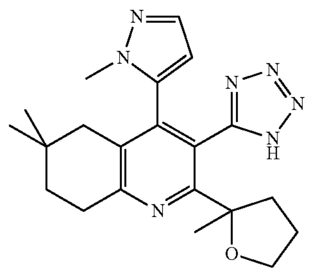 [SMILES: Cn1nccc1-c1c2c(nc(C3(C)CCCO3)c1-c1nnn[nH]1)CCC(C)(C)C2] | ESP [M + H]$^+$: 394.6 | C | N230 |
| 237 | 2-(1-(Methoxymethyl) cyclopentyl)-4-(1-methyl-1H-pyrazol-5-yl)-3-(2H-tetrazol-5-yl)-5,6,7,8-tetrahydroquinoline | 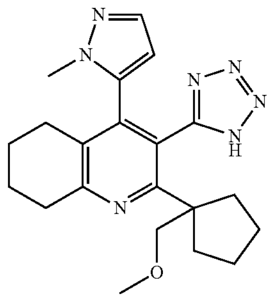 [SMILES: COCC1(c2nc3c(c(-c4ccnn4C)c2-c2nnn[nH]2)CCCC3)CCCC1] | ESP [M + H]$^+$: 394.7 | C | N237 |
| 238 | 2-(1-(Methoxymethyl) cyclohexyl)-4-(1-methyl-1H-pyrazol-5-yl)-3-(2H-tetrazol-5-yl)-5,6,7,8-tetrahydroquinoline | 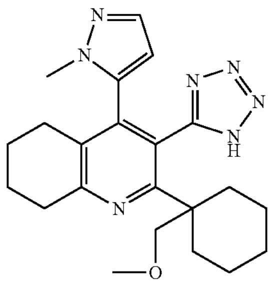 [SMILES: COCC1(c2nc3c(c(-c4ccnn4C)c2-c2nnn[nH]2)CCCC3)CCCCC1] | ESP [M + H]$^+$: 408.7 | C | N238 |
| 239 | 2-(1-(Methoxymethyl) cyclohexyl)-6,6-dimethyl-4-(1-methyl-1H-pyrazol-5-yl)-3-(2H-tetrazol-5-yl)-5,6,7,8-tetrahydroquinoline | 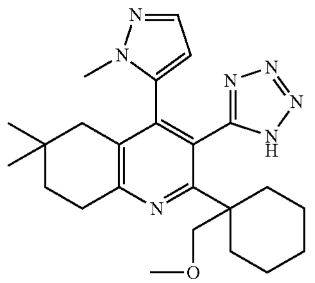 [SMILES: COCC1(c2nc3c(c(-c4ccnn4C)c2-c2nnn[nH]2)CC(C)(C)CC3)CCCCC1] | ESP [M + H]$^+$: 436.8 | C | N239 |
| 240 | 6,6-Difluoro-2-(1-(methoxymethyl)cyclohexyl)-4-(1-methyl-1H-pyrazol-5-yl)-3-(2H-tetrazol-5-yl)-5,6,7,8-tetrahydroquinoline | 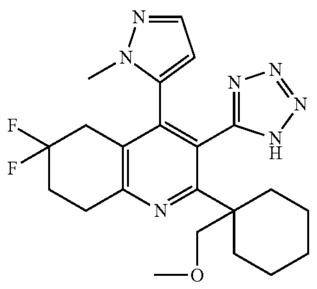 [SMILES: COCC1(c2nc3c(c(-c4ccnn4C)c2-c2nnn[nH]2)CC(F)(F)CC3)CCCCC1] | ESP [M + H]$^+$: 444.6 | C | N240 |

-continued

| Ex. | Name | Structure | MS | Method | Starting Material |
|---|---|---|---|---|---|
| 241 | 6,6-Difluoro-4-(1-methyl-1H-pyrazol-5-yl)-2-(2-methyltetrahydrofuran-2-yl)-3-(2H-tetrazol-5-yl)-5,6,7,8-tetrahydroquinoline | 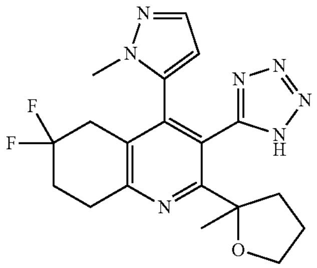 [SMILES: Cn1nccc1-c1c2c(nc(C3(C)CCCO3)c1-c1nnn[nH]1)CCC(F)(F)C2] | ESP [M + H]+: 402.7 | C | N241 |
| 242 | 2-(2-(Methoxymethyl) tetrahydrofuran-2-yl)-4-phenyl-3-(2H-tetrazol-5-yl)-5,6,7,8-tetrahydroquinoline | 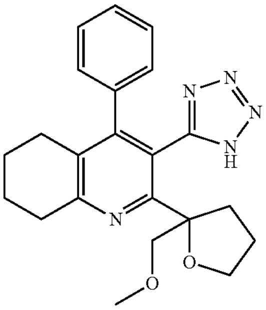 [SMILES: COCC1(c2nc3c(c(-c4ccccc4)c2-c2nnn[nH]2)CCCC3)CCCO1] | ESP [M + H]+: 392.7 | C | N242 |
| 243 | 2-(1-(Methoxymethyl) cyclohexyl)-4-(1-methyl-1H-pyrazol-4-yl)-3-(2H-tetrazol-5-yl)-5,6,7,8-tetrahydroquinoline | 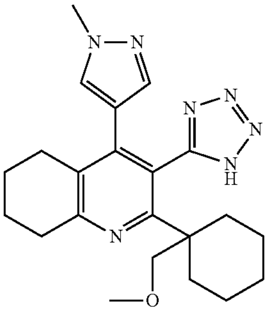 [SMILES: COCC1(c2nc3c(c(-c4cnn(C)c4)c2-c2nnn[nH]2)CCCC3)CCCCC1] | ESP [M + H]+: 408.6 | C | N243 |
| 244 | 2-(2-(Methoxymethyl) tetrahydrofuran-2-yl)-6,6-dimethyl-4-phenyl-3-(2H-tetrazol-5-yl)-5,6,7,8-tetrahydroquinoline | 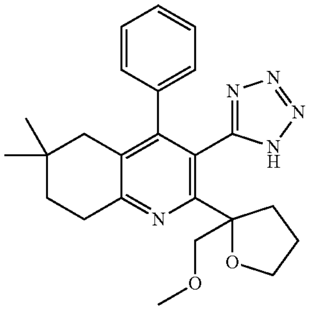 [SMILES: COCC1(c2nc3c(c(-c4ccccc4)c2-c2nnn[nH]2)CC(C)(C)CC3)CCCO1] | ESP [M + H]+: 420.6 | C | N244 |
| 245 | 6,6-Difluoro-2-(2-(methoxymethyl) tetrahydrofuran-2-yl)-4-phenyl-3-(2H-tetrazol-5-yl)-5,6,7,8-tetrahydroquinoline | 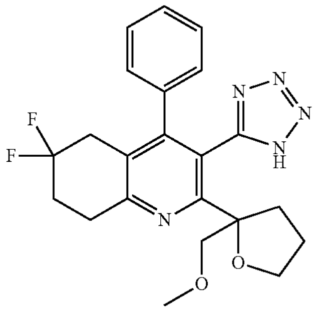 [SMILES: COCC1(c2nc3c(c(-c4ccccc4)c2-c2nnn[nH]2)CC(F)(F)CC3)CCCO1] | ESP [M + H]+: 428.6 | C | N245 |

-continued

| Ex. | Name | Structure | MS | Method | Starting Material |
|---|---|---|---|---|---|
| 246 | 2-(2-Ethyltetrahydrofuran-2-yl)-4-phenyl-3-(2H-tetrazol-5-yl)-5,6,7,8-tetrahydroquinoline | 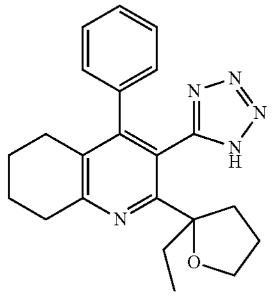 [SMILES: CCC1(c2nc3c(c(-c4ccccc4)c2-c2nnn[nH]2)CCCC3)CCCO1] | ESP [M + H]$^+$: 376.5 | C | N246 |
| 247 | 2-(2-Ethyltetrahydrofuran-2-yl)-6,6-dimethyl-4-phenyl-3-(2H-tetrazol-5-yl)-5,6,7,8-tetrahydroquinoline | 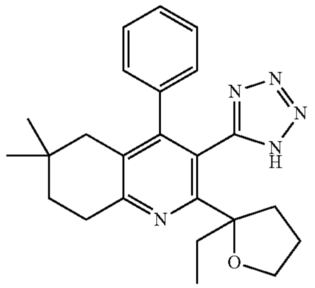 [SMILES: CCC1(c2nc3c(c(-c4ccccc4)c2-c2nnn[nH]2)CC(C)(C)CC3)CCCO1] | ESP [M + H]$^+$: 404.6 | C | N247 |
| 248 | 2-(2-Ethyltetrahydrofuran-2-yl)-6,6-difluoro-4-phenyl-3-(2H-tetrazol-5-yl)-5,6,7,8-tetrahydroquinoline | 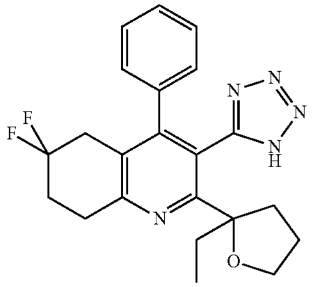 [SMILES: CCC1(c2nc3c(c(-c4ccccc4)c2-c2nnn[nH]2)CC(F)(F)CC3)CCCO1] | ESP [M + H]$^+$: 412.5 | C | N248 |
| 255 | 2-(2-Ethyltetrahydrofuran-2-yl)-4-(1-methyl-1H-pyrazol-5-yl)-3-(2H-tetrazol-5-yl)-5,6,7,8-tetrahydroquinoline | 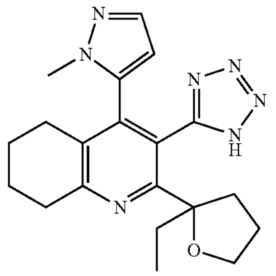 [SMILES: CCC1(c2nc3c(c(-c4ccnn4C)c2-c2nnn[nH]2)CCCC3)CCCO1] | ESP [M + H]$^+$: 380.6 | C | N255 |
| 256 | 2-(1-(Methoxymethyl) cyclopentyl)-4-(1-methyl-1H-pyrazol-4-yl)-3-(2H-tetrazol-5-yl)-5,6,7,8-tetrahydroquinoline | 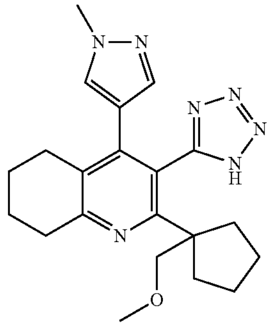 [SMILES: COCC1(c2nc3c(c(-c4cnn(C)c4)c2-c2nnn[nH]2)CCCC3)CCCC1] | ESP [M + H]$^+$: 394.6 | C | N256 |

-continued

| Ex. | Name | Structure | MS | Method | Starting Material |
|---|---|---|---|---|---|
| 257 | 4-(3-Chlorophenyl)-2-(2-(methoxymethyl) tetrahydrofuran-2-yl)-3-(2H-tetrazol-5-yl)-5,6,7,8-tetrahydroquinoline | 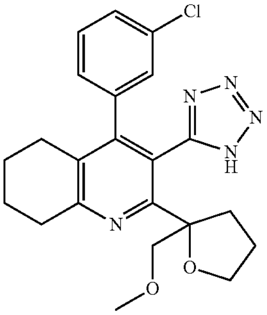 [SMILES: COCC1(c2nc3c(c(-c4cccc(Cl)c4)c2-c2nnn[nH]2)CCCC3)CCCO1] | ESP [M + H]$^+$: 426.5 | C | N257 |
| 258 | 4-(3-Chlorophenyl)-2-(2-methyltetrahydrofuran-2-yl)-3-(2H-tetrazol-5-yl)-5,6,7,8-tetrahydroquinoline | 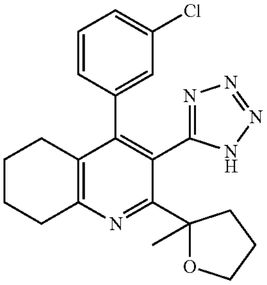 [SMILES: CC1(c2nc3c(c(-c4cccc(Cl)c4)c2-c2nnn[nH]2)CCCC3)CCCO1] | ESP [M + H]$^+$: 396.5 | C | N258 |
| 259 | 2-(2-(Methoxymethyl) tetrahydrofuran-2-yl)-4-(3-methoxyphenyl)-3-(2H-tetrazol-5-yl)-5,6,7,8-tetrahydroquinoline | 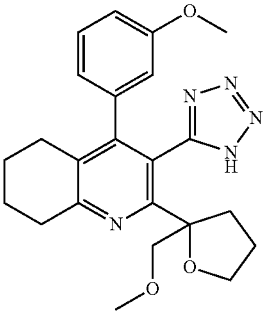 [SMILES: COCC1(c2nc3c(c(-c4cccc(OC)c4)c2-c2nnn[nH]2)CCCC3)CCCO1] | ESP [M + H]$^+$: 422.5 | C | N259 |
| 260 | 4-(4-Fluoro-3-methoxyphenyl)-2-(2-(methoxymethyl) tetrahydrofuran-2-yl)-3-(2H-tetrazol-5-yl)-5,6,7,8-tetrahydroquinoline | 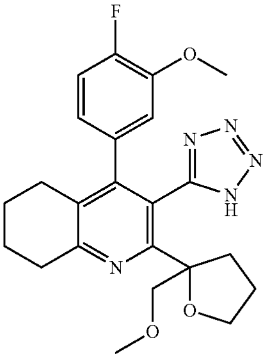 [SMILES: COCC1(c2nc3c(c(-c4ccc(F)c(OC)c4)c2-c2nnn[nH]2)CCCC3)CCCO1] | ESP [M + H]$^+$: 440.5 | C | N260 |

-continued

| Ex. | Name | Structure | MS | Method | Starting Material |
|---|---|---|---|---|---|
| 261 | 2-(1-(Methylsulfonylmethyl) cyclopentyl)-4-phenyl-3-(2H-tetrazol-5-yl)-5,6,7,8-tetrahydroquinoline | 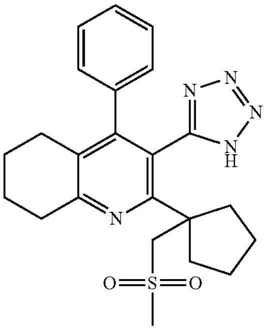 [SMILES: CS(=O)(=O)CC1(c2nc3c(c(-c4ccccc4)c2-c2nnn[nH]2)CCCC3)CCCC1] | ESP $[M + H]^+$: 438.5 | C | N261 |
| 264 | 2-(1-(Methoxymethyl) cyclopentyl)-4-(3-(methylsulfonyl)phenyl)-3-(2H-tetrazol-5-yl)-5,6,7,8-tetrahydroquinoline | 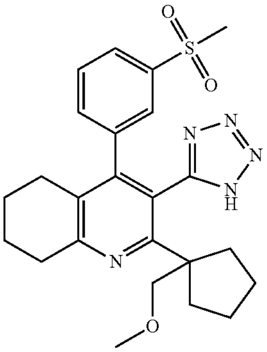 [SMILES: COCC1(c2nc3c(c(-c4cccc(S(C)(=O)=O)c4)c2-c2nnn[nH]2)CCCC3)CCCC1] | ESP $[M + H]^+$: 468.5 | C | N264 |
| 265 | 2-(1-(Methoxymethyl) cyclopentyl)-4-(3-methoxyphenyl)-3-(2H-tetrazol-5-yl)-5,6,7,8-tetrahydroquinoline | 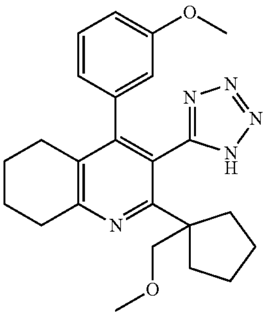 [SMILES: COCC1(c2nc3c(c(-c4cccc(OC)c4)c2-c2nnn[nH]2)CCCC3)CCCC1] | ESP $[M + H]^+$: 420.6 | C | N265 |
| 266 | 4-(2-Fluoro-5-methoxyphenyl)-2-(2-(methoxymethyl) tetrahydrofuran-2-yl)-3-(2H-tetrazol-5-yl)-5,6,7,8-tetrahydroquinoline | 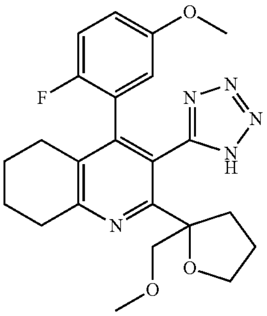 [SMILES: COCC1(c2nc3c(c(-c4cc(OC)ccc4F)c2-c2nnn[nH]2)CCCC3)CCCO1] | ESP $[M + H]^+$: 440.5 | C | N266 |

-continued

| Ex. | Name | Structure | MS | Method | Starting Material |
|---|---|---|---|---|---|
| 268 | 2-(1-(Ethoxymethyl) cyclopentyl)-4-phenyl-3-(2H-tetrazol-5-yl)-5,6,7,8-tetrahydroquinoline | 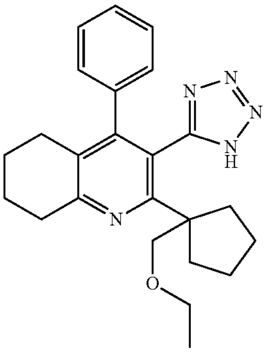 [SMILES: CCOCC1(c2nc3c(c(-c4ccccc4)c2-c2nnn[nH]2)CCCC3)CCCC1] | ESP [M + H]$^+$: 404.6 | C | N268 |
| 269 | 4-(3-Chlorophenyl)-2-(2-(methoxymethyl) tetrahydrofuran-2-yl)-6,6-dimethyl-3-(2H-tetrazol-5-yl)-5,6,7,8-tetrahydroquinoline | 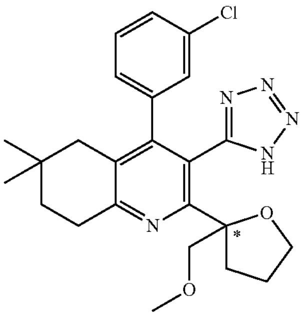 [SMILES: COCC1(c2nc3c(c(-c4cccc(Cl)c4)c2-c2nnn[nH]2)CC(C)(C)CC3)CCCO1] | ESP [M + H]$^+$: 454.5 | C | N269 |
| 270 | 4-(3-Chlorophenyl)-2-(2-(methoxymethyl) tetrahydrofuran-2-yl)-6,6-dimethyl-3-(2H-tetrazol-5-yl)-5,6,7,8-tetrahydroquinoline | 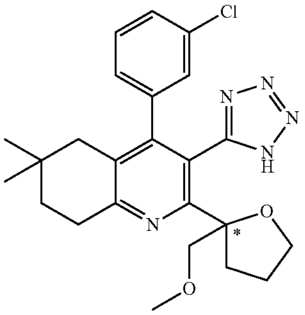 [SMILES: COCC1(c2nc3c(c(-c4cccc(Cl)c4)c2-c2nnn[nH]2)CC(C)(C)CC3)CCCO1] | ESP [M + H]$^+$: 454.5 | C | N270 |
| 271 | 2-(3,3-Difluorocyclobutyl)-4-(1-methyl-1H-pyrazol-4-yl)-3-(1H-tetrazol-5-yl)-6,7,8,9-tetrahydro-5H-cyclohepta[b]pyridine | 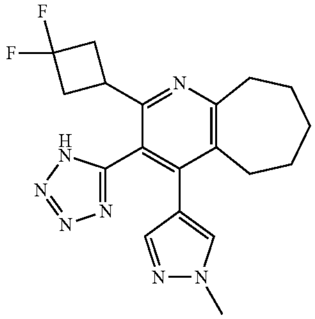 [SMILES: Cn1cc(-c2c3c(nc(C4CC(F)(F)C4)c2-c2nnn[nH]2)CCCCC3)cn1] | ESP [M + H]$^+$: 386.5 | C | N271 |

-continued

| Ex. | Name | Structure | MS | Method | Starting Material |
|---|---|---|---|---|---|
| 272 | 2-(1,5-Dimethyl-1H-pyrazol-4-yl)-4-phenyl-3-(2H-tetrazol-5-yl)-6,7,8,9-tetrahydro-5H-cyclohepta[b]pyridine | 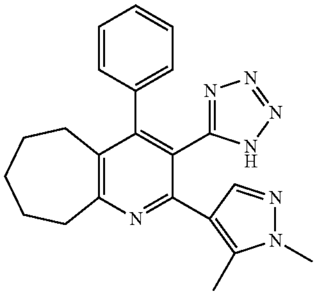 [SMILES: Cc1c(-c2nc3c(c(-c4ccccc4)c2-c2nnn[nH]2)CCCCC3)cnn1C] | ESN [M − H]$^-$: 384.6 | C | N272 |
| 273 | 2-tert-Butyl-4-(1-methyl-1H-pyrazol-4-yl)-3-(1H-tetrazol-5-yl)-6,7,8,9-tetrahydro-5H-cyclohepta[b]pyridine | 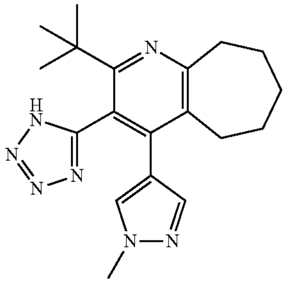 [SMILES: Cn1cc(-c2c3c(nc(C(C)(C)C)c2-c2nnn[nH]2)CCCCC3)cn1] | ESP [M + H]$^+$: 352.5 | C | N273 |
| 274 | 2-(3,3-Difluorocyclobutyl)-4-(2-methylpyridin-4-yl)-3-(1H-tetrazol-5-yl)-6,7,8,9-tetrahydro-5H-cyclohepta[b]pyridine | 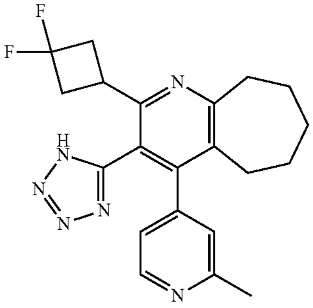 [SMILES: Cc1cc(-c2c3c(nc(C4CC(F)(F)C4)c2-c2nnn[nH]2)CCCCC3)ccn1] | ESP [M + H]$^+$: 397.5 | C | N274 |
| 275 | 2-sec-Butyl-4-(1-methyl-1H-pyrazol-4-yl)-3-(1H-tetrazol-5-yl)-6,7,8,9-tetrahydro-5H-cyclohepta[b]pyridine | 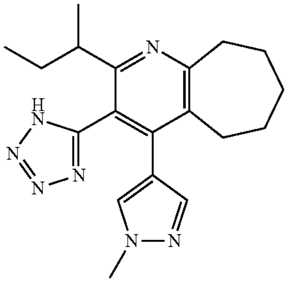 [SMILES: CCC(C)c1nc2c(c(-c3cnn(C)c3)c1-c1nnn[nH]1)CCCCC2] | ESP [M + H]$^+$: 352.6 | C | N275 |
| 276 | 2-tert-Butyl-6,6-difluoro-4-(2-methyl-pyridin-4-yl)-3-(1H-tetrazol-5-yl)-5,6,7,8-tetrahydro-quinoline | 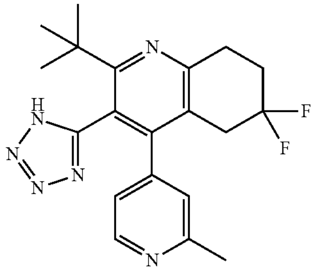 [SMILES: Cc1cc(-c2c3c(nc(C(C)(C)C)c2-c2nnn[nH]2)CCC(F)(F)C3)ccn1] | ESP [M + H]$^+$: 385.5 | C | N276 |

-continued

| Ex. | Name | Structure | MS | Method | Starting Material |
|---|---|---|---|---|---|
| 277 | 2-tert-Butyl-6,6-difluoro-4-(1-methyl-1H-pyrazol-4-yl)-3-(1H-tetrazol-5-yl)-5,6,7,8-tetrahydro-quinoline | 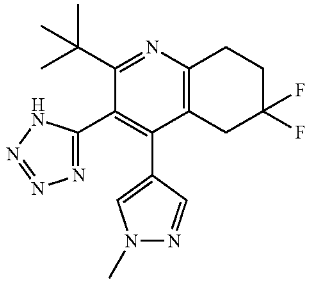 [SMILES: Cn1cc(-c2c3c(nc(C(C)(C)C)c2-c2nnn[nH]2)CCC(F)(F)C3)cn1] | ESP $[M + H]^+$: 374.5 | C | N277 |
| 278 | 2-tert-Butyl-6,6-difluoro-4-(2-methyl-2H-pyrazol-3-yl)-3-(1H-tetrazol-5-yl)-5,6,7,8-tetrahydro-quinoline | 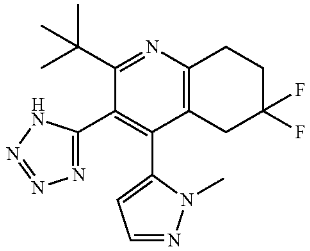 [SMILES: Cn1nccc1-c1c2c(nc(C(C)(C)C)c1-c1nnn[nH]1)CCC(F)(F)C2] | ESP $[M + H]^+$: 374.5 | C | N278 |
| 279 | 2-tert-Butyl-4-phenyl-3-(1H-tetrazol-5-yl)-7,8-dihydro-5H-thiopyrano[4,3-b]pyridine | 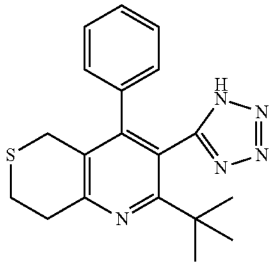 [SMILES: CC(C)(C)c1nc2c(c(-c3ccccc3)c1-c1nnn[nH]1)CSCC2] | ESP $[M + H]^+$: 352.6 | C | N279 |
| 280 | 2-tert-Butyl-8,8-dimethyl-4-phenyl-3-(1H-tetrazol-5-yl)-5,6,7,8-tetrahydroquinoline | 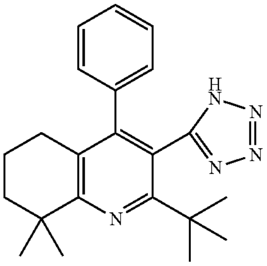 [SMILES: CC(C)(C)c1nc2c(c(-c3ccccc3)c1-c1nnn[nH]1)CCCC2(C)C] | ESP $[M + H]^+$: 362.6 | C | N280 |
| 281 | 2-tert-Butyl-7,7-dimethyl-4-phenyl-3-(1H-tetrazol-5-yl)-6,7-dihydro-5H-cyclopenta[b]pyridine | 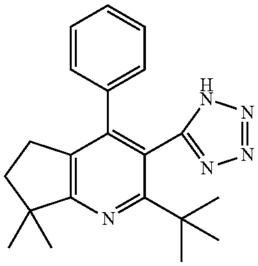 [SMILES: CC(C)(C)c1nc2c(c(-c3ccccc3)c1-c1nnn[nH]1)CCC2(C)C] | ESP $[M + H]^+$: 348.6 | C | N281 |

-continued

| Ex. | Name | Structure | MS | Method | Starting Material |
|---|---|---|---|---|---|
| 282 | 2-tert-Butyl-8,8-dimethyl-4-(2-methylpyridin-4-yl)-3-(1H-tetrazol-5-yl)-5,6,7,8-tetrahydroquinoline | 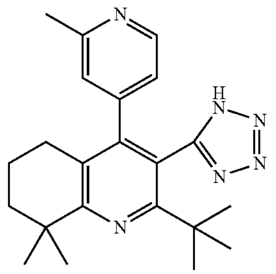 [SMILES: Cc1cc(-c2c3c(nc(C(C)(C)C)c2-c2nnn[nH]2)C(C)(C)CCC3)ccn1] | ESP $[M + H]^+$: 377.6 | C | N282 |
| 283 | 2-tert-Butyl-8,8-dimethyl-4-(1-methyl-1H-pyrazol-4-yl)-3-(1H-tetrazol-5-yl)-5,6,7,8-tetrahydroquinoline | 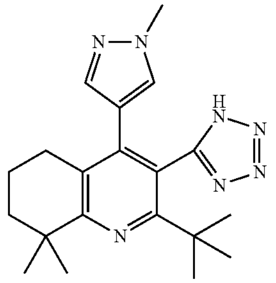 [SMILES: Cn1cc(-c2c3c(nc(C(C)(C)C)c2-c2nnn[nH]2)C(C)(C)CCC3)cn1] | ESP $[M + H]^+$: 366.2 | C | N283 |
| 284 | 2-(1-(Methoxymethyl) cyclobutyl)-4-phenyl-3-(1H-tetrazol-5-yl)-6,7,8,9-tetrahydro-5H-cyclohepta[b]pyridine | 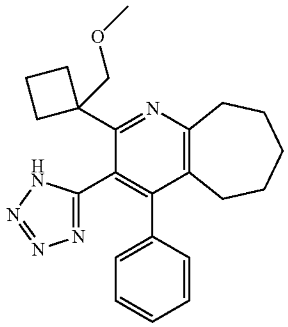 [SMILES: COCC1(c2nc3c(c(-c4ccccc4)c2-c2nnn[nH]2)CCCCC3)CCC1] | ESN $[M - H]^-$: 388.6 | C | N284 |
| 285 | 2-(1-(Methoxymethyl) cyclobutyl)-4-(2-methylpyridin-4-yl)-3-(1H-tetrazol-5-yl)-6,7,8,9-tetrahydro-5H-cyclohepta[b]pyridine | 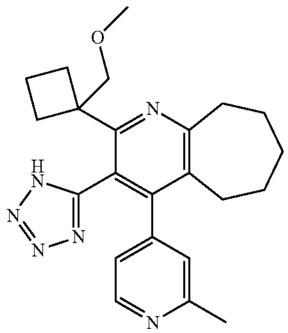 [SMILES: COCC1(c2nc3c(c(-c4ccnc(C)c4)c2-c2nnn[nH]2)CCCCC3)CCC1] | ESP $[M + H]^+$: 405.2 | C | N285 |
| 286 | 2-(1-(Methoxymethyl) cyclobutyl)-4-(1-methyl-1H-pyrazol-4-yl)-3-(1H-tetrazol-5-yl)-6,7,8,9-tetrahydro-5H-cyclohepta[b]pyridine | 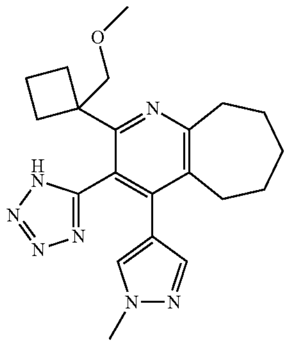 [SMILES: COCC1(c2nc3c(c(-c4cnn(C)c4)c2-c2nnn[nH]2)CCCCC3)CCC1] | ESP $[M + H]^+$: 394.6 | C | N286 |

-continued

| Ex. | Name | Structure | MS | Method | Starting Material |
|---|---|---|---|---|---|
| 287 | 2-(Perfluoroethyl)-4-phenyl-3-(1H-tetrazol-5-yl)-6,7,8,9-tetrahydro-5H-cyclohepta[b]pyridine | 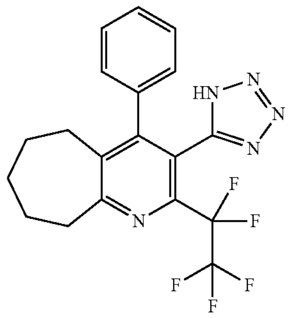 [SMILES: FC(F)(F)C(F)(F)c1nc2c(c(-c3ccccc3)c1-c1nnn[nH]1)CCCCC2] | ESN [M − H]⁻: 408.7 | C | N287 |
| 288 | 2-tert-Butyl-8,8-dimethyl-4-(1-methyl-1H-pyrazol-5-yl)-3-(1H-tetrazol-5-yl)-5,6,7,8-tetrahydroquinoline | 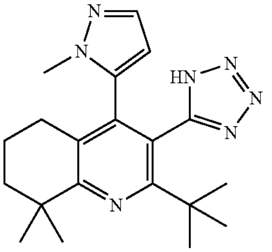 [SMILES: Cn1nccc1-c1c2c(nc(C(C)(C)C)c1-c1nnn[nH]1)C(C)(C)CCC2] | ESN [M − H]⁻: 364.8 | C | N288 |
| 289 | 2,4-Bis(2-methylpyridin-4-yl)-3-(1H-tetrazol-5-yl)-6,7,8,9-tetrahydro-5H-cyclohepta[b]pyridine triethylamine sal | 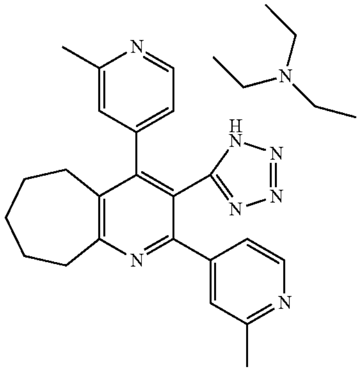 | ESP [M + H]⁺: 398.6 | C | N289 |
| 290 | 2-Isopropoxy-4-phenyl-3-(1H-tetrazol-5-yl)-6,7,8,9-tetrahydro-5H-cyclohepta[b]pyridine | 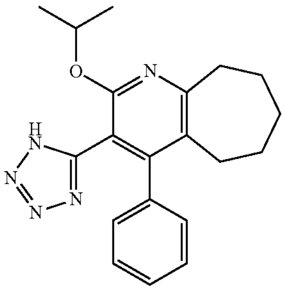 [SMILES: CC(C)Oc1nc2c(c(-c3ccccc3)c1-c1nnn[nH]1)CCCCC2] | ESN [M − H]⁻: 348.5 | C | N290 |
| 291 | 2-Methoxy-4-phenyl-3-(1H-tetrazol-5-yl)-6,7,8,9-tetrahydro-5H-cyclohepta[b]pyridine | 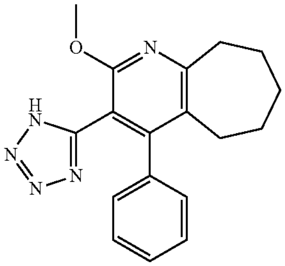 [SMILES: COc1nc2c(c(-c3ccccc3)c1-c1nnn[nH]1)CCCCC2] | ESP [M + H]⁺: 322.4 | C | N291 |

-continued

| Ex. | Name | Structure | MS | Method | Starting Material |
|---|---|---|---|---|---|
| 292 | 2-Ethoxy-4-phenyl-3-(1H-tetrazol-5-yl)-6,7,8,9-tetrahydro-5H-cyclohepta[b]pyridine | 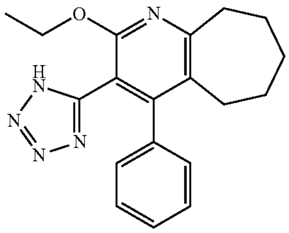 [SMILES: CCOc1nc2c(c(-c3ccccc3)c1-c1nnn[nH]1)CCCCC2] | ESP $[M + H]^+$: 336.5 | C | N292 |
| 293 | (S)-4-Phenyl-2-(tetrahydrofuran-3-yloxy)-3-(1H-tetrazol-5-yl)-6,7,8,9-tetrahydro-5H-cyclohepta[b]pyridine | 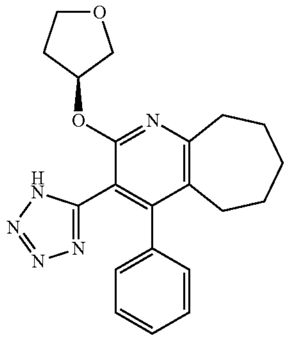 [SMILES: c1ccc(-c2c3c(nc(O[C@H]4CCOC4)c2-c2nnn[nH]2)CCCCC3)cc1] | ESP $[M + H]^+$: 378.6 | C | N293 |
| 294 | (R)-4-Phenyl-2-(tetrahydrofuran-3-yloxy)-3-(1H-tetrazol-5-yl)-6,7,8,9-tetrahydro-5H-cyclohepta[b]pyridine | 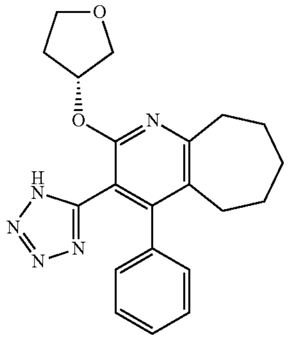 [SMILES: c1ccc(-c2c3c(nc(O[C@@H]4CCOC4)c2-c2nnn[nH]2)CCCCC3)cc1] | ESP $[M + H]^+$: 378.5 | C | N294 |
| 295 | 2-Ethoxy-4-(1-methyl-1H-pyrazol-4-yl)-3-(1H-tetrazol-5-yl)-6,7,8,9-tetrahydro-5H-cyclohepta[b]pyridine | 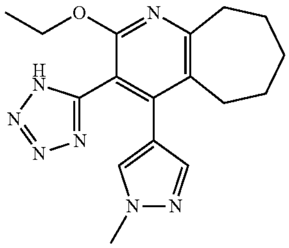 [SMILES: CCOc1nc2c(c(-c3cnn(C)c3)c1-c1nnn[nH]1)CCCCC2] | ESP $[M + H]^+$: 340.5 | C | N295 |
| 296 | 2-Isopropoxy-4-(1-methyl-1H-pyrazol-4-yl)-3-(1H-tetrazol-5-yl)-6,7,8,9-tetrahydro-5H-cyclohepta[b]pyridine | 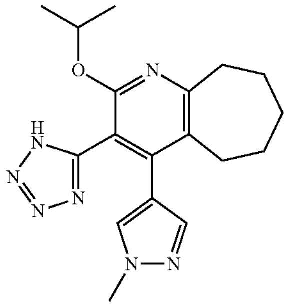 [SMILES: CC(C)Oc1nc2c(c(-c3cnn(C)c3)c1-c1nnn[nH]1)CCCCC2] | ESP $[M + H]^+$: 354.6 | C | N296 |

-continued

| Ex. | Name | Structure | MS | Method | Starting Material |
|---|---|---|---|---|---|
| 297 | 2-Ethoxy-4-(2-methylpyridin-4-yl)-3-(1H-tetrazol-5-yl)-6,7,8,9-tetrahydro-5H-cyclohepta[b]pyridine | 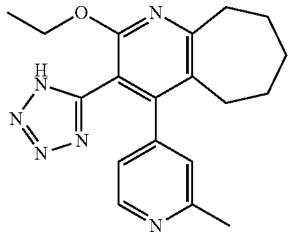 [SMILES: CCOc1nc2c(c(-c3ccnc(C)c3)c1-c1nnn[nH]1)CCCCC2] | ESP [M + H]$^+$: 351.5 | C | N297 |
| 298 | 2-(2-Methoxyethoxy)-4-phenyl-3-(1H-tetrazol-5-yl)-6,7,8,9-tetrahydro-5H-cyclohepta[b]pyridine | 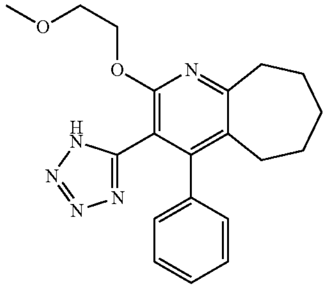 [SMILES: COCCOc1nc2c(c(-c3ccccc3)c1-c1nnn[nH]1)CCCCC2] | ESP [M + H]$^+$: 366.5 | C | N298 |
| 299 | 4-Phenyl-2-((tetrahydrofuran-2-yl)methoxy)-3-(1H-tetrazol-5-yl)-6,7,8,9-tetrahydro-5H-cyclohepta[b]pyridine | 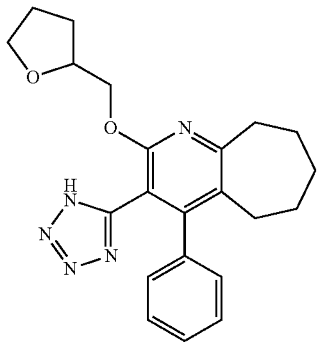 [SMILES: c1ccc(-c2c3c(nc(OCC4CCCO4)c2-c2nnn[nH]2)CCCCC3)cc1] | ESP [M + H]$^+$: 392.5 | C | N299 |
| 300 | 2-(3-Fluoropropoxy)-4-phenyl-3-(1H-tetrazol-5-yl)-6,7,8,9-tetrahydro-5H-cyclohepta[b]pyridine | 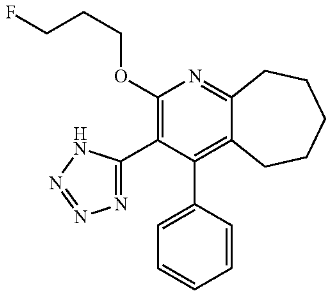 [SMILES: FCCCOc1nc2c(c(-c3ccccc3)c1-c1nnn[nH]1)CCCCC2] | ESP [M + H]$^+$: 368.5 | C | N300 |
| 301 | 2-(2,2-Difluoroethoxy)-4-phenyl-3-(1H-tetrazol-5-yl)-6,7,8,9-tetrahydro-5H-cyclohepta[b]pyridine | 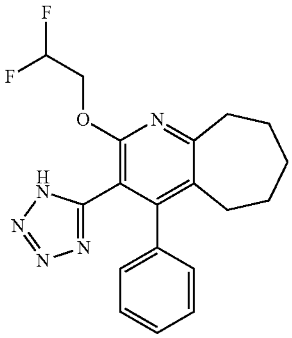 [SMILES: FC(F)COc1nc2c(c(-c3ccccc3)c1-c1nnn[nH]1)CCCCC2] | ESP [M + H]$^+$: 372.5 | C | N301 |

-continued

| Ex. | Name | Structure | MS | Method | Starting Material |
|---|---|---|---|---|---|
| 302 | (S)-4-Phenyl-2-(tetrahydrofuran-3-yloxy)-3-(1H-tetrazol-5-yl)-5,6,7,8-tetrahydroquinoline | 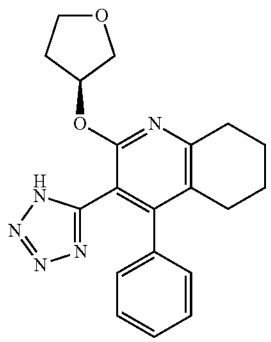 [SMILES: c1ccc(-c2c3c(nc(O[C@H]4CCOC4)c2-c2nnn[nH]2)CCCC3)cc1] | ESP [M + H]$^+$: 364.5 | C | N302 |
| 303 | 4-(2-Methylpyridin-4-yl)-2-(tetrahydro-2H-pyran-4-yloxy)-3-(1H-tetrazol-5-yl)-6,7,8,9-tetrahydro-5H-cyclohepta[b]pyridine | 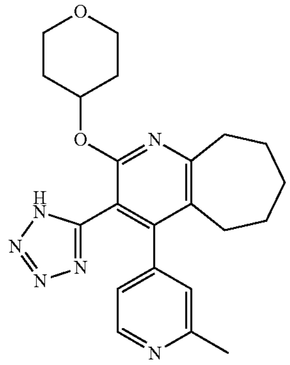 [SMILES: Cc1cc(-c2c3c(nc(OC4CCOCC4)c2-c2nnn[nH]2)CCCCC3)ccn1] | ESP [M + H]$^+$: 407.5 | C | N303 |
| 304 | (S)-4-(2-Methylpyridin-4-yl)-2-(tetrahydrofuran-3-yloxy)-3-(1H-tetrazol-5-yl)-6,7,8,9-tetrahydro-5H-cyclohepta[b]pyridine | 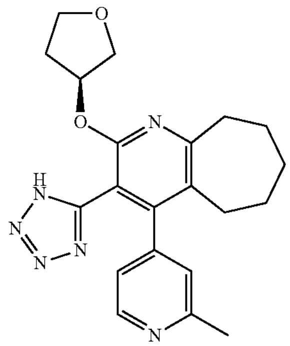 [SMILES: Cc1cc(-c2c3c(nc(O[C@H]4CCOC4)c2-c2nnn[nH]2)CCCCC3)ccn1] | ESP [M + H]$^+$: 393.5 | C | N304 |
| 305 | (S)-4-(2-Methylpyridin-4-yl)-2-(tetrahydrofuran-3-yloxy)-3-(1H-tetrazol-5-yl)-5,6,7,8-tetrahydroquinoline | 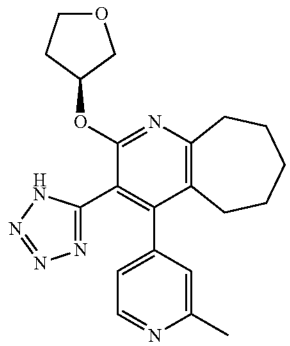 | ESP [M + H]$^+$: 379.5 | C | N305 |

-continued

| Ex. | Name | Structure | MS | Method | Starting Material |
|---|---|---|---|---|---|
| 306 | 2-(2-Methoxyethoxy)-3-(1H-tetrazol-5-yl)-4-(4-(trifluoromethyl)phenyl)-6,7,8,9-tetrahydro-5H-cyclohepta[b]pyridine | 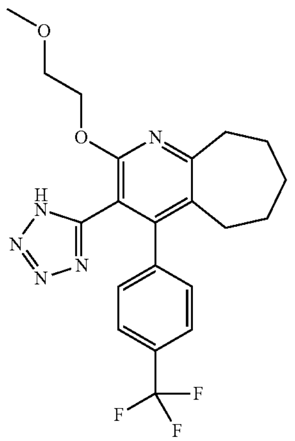 [SMILES: COCCOc1nc2c(c(-c3ccc(C(F)(F)F)cc3)c1-c1nnn[nH]1)CCCCC2] | ESP $[M + H]^+$: 434.5 | C | N306 |
| 307 | 4-(3-Fluorophenyl)-2-(2-methoxyethoxy)-3-(1H-tetrazol-5-yl)-6,7,8,9-tetrahydro-5H-cyclohepta[b]pyridine | 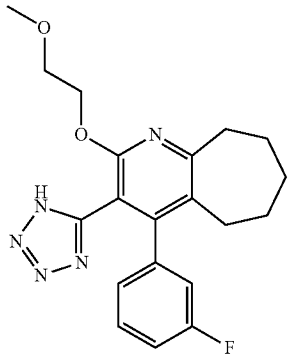 [SMILES: COCCOc1nc2c(c(-c3cccc(F)c3)c1-c1nnn[nH]1)CCCCC2] | ESP $[M + H]^+$: 384.5 | C | N307 |
| 308 | (S)-4-(3-Fluorophenyl)-2-(tetrahydrofuran-3-yloxy)-3-(1H-tetrazol-5-yl)-5,6,7,8-tetrahydroquinoline | 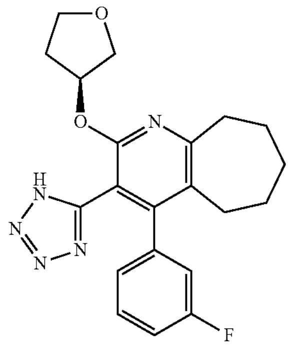 [SMILES: Fc1cccc(-c2c3c(nc(O[C@H]4CCOC4)c2-c2nnn[nH]2)CCCCC3)c1] | ESN $[M - H]^-$: 380.5 | C | N308 |
| 309 | 4-(3,5-Difluorophenyl)-2-(2-methoxyethoxy)-3-(1H-tetrazol-5-yl)-6,7,8,9-tetrahydro-5H-cyclohepta[b]pyridine | 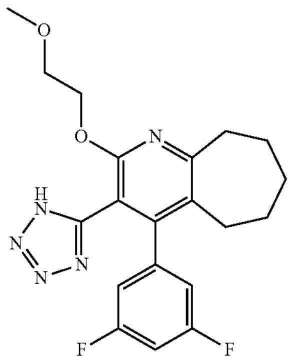 [SMILES: COCCOc1nc2c(c(-c3cc(F)cc(F)c3)c1-c1nnn[nH]1)CCCCC2] | ESP $[M + H]^+$: 402.5 | C | N309 |

-continued

| Ex. | Name | Structure | MS | Method | Starting Material |
|---|---|---|---|---|---|
| 310 | (S)-4-(3-Fluorophenyl)-2-(tetrahydrofuran-3-yloxy)-3-(1H-tetrazol-5-yl)-6,7,8,9-tetrahydro-5H-cyclohepta[b]pyridine | 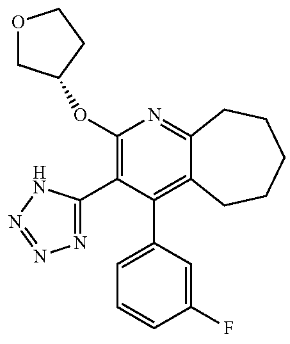 [SMILES: Fc1cccc(-c2c3c(nc(O[C@H]4CCOC4)c2-c2nnn[nH]2)CCCCC3)c1] | ESP $[M + H]^+$: 396.5 | C | N310 |
| 311 | (S)-4-(3,5-Difluorophenyl)-2-(tetrahydrofuran-3-yloxy)-3-(1H-tetrazol-5-yl)-6,7,8,9-tetrahydro-5H-cyclohepta[b]pyridine | 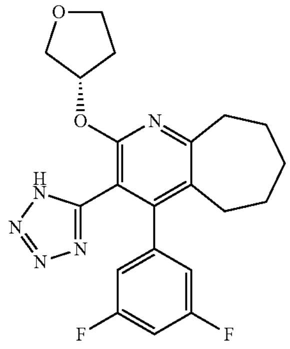 [SMILES: Fc1cc(F)cc(-c2c3c(nc(O[C@H]4CCOC4)c2-c2nnn[nH]2)CCCCC3)c1] | ESP $[M + H]^+$: 414.5 | C | N311 |
| 312 | 4-(2-Fluorophenyl)-2-((S)-tetrahydrofuran-3-yloxy)-3-(1H-tetrazol-5-yl)-6,7,8,9-tetrahydro-5H-cyclohepta[b]pyridine | 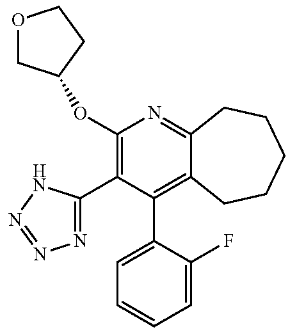 [SMILES: Fc1ccccc1-c1c2c(nc(O[C@H]3CCOC3)c1-c1nnn[nH]1)CCCCC2] | ESP $[M + H]^+$: 396.5 | C | N312 |
| 313 | 4-(2-Fluorophenyl)-2-(2-methoxyethoxy)-3-(1H-tetrazol-5-yl)-6,7,8,9-tetrahydro-5H-cyclohepta[b]pyridine | 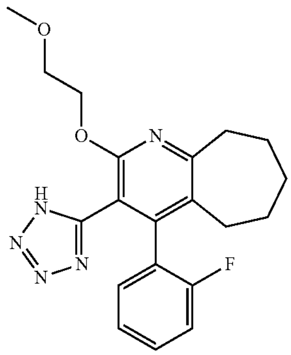 [SMILES: COCCOc1nc2c(c(-c3ccccc3F)c1-c1nnn[nH]1)CCCCC2] | ESP $[M + H]^+$: 384.4 | C | N313 |

-continued

| Ex. | Name | Structure | MS | Method | Starting Material |
|---|---|---|---|---|---|
| 314 | (S)-2-(Tetrahydrofuran-3-yloxy)-3-(1H-tetrazol-5-yl)-4-(thiophen-2-yl)-6,7,8,9-tetrahydro-5H-cyclohepta[b]pyridine | 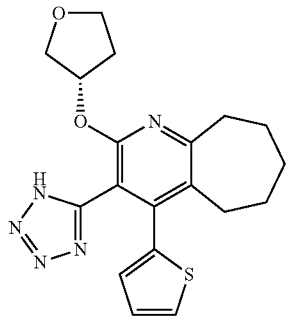 [SMILES: c1csc(-c2c3c(nc(O[C@H]4CCOC4)c2-c2nnn[nH]2)CCCCC3)c1] | ESP [M + H]$^+$: 384.4 | C | N314 |
| 315 | 2-(3-Fluoropropoxy)-3-(1H-tetrazol-5-yl)-4-(thiophen-2-yl)-6,7,8,9-tetrahydro-5H-cyclohepta[b]pyridine | 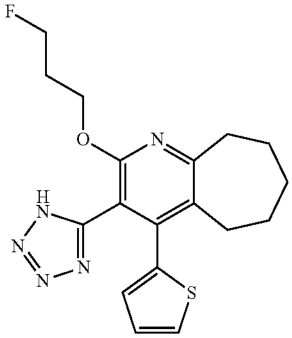 [SMILES: FCCCOc1nc2c(c(-c3cccs3)c1-c1nnn[nH]1)CCCCC2] | ESP [M + H]$^+$: 374.4 | C | N315 |
| 316 | (S)-2-(Tetrahydrofuran-3-yloxy)-3-(1H-tetrazol-5-yl)-4-(thiophen-3-yl)-6,7,8,9-tetrahydro-5H-cyclohepta[b]pyridine | 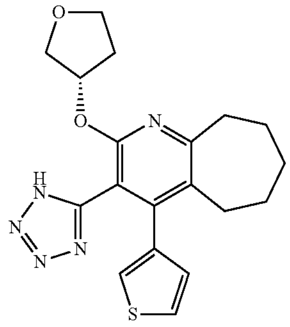 [SMILES: c1cc(-c2c3c(nc(O[C@H]4CCOC4)c2-c2nnn[nH]2)CCCCC3)cs1] | ESP [M + H]$^+$: 384.4 | C | N316 |
| 317 | 4-Phenyl-2-(tetrahydro-2H-pyran-4-yloxy)-3-(1H-tetrazol-5-yl)-6,7,8,9-tetrahydro-5H-cyclohepta[b]pyridine | 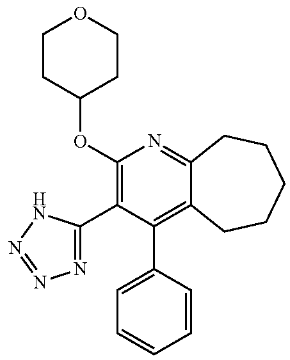 [SMILES: c1ccc(-c2c3c(nc(OC4CCOCC4)c2-c2nnn[nH]2)CCCCC3)cc1] | ESP [M + H]$^+$: 392.5 | C | N317 |

-continued

| Ex. | Name | Structure | MS | Method | Starting Material |
|---|---|---|---|---|---|
| 318 | 2-(1-Methylcyclopentyl)-4-phenyl-6,7,8,9-tetrahydro-5H-cyclohepta[b]pyridine-3-carboxylic acid | 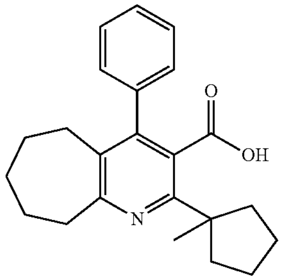 [SMILES: CC1(c2nc3c(c(-c4ccccc4)c2C(=O)O)CCCCC3)CCCC1] | ESP $[M + H]^+$: 350.6 | Z | N167 |
| 319 | 4-(3-Chlorophenyl)-2-(1-methylcyclopentyl)-6,7,8,9-tetrahydro-5H-cyclohepta[b]pyridine-3-carboxylic acid | 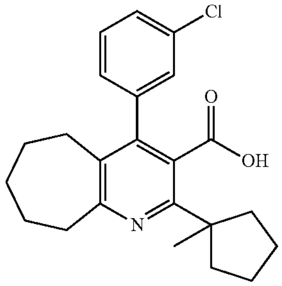 [SMILES: CC1(c2nc3c(c(-c4cccc(Cl)c4)c2C(=O)O)CCCCC3)CCCC1] | ESP $[M + H]^+$: 384.5 | Z | N170 |
| 320 | 4-(1-Methyl-1H-pyrazol-5-yl)-2-(1-methylcyclohexyl)-6,7,8,9-tetrahydro-5H-cyclohepta[b]pyridine-3-carboxylic acid | 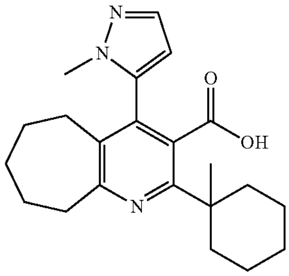 [SMILES: Cn1nccc1-c1c2c(nc(C3(C)CCCCC3)c1C(=O)O)CCCCC2] | ESP $[M + H]^+$: 368.6 | Z | N171 |
| 321 | 2-(1-Methylcyclohexyl)-4-phenyl-6,7,8,9-tetrahydro-5H-cyclohepta[b]pyridine-3-carboxylic acid | 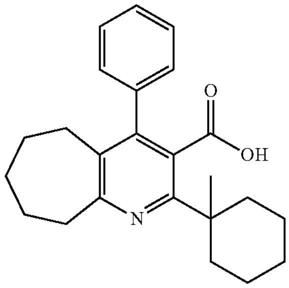 [SMILES: CC1(c2nc3c(c(-c4ccccc4)c2C(=O)O)CCCCC3)CCCCC1] | ESP $[M + H]^+$: 364.6 | Z | N321 |
| 322 | 2-Cyclohexyl-4-phenyl-6,7,8,9-tetrahydro-5H-cyclohepta[b]pyridine-3-carboxylic acid | 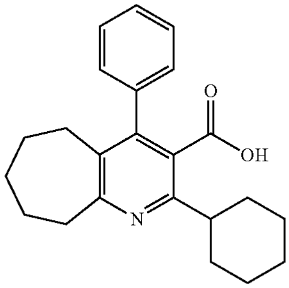 | ESP $[M + H]^+$: 350.6 | Z | from impurity in N321 |

-continued

| Ex. | Name | Structure | MS | Method | Starting Material |
|---|---|---|---|---|---|
| 323 | 2-(1-Methylcyclohexyl)-4-(2-methylpyridin-4-yl)-6,7,8,9-tetrahydro-5H-cyclohepta[b]pyridine-3-carboxylic acid | 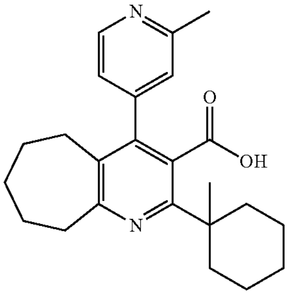 [SMILES: Cc1cc(-c2c3c(nc(C4(C)CCCCC4)c2C(=O)O)CCCCC3)ccn1] | ESP $[M + H]^+$: 379.5 | Z | N172 |
| 324 | 2-Cyclohexyl-4-(2-methylpyridin-4-yl)-6,7,8,9-tetrahydro-5H-cyclohepta[b]pyridine-3-carboxylic acid | 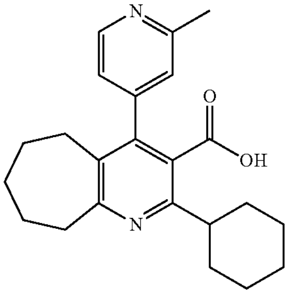 [SMILES: Cc1cc(-c2c3c(nc(C4CCCCC4)c2C(=O)O)CCCCC3)ccn1] | ESP $[M + H]^+$: 365.5 | Z | from impurity in N172 |
| 325 | 2-Cyclopentyl-4-phenyl-5,6,7,8-tetrahydroquinoline-3-carboxylic acid | 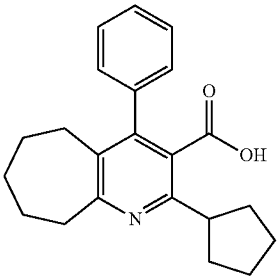 [SMILES: O=C(O)c1c(C2CCCC2)nc2c(c1-c1ccccc1)CCCCC2] | ESP $[M + H]^+$: 322.6 | A | E325 |
| 326 | 2-(1-(Methoxymethyl)cyclopentyl)-6-pentyl-4-phenyl-3-(1H-tetrazol-5-yl)-5,6,7,8-tetrahydroquinoline | 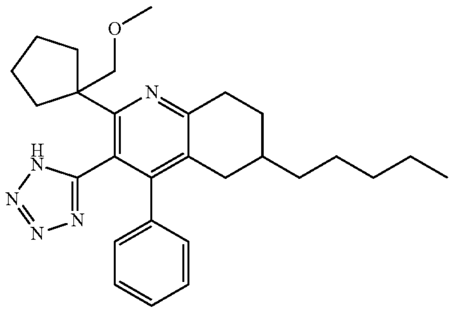 [SMILES: CCCCCC1CCc2nc(C3(COC)CCCC3)c(-c3nnn[nH]3)c(-c3ccccc3)c2C1] | ESP $[M + H]^+$: 460.7 | C | N326 |

-continued

| Ex. | Name | Structure | MS | Method | Starting Material |
|---|---|---|---|---|---|
| 327 | tert-Butyl 2-methyl-2-(4-(2-methylpyridin-4-yl)-3-(1H-tetrazol-5-yl)-6,7,8,9-tetrahydro-5H-cyclohepta[b]pyridin-2-yl)propanoate | 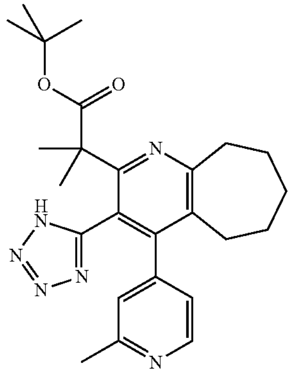 [SMILES: Cc1cc(-c2c3c(nc(C(C)(C)C(=O)OC(C)(C)C)c2-c2nnn[nH]2)CCCCC3)ccn1] | ESP $[M + H]^+$: 449.4 | C | N327 |

General Method X

Tetrazole compounds containing stereogenic centers and/or axis can be separated by preparative HPLC using one of the following conditions.

X1: Reprosil Chiral NR, 15% iPrOH in heptane

X2: Chiralpak AD-H, 10% EtOH in heptane

X3: Chiralpak AD, 10% iPrOH in heptane

X4: Chiralpak AD, 10% EtOH in heptane

X5: Chiralpak AD, 5% EtOH in heptane

X6: Chiralpak AD, 15% iPrOH in heptane

| Ex. | Name | Structure | MS | Method | Starting Material |
|---|---|---|---|---|---|
| 146 | 4-Phenyl-2-(R)-tetrahydro-furan-2-yl-3-(1H-tetrazol-5-yl)-6,7,8,9-tetrahydro-5H-cyclohepta[b]pyridine | 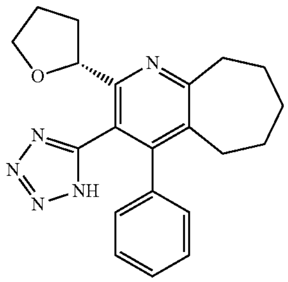 [SMILES: c1ccc(-c2c3c(nc([C@H]4CCCO4)c2-c2nnn[nH]2)CCCCC3)cc1] | ESP $[M + H]^+$: 362.5 | X1 1. Peak | Ex. 85 |
| 147 | 4-Phenyl-2-(S)-tetrahydro-furan-2-yl-3-(1H-tetrazol-5-yl)-6,7,8,9-tetrahydro-5H-cyclohepta[b]pyridine | 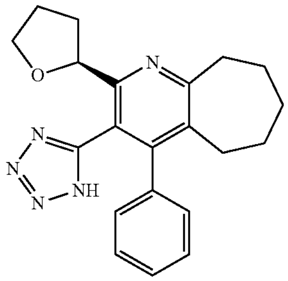 [SMILES: c1ccc(-c2c3c(nc([C@@H]4CCCO4)c2-c2nnn[nH]2)CCCCC3)cc1] | ESP $[M + H]^+$: 362.5 | X1 2. Peak | Ex. 85 |
| 152 | 4-Phenyl-2-(tetrahydrofuran-2-yl)-3-(1H-tetrazol-5-yl)-5,6,7,8,9,10-hexahydrocycloocta[b] pyridine | 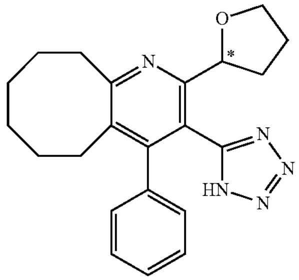 [SMILES: c1ccc(-c2c3c(nc(C4CCCO4)c2-c2nnn[nH]2)CCCCCC3)cc1] | ESP $[M + H]^+$: 376.6 | X2 1. Peak | Ex. 151 |

-continued

| Ex. | Name | Structure | MS | Method | Starting Material |
|---|---|---|---|---|---|
| 153 | 4-Phenyl-2-(tetrahydrofuran-2-yl)-3-(1H-tetrazol-5-yl)-5,6,7,8,9,10-hexahydrocycloocta[b]pyridine | 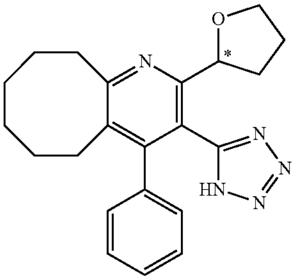 [SMILES: c1ccc(-c2c3c(nc(C4CCCO4)c2-c2nnn[nH]2)CCCCCC3)cc1] | ESP [M + H]$^+$: 376.6 | X2 2. Peak | Ex. 151 |
| 155 | 2-(2-Methyl-tetrahydro-furan-2-yl)-4-phenyl-3-(1H-tetrazol-5-yl)-6,7,8,9-tetrahydro-5H-cyclohepta[b]pyridine | 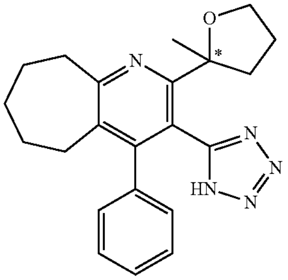 [SMILES: CC1(c2nc3c(c(-c4ccccc4)c2-c2nnn[nH]2)CCCCC3)CCCO1] | ESP [M + H]$^+$: 376.5 | X3 1. Peak | Ex. 154 |
| 156 | 2-(2-Methyl-tetrahydro-furan-2-yl)-4-phenyl-3-(1H-tetrazol-5-yl)-6,7,8,9-tetrahydro-5H-cyclohepta[b]pyridine | 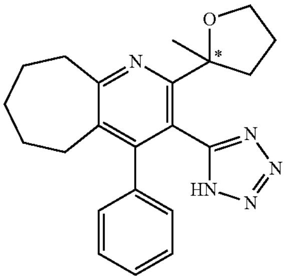 [SMILES: CC1(c2nc3c(c(-c4ccccc4)c2-c2nnn[nH]2)CCCCC3)CCCO1] | ESP [M + H]$^+$: 376.6 | X3 2. Peak | Ex. 154 |
| 158 | 4-(3-Methoxy-phenyl)-2-(2-methyl-tetrahydro-furan-2-yl)-3-(1H-tetrazol-5-yl)-6,7,8,9-tetrahydro-5H-cyclohepta[b]pyridine | 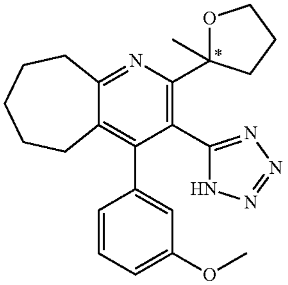 [SMILES: COc1cccc(-c2c3c(nc(C4(C)CCCO4)c2-c2nnn[nH]2)CCCCC3)c1] | ESP [M + H]$^+$: 406.6 | X4 1. Peak | Ex. 157 |
| 159 | 4-(3-Methoxy-phenyl)-2-(2-methyl-tetrahydro-furan-2-yl)-3-(1H-tetrazol-5-yl)-6,7,8,9-tetrahydro-5H-cyclohepta[b]pyridine | 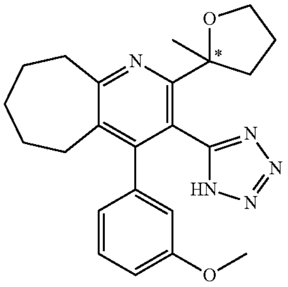 [SMILES: COc1cccc(-c2c3c(nc(C4(C)CCCO4)c2-c2nnn[nH]2)CCCCC3)c1] | ESP [M + H]$^+$: 406.6 | X4 2. Peak | Ex. 157 |

-continued

| Ex. | Name | Structure | MS | Method | Starting Material |
|---|---|---|---|---|---|
| 164 | 4-(3-Chloro-phenyl)-2-(2-methyl-tetrahydro-furan-2-yl)-3-(1H-tetrazol-5-yl)-6,7,8,9-tetrahydro-5H-cyclohepta[b]pyridine | 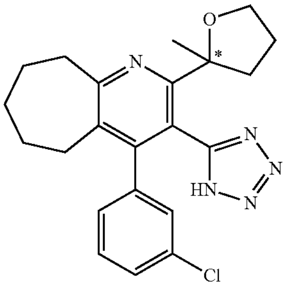 [SMILES: CC1(c2nc3c(c(-c4cccc(Cl)c4)c2-c2nnn[nH]2)CCCCC3)CCCO1] | ESP [M + H]+: 410.5 | X5 1. Peak | Ex. 163 |
| 165 | 4-(3-Chloro-phenyl)-2-(2-methyl-tetrahydro-furan-2-yl)-3-(1H-tetrazol-5-yl)-6,7,8,9-tetrahydro-5H-cyclohepta[b]pyridine | 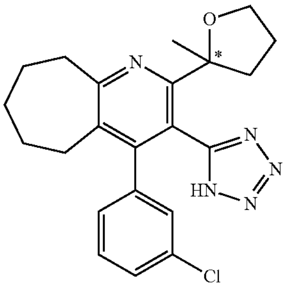 [SMILES: CC1(c2nc3c(c(-c4cccc(Cl)c4)c2-c2nnn[nH]2)CCCCC3)CCCO1] | ESP [M + H]+: 410.5 | X5 2. Peak | Ex. 163 |
| 231 | 2-(2-Methyltetrahydrofuran-2-yl)-4-phenyl-3-(2H-tetrazol-5-yl)-5,6,7,8-tetrahydroquinoline | 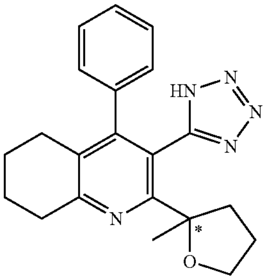 [SMILES: CC1(c2nc3c(c(-c4ccccc4)c2-c2nnn[nH]2)CCCC3)CCCO1] | ESP [M + H]+: 362.7 | X3 1. Peak | Ex. 226 |
| 232 | 2-(2-Methyltetrahydrofuran-2-yl)-4-phenyl-3-(2H-tetrazol-5-yl)-5,6,7,8-tetrahydroquinoline | 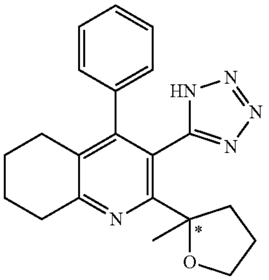 [SMILES: CC1(c2nc3c(c(-c4ccccc4)c2-c2nnn[nH]2)CCCC3)CCCO1] | ESP [M + H]+: 362.7 | X3 2. Peak | Ex. 226 |
| 233 | 6,6-Difluoro-2-(2-methyltetrahydrofuran-2-yl)-4-phenyl-3-(2H-tetrazol-5-yl)-5,6,7,8-tetrahydroquinoline | 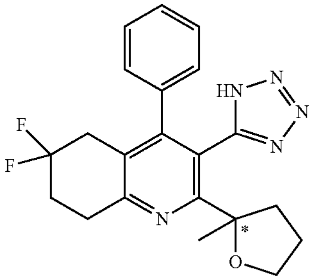 [SMILES: CC1(c2nc3c(c(-c4ccccc4)c2-c2nnn[nH]2)CC(F)(F)CC3)CCCO1] | ESP [M + H]+: 398.7 | X3 1. Peak | Ex. 227 |

-continued

| Ex. | Name | Structure | MS | Method | Starting Material |
|---|---|---|---|---|---|
| 234 | 6,6-Difluoro-2-(2-methyltetrahydrofuran-2-yl)-4-phenyl-3-(2H-tetrazol-5-yl)-5,6,7,8-tetrahydroquinoline | 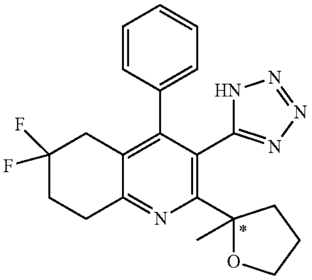 [SMILES: CC1(c2nc3c(c(-c4ccccc4)c2-c2nnn[nH]2)CC(F)(F)CC3)CCCO1] | ESP $[M + H]^+$: 398.7 | X3 2. Peak | Ex. 227 |
| 235 | 6,6-Dimethyl-2-(2-methyltetrahydrofuran-2-yl)-4-phenyl-3-(2H-tetrazol-5-yl)-5,6,7,8-tetrahydroquinoline | 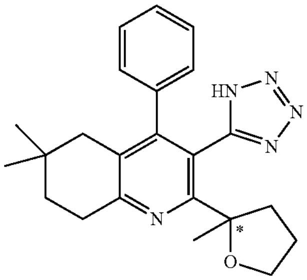 [SMILES: CC1(C)CCc2nc(C3(C)CCCO3)c(-c3nnn[nH]3)c(-c3ccccc3)c2C1] | ESP $[M + H]^+$: 390.7 | X3 1. Peak | Ex. 228 |
| 236 | 6,6-Dimethyl-2-(2-methyltetrahydrofuran-2-yl)-4-phenyl-3-(2H-tetrazol-5-yl)-5,6,7,8-tetrahydroquinoline | 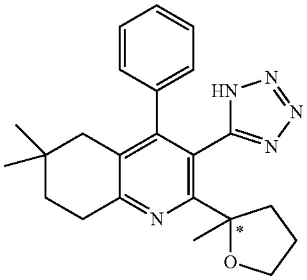 [SMILES: CC1(C)CCc2nc(C3(C)CCCO3)c(-c3nnn[nH]3)c(-c3ccccc3)c2C1] | ESP $[M + H]^+$: 390.7 | X3 2. Peak | Ex. 228 |
| 249 | 2-(2-(Methoxymethyl) tetrahydrofuran-2-yl)-4-phenyl-3 - (2H-tetrazol-5-yl)-5,6,7,8-tetrahydroquinoline | 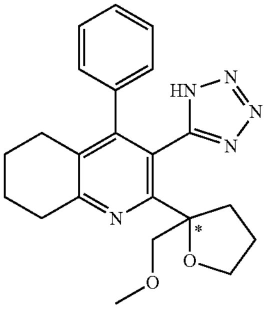 [SMILES: COCC1(c2nc3c(c(-c4ccccc4)c2-c2nnn[nH]2)CCCC3)CCCO1] | ESP $[M + H]^+$: 392.6 | X3 1. Peak | Ex. 242 |
| 250 | (S)-2-(2-(Methoxymethyl) tetrahydrofuran-2-yl)-4-phenyl-3 - (2H-tetrazol-5-yl)-5,6,7,8-tetrahydroquinoline | 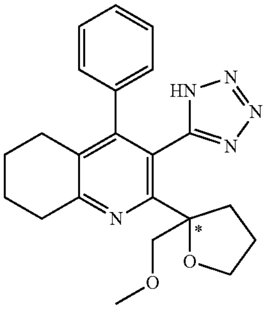 [SMILES: COCC1(c2nc3c(c(-c4ccccc4)c2-c2nnn[nH]2)CCCC3)CCCO1] | ESP $[M + H]^+$: 392.6 | X3 2. Peak | Ex. 242 |

-continued

| Ex. | Name | Structure | MS | Method | Starting Material |
|---|---|---|---|---|---|
| 251 | 6,6-Difluoro-2-(2-(methoxymethyl) tetrahydrofuran-2-yl)-4-phenyl-3-(2H-tetrazol-5-yl)-5,6,7,8-tetrahydroquinoline | 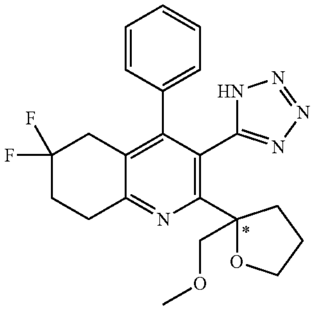 [SMILES: COCC1(c2nc3c(c(-c4ccccc4)c2-c2nnn[nH]2)CC(F)(F)CC3)CCCO1] | ESP [M + H]$^+$: 428.5 | X3 1. Peak | Ex. 245 |
| 252 | 6,6-Difluoro-2-(2-(methoxymethyl) tetrahydrofuran-2-yl)-4-phenyl-3-(2H-tetrazol-5-yl)-5,6,7,8-tetrahydroquinoline | 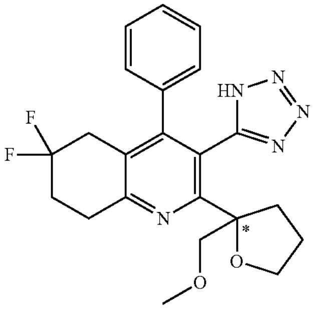 [SMILES: COCC1(c2nc3c(c(-c4ccccc4)c2-c2nnn[nH]2)CC(F)(F)CC3)CCCO1] | ESP [M + H]$^+$: 428.5 | X3 2. Peak | Ex. 245 |
| 253 | 2-(2-(Methoxymethyl) tetrahydrofuran-2-yl)-6,6-dimethyl-4-phenyl-3-(2H-tetrazol-5-yl)-5,6,7,8-tetrahydroquinoline | 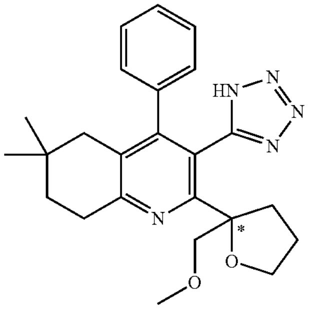 [SMILES: COCC1(c2nc3c(c(-c4ccccc4)c2-c2nnn[nH]2)CC(C)(C)CC3)CCCO1] | ESP [M + H]$^+$: 420.6 | X3 1. Peak | Ex. 244 |
| 254 | 2-(2-(Methoxymethyl) tetrahydrofuran-2-yl)-6,6-dimethyl-4-phenyl-3-(2H-tetrazol-5-yl)-5,6,7,8-tetrahydroquinoline | 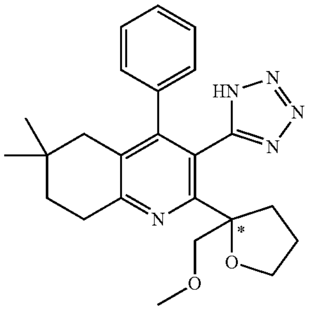 [SMILES: COCC1(c2nc3c(c(-c4ccccc4)c2-c2nnn[nH]2)CC(C)(C)CC3)CCCO1] | ESP [M + H]$^+$: 420.6 | X3 2. Peak | Ex. 244 |

-continued

| Ex. | Name | Structure | MS | Method | Starting Material |
|---|---|---|---|---|---|
| 262 | 4-(4-Fluoro-3-methoxyphenyl)-2-(2-(methoxymethyl) tetrahydrofuran-2-yl)-3-(2H-tetrazol-5-yl)-5,6,7,8-tetrahydroquinoline | 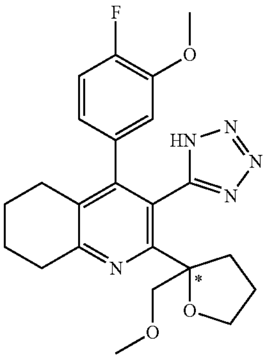 [SMILES: COCC1(c2nc3c(c(-c4ccc(F)c(OC)c4)c2-c2nnn[nH]2)CCCC3)CCCO1] | ESP $[M + H]^+$: 440.5 | X6 1. Peak | Ex. 260 |
| 263 | 4-(4-Fluoro-3-methoxyphenyl)-2-(2-(methoxymethyl) tetrahydrofuran-2-yl)-3-(2H-tetrazol-5-yl)-5,6,7,8-tetrahydroquinoline | 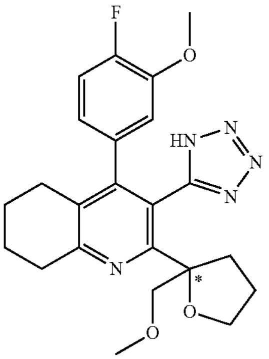 [SMILES: COCC1(c2nc3c(c(-c4ccc(F)c(OC)c4)c2-c2nnn[nH]2)CCCC3)CCCO1] | ESP $[M + H]^+$: 440.5 | X6 2. Peak | Ex. 260 |
| 267 | 4-(2-Fluoro-5-methoxyphenyl)-2-(2-(methoxymethyl) tetrahydrofuran-2-yl)-3-(2H-tetrazol-5-yl)-5,6,7,8-tetrahydroquinoline | 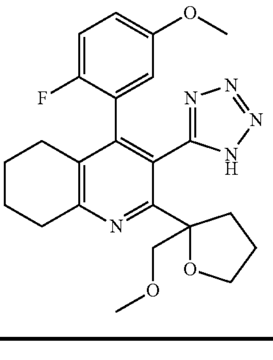 | ESP $[M + H]^+$: 440.5 | X3 1. Peak (absolute configuration not assigned) | Ex. 266 |

Example 169

4-(2-(1-Methylcyclopentyl)-3-(1H-tetrazol-5-yl)-6,7,8,9-tetrahydro-5H-cyclohepta[b]pyridin-4-yl)pyridin-2(1H)-one

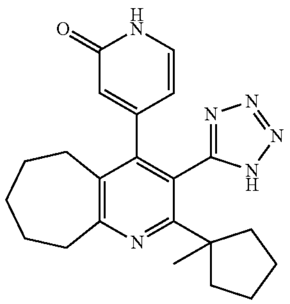 [SMILES: CC1(c2nc3c(c(-c4cc[nH]c(=O)c4)c2-c2nnn[nH]2)CCCCC3)CCCC1]

4-(2-Methoxypyridin-4-yl)-2-(1-methylcyclopentyl)-3-(1H-tetrazol-5-yl)-6,7,8,9-tetrahydro-5H-cyclohepta[b]pyridine (Example 168, 68.9 mg) was mixed with hydrobromic acid, 33% in acetic acid (1.42 g) and the suspension was stirred at 70° C. for 18 h. The reaction mixture was evaporated, twice evaporated with water and purified by preparative HPLC to give the title compound (26 mg) as a colorless solid. MS (ESP)=391.7 $[M+H]^+$ Example 211

(S)-4-Phenyl-2-(pyrrolidin-2-yl)-3-(1H-tetrazol-5-yl)-6,7,8,9-tetrahydro-5H-cyclohepta[b]pyridine 2,2,2-trifluoroacetate

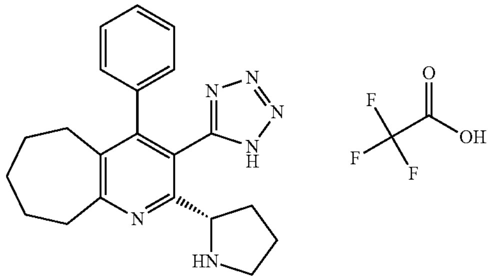 [SMILES: c1ccc(-c2c3c(nc([C@@H]4CCCN4)c2-c2nnn[nH]2)CCCCC3)cc1 ; O=C(O)C(F)(F)F]

(S)-tert-Butyl 2-(4-phenyl-3-(1H-tetrazol-5-yl)-6,7,8,9-tetrahydro-5H-cyclohepta[b]pyridin-2-yl)pyrrolidine-1-carboxylate (Example 210, 140 mg) was dissolved in DCM (2 ml). After addition of TFA (1.48 g) the reaction mixture was stirred for 1 h at rt. The solvent was evaporated and the product was purified by preparative HPLC to give the title compound (55 mg) as an off-white solid. MS (ESP): m/z=361.6 $[M+H]^+$.

Example 328

2-Methyl-2-(4-(2-methylpyridin-4-yl)-3-(1H-tetrazol-5-yl)-6,7,8,9-tetrahydro-5H-cyclohepta[b]pyridin-2-yl)propanoic acid

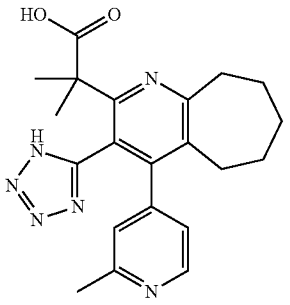 [SMILES: Cc1cc(-c2c3c(nc(C(C)(C)C(=O)O)c2-c2nnn[nH]2)CCCCC3)ccn1]

tert-Butyl 2-methyl-2-(4-(2-methylpyridin-4-yl)-3-(1H-tetrazol-5-yl)-6,7,8,9-tetrahydro-5H-cyclohepta[b]pyridin-2-yl)propanoate (Example 327, 28 mg) was dissolved in DCM (3 ml). After addition of TFA (7.12 mg) the reaction mixture was stirred for 27 h at rt. The solvent was evaporated and the product was purified by preparative HPLC to afford the title compound (8 mg) as a white solid. MS (ESP): m/z=393.5 $[M+H]^+$.

Intermediate B154

3-(2-Methyltetrahydrofuran-2-yl)-3-oxo-propanenitrile

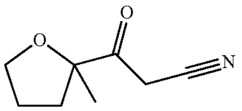

In analogy to the synthesis of Intermediate B79, methyl 2-methyltetrahydrofuran-2-carboxylate (CAS#1218915-91-3) was converted to the title compound by reaction with sodium hydride and acetonitrile in THF. Colorless liquid. MS (ESP): m/z=154.2 $[M+H]^+$.

Intermediate B166

3-(1-Methylcyclopentyl)-3-oxopropanenitrile

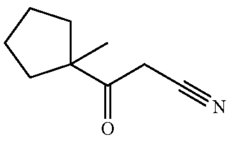

In analogy to the synthesis of Intermediate B79, methyl 1-methylcyclopentanecarboxylate (CAS#4630-83-5) was converted to the title compound by reaction with sodium hydride and acetonitrile in THF. Yellow oil. MS (ESN): m/z=150.3 $[M-H]^-$.

Intermediate B191

4-Ethyl-4-(methoxymethyl)-3-oxohexanenitrile

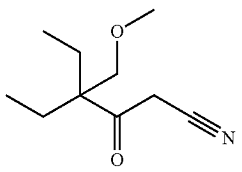

In analogy to the synthesis of Intermediate B218, ethyl 2-ethylbutanoate (CAS#2983-38-2) was reacted with lithium diisopropylamide and chloromethyl methyl ether to obtain ethyl 2-ethyl-2-(methoxymethyl)butanoate which was converted to the title compound by reaction with sodium hydride and acetonitrile in THF. Light yellow liquid. MS (ESP): m/z=189.3 [M+H]$^+$.

Intermediate B200

3-(1-Methoxycyclopentyl)-3-oxopropanenitrile

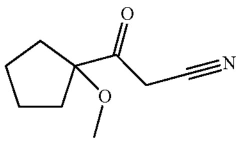

In analogy to the synthesis of Intermediate B79, methyl 1-methoxycyclopentanecarboxylate (CAS#17860-29-6) was converted to the title compound by reaction with sodium hydride and acetonitrile in THF. Light yellow liquid. MS (ESN): m/z=166.3 [M−H]$^-$.

Intermediate B218

3-(1-(Methoxymethyl)cyclohexyl)-3-oxopropanenitrile

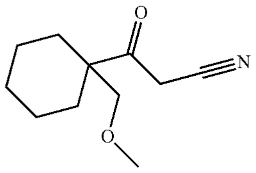

To a solution of diisopropylamine (3.66 g, 5.15 ml, 36.1 mmol) in THF (50 ml) under Argon was slowly added n-butyllithium (1.6 M in n-hexane, 22.5 ml, 36.0 mmol) at −78° C. and the mixture was stirred for 30 minutes. Then a solution of methyl cyclohexanecarboxylate (5 g, 35.2 mmol) in THF (25 ml) was added dropwise. The mixture was allowed to warm to −40° C. and stirred for 30 minutes at this temperature. Then a solution of chloromethyl methyl ether (2.83 g, 35.2 mmol) in THF (12.5 ml) was added dropwise. After the addition was completed, the reaction mixture was allowed to warm to rt. Water was added and the mixture was extracted with EtOAc. The combined organic extracts were washed with water and brine, dried with $Na_2SO_4$ and evaporated to give methyl 1-(methoxymethyl)cyclohexanecarboxylate as a light yellow oil which was converted to the title compound in analogy to the synthesis of Intermediate B79 by reaction with sodium hydride and acetonitrile in THF. Light yellow oil. MS (ESP): m/z=196.5 [M+H]$^+$.

Intermediate B242

3-(2-(Methoxymethyl)tetrahydrofuran-2-yl)-3-oxopropanenitrile

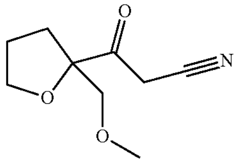

In analogy to the synthesis of Intermediate B218, methyl tetrahydrofuran-2-carboxylate (CAS#37443-42-8) was reacted with lithium diisopropylamide and chloromethyl methyl ether to obtain methyl 2-(methoxymethyl)tetrahydrofuran-2-carboxylate which was converted to the title compound by reaction with sodium hydride and acetonitrile in THF. Light yellow oil. MS (ESN): m/z=182.3 [M−H]$^-$.

Intermediate B246

3-(2-Ethyltetrahydrofuran-2-yl)-3-oxopropanenitrile

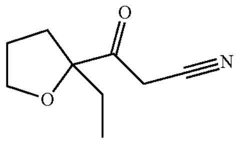

In analogy to the synthesis of Intermediate B218, methyl tetrahydrofuran-2-carboxylate (CAS#37443-42-8) was reacted with lithium diisopropylamide and iodoethane to obtain methyl 2-ethyltetrahydrofuran-2-carboxylate which was converted to the title compound by reaction with sodium hydride and acetonitrile in THFE Light yellow oil. MS (ESN): m/z=166.4 [M−H]$^-$.

Intermediate B261

3-(1-(Methylsulfonylmethyl)cyclopentyl)-3-oxopropanenitrile

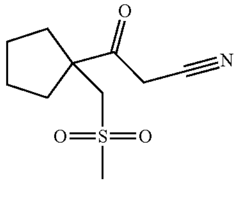

In analogy to the synthesis of Intermediate B218, methyl cyclopentanecarboxylate was reacted with lithium diisopropylamide and (chloromethyl)(methyl)sulfane to obtain methyl 1-(methylthiomethyl)cyclopentanecarboxylate which was converted to 3-(1-(methylthiomethyl)cyclopentyl)-3-oxopropanenitrile by reaction with sodium hydride and acetonitrile in THF. The 3-(1-(methylthiomethyl)cyclopentyl)-3-oxopropanenitrile (210 mg, 1.06 mmol) was then dissolved in dichloromethane (10 ml) and m-chloroperbenzoic acid (656 mg, 2.66 mmol) was added in one portion and the mixture was stirred at room temperature overnight. The resulting white suspension was diluted with water and extracted with DCM. The organic extracts were washed with $Na_2SO_3$ (15% g/g solution) and sat. aqueous $NaHCO_3$ solution, dried with $Na_2SO_4$ (containing solid $Na_2SO_3$) and evaporated to obtain the title compound as white solid. MS (ESN): m/z=228.3 $[M-H]^-$.

Intermediate B268

3-[1-(Ethoxymethyl)cyclopentyl]-3-oxo-propanenitrile

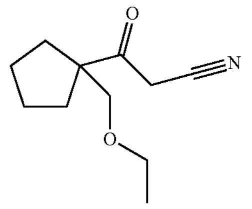

In analogy to the synthesis of Intermediate B79, methyl 1-(ethoxymethyl)cyclopentanecarboxylate (CAS#1360569-15-8) was converted to the title compound by reaction with sodium hydride and acetonitrile in THF. Yellow liquid. MS (ESN): m/z=194.3 $[M-H]^-$.

Intermediate B284

3-(1-(Methoxymethyl)cyclobutyl)-3-oxopropanenitrile

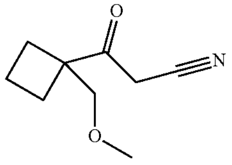

In analogy to the synthesis of Intermediate B218, methyl cyclobutanecarboxylate (CAS#765-85-5) was reacted with lithium diisopropylamide and chloromethyl methyl ether to obtain methyl 1-(methoxymethyl)cyclobutanecarboxylate which was converted to the title compound by reaction with sodium hydride and acetonitrile in THF. Yellow liquid. MS (ESN): m/z=166.3 $[M-H]^-$.

Intermediate B327 tert-Butyl 4-cyano-2,2-dimethyl-3-oxobutanoate

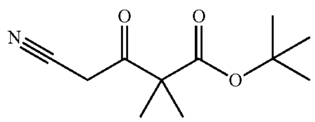

A solution of acetonitrile (0.60 g, 14.6 mmol) in THF (29 ml) was cooled in a dry ice bath. n-BuLi (9 ml of a 1.6 M solution in hexane, 14.4 mmol) was added dropwise and stirring was continued for 30 min. Then a solution of 1-tert-butyl 3-methyl 2,2-dimethylmalonate (CAS#85293-46-5) (1.5 g, 7.3 mmol) in THF (7 ml) was added slowly. The mixture was stirred for 2 h at −78° C. Acetic acid (2.4 ml, excess) was added and the reaction mixture was allowed to reach rt. After extractive workup (AcOEt/sat. aq. Seignette salt solution) the organic phase was dried ($Na_2SO_4$) and concentrated to furnish a light orange liquid (1.4 g) which was used in the next step without further purification.

Additional Intermediates K (Via Knoevenagel Condensation)

General Method Z2: Knoevenagel Products by Reaction of Alkyl Cyanoacetate with Aldehyde and $NH_4OAc$ at Rt A mixture of the aldehyde (1 eq), alkyl 2-cyanoacetate (1 eq), ammonium acetate (1.5 eq) and an alcohol (typically ethanol) is stirred at rt for 1 h. After extractive workup ($AcOEt/H_2O$) the organic phase is dried ($Na_2SO_4$), filtered and concentrated to dryness to obtain the title compound as a solid which can be used as such. If necessary, it can be further purified by chromatography and/or recrystallization.

| Intermediate | Name and Structure | MS | Method | Reagents |
|---|---|---|---|---|
| K297 | Ethyl 2-cyano-3-(2-methylpyridin-4-yl)acrylate 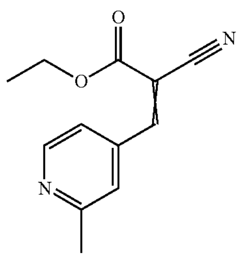 [SMILES: CCOC(=O)C(C#N)=Cc1ccnc(C)c1] | ESP $[M + H]^+$: 217.5 | Z2 | 2-Methylisonicotinaldehyde, ethyl 2-cyanoacetate |

Additional Intermediates P (Pyridones)

General Method Z1: Pyridones from Ketones, Knoevenagel Adducts, $NH_4OAc$ (78° C.) Followed by Reaction with Ceric Ammonium Nitrate A mixture of the ketone (1 eq), the Knoevenagel adduct (Intermediate K, 1 eq), ammonium acetate (3 eq) and an alcohol (typically ethanol) is refluxed for 2 to 12 h. The suspension is cooled in an ice bath and filtered to obtain precipitate 1. The mother liquor is concentrated, dissolved in acetone/water (1/1) and cooled in an ice bath. Ceric ammonium nitrate (1 eq) is added and stirring is continued for 20 min to 2 h at rt. The reaction mixture is filtered to obtain precipitate 2. The combined solids are dried and can be used as such. If necessary, the raw product can be further purified by chromatography and/or crystallization to obtain a pure specimen of the title compound.

| Intermediate | Name and Structure | MS | Method | Reagents |
|---|---|---|---|---|
| P295 | 4-(1-Methyl-1H-pyrazol-4-yl)-2-oxo-2,5,6,7,8,9-hexahydro-1H-cyclohepta[b]pyridine-3-carbonitrile 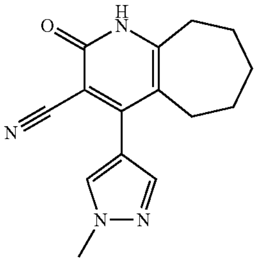 [SMILES: Cn1cc(-c2c3c([nH]c(=O)c2C#N)CCCCC3)cn1] | ESP $[M + H]^+$: 269.5 | Z1 | Ethyl 2-cyano-3-(1-methyl-1H-pyrazol-4-yl)acrylate, (CAS# 1005866-02-3), cycloheptanone |
| P297 | 4-(2-Methylpyridin-4-yl)-2-oxo-2,5,6,7,8,9-hexahydro-1H-cyclohepta[b]pyridine-3-carbonitrile 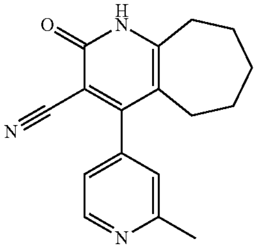 [SMILES: Cc1cc(-c2c3c([nH]c(=O)c2C#N)CCCCC3)ccn1] | ESP $[M + H]^+$: 280.5 | Z1 | Ethyl 2-cyano-3-(2-methylpyridin-4-yl)acrylate (Intermediate K297), cycloheptanone |
| P302 | 2-Oxo-4-phenyl-1,2,5,6,7,8-hexahydroquinoline-3-carbonitrile 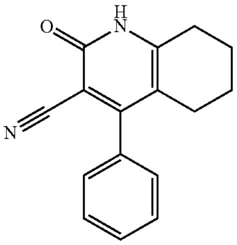 [SMILES: N#Cc1c(-c2ccccc2)c2c([nH]c1=O)CCCC2] | ESP $[M + H]^+$: 251.5 | Z1 | Ethyl 2-cyano-3-phenylacrylate (CAS# 2025-40-3), cyclohexanone |

-continued

| Intermediate | Name and Structure | MS | Method | Reagents |
|---|---|---|---|---|
| P305 | 4-(2-Methylpyridin-4-yl)-2-oxo-1,2,5,6,7,8-hexahydroquinoline-3-carbonitrile 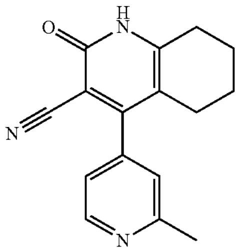 [SMILES: Cc1cc(-c2c3c([nH]c(=O)c2C#N)CCCC3)ccn1] | ESP $[M + H]^+$: 266.5 | Z1 | Ethyl 2-cyano-3-(2-methylpyridin-4-yl)acrylate (Intermediate K297), cyclohexanone |
| P306 | 2-Oxo-4-(4-(trifluoromethyl)phenyl)-2,5,6,7,8,9-hexahydro-1H-cyclohepta[b]pyridine-3-carbonitrile 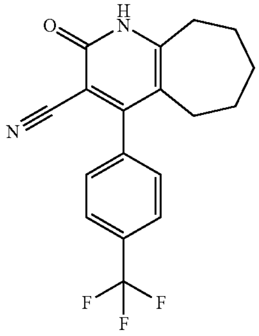 [SMILES: N#Cc1c(-c2ccc(C(F)(F)F)cc2)c2c([nH]c1=O)CCCCC2] | ESN [M − H]: 331.4 | Z1 | Ethyl 2-cyano-3-(4-(trifluoromethyl)phenyl) acrylate (CAS# 149550-21-0), cycloheptanone |
| P307 | 4-(3-Fluorophenyl)-2-oxo-2,5,6,7,8,9-hexahydro-1H-cyclohepta[b]pyridine-3-carbonitrile 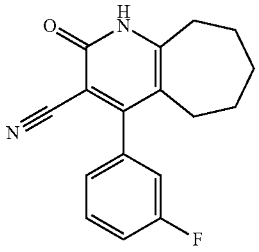 [SMILES: N#Cc1c(-c2cccc(F)c2)c2c([nH]c1=O)CCCCC2] | ESP $[M + H]^+$: 283.4 | Z1 | Ethyl 2-cyano-3-(3-fluorophenyl)acrylate (CAS# 19310-52-2), cycloheptanone |
| P308 | 4-(3-Fluorophenyl)-2-oxo-1,2,5,6,7,8-hexahydroquinoline-3-carbonitrile 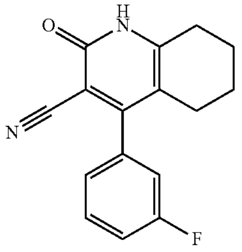 [SMILES: N#Cc1c(-c2cccc(F)c2)c2c([nH]c1=O)CCCC2] | ESP $[M + H]^+$: 269.3 | Z1 | Ethyl 2-cyano-3-(3-fluorophenyl)acrylate (CAS# 19310-52-2), cyclohexanone |

-continued

| Intermediate | Name and Structure | MS | Method | Reagents |
|---|---|---|---|---|
| P309 | 4-(3,5-Difluorophenyl)-2-oxo-2,5,6,7,8,9-hexahydro-1H-cyclohepta[b]pyridine-3-carbonitrile 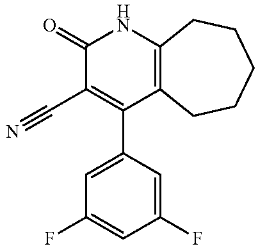 [SMILES: N#Cc1c(-c2cc(F)cc(F)c2)c2c([nH]c1=O)CCCCC2] | ESP $[M + H]^+$: 301.4 | Z1 | Ethyl 2-cyano-3-(3,5-difluorophenyl)acrylate (CAS# 623572-49-6), cycloheptanone |
| P312 | 4-(2-Fluorophenyl)-2-oxo-2,5,6,7,8,9-hexahydro-1H-cyclohepta[b]pyridine-3-carbonitrile 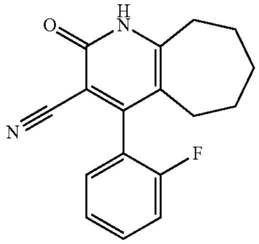 [SMILES: N#Cc1c(-c2ccccc2F)c2c([nH]c1=O)CCCCC2] | ESP $[M + H]^+$: 283.3 | Z1 | Ethyl 2-cyano-3-(2-fluorophenyl)acrylate (CAS# 84186-23-2), cycloheptanone |
| P314 | 2-Oxo-4-(thiophen-2-yl)-2,5,6,7,8,9-hexahydro-1H-cyclohepta[b]pyridine-3-carbonitrile 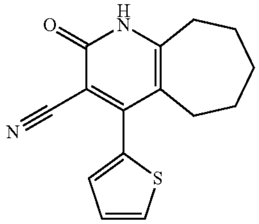 [SMILES: N#Cc1c(-c2cccs2)c2c([nH]c1=O)CCCCC2] | ESN $[M - H]^-$: 269.4 | Z1 | Ethyl 2-cyano-3-(thiophen-2-yl)acrylate (CAS#31330-51-5), cycloheptanone |
| P316 | 2-Oxo-4-(thiophen-3-yl)-2,5,6,7,8,9-hexahydro-1H-cyclohepta[b]pyridine-3-carbonitrile 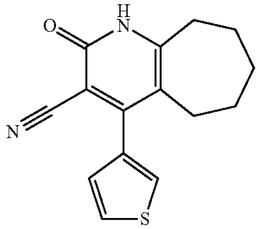 [SMILES: N#Cc1c(-c2ccsc2)c2c([nH]c1=O)CCCCC2] | ESP $[M + H]^+$: 271.4 | Z1 | Ethyl 2-cyano-3-(thiophen-3-yl)acrylate (CAS#117106-47-5), cycloheptanone |

Additional Intermediates E/N

General Method Y: Conversion of pyridones into 2-alkoxypyridines via 2-chloropyridines Step 1: To a suspension of pyridone (Intermediate P, 54.1 mmol) in phosphorous oxychloride (377 mmol, 7 eq) is slowly added DMF (23.1 mmol, 0.43 eq). After the exothermic reaction has ceased the mixture is heated to 105° C. for 4 h. All volatiles are evaporated and the oily residue is slowly poured onto water. The suspension is stirred for 1 h, filtered, washed with water and dried to obtain the 2-chloropyridine as a brown solid. The compound can be used as such or further purified by chromatography.

Step 2: The respective alcohol (4.2 mmol, 4 eq) is dissolved in THF (2 ml). Sodium hydride (4 eq of a 55% dispersion in mineral oil) is added. The mixture is stirred at room temperature for 1 h followed by addition of a suspension of the chloropyridine obtained in step 1 (1.1 mmol, 1 eq) in THF (3 ml). The reaction mixture is stirred at rt for 3 h. Extractive workup (water/sat aq. sodium bicarbonate solution) followed by chromatography affords the target compound.

| Intermediate | Name and Structure | MS | Method | Reagents |
| --- | --- | --- | --- | --- |
| N149R | 4-(2-Chloropyridin-4-yl)-2-(tetrahydrofuran-2-yl)-6,7,8,9-tetrahydro-5H-cyclohepta[b]pyridine-3-carbonitrile 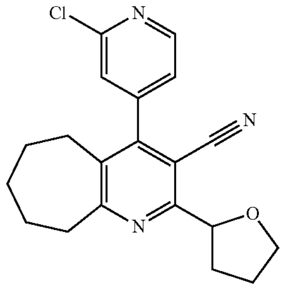 [SMILES: N#Cc1c(C2CCCO2)nc2c(c1-c1ccnc(Cl)c1)CCCCC2] | ESP $[M + H]^+$: 354.6 | V | Intermediate B85, 2-chloroisonicotinaldehyde, cycloheptanone |
| N151 | 4-Phenyl-2-(tetrahydrofuran-2-yl)-5,6,7,8,9,10-hexahydrocycloocta[b]pyridine-3-carbonitrile 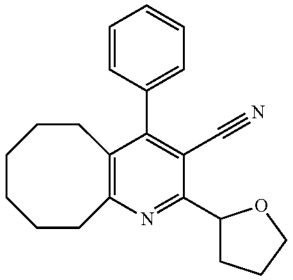 [SMILES: N#Cc1c(C2CCCO2)nc2c(c1-c1ccccc1)CCCCCC2] | ESP $[M + H]^+$: 333.5 | V | Intermediate B85, benzaldehyde, cyclooctanone |
| N154 | 2-(2-Methyltetrahydrofuran-2-yl)-4-phenyl-6,7,8,9-tetrahydro-5H-cyclohepta[b]pyridine-3-carbonitrile 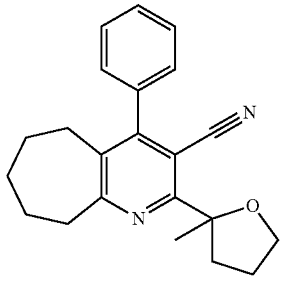 [SMILES: CC1(c2nc3c(c(-c4ccccc4)c2C#N)CCCCC3)CCCO1] | ESP $[M + H]^+$: 333.6 | V | Intermediate B154, benzaldehyde, cycloheptanone |

-continued

| Intermediate | Name and Structure | MS | Method | Reagents |
|---|---|---|---|---|
| N157 | 4-(3-Methoxyphenyl)-2-(2-methyltetrahydrofuran-2-yl)-6,7,8,9-tetrahydro-5H-cyclohepta[b]pyridine-3-carbonitrile 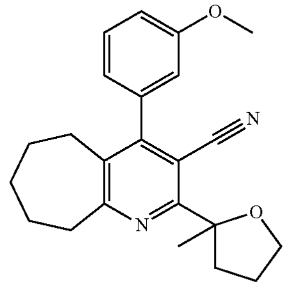 [SMILES: COc1cccc(-c2c(C#N)c(C3(C)CCCO3)nc3c2CCCCC3)c1] | ESP $[M + H]^+$: 363.5 | V | Intermediate B154, 3-methoxybenzaldehyde, cycloheptanone |
| N160 | 4-(2-Methylpyridin-4-yl)-2-(2-methyltetrahydrofuran-2-yl)-6,7,8,9-tetrahydro-5H-cyclohepta[b]pyridine-3-carbonitrile 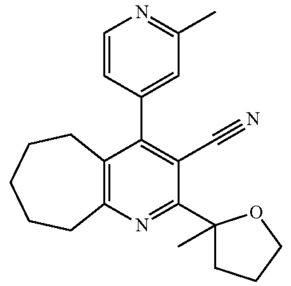 [SMILES: Cc1cc(-c2c(C#N)c(C3(C)CCCO3)nc3c2CCCCC3)ccn1] | ESP $[M + H]^+$: 348.5 | V | Intermediate B154, 2-methylisonicotinaldehyde, cycloheptanone |
| N163 | 4-(3-Chlorophenyl)-2-(2-methyltetrahydrofuran-2-yl)-6,7,8,9-tetrahydro-5H-cyclohepta[b]pyridine-3-carbonitrile 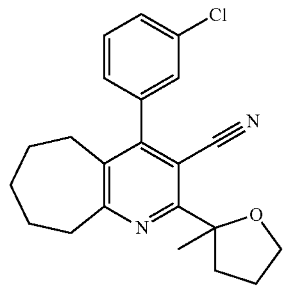 [SMILES: CC1(c2nc3c(c(-c4cccc(Cl)c4)c2C#N)CCCCC3)CCCO1] | ESP $[M + H]^+$: 367.5 | V | Intermediate B154, 3-chlorobenzaldehyde, cycloheptanone |
| N166 | 2-(1-Methylcyclopentyl)-4-(2-methylpyridin-4-yl)-6,7,8,9-tetrahydro-5H-cyclohepta[b]pyridine-3-carbonitrile 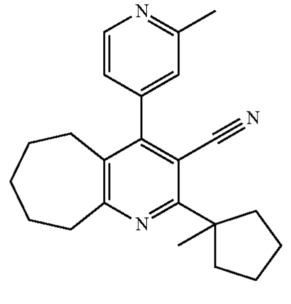 [SMILES: Cc1cc(-c2c(C#N)c(C3(C)CCCC3)nc3c2CCCCC3)ccn1] | ESP $[M + H]^+$: 346.5 | V | Intermediate B166, 2-methylisonicotinaldehyde, cycloheptanone |

-continued

| Intermediate | Name and Structure | MS | Method | Reagents |
|---|---|---|---|---|
| N167 | 2-(1-Methylcyclopentyl)-4-phenyl-6,7,8,9-tetrahydro-5H-cyclohepta[b]pyridine-3-carbonitrile 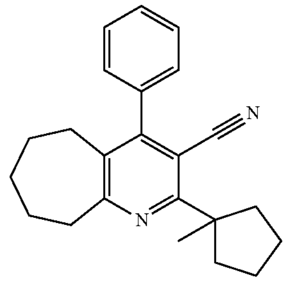 [SMILES: CC1(c2nc3c(c(-c4ccccc4)c2C#N)CCCCC3)CCCC1] | ESP $[M + NH_4]^+$: 349.5 | V | Intermediate B166, benzaldehyde, cycloheptanone |
| N168 | 4-(2-Methoxypyridin-4-yl)-2-(1-methylcyclopentyl)-6,7,8,9-tetrahydro-5H-cyclohepta[b]pyridine-3-carbonitrile 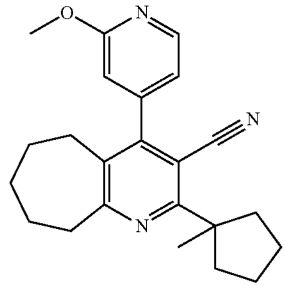 [SMILES: COc1cc(-c2c(C#N)c(C3(C)CCCC3)nc3c2CCCCC3)ccn1] | ESP $[M + H]^+$: 362.7 | V | Intermediate B166, 2-methoxyisonicotinaldehyde, cycloheptanone |
| N170 | 4-(3-Chlorophenyl)-2-(1-methylcyclopentyl)-6,7,8,9-tetrahydro-5H-cyclohepta[b]pyridine-3-carbonitrile 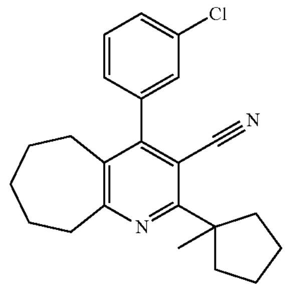 [SMILES: CC1(c2nc3c(c(-c4cccc(Cl)c4)c2C#N)CCCCC3)CCCC1] | | V | Intermediate B166, 3-chlorobenzaldehyde, cycloheptanone |
| N171 | 4-(1-Methyl-1H-pyrazol-5-yl)-2-(1-methylcyclohexyl)-6,7,8,9-tetrahydro-5H-cyclohepta[b]pyridine-3-carbonitrile 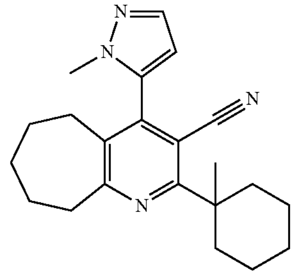 [SMILES: Cn1nccc1-c1c(C#N)c(C2(C)CCCCC2)nc2c1CCCCC2] | ESP $[M + H]^+$: 349.6 | V | 3-(1-Methylcyclohexyl)-3-oxopropanenitrile (CAS# 95882-32-9), 1-methyl-1H-pyrazole-5-carbaldehyde, cycloheptanone |

-continued

| Intermediate | Name and Structure | MS | Method | Reagents |
|---|---|---|---|---|
| N172 | 2-(1-Methylcyclohexyl)-4-(2-methyl-4-pyridyl)-6,7,8,9-tetrahydro-5H-cyclohepta[b]pyridine-3-carbonitrile, contains traces of 2-Cyclohexyl-4-(2-methyl-4-pyridyl)-6,7,8,9-tetrahydro-5H-cyclohepta[b]pyridine-3-carbonitrile 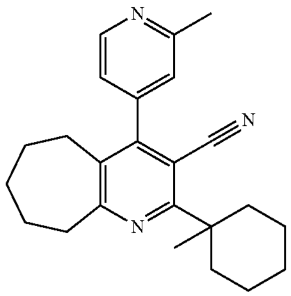 [SMILES: Cc1cc(-c2c(C#N)c(C3(C)CCCCC3)nc3c2CCCCC3)ccn1] | ESP [M + H]$^+$: 360.5 | V | 3-(1-Methylcyclohexyl)-3-oxopropanenitrile (CAS# 95882-32-9), 2-methylisonicotinaldehyde, cycloheptanone |
| N173 | 2-(1-(Methoxymethyl)cyclopentyl)-4-(1-methyl-1H-pyrazol-5-yl)-6,7,8,9-tetrahydro-5H-cyclohepta[b]pyridine-3-carbonitrile 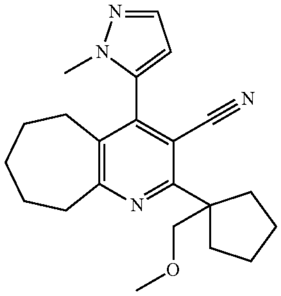 [SMILES: COCC1(c2nc3c(c(-c4ccnn4C)c2C#N)CCCCC3)CCCC1] | ESP [M + H]$^+$: 365.6 | V | Intermediate B94, 1-methyl-1H-pyrazole-5-carbaldehyde, cycloheptanone |
| N174 | 4-(3-Fluoropyridin-4-yl)-2-(1-(methoxymethyl)cyclopentyl)-6,7,8,9-tetrahydro-5H-cyclohepta[b]pyridine-3-carbonitrile 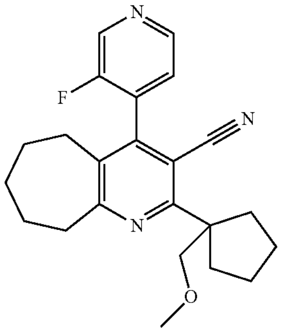 [SMILES: COCC1(c2nc3c(c(-c4ccncc4F)c2C#N)CCCCC3)CCCC1] | ESP [M + H]$^+$: 380.5 | V | Intermediate B94, 3-fluoroisonicotinaldehyde, cycloheptanone |

-continued

| Intermediate | Name and Structure | MS | Method | Reagents |
|---|---|---|---|---|
| N175 | 2-(1-(Methoxymethyl)cyclopentyl)-4-(4-methyl-1H-pyrazol-3-yl)-6,7,8,9-tetrahydro-5H-cyclohepta[b]pyridine-3-carbonitrile 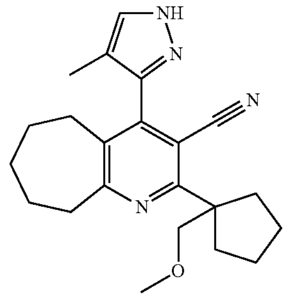 [SMILES: COCC1(c2nc3c(c(-c4n[nH]cc4C)c2C#N)CCCCC3)CCCC1] | ESP $[M + H]^+$: 365.6 | V | Intermediate B94, 4-methyl-1H-pyrazole-5-carbaldehyde, cycloheptanone |
| N176 | 4-(1H-Indol-4-yl)-2-(1-(methoxymethyl)cyclopentyl)-6,7,8,9-tetrahydro-5H-cyclohepta[b]pyridine-3-carbonitrile 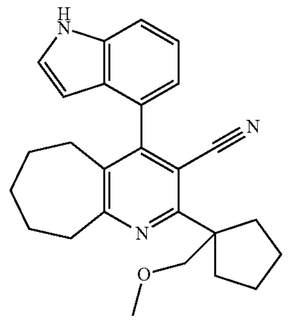 [SMILES: COCC1(c2nc3c(c(-c4cccc5[nH]ccc45)c2C#N)CCCCC3)CCCC1] | ESP $[M + H]^+$: 400.7 | V | Intermediate B94, 1H-indole-4-carbaldehyde, cycloheptanone |
| N177 | 4-(2-Chloro-4-pyridyl)-2-[1-(methoxymethyl)cyclopentyl]-6,7,8,9-tetrahydro-5H-cyclohepta[b]pyridine-3-carbonitrile 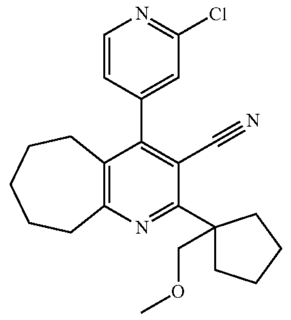 [SMILES: COCC1(c2nc3c(c(-c4ccnc(Cl)c4)c2C#N)CCCCC3)CCCC1] | ESP $[M + H]^+$: 396.5 | V | Intermediate B94, 2-chloroisonicotinaldehyde, cycloheptanone |

-continued

| Intermediate | Name and Structure | MS | Method | Reagents |
|---|---|---|---|---|
| N178 | 4-(2-Ethyl-4-pyridyl)-2-[1-(methoxymethyl)cyclopentyl]-6,7,8,9-tetrahydro-5H-cyclohepta[b]pyridine-3-carbonitrile 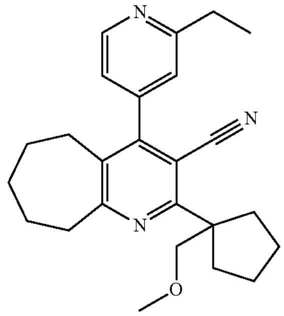 [SMILES: CCc1cc(-c2c(C#N)c(C3(COC)CCCC3)nc3c2CCCCC3)ccn1] | ESP [M + H]$^+$: 390.6 | V | Intermediate B94, 2-ethylisonicotinaldehyde, cycloheptanone |
| N179 | 4-(3-Hydroxy-2-methylphenyl)-2-(1-(methoxymethyl)cyclopentyl)-6,7,8,9-tetrahydro-5H-cyclohepta[b]pyridine-3-carbonitrile 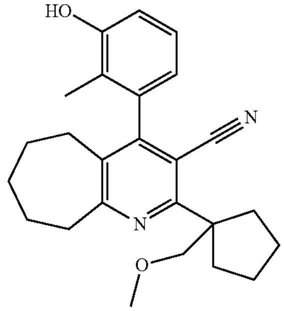 [SMILES: COCC1(c2nc3c(c(-c4cccc(O)c4C)c2C#N)CCCCC3)CCCC1] | ESP [M + H]$^+$: 391.7 | V | Intermediate B94, 3-hydroxy-2-methylbenzaldehyde, cycloheptanone |
| N180 | 2-(1-(Methoxymethyl)cyclopentyl)-4-(2-methyloxazol-4-yl)-6,7,8,9-tetrahydro-5H-cyclohepta[b]pyridine-3-carbonitrile 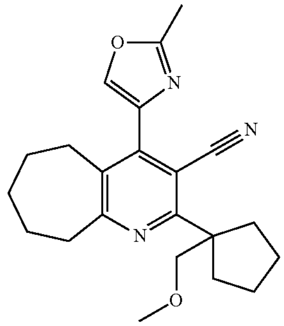 [SMILES: COCC1(c2nc3c(c(-c4coc(C)n4)c2C#N)CCCCC3)CCCC1] | ESP [M + H]$^+$: 366.6 | V | Intermediate B94, 2-methyloxazole-4-carbaldehyde, cycloheptanone |

-continued

| Intermediate | Name and Structure | MS | Method | Reagents |
|---|---|---|---|---|
| N181 | 4-(1H-Indazol-4-yl)-2-(1-(methoxymethyl)cyclopentyl)-6,7,8,9-tetrahydro-5H-cyclohepta[b]pyridine-3-carbonitrile 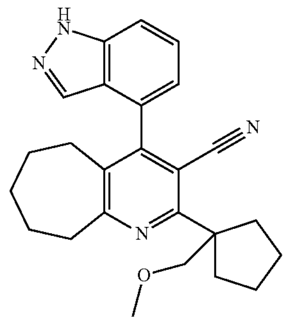 [SMILES: COCC1(c2nc3c(c(-c4cccc5[nH]ncc45)c2C#N)CCCCC3)CCCC1] | ESP $[M + H]^+$: 401.7 | V | Intermediate B94, 1H-indazole-4-carbaldehyde, cycloheptanone |
| N182 | 2-[1-(Methoxymethyl)cyclopentyl]-4-[2-(trifluoromethyl)-4-pyridyl]-6,7,8,9-tetrahydro-5H-cyclohepta[b]pyridine-3-carbonitrile 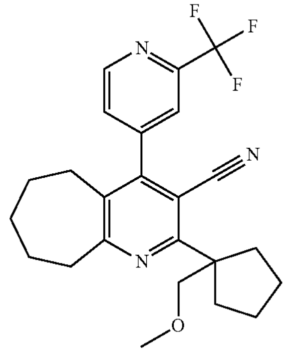 [SMILES: COCC1(c2nc3c(c(-c4ccnc(C(F)(F)F)c4)c2C#N)CCCCC3)CCCC1] | | V | Intermediate B94, 2-(trifluoromethyl) isonicotinaldehyde, cycloheptanone |
| N183 | 2-(1-(Methoxymethyl)cyclopentyl)-4-(2-(2,2,2-trifluoroethoxy)pyridin-4-yl)-6,7,8,9-tetrahydro-5H-cyclohepta[b]pyridine-3-carbonitrile 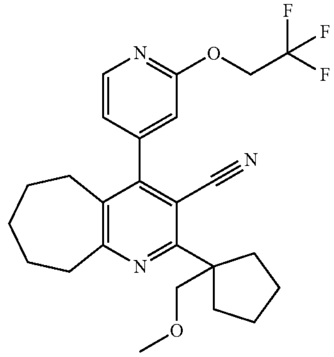 [SMILES: COCC1(c2nc3c(c(-c4ccnc(OCC(F)(F)F)c4)c2C#N)CCCCC3)CCCC1] | ESP $[M + H]^+$: 460.6 | V | Intermediate B94, 2-(2,2,2-trifluoroethoxy) isonicotinaldehyde, cycloheptanone |

-continued

| Intermediate | Name and Structure | MS | Method | Reagents |
|---|---|---|---|---|
| N184 | 2-(1-(Methoxymethyl)cyclopentyl)-4-phenyl-6,7,8,9-tetrahydro-5H-cyclohepta[b]pyridine-3-carbonitrile 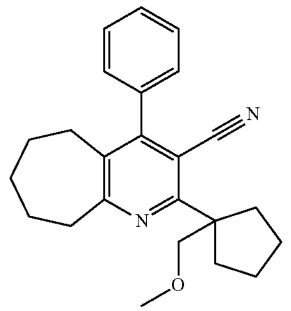 [SMILES: COCC1(c2nc3c(c(-c4ccccc4)c2C#N)CCCCC3)CCCC1] | ESP [M + H]$^+$: 361.6 | V | Intermediate B94, benzaldehyde, cycloheptanone |
| N185 | 4-(2-Ethoxypyridin-4-yl)-2-(1-(methoxymethyl)cyclopentyl)-6,7,8,9-tetrahydro-5H-cyclohepta[b]pyridine-3-carbonitrile 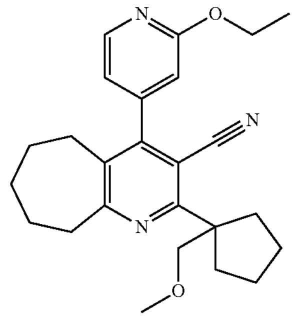 [SMILES: CCOc1cc(-c2c(C#N)c(C3(COC)CCCC3)nc3c2CCCCC3)ccn1] | ESP [M + H]$^+$: 406.6 | V | Intermediate B94, 2-ethoxyisonicotinaldehyde, cycloheptanone |
| N186 | 4-(4-Fluoro-3-methoxy-phenyl)-2-[1-(methoxymethyl)cyclopentyl]-6,7,8,9-tetrahydro-5H-cyclohepta[b]pyridine-3-carbonitrile 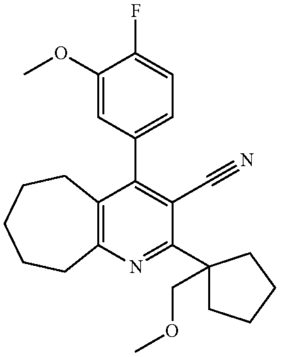 [SMILES: COCC1(c2nc3c(c(-c4ccc(F)c(OC)c4)c2C#N)CCCCC3)CCCC1] | ESP [M + H]$^+$: 409.6 | V | Intermediate B94, 4-fluoro-3-methoxybenzaldehyde, cycloheptanone |

-continued

| Intermediate | Name and Structure | MS | Method | Reagents |
|---|---|---|---|---|
| N187 | 4-(4-Fluorophenyl)-2-(1-(methoxymethyl)cyclopentyl)-6,7,8,9-tetrahydro-5H-cyclohepta[b]pyridine-3-carbonitrile 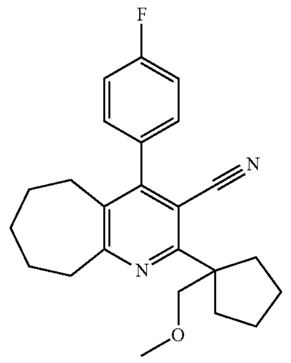 [SMILES: COCC1(c2nc3c(c(-c4ccc(F)cc4)c2C#N)CCCCC3)CCCC1] | ESP [M + H]$^+$: 379.6 | V | Intermediate B94, 4-fluorobenzaldehyde, cycloheptanone |
| N188 | 2-(1-(Methoxymethyl)cyclopentyl)-4-(3-methoxyphenyl)-6,7,8,9-tetrahydro-5H-cyclohepta[b]pyridine-3-carbonitrile 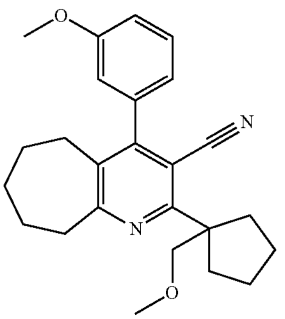 [SMILES: COCC1(c2nc3c(c(-c4cccc(OC)c4)c2C#N)CCCCC3)CCCC1] | ESP [M + H]$^+$: 391.6 | V | Intermediate B94, 3-methoxybenzaldehyde, cycloheptanone |
| N189 | 4-(2-Fluoro-5-methoxyphenyl)-2-(1-(methoxymethyl)cyclopentyl)-6,7,8,9-tetrahydro-5H-cyclohepta[b]pyridine-3-carbonitrile 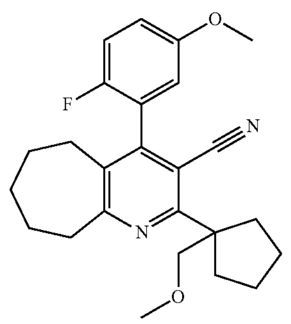 [SMILES: COCC1(c2nc3c(c(-c4cc(OC)ccc4F)c2C#N)CCCCC3)CCCC1] | ESP [M + H]$^+$: 409.6 | V | Intermediate B94, 2-fluoro-5-methoxybenzaldehyde, cycloheptanone |

-continued

| Intermediate | Name and Structure | MS | Method | Reagents |
|---|---|---|---|---|
| N190 | 4-(3-Chlorophenyl)-2-(1-(methoxymethyl)cyclopentyl)-6,7,8,9-tetrahydro-5H-cyclohepta[b]pyridine-3-carbonitrile 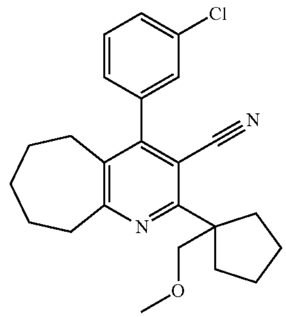 [SMILES: COCC1(c2nc3c(c(-c4cccc(Cl)c4)c2C#N)CCCCC3)CCCC1] | | V | Intermediate B94, 3-chlorobenzaldehyde, cycloheptanone |
| N191 | 2-(3-(Methoxymethyl)pentan-3-yl)-4-(1-methyl-1H-pyrazol-5-yl)-6,7,8,9-tetrahydro-5H-cyclohepta[b]pyridine-3-carbonitrile 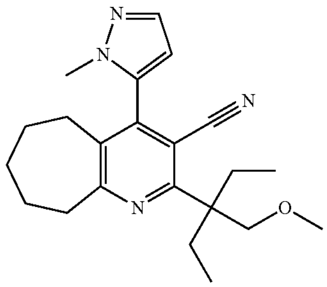 [SMILES: CCC(CC)(COC)c1nc2c(c(-c3ccnn3C)c1C#N)CCCCC2] | ESP $[M + H]^+$: 367.6 | V | Intermediate B191, 1-methyl-1H-pyrazole-5-carbaldehyde, cycloheptanone |
| N192 | 2-[1-Ethyl-1-(methoxymethyl)propyl]-4-phenyl-6,7,8,9-tetrahydro-5H-cyclohepta[b]pyridine-3-carbonitrile 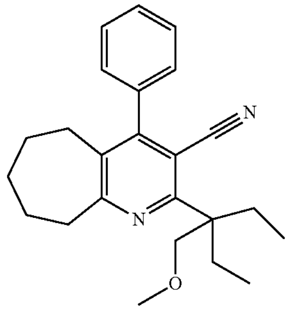 [SMILES: CCC(CC)(COC)c1nc2c(c(-c3ccccc3)c1C#N)CCCCC2] | | V | Intermediate B191, benzaldehyde, cycloheptanone |
| N193 | 2-Cyclopentyl-4-(2-ethylpyridin-4-yl)-6,7,8,9-tetrahydro-5H-cyclohepta[b]pyridine-3-carbonitrile 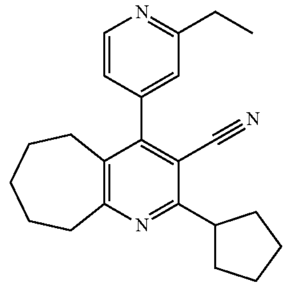 [SMILES: CCc1cc(-c2c(C#N)c(C3CCCC3)nc3c2CCCCC3)ccn1] | ESP $[M + H]^+$: 346.5 | V | 3-Cyclopentyl-3-oxopropanenitrile (CAS# 95882-33-0), 2-ethylisonicotinaldehyde, cycloheptanone |

-continued

| Intermediate | Name and Structure | MS | Method | Reagents |
|---|---|---|---|---|
| N195 | 2-Cyclopentyl-4-(2-(trifluoromethyl)pyridin-4-yl)-6,7,8,9-tetrahydro-5H-cyclohepta[b]pyridine-3-carbonitrile 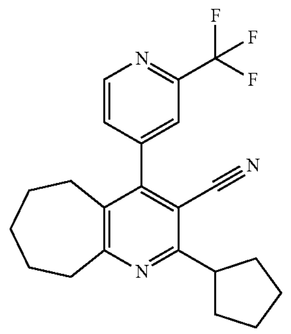 [SMILES: N#Cc1c(C2CCCC2)nc2c(c1-c1ccnc(C(F)(F)F)c1)CCCCC2] | ESP $[M + H]^+$: 386.5 | V | 3-Cyclopentyl-3-oxopropanenitrile (CAS# 95882-33-0), 2-(trifluoromethyl) isonicotinaldehyde, cycloheptanone |
| N196 | 4-(1-Methyl-1H-pyrazol-5-yl)-2-(3-methylpentan-3-yl)-6,7,8,9-tetrahydro-5H-cyclohepta[b]pyridine-3-carbonitrile 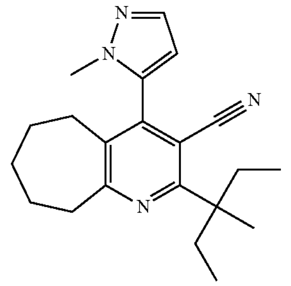 [SMILES: CCC(C)(CC)c1nc2c(c(-c3ccnn3C)c1C#N)CCCCC2] | ESP $[M + H]^+$: 337.7 | V | 4-Ethyl-4-methyl-3-oxohexanenitrile (CAS#87539-07-9), 1-methyl-1H-pyrazole-5-carbaldehyde, cycloheptanone |
| N197 | 4-(2-Ethyl-4-pyridyl)-2-isopropyl-6,7,8,9-tetrahydro-5H-cyclohepta[b]pyridine-3-carbonitrile 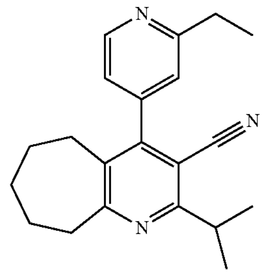 [SMILES: CCc1cc(-c2c(C#N)c(C(C)C)nc3c2CCCCC3)ccn1] | ESP $[M + H]^+$: 320.5 | V | 4-Methyl-3-oxopentanenitrile (CAS# 29509-06-6), 2-ethylisonicotinaldehyde, cycloheptanone |
| N198 | 2-Isopropyl-4-(2-(2,2,2-trifluoroethoxy)pyridin-4-yl)-6,7,8,9-tetrahydro-5H-cyclohepta[b]pyridine-3-carbonitrile 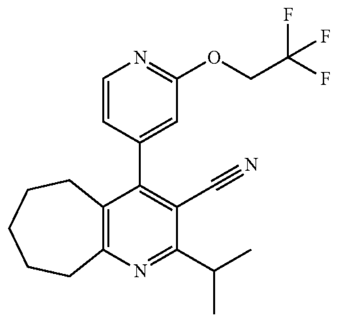 [SMILES: CC(C)c1nc2c(c(-c3ccnc(OCC(F)(F)F)c3)c1C#N)CCCCC2] | ESP $[M + H]^+$: 390.5 | V | 4-Methyl-3-oxopentanenitrile (CAS# 29509-06-6), 2-(2,2,2-trifluoroethoxy) isonicotinaldehyde, cycloheptanone |

-continued

| Intermediate | Name and Structure | MS | Method | Reagents |
|---|---|---|---|---|
| N199 | 4-(2-Ethoxypyridin-4-yl)-2-isopropyl-6,7,8,9-tetrahydro-5H-cyclohepta[b]pyridine-3-carbonitrile 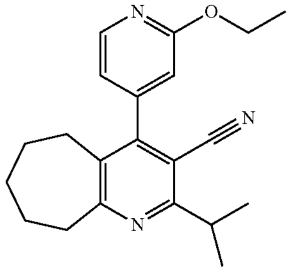 [SMILES: CCOc1cc(-c2c(C#N)c(C(C)C)nc3c2CCCCC3)ccn1] | ESP $[M + H]^+$: 336.6 | V | 4-Methyl-3-oxopentanenitrile (CAS# 29509-06-6), 2-ethoxyisonicotinaldehyde. cycloheptanone |
| N200 | 2-(1-Methoxycyclopentyl)-4-phenyl-6,7,8,9-tetrahydro-5H-cyclohepta[b]pyridine-3-carbonitrile 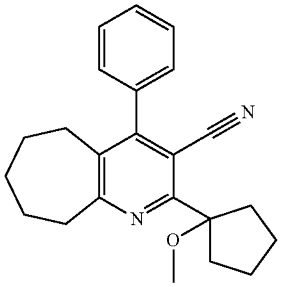 [SMILES: COC1(c2nc3c(c(-c4ccccc4)c2C#N)CCCCC3)CCCC1] | ESP $[M + H]^+$: 347.7 | V | Intermediate B200, benzaldehyde, cycloheptanone |
| N201 | 2-(1-Methoxycyclopentyl)-4-phenyl-5,6,7,8-tetrahydroquinoline-3-carbonitrile 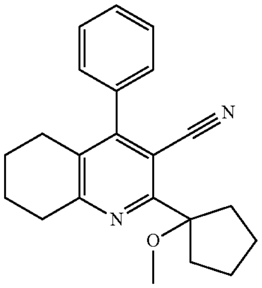 | ESP $[M + H]^+$: 336.6 | V | Intermediate B200, benzaldehyde, cyclohexanone |
| N202 | 2-(1-Methoxycyclopentyl)-4-(2-methoxypyridin-4-yl)-6,7,8,9-tetrahydro-5H-cyclohepta[b]pyridine-3-carbonitrile 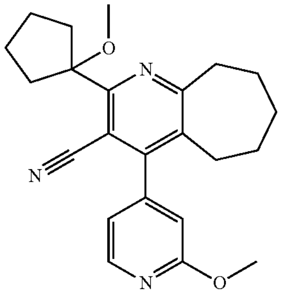 [SMILES: COc1cc(-c2c(C#N)c(C3(OC)CCCC3)nc3c2CCCCC3)ccn1] | ESP $[M + H]^+$: 378.5 | V | Intermediate B200, 2-methoxyisonicotinaldehyde, cycloheptanone |

-continued

| Intermediate | Name and Structure | MS | Method | Reagents |
|---|---|---|---|---|
| N203 | 4-(2-Chloro-4-pyridyl)-2-(1-methoxycyclopentyl)-6,7,8,9-tetrahydro-5H-cyclohepta[b]pyridine-3-carbonitrile 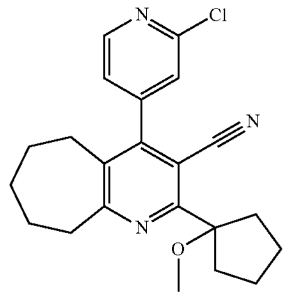 [SMILES: COC1(c2nc3c(c(-c4ccnc(Cl)c4)c2C#N)CCCCC3)CCCC1] | ESP $[M + H]^+$: 382.5 | V | Intermediate B200, 2-chloroisonicotinaldehyde, cycloheptanone |
| N204 | 2-(1-Methoxycyclopentyl)-4-(2-methylpyridin-4-yl)-6,7,8,9-tetrahydro-5H-cyclohepta[b]pyridine-3-carbonitrile 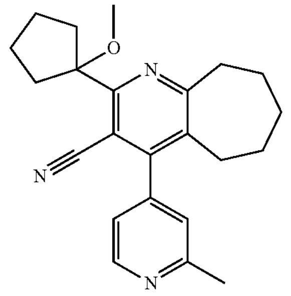 [SMILES: COC1(c2nc3c(c(-c4ccnc(C)c4)c2C#N)CCCCC3)CCCC1] | ESP $[M + H]^+$: 362.5 | V | Intermediate B200, 2-methylisonicotinaldehyde, cycloheptanone |
| N210 | (S)-tert-Butyl 2-(3-cyano-4-phenyl-6,7,8,9-tetrahydro-5H-cyclohepta[b]pyridin-2-yl)pyrrolidine-1-carboxylate 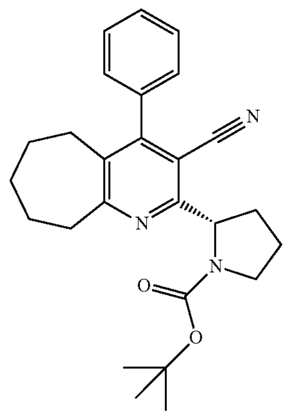 [SMILES: CC(C)(C)OC(=O)N1CCC[C@H]1c1nc2c(c(-c3ccccc3)c1C#N)CCCCC2] | ESP $[M + H]^+$: 418.7 | V | (S)-tert-Butyl 2-(2-cyanoacetyl) pyrrolidine-1-carboxylate (CAS# 173690-69-2), benzaldehyde, cycloheptanone |

-continued

| Intermediate | Name and Structure | MS | Method | Reagents |
|---|---|---|---|---|
| N213 | 2-(1-Methoxy-2-methylpropan-2-yl)-6,6-dimethyl-4-(1-methyl-1H-pyrazol-5-yl)-5,6,7,8-tetrahydroquinoline-3-carbonitrile 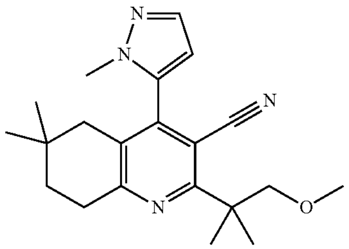 | ESP [M + H]$^+$: 353.5 | V | 5-Methoxy-4,4-dimethyl-3-oxopentanenitrile (CAS# 90087-79-9), 1-methyl-1H-pyrazole-5-carbaldehyde, 4,4-dimethylcyclohexanone |
| N214 | 6,6-Dimethyl-4-(1-methyl-1H-pyrazol-5-yl)-2-tert-pentyl-5,6,7,8-tetrahydroquinoline-3-carbonitrile 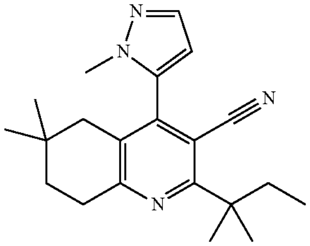 [SMILES: CCC(C)(C)c1nc2c(c(-c3ccnn3C)c1C#N)CC(C)(C)CC2] | ESP [M + H]$^+$: 337.5 | V | 4,4-Dimethyl-3-oxohexanenitrile (CAS# 876299-62-6), 1-methyl-1H-pyrazole-5-carbaldehyde, 4,4-dimethylcyclohexanone |
| N215 | 2-(1-Methoxy-2-methylpropan-2-yl)-6,6-dimethyl-4-(2-methylpyridin-4-yl)-5,6,7,8-tetrahydroquinoline-3-carbonitrile 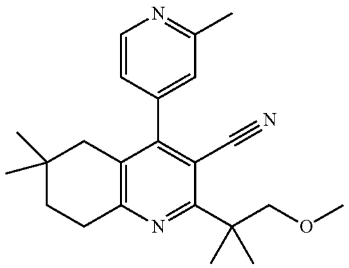 | ESP [M + H]$^+$: 364.6 | V | 5-Methoxy-4,4-dimethyl-3-oxopentanenitrile (CAS# 90087-79-9), 2-methylpyridine-4-carbaldehyde, 4,4-dimethylcyclohexanone |
| N216 | 2-(1-(Methoxymethyl)cyclopentyl)-4-phenyl-5,6,7,8-tetrahydroquinoline-3-carbonitrile 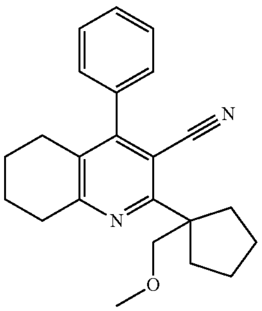 [SMILES: COCC1(c2nc3c(c(-c4ccccc4)c2C#N)CCCC3)CCCC1] | ESP [M + H]$^+$: 347.6 | V | Intermediate B94, benzaldehyde, cyclohexanone |

-continued

| Intermediate | Name and Structure | MS | Method | Reagents |
|---|---|---|---|---|
| N217 | 6,6-Difluoro-2-(1-(methoxymethyl)cyclopentyl)-4-phenyl-5,6,7,8-tetrahydroquinoline-3-carbonitrile 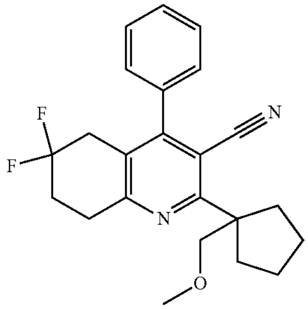 [SMILES: COCC1(c2nc3c(c(-c4ccccc4)c2C#N)CC(F)(F)CC3)CCCC1] | ESP [M + H]$^+$: 383.6 | V | Intermediate B94, benzaldehyde, 4,4-difluorocyclohexanone |
| N218 | 6,6-Difluoro-2-(1-(methoxymethyl)cyclohexyl)-4-phenyl-5,6,7,8-tetrahydroquinoline-3-carbonitrile 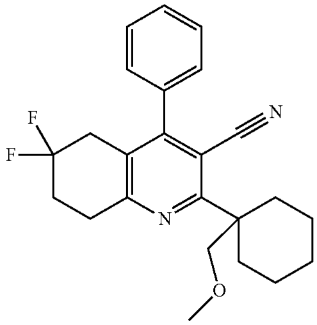 [SMILES: COCC1(c2nc3c(c(-c4ccccc4)c2C#N)CC(F)(F)CC3)CCCCC1] | ESP [M + H]$^+$: 397.6 | V | Intermediate B218, benzaldehyde, 4,4-difluorocyclohexanone |
| N219 | 6,6-Difluoro-2-(1-(methoxymethyl)cyclopentyl)-4-(2-methylpyridin-4-yl)-5,6,7,8-tetrahydroquinoline-3-carbonitrile 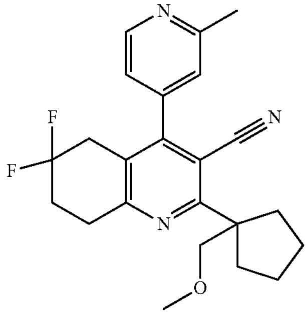 [SMILES: COCC1(c2nc3c(c(-c4ccnc(C)c4)c2C#N)CC(F)(F)CC3)CCCC1] | ESP [M + H]$^+$: 398.5 | V | Intermediate B94, 2-methylpyridine-4-carbaldehyde, 4,4-difluorocyclohexanone |

-continued

| Intermediate | Name and Structure | MS | Method | Reagents |
|---|---|---|---|---|
| N220 | 2-(4-Methyltetrahydro-2H-pyran-4-yl)-4-phenyl-5,6,7,8-tetrahydroquinoline-3-carbonitrile 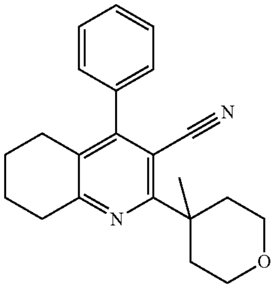 [SMILES: CC1(c2nc3c(c(-c4ccccc4)c2C#N)CCCC3)CCOCC1] | ESP [M + H]$^+$: 333.5 | V | Intermediate B220, benzaldehyde, cyclohexanone |
| N221 | 6,6-Difluoro-2-(4-methyltetrahydro-2H-pyran-4-yl)-4-phenyl-5,6,7,8-tetrahydroquinoline-3-carbonitrile 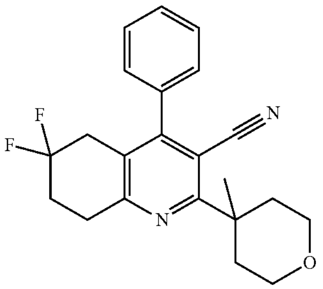 [SMILES: CC1(c2nc3c(c(-c4ccccc4)c2C#N)CC(F)(F)CC3)CCOCC1] | ESP [M + H]$^+$: 369.5 | V | Intermediate B220, benzaldehyde, 4,4-difluorocyclohexanone |
| N222 | 2-(1-(Methoxymethyl)cyclopentyl)-6-methyl-4-(2-methylpyridin-4-yl)-5,6,7,8-tetrahydroquinoline-3-carbonitrile 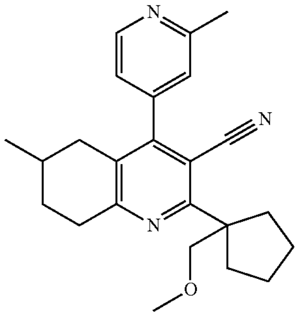 [SMILES: COCC1(c2nc3c(c(-c4ccnc(C)c4)c2C#N)CC(C)CC3)CCCC1] | ESP [M + H]$^+$: 376.5 | V | Intermediate B94, 2-methylpyridine-4-carbaldehyde, 4-methylcyclohexanone |
| N223 | 2-(1-(Methoxymethyl)cyclohexyl)-4-phenyl-5,6,7,8-tetrahydroquinoline-3-carbonitrile 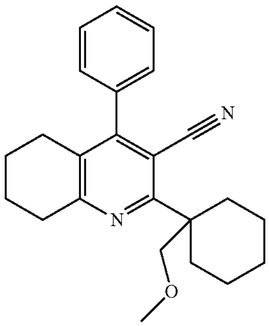 [SMILES: COCC1(c2nc3c(c(-c4ccccc4)c2C#N)CCCC3)CCCCC1] | ESP [M + H]$^+$: 361.7 | V | Intermediate B218, benzaldehyde, cyclohexanone |

-continued

| Intermediate | Name and Structure | MS | Method | Reagents |
|---|---|---|---|---|
| N224 | 6,6-Difluoro-2-(1-(methoxymethyl)cyclopentyl)-4-(1-methyl-1H-pyrazol-5-yl)-5,6,7,8-tetrahydroquinoline-3-carbonitrile 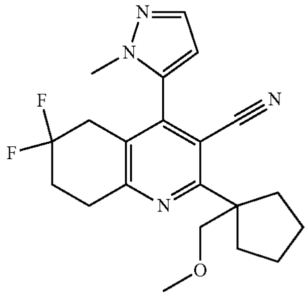 [SMILES: COCC1(c2nc3c(c(-c4ccnn4C)c2C#N)CC(F)(F)CC3)CCCC1] | ESP $[M + H]^+$: 387.6 | V | Intermediate B94, 1-methyl-1H-pyrazole-5-carbaldehyde, 4,4-difluorocyclohexanone |
| N225 | 2-(1-(Methoxymethyl)cyclopentyl)-6,6-dimethyl-4-(1-methyl-1H-pyrazol-5-yl)-5,6,7,8-tetrahydroquinoline-3-carbonitrile 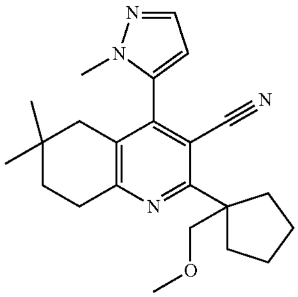 [SMILES: COCC1(c2nc3c(c(-c4ccnn4C)c2C#N)CC(C)(C)CC3)CCCC1] | ESP $[M + H]^+$: 379.6 | V | Intermediate B94, 1-methyl-1H-pyrazole-5-carbaldehyde, 4,4-dimethylcyclohexanone |
| N226 | 2-(2-Methyltetrahydrofuran-2-yl)-4-phenyl-5,6,7,8-tetrahydroquinoline-3-carbonitrile 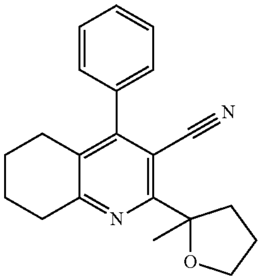 [SMILES: CC1(c2nc3c(c(-c4ccccc4)c2C#N)CCCC3)CCCO1] | ESP $[M + H]^+$: 319.5 | V | Intermediate B154, benzaldehyde, cyclohexanone |
| N227 | 6,6-Difluoro-2-(2-methyltetrahydrofuran-2-yl)-4-phenyl-5,6,7,8-tetrahydroquinoline-3-carbonitrile 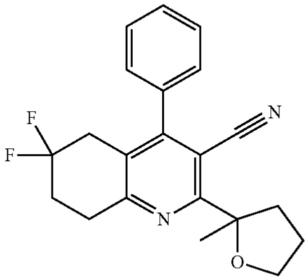 [SMILES: CC1(c2nc3c(c(-c4ccccc4)c2C#N)CC(F)(F)CC3)CCCO1] | ESP $[M + H]^+$: 355.5 | V | Intermediate B154, benzaldehyde, 4,4-difluorocyclohexanone |

-continued

| Intermediate | Name and Structure | MS | Method | Reagents |
|---|---|---|---|---|
| N228 | 6,6-Dimethyl-2-(2-methyltetrahydrofuran-2-yl)-4-phenyl-5,6,7,8-tetrahydroquinoline-3-carbonitrile 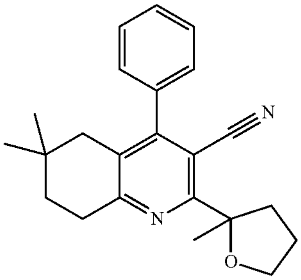 [SMILES: CC1(C)CCc2nc(C3(C)CCCO3)c(C#N)c(-c3ccccc3)c2C1] | ESP $[M + H]^+$: 347.6 | V | Intermediate B154, benzaldehyde, 4,4-dimethylcyclohexanone |
| N229 | 4-(1-Methyl-1H-pyrazol-5-yl)-2-(2-methyltetrahydrofuran-2-yl)-5,6,7,8-tetrahydroquinoline-3-carbonitrile 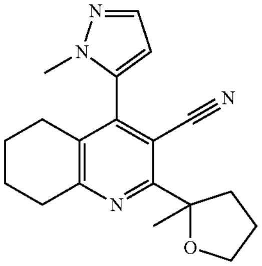 [SMILES: Cn1nccc1-c1c(C#N)c(C2(C)CCCO2)nc2c1CCCC2] | ESP $[M + H]^+$: 323.6 | V | Intermediate B154, 1-methyl-1H-pyrazole-5-carbaldehyde, cyclohexanone |
| N230 | 6,6-Dimethyl-4-(1-methyl-1H-pyrazol-5-yl)-2-(2-methyltetrahydrofuran-2-yl)-5,6,7,8-tetrahydroquinoline-3-carbonitrile 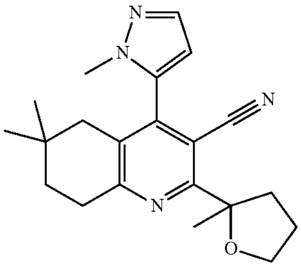 [SMILES: Cn1nccc1-c1c(C#N)c(C2(C)CCCO2)nc2c1CC(C)(C)CC2] | ESP $[M + H]^+$: 351.6 | V | Intermediate B154, 1-methyl-1H-pyrazole-5-carbaldehyde, 4,4-dimethylcyclohexanone |
| N237 | 2-(1-(Methoxymethyl)cyclopentyl)-4-(1-methyl-1H-pyrazol-5-yl)-5,6,7,8-tetrahydroquinoline-3-carbonitrile 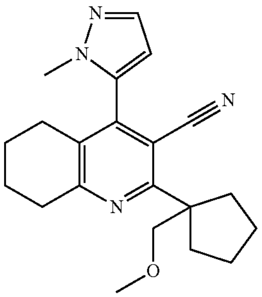 [SMILES: COCC1(c2nc3c(c(-c4ccnn4C)c2C#N)CCCC3)CCCC1] | ESP $[M + H]^+$: 351.7 | V | Intermediate B94, 1-methyl-1H-pyrazole-5-carbaldehyde, cyclohexanone |

-continued

| Intermediate | Name and Structure | MS | Method | Reagents |
|---|---|---|---|---|
| N238 | 2-(1-(Methoxymethyl)cyclohexyl)-4-(1-methyl-1H-pyrazol-5-yl)-5,6,7,8-tetrahydroquinoline-3-carbonitrile 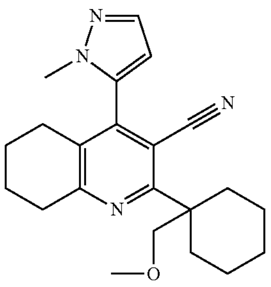 [SMILES: COCC1(c2nc3c(c(-c4ccnn4C)c2C#N)CCCC3)CCCCC1] | ESP [M + H]$^+$: 365.6 | V | Intermediate B218, 1-methyl-1H-pyrazole-5-carbaldehyde, cyclohexanone |
| N239 | 2-(1-(Methoxymethyl)cyclohexyl)-6,6-dimethyl-4-(1-methyl-1H-pyrazol-5-yl)-5,6,7,8-tetrahydroquinoline-3-carbonitrile 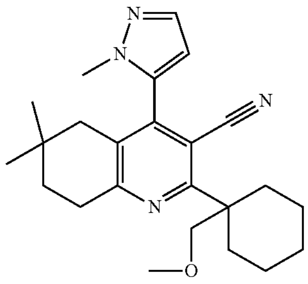 [SMILES: COCC1(c2nc3c(c(-c4ccnn4C)c2C#N)CC(C)(C)CC3)CCCCC1] | ESP [M + H]$^+$: 393.7 | V | Intermediate B218, 1-methyl-1H-pyrazole-5-carbaldehyde, 4,4-dimethylcyclohexanone |
| N240 | 6,6-Difluoro-2-(1-(methoxymethyl)cyclohexyl)-4-(1-methyl-1H-pyrazol-5-yl)-5,6,7,8-tetrahydroquinoline-3-carbonitrile 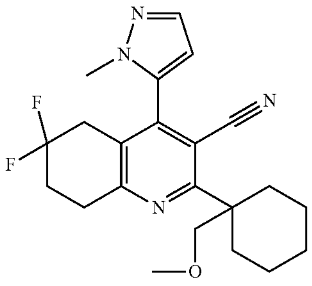 [SMILES: COCC1(c2nc3c(c(-c4ccnn4C)c2C#N)CC(F)(F)CC3)CCCCC1] | ESP [M + H]$^+$: 401.6 | V | Intermediate B218, 1-methyl-1H-pyrazole-5-carbaldehyde, 4,4-difluorocyclohexanone |
| N241 | 6,6-Difluoro-4-(1-methyl-1H-pyrazol-5-yl)-2-(2-methyltetrahydrofuran-2-yl)-5,6,7,8-tetrahydroquinoline-3-carbonitrile 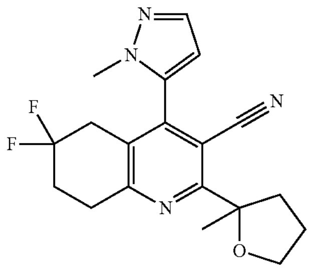 [SMILES: Cn1nccc1-c1c(C#N)c(C2(C)CCCO2)nc2c1CC(F)(F)CC2] | ESP [M + H]$^+$: 359.5 | V | Intermediate B154, 1-methyl-1H-pyrazole-5-carbaldehyde, 4,4-difluorocyclohexanone |

-continued

| Intermediate | Name and Structure | MS | Method | Reagents |
|---|---|---|---|---|
| N242 | 2-(2-(Methoxymethyl)tetrahydrofuran-2-yl)-4-phenyl-5,6,7,8-tetrahydroquinoline-3-carbonitrile 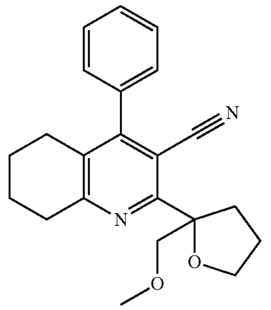 [SMILES: COCC1(c2nc3c(c(-c4ccccc4)c2C#N)CCCC3)CCCO1] | ESP $[M + H]^+$: 349.5 | V | Intermediate B242, benzaldehyde, cyclohexanone |
| N243 | 2-(1-(Methoxymethyl)cyclohexyl)-4-(1-methyl-1H-pyrazol-4-yl)-5,6,7,8-tetrahydroquinoline-3-carbonitrile 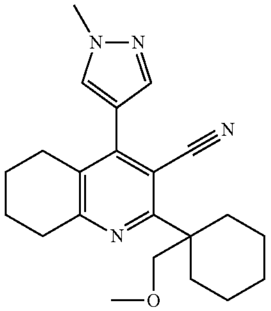 [SMILES: COCC1(c2nc3c(c(-c4cnn(C)c4)c2C#N)CCCC3)CCCCC1] | ESP $[M + H]^+$: 365.7 | V | Intermediate B218, 1-methyl-1H-pyrazole-4-carbaldehyde, cyclohexanone |
| N244 | 2-(2-(Methoxymethyl)tetrahydrofuran-2-yl)-6,6-dimethyl-4-phenyl-5,6,7,8-tetrahydroquinoline-3-carbonitrile 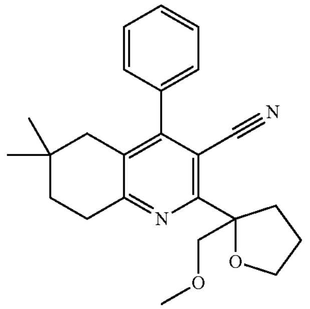 [SMILES: COCC1(c2nc3c(c(-c4ccccc4)c2C#N)CC(C)(C)CC3)CCCO1] | ESP $[M + H]^+$: 377.7 | V | Intermediate B242, benzaldehyde, 4,4-dimethylcyclohexanone |

-continued

| Intermediate | Name and Structure | MS | Method | Reagents |
|---|---|---|---|---|
| N245 | 6,6-Difluoro-2-(2-(methoxymethyl)tetrahydrofuran-2-yl)-4-phenyl-5,6,7,8-tetrahydroquinoline-3-carbonitrile 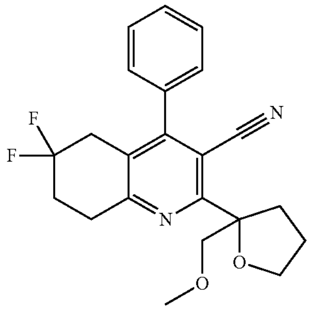 [SMILES: COCC1(c2nc3c(c(-c4ccccc4)c2C#N)CC(F)(F)CC3)CCCO1] | ESP $[M + H]^+$: 385.5 | V | Intermediate B242, benzaldehyde, 4,4-difluorocyclohexanone |
| N246 | 2-(2-Ethyltetrahydrofuran-2-yl)-4-phenyl-5,6,7,8-tetrahydroquinoline-3-carbonitrile 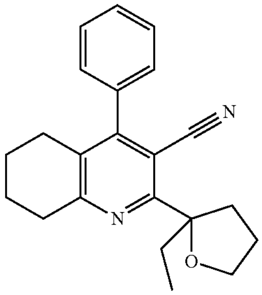 [SMILES: CCC1(c2nc3c(c(-c4ccccc4)c2C#N)CCCC3)CCCO1] | ESP $[M + H]^+$: 333.6 | V | Intermediate B246, benzaldehyde, cyclohexanone |
| N247 | 2-(2-Ethyltetrahydrofuran-2-yl)-6,6-dimethyl-4-phenyl-5,6,7,8-tetrahydroquinoline-3-carbonitrile 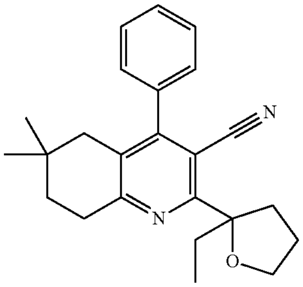 [SMILES: CCC1(c2nc3c(c(-c4ccccc4)c2C#N)CC(C)(C)CC3)CCCO1] | ESP $[M + H]^+$: 361.6 | V | Intermediate B246, benzaldehyde, 4,4-dimethylcyclohexanone |
| N248 | 2-(2-Ethyltetrahydrofuran-2-yl)-6,6-difluoro-4-phenyl-5,6,7,8-tetrahydroquinoline-3-carbonitrile 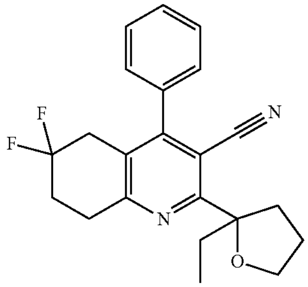 [SMILES: CCC1(c2nc3c(c(-c4ccccc4)c2C#N)CC(F)(F)CC3)CCCO1] | ESP $[M + H]^+$: 369.6 | V | Intermediate B246, benzaldehyde, 4,4-difluorocyclohexanone |

-continued

| Intermediate | Name and Structure | MS | Method | Reagents |
|---|---|---|---|---|
| N255 | 2-(2-Ethyltetrahydrofuran-2-yl)-4-(1-methyl-1H-pyrazol-5-yl)-5,6,7,8-tetrahydroquinoline-3-carbonitrile 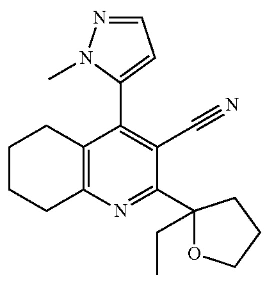 [SMILES: CCC1(c2nc3c(c(-c4ccnn4C)c2C#N)CCCC3)CCCO1] | ESP [M + H]$^+$: 337.6 | V | Intermediate B246, 1-methyl-1H-pyrazole-5-carbaldehyde, cyclohexanone |
| N256 | 2-(1-(Methoxymethyl)cyclopentyl)-4-(1-methyl-1H-pyrazol-4-yl)-5,6,7,8-tetrahydroquinoline-3-carbonitrile 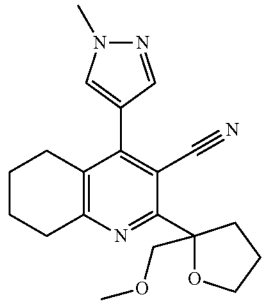 [SMILES: COCC1(c2nc3c(c(-c4cnn(C)c4)c2C#N)CCCC3)CCCO1] | ESP [M + H]$^+$: 351.6 | V | Intermediate B94, 1-methyl-1H-pyrazole-4-carbaldehyde, cyclohexanone |
| N257 | 4-(3-Chlorophenyl)-2-(2-(methoxymethyl)tetrahydrofuran-2-yl)-5,6,7,8-tetrahydroquinoline-3-carbonitrile 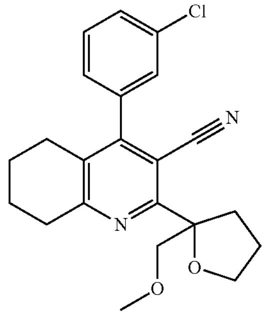 [SMILES: COCC1(c2nc3c(c(-c4cccc(Cl)c4)c2C#N)CCCC3)CCCO1] | ESP [M + H]$^+$: 383.5 | V | Intermediate B242, 3-chlorobenzaldehyde, cyclohexanone |
| N258 | 4-(3-Chlorophenyl)-2-(2-methyltetrahydrofuran-2-yl)-5,6,7,8-tetrahydroquinoline-3-carbonitrile 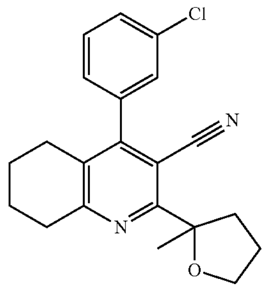 [SMILES: CC1(c2nc3c(c(-c4cccc(Cl)c4)c2C#N)CCCC3)CCCO1] | ESP [M + H]$^+$: 353.5 | V | Intermediate B154, 3-chlorobenzaldehyde, cyclohexanone |

-continued

| Intermediate | Name and Structure | MS | Method | Reagents |
|---|---|---|---|---|
| N259 | 2-(2-(Methoxymethyl)tetrahydrofuran-2-yl)-4-(3-methoxyphenyl)-5,6,7,8-tetrahydroquinoline-3-carbonitrile 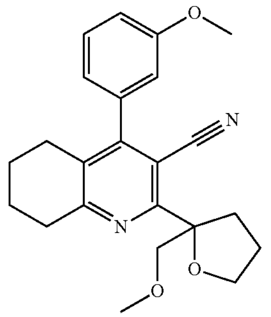 [SMILES: COCC1(c2nc3c(c(-c4cccc(OC)c4)c2C#N)CCCC3)CCCO1] | ESP $[M + H]^+$: 379.5 | V | Intermediate B242, 3-methoxybenzaldehyde, cyclohexanone |
| N260 | 4-(4-Fluoro-3-methoxyphenyl)-2-(2-(methoxymethyl)tetrahydrofuran-2-yl)-5,6,7,8-tetrahydroquinoline-3-carbonitrile 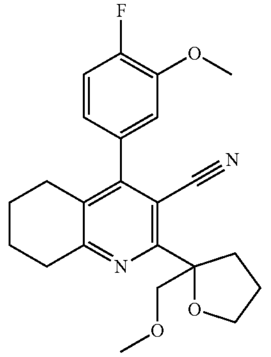 [SMILES: COCC1(c2nc3c(c(-c4ccc(F)c(OC)c4)c2C#N)CCCC3)CCCO1] | ESP $[M + H]^+$: 397.5 | V | Intermediate B242, 4-fluoro-3-methoxybenzaldehyde, cyclohexanone |
| N261 | 2-(1-(Methylsulfonylmethyl)cyclopentyl)-4-phenyl-5,6,7,8-tetrahydroquinoline-3-carbonitrile 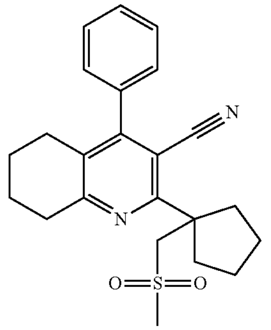 [SMILES: CS(=O)(=O)CC1(c2nc3c(c(-c4ccccc4)c2C#N)CCCC3)CCCC1] | ESP $[M + H]^+$: 395.5 | V | Intermediate B261, benzaldehyde, cyclohexanone |

-continued

| Intermediate | Name and Structure | MS | Method | Reagents |
|---|---|---|---|---|
| N264 | 2-[1-(Methoxymethyl)cyclopentyl]-4-(3-methylsulfonylphenyl)-5,6,7,8-tetrahydroquinoline-3-carbonitrile 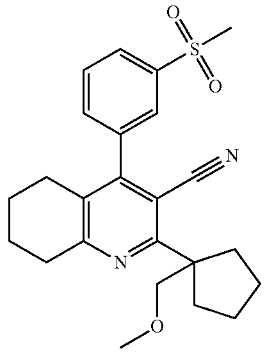 [SMILES: COCC1(c2nc3c(c(-c4cccc(S(C)(=O)=O)c4)c2C#N)CCCC3)CCCC1] | ESP $[M + H]^+$: 425.6 | V | Intermediate B94, 3-(methylsulfonyl) benzaldehyde, cyclohexanone |
| N265 | 2-[1-(Methoxymethyl)cyclopentyl]-4-(3-methoxyphenyl)-5,6,7,8-tetrahydroquinoline-3-carbonitrile 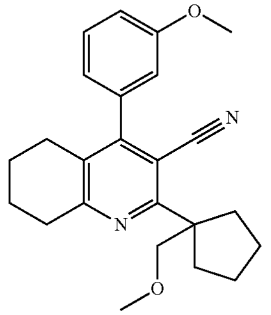 [SMILES: COCC1(c2nc3c(c(-c4cccc(OC)c4)c2C#N)CCCC3)CCCC1] | ESP $[M + H]^+$: 377.6 | V | Intermediate B94, 3-methoxybenzaldehyde, cyclohexanone |
| N266 | 4-(2-Fluoro-5-methoxyphenyl)-2-(2-(methoxymethyl)tetrahydrofuran-2-yl)-5,6,7,8-tetrahydroquinoline-3-carbonitrile 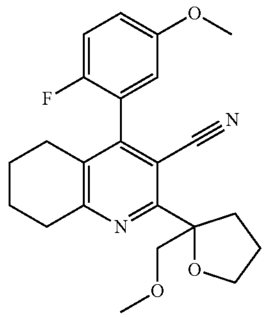 [SMILES: COCC1(c2nc3c(c(-c4cc(OC)ccc4F)c2C#N)CCCC3)CCCO1] | ESP $[M + H]^+$: 397.6 | V | Intermediate B242, 2-fluoro-5-methoxybenzaldehyde, cyclohexanone |

-continued

| Intermediate | Name and Structure | MS | Method | Reagents |
| --- | --- | --- | --- | --- |
| N268 | 2-(1-(Ethoxymethyl)cyclopentyl)-4-phenyl-5,6,7,8-tetrahydroquinoline-3-carbonitrile 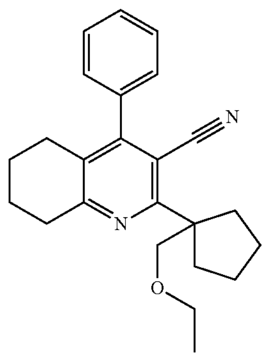 [SMILES: CCOCC1(c2nc3c(c(-c4ccccc4)c2C#N)CCCC3)CCCC1] | ESP [M + H]$^+$: 361.5 | V | Intermediate B268, benzaldehyde, cyclohexanone |
| N269R | 4-(3-Chlorophenyl)-2-(2-(methoxymethyl)tetrahydrofuran-2-yl)-6,6-dimethyl-5,6,7,8-tetrahydroquinoline-3-carbonitrile 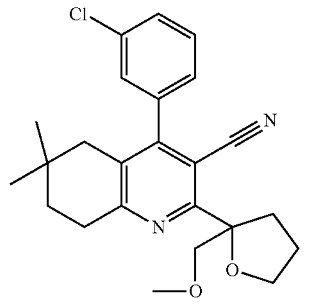 [SMILES: COCC1(c2nc3c(c(-c4cccc(Cl)c4)c2C#N)CC(C)(C)CC3)CCCO1] | ESP [M + H]$^+$: 411.5 | V | Intermediate B242, 3-chlorobenzaldehyde, 4,4-dimethylcyclohexanone |
| N271 | 2-(3,3-Difluorocyclobutyl)-4-(1-methyl-1H-pyrazol-4-yl)-6,7,8,9-tetrahydro-5H-cyclohepta[b]pyridine-3-carbonitrile 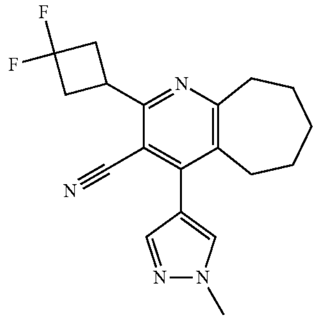 [SMILES: Cn1cc(-c2c(C#N)c(C3CC(F)(F)C3)nc3c2CCCCC3)cn1] | ESP [M + H]$^+$: 343.5 | V | 3-(3,3-Difluorocyclobutyl)-3-oxopropanenitrile (CAS# 1234616-26-2), 1-methyl-1H-pyrazole-4-carbaldehyde, cycloheptanone |

-continued

| Intermediate | Name and Structure | MS | Method | Reagents |
|---|---|---|---|---|
| N272 | 2-(1,5-Dimethyl-1H-pyrazol-4-yl)-4-phenyl-6,7,8,9-tetrahydro-5H-cyclohepta[b]pyridine-3-carbonitrile 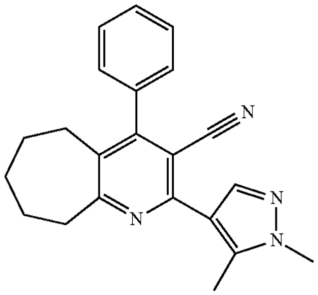 [SMILES: Cc1c(-c2nc3c(c(-c4ccccc4)c2C#N)CCCCC3)cnn1C] | ESP $[M + H]^+$: 343.6 | V | 3-(1,5-Dimethyl-1H-pyrazol-4-yl)-3-oxopropanenitrile (CAS# 1006485-37-5), benzaldehyde, cycloheptanone |
| N273 | 2-tert-Butyl-4-(1-methyl-1H-pyrazol-4-yl)-6,7,8,9-tetrahydro-5H-cyclohepta[b]pyridine-3-carbonitrile 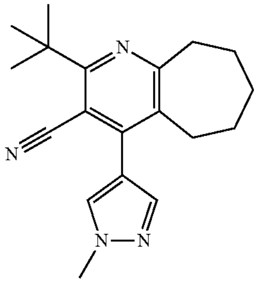 [SMILES: Cn1cc(-c2c(C#N)c(C(C)(C)C)nc3c2CCCCC3)cn1] | ESP $[M + H]^+$: 309.5 | V | 4,4-Dimethyl-3-oxopentanenitrile (CAS# 59997-51-2), 1-methyl-1H-pyrazole-4-carbaldehyde, cycloheptanone |
| N274 | 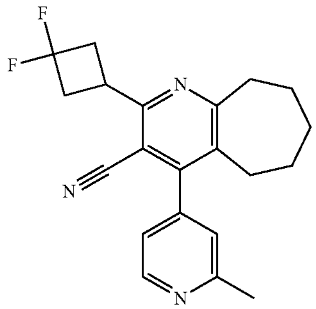 [SMILES: Cc1cc(-c2c(C#N)c(C3CC(F)(F)C3)nc3c2CCCCC3)ccn1] 2-(3,3-Difluorocyclobutyl)-4-(2-methylpyridin-4-yl)-6,7,8,9-tetrahydro-5H-cyclohepta[b]pyridine-3-carbonitrile | ESP $[M + H]^+$: 354.5 | V | 3-(3,3-Difluorocyclobutyl)-3-oxopropanenitrile (CAS# 1234616-26-2), 2-methylisonicotinaldehyde, cycloheptanone |
| N275 | 2-sec-Butyl-4-(1-methyl-1H-pyrazol-4-yl)-6,7,8,9-tetrahydro-5H-cyclohepta[b]pyridine-3-carbonitrile 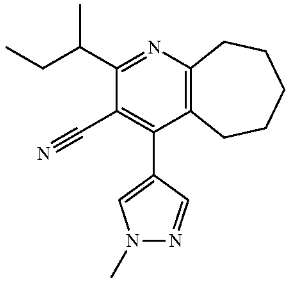 [SMILES: CCC(C)c1nc2c(c(-c3cnn(C)c3)c1C#N)CCCCC2] | ESP $[M + H]^+$: 309.5 | V | 4-Methyl-3-oxohexanenitrile (CAS# 42124-66-3), 1-methyl-1H-pyrazole-4-carbaldehyde, cycloheptanone |

-continued

| Intermediate | Name and Structure | MS | Method | Reagents |
|---|---|---|---|---|
| N276 | 2-tert-Butyl-6,6-difluoro-4-(2-methyl-pyridin-4-yl)-5,6,7,8-tetrahydro-quinoline-3-carbonitrile 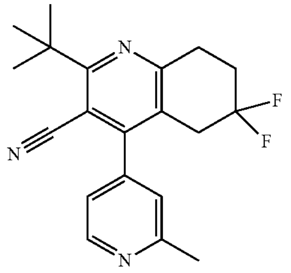 [SMILES: Cc1cc(-c2c(C#N)c(C(C)(C)C)nc3c2CC(F)(F)CC3)ccn1] | ESP $[M + H]^+$: 342.5 | V | 4,4-Dimethyl-3-oxopentanenitrile (CAS# 59997-51-2), 2-methylisonicotinaldehyde (CAS#63875-01-4), 4,4-difluorocyclohexanone (CAS# 22515-18-0) |
| N277 | 2-tert-Butyl-6,6-difluoro-4-(1-methyl-1H-pyrazol-4-yl)-5,6,7,8-tetrahydro-quinoline-3-carbonitrile 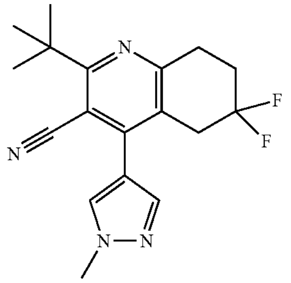 [SMILES: Cn1cc(-c2c(C#N)c(C(C)(C)C)nc3c2CC(F)(F)CC3)cn1] | ESP $[M + H]^+$: 331.0 | V | 4,4-Dimethyl-3-oxopentanenitrile (CAS# 59997-51-2), 1-methyl-1H-pyrazole-4-carbaldehyde, 4,4-difluorocyclohexanone (CAS# 22515-18-0) |
| N278 | 2-tert-Butyl-6,6-difluoro-4-(2-methyl-2H-pyrazol-3-yl)-5,6,7,8-tetrahydro-quinoline-3-carbonitrile 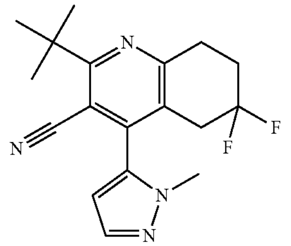 [SMILES: Cn1nccc1-c1c(C#N)c(C(C)(C)C)nc2c1CC(F)(F)CC2] | ESP $[M + H]^+$: 331.5 | V | 4,4-Dimethyl-3-oxopentanenitrile (CAS# 59997-51-2), 1-methyl-1H-pyrazole-5-carbaldehyde, 4,4-difluorocyclohexanone (CAS# 27258-33-9) |
| N279 | 2-tert-Butyl-4-phenyl-7,8-dihydro-5H-thiopyrano[4,3-b]pyridine-3-carbonitrile 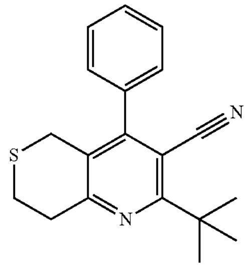 [SMILES: CC(C)(C)c1nc2c(c(-c3ccccc3)c1C#N)CSCC2] | ESP $[M + H]^+$: 309.5 | V | 4,4-Dimethyl-3-oxopentanenitrile (CAS# 59997-51-2), benzaldehyde, dihydro-2H-thiopyran-4(3H)-one (CAS# 1072-72-6) |

-continued

| Intermediate | Name and Structure | MS | Method | Reagents |
|---|---|---|---|---|
| N280 | 2-tert-Butyl-8,8-dimethyl-4-phenyl-5,6,7,8-tetrahydroquinoline-3-carbonitrile 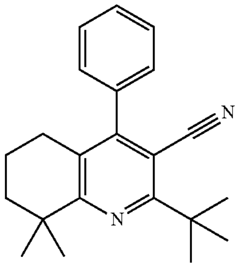 [SMILES: CC(C)(C)c1nc2c(c(-c3ccccc3)c1C#N)CCCC2(C)C] | ESP $[M + H]^+$: 319.6 | V | 4,4-Dimethyl-3-oxopentanenitrile (CAS# 59997-51-2), benzaldehyde, 2,2-dimethylcyclohexanone (CAS# 1193-47-1) |
| N281 | 2-tert-Butyl-7,7-dimethyl-4-phenyl-6,7-dihydro-5H-cyclopenta[b]pyridine-3-carbonitrile 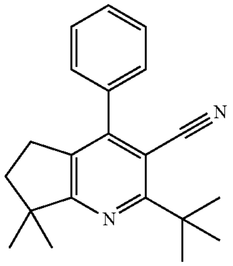 [SMILES: CC(C)(C)c1nc2c(c(-c3ccccc3)c1C#N)CCC2(C)C] | ESP $[M + H]^+$: 305.6 | V | 4,4-Dimethyl-3-oxopentanenitrile (CAS# 59997-51-2), benzaldehyde, 2,2-dimethylcyclopentanone (CAS# 4541-20-1) |
| N282 | 2-tert-Butyl-8,8-dimethyl-4-(2-methylpyridin-4-yl)-5,6,7,8-tetrahydroquinoline-3-carbonitrile 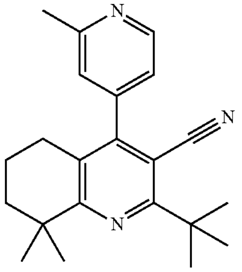 [SMILES: Cc1cc(-c2c(C#N)c(C(C)(C)C)nc3c2CCCC3(C)C)ccn1] | ESP $[M + H]^+$: 334.6 | V | 4,4-Dimethyl-3-oxopentanenitrile, 2-methylisonicotinaldehyde, 2,2-dimethylcyclohexanone |
| N283 | 2-tert-Butyl-8,8-dimethyl-4-(1-methyl-1H-pyrazol-4-yl)-5,6,7,8-tetrahydroquinoline-3-carbonitrile 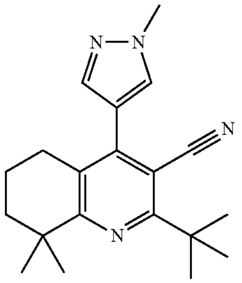 [SMILES: Cn1cc(-c2c(C#N)c(C(C)(C)C)nc3c2CCCC3(C)C)cn1] | ESP $[M + H]^+$: 323.5 | V | 4,4-Dimethyl-3-oxopentanenitrile, 2,2-dimethylcyclohexanone, 1-methyl-1H-pyrazole-4-carbaldehyde (CAS# 25016-11-9) |

-continued

| Intermediate | Name and Structure | MS | Method | Reagents |
|---|---|---|---|---|
| N284 | 2-(1-(Methoxymethyl)cyclobutyl)-4-phenyl-6,7,8,9-tetrahydro-5H-cyclohepta[b]pyridine-3-carbonitrile 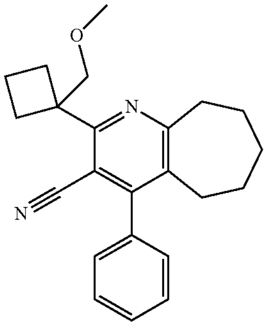 [SMILES: COCC1(c2nc3c(c(-c4ccccc4)c2C#N)CCCCC3)CCC1] | ESP $[M + H]^+$: 347.2 | V | Intermediate B284 (3-(1-(methoxymethyl) cyclobutyl)-3-oxopropanenitrile), benzaldehyde, cycloheptanone |
| N285 | 2-(1-(Methoxymethyl)cyclobutyl)-4-(2-methylpyridin-4-yl)-6,7,8,9-tetrahydro-5H-cyclohepta[b]pyridine-3-carbonitrile 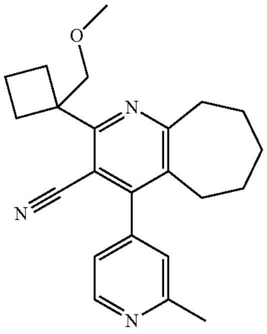 [SMILES: COCC1(c2nc3c(c(-c4ccnc(C)c4)c2C#N)CCCCC3)CCC1] | ESP $[M + H]^+$: 362.6 | V | Intermediate B284 (3-(1-(methoxymethyl) cyclobutyl)-3-oxopropanenitrile), 2-methylisonicotinaldehyde, cycloheptanone |
| N286 | 2-(1-(Methoxymethyl)cyclobutyl)-4-(1-methyl-1H-pyrazol-4-yl)-6,7,8,9-tetrahydro-5H-cyclohepta[b]pyridine-3-carbonitrile 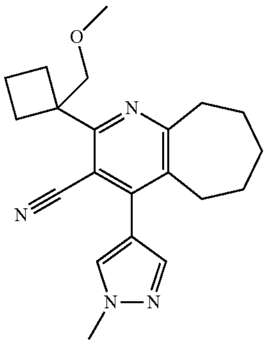 [SMILES: COCC1(c2nc3c(c(-c4cnn(C)c4)c2C#N)CCCCC3)CCC1] | ESP $[M + H]^+$: 351.6 | V | Intermediate B284 (3-(1-(methoxymethyl) cyclobutyl)-3-oxopropanenitrile), 1-methyl-1H-pyrazole-4-carbaldehyde, cycloheptanone |

-continued

| Intermediate | Name and Structure | MS | Method | Reagents |
|---|---|---|---|---|
| N287 | 2-(Perfluoroethyl)-4-phenyl-3-(1H-tetrazol-5-yl)-6,7,8,9-tetrahydro-5H-cyclohepta[b]pyridine 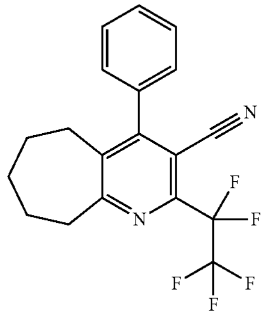 [SMILES: N#Cc1c(C(F)(F)C(F)(F)F)nc2c(c1-c1ccccc1)CCCCC2] | ESP $[M]^+$: 366 | V | 4,4,5,5,5-Pentafluoro-3-oxo-pentanenitrile (CAS# 110234-69-0), benzaldehyde, cycloheptanone |
| N288 | 2-tert-Butyl-8,8-dimethyl-4-(1-methyl-1H-pyrazol-5-yl)-5,6,7,8-tetrahydroquinoline-3-carbonitrile 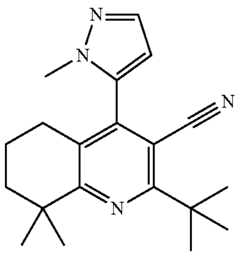 [SMILES: Cn1nccc1-c1c(C#N)c(C(C)(C)C)nc2c1CCCC2(C)C] | ESP $[M + H]^+$: 323.6 | V | 4,4-Dimethyl-3-oxopentanenitrile (CAS# 59997-51-2), 1-methyl-1H-pyrazole-5-carbaldehyde (CAS# 27258-33-9), 2,2-dimethylcyclohexanone |
| N289 | 2,4-Bis(2-methylpyridin-4-yl)-6,7,8,9-tetrahydro-5H-cyclohepta[b]pyridine-3-carbonitrile 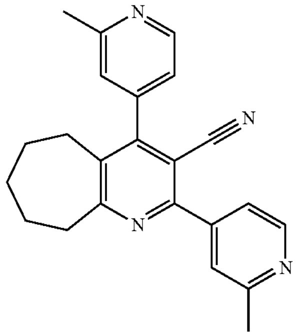 [SMILES: Cc1cc(-c2nc3c(c(-c4ccnc(C)c4)c2C#N)CCCCC3)ccn1] | ESP $[M + H]^+$: 355.6 | V | 3-(2-Methylpyridin-4-yl)-3-oxopropanenitrile (CAS# 1240521-95-2), 2-methylisonicotinaldehyde, cycloheptanone |
| N290 | 2-Isopropoxy-4-phenyl-6,7,8,9-tetrahydro-5H-cyclohepta[b]pyridine-3-carbonitrile 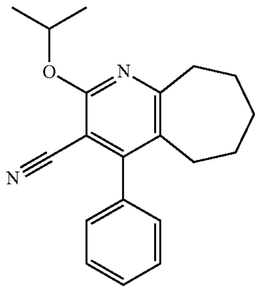 [SMILES: CC(C)Oc1nc2c(c(-c3ccccc3)c1C#N)CCCCC2] | ESP $[M + H]^+$: 307.5 | Y | 2-Oxo-4-phenyl-2,5,6,7,8,9-hexahydro-1H-cyclohepta[b]pyridine-3-carbonitrile (Intermediate P30), isopropanol |

-continued

| Intermediate | Name and Structure | MS | Method | Reagents |
|---|---|---|---|---|
| N291 | 2-Methoxy-4-phenyl-6,7,8,9-tetrahydro-5H-cyclohepta[b]pyridine-3-carbonitrile 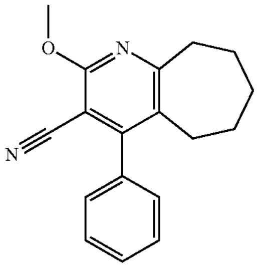 [SMILES: COc1nc2c(c(-c3ccccc3)c1C#N)CCCCC2] | ESP $[M + H]^+$: 279.5 | Y | 2-Oxo-4-phenyl-2,5,6,7,8,9-hexahydro-1H-cyclohepta[b]pyridine-3-carbonitrile (Intermediate P30), methanol |
| N292 | 2-Ethoxy-4-phenyl-6,7,8,9-tetrahydro-5H-cyclohepta[b]pyridine-3-carbonitrile 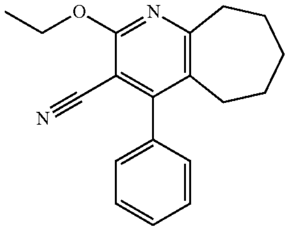 [SMILES: CCOc1nc2c(c(-c3ccccc3)c1C#N)CCCCC2] | ESP $[M + H]^+$: 293.5 | Y | 2-Oxo-4-phenyl-2,5,6,7,8,9-hexahydro-1H-cyclohepta[b]pyridine-3-carbonitrile (Intermediate P30), ethanol |
| N293 | (S)-4-Phenyl-2-(tetrahydrofuran-3-yloxy)-6,7,8,9-tetrahydro-5H-cyclohepta[b]pyridine-3-carbonitrile 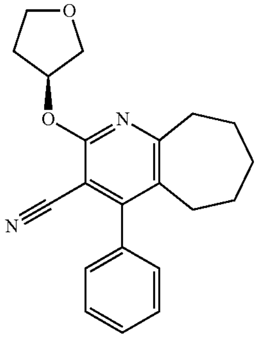 [SMILES: N#Cc1c(O[C@H]2CCOC2)nc2c(c1-c1ccccc1)CCCCC2] | ESP $[M + H]^+$: 335.5 | Y | 2-Oxo-4-phenyl-2,5,6,7,8,9-hexahydro-1H-cyclohepta[b] pyridine-3-carbonitrile (Intermediate P30), (S)-tetrahydrofuran-3-ol |
| N294 | (R)-4-Phenyl-2-(tetrahydrofuran-3-yloxy)-6,7,8,9-tetrahydro-5H-cyclohepta[b]pyridine-3-carbonitrile 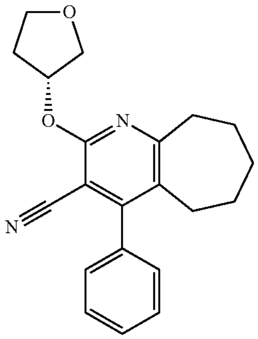 [SMILES: N#Cc1c(O[C@@H]2CCOC2)nc2c(c1-c1ccccc1)CCCCC2] | ESP $[M + H]^+$: 335.6 | Y | 2-Oxo-4-phenyl-2,5,6,7,8,9-hexahydro-1H-cyclohepta[b] pyridine-3-carbonitrile (Intermediate P30), (R)-tetrahydrofuran-3-ol |

-continued

| Intermediate | Name and Structure | MS | Method | Reagents |
|---|---|---|---|---|
| N295 | 2-Ethoxy-4-(1-methyl-1H-pyrazol-4-yl)-6,7,8,9-tetrahydro-5H-cyclohepta[b]pyridine-3-carbonitrile 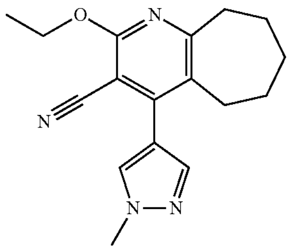 [SMILES: CCOc1nc2c(c(-c3cnn(C)c3)c1C#N)CCCCC2] | ESP [M + H]$^+$: 297.5 | Y | Intermediate P295, ethanol |
| N296 | 2-Isopropoxy-4-(1-methyl-1H-pyrazol-4-yl)-6,7,8,9-tetrahydro-5H-cyclohepta[b]pyridine-3-carbonitrile 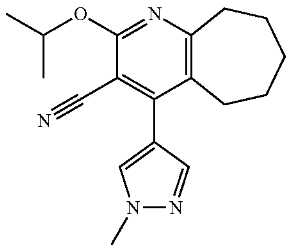 [SMILES: CC(C)Oc1nc2c(c(-c3cnn(C)c3)c1C#N)CCCCC2] | ESP [M + H]$^+$: 311.5 | Y | Intermediate P295, isopropanol |
| N297 | 2-Ethoxy-4-(2-methylpyridin-4-yl)-6,7,8,9-tetrahydro-5H-cyclohepta[b]pyridine-3-carbonitrile 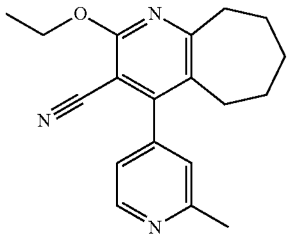 [SMILES: CCOc1nc2c(c(-c3ccnc(C)c3)c1C#N)CCCCC2] | ESP [M + H]$^+$: 308.5 | Y | Intermediate P297, ethanol |
| N298 | 2-(2-Methoxyethoxy)-4-phenyl-6,7,8,9-tetrahydro-5H-cyclohepta[b]pyridine-3-carbonitrile 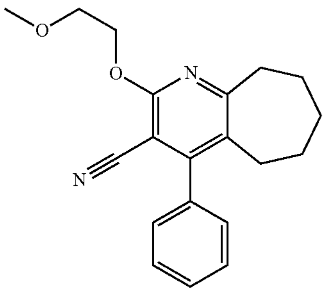 [SMILES: COCCOc1nc2c(c(-c3ccccc3)c1C#N)CCCCC2] | ESP [M + H]$^+$: 323.5 | Y | 2-Oxo-4-phenyl-2,5,6,7,8,9-hexahydro-1H-cyclohepta[b] pyridine-3-carbonitrile (Intermediate P30), methoxyethanol |

-continued

| Intermediate | Name and Structure | MS | Method | Reagents |
|---|---|---|---|---|
| N299 | 4-Phenyl-2-((tetrahydrofuran-2-yl)methoxy)-6,7,8,9-tetrahydro-5H-cyclohepta[b]pyridine-3-carbonitrile 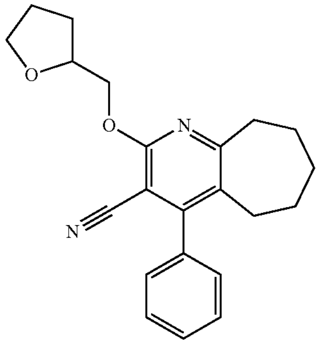 [SMILES: N#Cc1c(OCC2CCCO2)nc2c(c1-c1ccccc1)CCCCC2] | ESP [M + H]$^+$: 249.6 | Y | 2-Oxo-4-phenyl-2,5,6,7,8,9-hexahydro-1H-cyclohepta[b] pyridine-3-carbonitrile (Intermediate P30), tetrahydrofuran-2-ylmethanol |
| N300 | 2-(3-Fluoropropoxy)-4-phenyl-6,7,8,9-tetrahydro-5H-cyclohepta[b]pyridine-3-carbonitrile 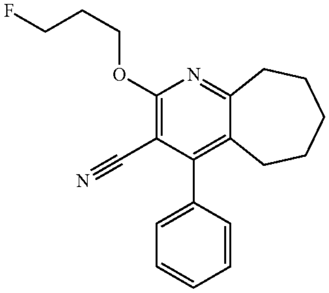 [SMILES: N#Cc1c(OCCCF)nc2c(c1-c1ccccc1)CCCCC2] | ESP [M + H]$^+$: 325.5 | Y | 2-Oxo-4-phenyl-2,5,6,7,8,9-hexahydro-1H-cyclohepta[b] pyridine-3-carbonitrile (Intermediate P30),3-fluoro-1-propanol |
| N301 | 2-(2,2-Difluoroethoxy)-4-phenyl-6,7,8,9-tetrahydro-5H-cyclohepta[b]pyridine-3-carbonitrile 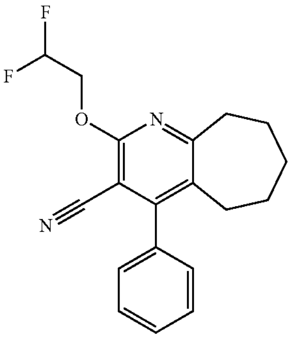 [SMILES: N#Cc1c(OCC(F)F)nc2c(c1-c1ccccc1)CCCCC2] | ESP [M + H]$^+$: 329.5 | Y | 2-Oxo-4-phenyl-2,5,6,7,8,9-hexahydro-1H-cyclohepta[b] pyridine-3-carbonitrile (Intermediate P30), 2,2-difluoroethanol |

-continued

| Intermediate | Name and Structure | MS | Method | Reagents |
|---|---|---|---|---|
| N302 | (S)-4-Phenyl-2-(tetrahydrofuran-3-yloxy)-5,6,7,8-tetrahydroquinoline-3-carbonitrile 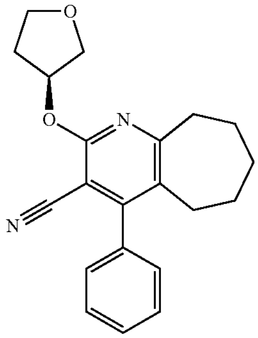 [SMILES: N#Cc1c(O[C@H]2CCOC2)nc2c(c1-c1ccccc1)CCCCC2] | ESP $[M + H]^+$: 321.5 | Y | 2-Oxo-4-phenyl-1,2,5,6,7,8-hexahydroquinoline-3-carbonitrile (intermediate P302), (S)-tetrahydrofuran-3-ol |
| N303 | 4-(2-Methylpyridin-4-yl)-2-(tetrahydro-2H-pyran-4-yloxy)-6,7,8,9-tetrahydro-5H-cyclohepta[b]pyridine-3-carbonitrile 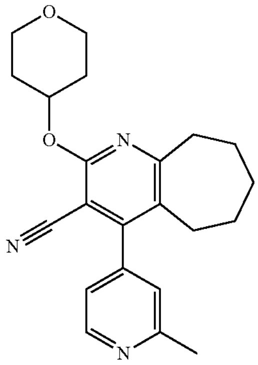 [SMILES: Cc1cc(-c2c(C#N)c(OC3CCOCC3)nc3c2CCCCC3)ccn1] | ESP $[M + H]^+$: 364.5 | Y | 4-(2-Methylpyridin-4-yl)-2-oxo-2,5,6,7,8,9-hexahydro-1H-cyclohepta[b] pyridine-3-carbonitrile (Intermediate P297), tetrahydro-2H-pyran-4-ol |
| N304 | (S)-4-(2-Methylpyridin-4-yl)-2-(tetrahydrofuran-3-yloxy)-6,7,8,9-tetrahydro-5H-cyclohepta[b]pyridine-3-carbonitrile 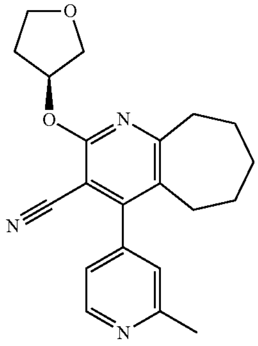 [SMILES: Cc1cc(-c2c(C#N)c(O[C@H]3CCOC3)nc3c2CCCCC3)ccn1] | ESP $[M + H]^+$: 350.5 | Y | 4-(2-Methylpyridin-4-yl)-2-oxo-2,5,6,7,8,9-hexahydro-1H-cyclohepta[b] pyridine-3-carbonitrile (Intermediate P297), (S)-tetrahydrofuran-3-ol |

-continued

| Intermediate | Name and Structure | MS | Method | Reagents |
| --- | --- | --- | --- | --- |
| N305 | (S)-4-(2-Methylpyridin-4-yl)-2-(tetrahydrofuran-3-yloxy)-5,6,7,8-tetrahydroquinoline-3-carbonitrile 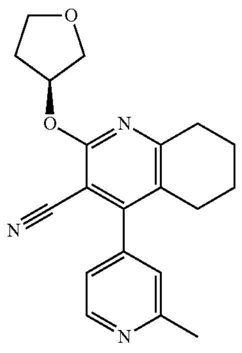 | ESP $[M + H]^+$: 379.5 | Y | 4-(2-Methylpyridin-4-yl)-2-oxo-1,2,5,6,7,8-hexahydroquinoline-3-carbonitrile (Intermediate P305), (S)-tetrahydrofuran-3-ol |
| N306 | 2-(2-Methoxyethoxy)-4-(4-(trifluoromethyl)phenyl)-6,7,8,9-tetrahydro-5H-cyclohepta[b]pyridine-3-carbonitrile 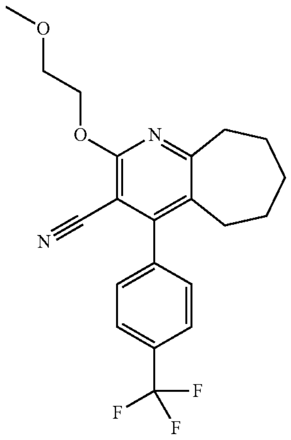 [SMILES: COCCOc1nc2c(c(-c3ccc(C(F)(F)F)cc3)c1C#N)CCCCC2] | ESP $[M + H]^+$: 391.4 | Y | 2-Oxo-4-(4-(trifluoromethyl)phenyl)-2,5,6,7,8,9-hexahydro-1H-cyclohepta[b]pyridine-3-carbonitrile (Intermediate P306), 2-methoxyethanol |
| N307 | 4-(3-Fluorophenyl)-2-(2-methoxyethoxy)-6,7,8,9-tetrahydro-5H-cyclohepta[b]pyridine-3-carbonitrile 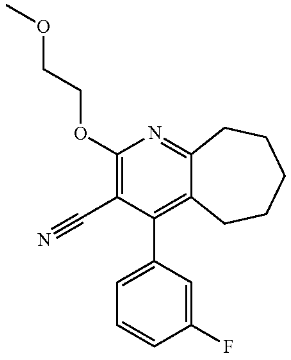 [SMILES: COCCOc1nc2c(c(-c3cccc(F)c3)c1C#N)CCCCC2] | ESP $[M + H]^+$: 341.4 | Y | 4-(3-Fluorophenyl)-2-oxo-2,5,6,7,8,9-hexahydro-1H-cyclohepta[b]pyridine-3-carbonitrile (Intermediate P307), 2-methoxyethanol |

-continued

| Intermediate | Name and Structure | MS | Method | Reagents |
|---|---|---|---|---|
| N308 | (S)-4-(3-Fluorophenyl)-2-(tetrahydrofuran-3-yloxy)-5,6,7,8-tetrahydroquinoline-3-carbonitrile 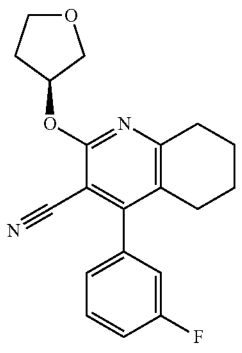 [SMILES: N#Cc1c(O[C@H]2CCOC2)nc2c(c1-c1cccc(F)c1)CCCC2] | ESP $[M + H]^+$: 339.4 | Y | (S)-4-(3-Fluorophenyl)-2-(tetrahydrofuran-3-yloxy)-5,6,7,8-tetrahydroquinoline-3-carbonitrile (Intermediate P308), 2-(S)-tetrahydrofuran-3-ol |
| N309 | 4-(3,5-Difluorophenyl)-2-(2-methoxyethoxy)-6,7,8,9-tetrahydro-5H-cyclohepta[b]pyridine-3-carbonitrile 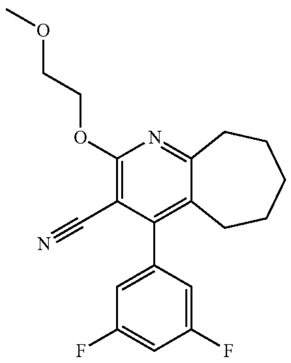 [SMILES: COCCOc1nc2c(c(-c3cc(F)cc(F)c3)c1C#N)CCCCC2] | ESP $[M + H]^+$: 359.4 | Y | 4-(3,5-Difluorophenyl)-2-oxo-2,5,6,7,8,9-hexahydro-1H-cyclohepta[b]pyridine-3-carbonitrile (Intermediate P309), 2-methoxyethanol, |
| N310 | (S)-4-(3-Fluorophenyl)-2-(tetrahydrofuran-3-yloxy)-6,7,8,9-tetrahydro-5H-cyclohepta[b]pyridine-3-carbonitrile 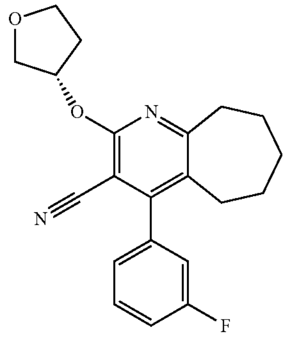 [SMILES: N#Cc1c(O[C@H]2CCOC2)nc2c(c1-c1cccc(F)c1)CCCCC2] | ESP $[M + H]^+$: 353.5 | Y | 4-(3-Fluorophenyl)-2-oxo-2,5,6,7,8,9-hexahydro-1H-cyclohepta[b]pyridine-3-carbonitrile (Intermediate P307), (S)-tetrahydrofuran-3-ol |

-continued

| Intermediate | Name and Structure | MS | Method | Reagents |
|---|---|---|---|---|
| N311 | (S)-4-(3,5-Difluorophenyl)-2-(tetrahydrofuran-3-yloxy)-6,7,8,9-tetrahydro-5H-cyclohepta[b]pyridine-3-carbonitrile 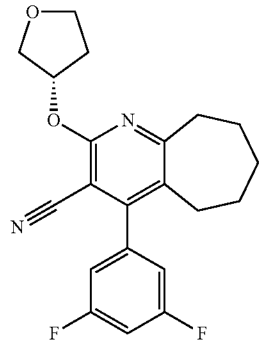 [SMILES: N#Cc1c(O[C@H]2CCOC2)nc2c(c1-c1cc(F)cc(F)c1)CCCCC2] | ESP [M + H]$^+$: 371.4 | Y | 4-(3,5-Difluorophenyl)-2-oxo-2,5,6,7,8,9-hexahydro-1H-cyclohepta[b] pyridine-3-carbonitrile (Intermediate 309), (S)-tetrahydrofuran-3-ol |
| N312 | 4-(2-Fluorophenyl)-2-((S)-tetrahydrofuran-3-yloxy)-6,7,8,9-tetrahydro-5H-cyclohepta[b]pyridine-3 carbonitrile 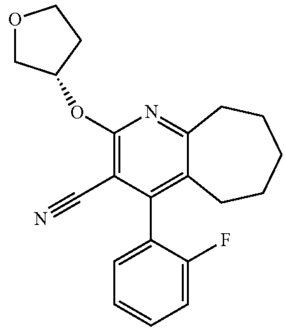 [SMILES: N#Cc1c(O[C@H]2CCOC2)nc2c(c1-c1ccccc1F)CCCCC2] | ESP [M + H]$^+$: 353.5 | Y | 4-(2-Fluorophenyl)-2-oxo-2,5,6,7,8,9-hexahydro-1H-cyclohepta[b] pyridine-3-carbonitrile (Intermediate P312), (S)-tetrahydrofuran-3-ol |
| N313 | 4-(2-Fluorophenyl)-2-(2-methoxyethoxy)-6,7,8,9-tetrahydro-5H-cyclohepta[b]pyridine-3-carbonitrile 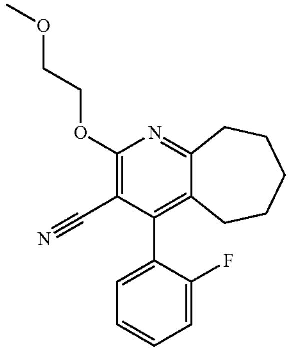 [SMILES: COCCOc1nc2c(c(-c3ccccc3F)c1C#N)CCCCC2] | ESP [M + H]$^+$: 341.4 | Y | 4-(2-Fluorophenyl)-2-oxo-2,5,6,7,8,9-hexahydro-1H-cyclohepta[b] pyridine-3-carbonitrile (Intermediate P312), 2-methoxyethanol |

-continued

| Intermediate | Name and Structure | MS | Method | Reagents |
|---|---|---|---|---|
| N314 | (S)-2-(Tetrahydrofuran-3-yloxy)-4-(thiophen-2-yl)-6,7,8,9-tetrahydro-5H-cyclohepta[b]pyridine-3-carbonitrile 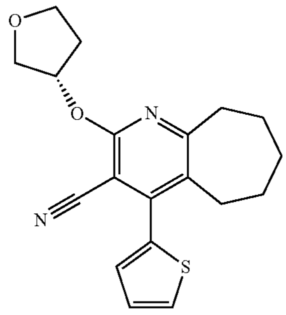 [SMILES: N#Cc1c(O[C@H]2CCOC2)nc2c(c1-c1cccs1)CCCCC2] | ESP $[M + H]^+$: 341.4 | Y | 2-Oxo-4-(thiophen-2-yl)-2,5,6,7,8,9-hexahydro-1H-cyclohepta[b] pyridine-3-carbonitrile, (Intermediate P314), (S)-tetrahydrofuran-3-ol |
| N315 | 2-(3-Fluoropropoxy)-4-(thiophen-2-yl)-6,7,8,9-tetrahydro-5H-cyclohepta[b]pyridine-3-carbonitrile 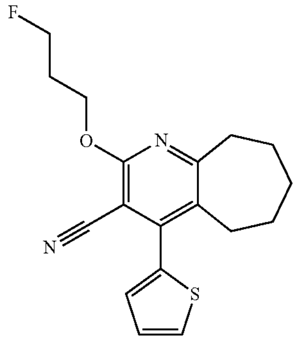 [SMILES: N#Cc1c(OCCCF)nc2c(c1-c1cccs1)CCCCC2] | ESP $[M + H]^+$: 331.5 | Y | 2-Oxo-4-(thiophen-2-yl)-2,5,6,7,8,9-hexahydro-1H-cyclohepta[b] pyridine-3-carbonitrile, (Intermediate P314), 3-fluoropropan-1-ol |
| N316 | (S)-2-(Tetrahydrofuran-3-yloxy)-4-(thiophen-3-yl)-6,7,8,9-tetrahydro-5H-cyclohepta[b]pyridine-3-carbonitrile 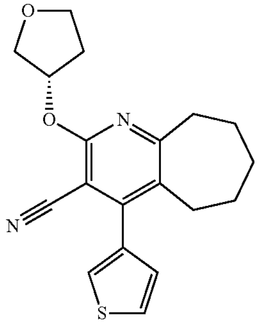 [SMILES: N#Cc1c(O[C@H]2CCOC2)nc2c(c1-c1ccsc1)CCCCC2] | ESP $[M + H]^+$: 341.3 | Y | 2-Oxo-4-(3-thienyl)-1,5,6,7,8,9-hexahydrocyclohepta[b] pyridine-3-carbonitrile (Intermediate P316), (S)-tetrahydrofuran-3-ol |

-continued

| Intermediate | Name and Structure | MS | Method | Reagents |
|---|---|---|---|---|
| N317 | 4-phenyl-2-(tetrahydro-2H-pyran-4-yloxy)-6,7,8,9-tetrahydro-5H-cyclohepta[b]pyridine-3-carbonitrile 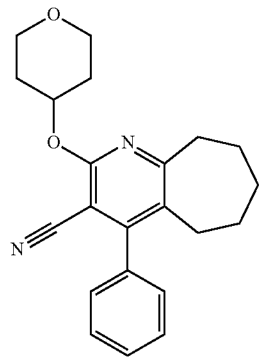 [SMILES: N#Cc1c(OC2CCOCC2)nc2c(c1-c1ccccc1)CCCCC2] | ESP $[M+H]^+$: 349.5 | Y | 2-Oxo-4-phenyl-2,5,6,7,8,9-hexahydro-1H-cyclohepta[b] pyridine-3-carbonitrile (Intermediate P30), tetrahydro-2H-pyran-4-ol |
| N321 | 2-(1-Methylcyclohexyl)-4-phenyl-6,7,8,9-tetrahydro-5H-cyclohepta[b]pyridine-3-carbonitrile, contains traces of 2-cyclohexyl-4-phenyl-6,7,8,9-tetrahydro-5H-cyclohepta[b]pyridine-3-carbonitrile 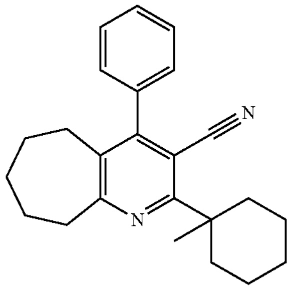 [SMILES: CC1(c2nc3c(c(-c4ccccc4)c2C#N)CCCCC3)CCCCC1] | | V | Intermediate B171, benzaldehyde, cycloheptanone |
| E325 | Methyl 2-cyclopentyl-4-phenyl-5,6,7,8-tetrahydroquinoline-3-carboxylate 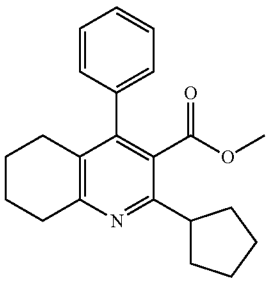 [SMILES: COC(=O)c1c(C2CCCC2)nc2c(c1-c1ccccc1)CCCC2] | ESP $[M+H]^+$: 336.6 | P | Intermediate K6, cyclohexanone |

-continued

| Intermediate | Name and Structure | MS | Method | Reagents |
|---|---|---|---|---|
| N326 | 2-(1-(Methoxymethyl)cyclopentyl)-6-pentyl-4-phenyl-5,6,7,8-tetrahydroquinoline-3-carbonitrile 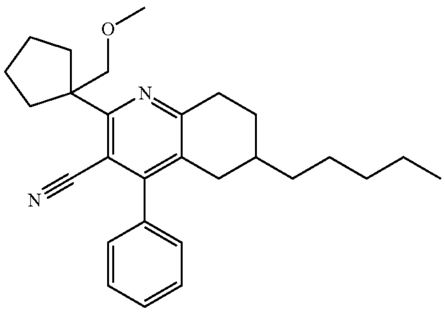 [SMILES: CCCCCC1CCc2nc(C3(COC)CCCC3)c(C#N)c(-c3ccccc3)c2C1] | | V | Intermediate B94, benzaldehyde, 4-pentylcyclohexanone |
| N327 | tert-Butyl 2-(3-cyano-4-(2-methylpyridin-4-yl)-6,7,8,9-tetrahydro-5H-cyclohepta[b]pyridin-2-yl)-2-methylpropanoate 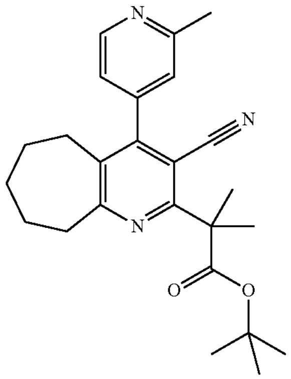 [SMILES: Cc1cc(-c2c(C#N)c(C(C)(C)C(=O)OC(C)(C)C)nc3c2CCCCC3)ccn1] | ESP [M + H]$^+$: 406.6 | V | tert-Butyl 4-cyano-2,2-dimethyl-3-oxobutanoate (Intermediate B327), 2-methylisonicotinaldehyde, cycloheptanone |

Intermediates N149 and N150

(R)-4-(2-chloropyridin-4-yl)-2-(tetrahydrofuran-2-yl)-6,7,8,9-tetrahydro-5H-cyclohepta[b]pyridine-3-carbonitrile and (S)-4-(2-chloropyridin-4-yl)-2-(tetrahydrofuran-2-yl)-6,7,8,9-tetrahydro-5H-cyclohepta[b]pyridine-3-carbonitrile

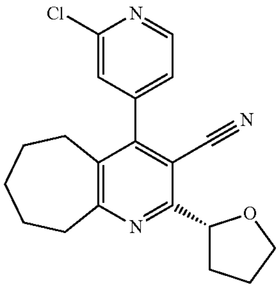

and

-continued

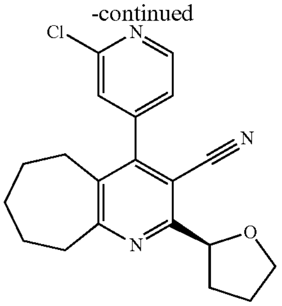

Intermediate N149R was separated into the enantiomers using chiral chromatography (Chiralpak AD, isopropanol/heptane 1:9) to give the title compounds as off-white solids.

N149 First-eluting enantiomer (+), ESP [M+H]$^+$: 354.5

N150 Second-eluting enantiomer (−), ESP [M+H]$^+$: 354.5

Intermediates N161 and N162

2-[(2S)-2-methyloxolan-2-yl]-4-(2-methylpyridin-4-yl)-6,7,8,9-tetrahydro-5H-cyclohepta[b]pyridine-3-carbonitrile and 2-[(2R)-2-methyloxolan-2-yl]-4-(2-methylpyridin-4-yl)-6,7,8,9-tetrahydro-5H-cyclohepta[b]pyridine-3-carbonitrile

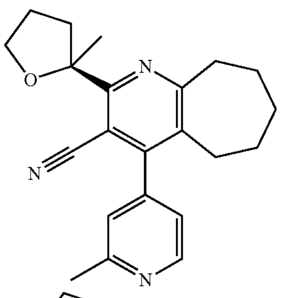

and

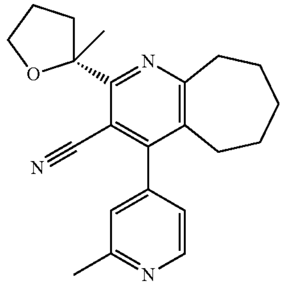

Intermediate N160 was separated into the enantiomers using chiral chromatography (Reprosil Chiral NR, 15% EtOH in heptane) to give the title compounds as light yellow solids.

N161 First-eluting enantiomer (−), ESP $[M+H]^+$: 348.5

N162 Second-eluting enantiomer (+), ESP $[M+H]^+$: 348.5

Intermediate N194

2-Cyclopentyl-4-(2-(methylamino)pyridin-4-yl)-6,7,8,9-tetrahydro-5H-cyclohepta[b]pyridine-3-carbonitrile

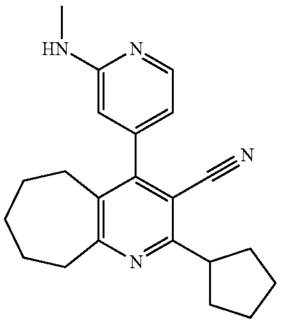 [SMILES: CNc1cc(-c2c(C#N)c(C3CCCC3)nc3c2CCCCC3)ccn1]

4-(2-Chloropyridin-4-yl)-2-cyclopentyl-6,7,8,9-tetrahydro-5H-cyclohepta[b]pyridine-3-carbonitrile (Intermediate N103, 209 mg) and methylamine (8M in ethanol, 5 ml) were stirred 18 h in a stainless steel autoclave at 150° C. The reaction mixture was evaporated and purified by chromatography ($SiO_2$, 0-50% EtOAc in heptane) to give the title compound (66 mg) as a light yellow solid. ESP $[M+H]^+$: 347.6

Intermediate N205

2-[1-(Hydroxymethyl)cyclopentyl]-4-phenyl-6,7,8,9-tetrahydro-5H-cyclohepta[b]pyridine-3-carbonitrile

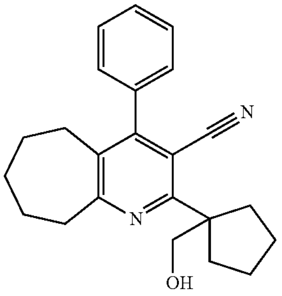 [SMILES: N#Cc1c(C2(CO)CCCC2)nc2c(c1-c1ccccc1)CCCCC2]

2-(1-(Methoxymethyl)cyclopentyl)-4-phenyl-6,7,8,9-tetrahydro-5H-cyclohepta[b]pyridine-3-carbonitrile (Intermediate N184, 200 mg) was combined with acetonitrile (2.5 ml) to give a colorless solution. Then a suspension of sodium iodide (166 mg) in acetonitrile (2.5 ml) and trimethylchlorosilane (121 mg) were added at r.t. After stirring at r.t. for 1.5 h, the mixture was stirred for 33 h at 60° C. and for 17 days at r.t. Additional portions of trimethylchlorosilane (121 mg) and sodium iodide (166 mg) were added twice during this time. 5 g Silica gel was added and the reaction mixture was evaporated. The crude material was purified by flash chromatography (silical gel, 0% to 50% EtOAc in n-heptane)

followed by preparative TLC (silica gel, 2.0 mm, 1:1 n-heptane/AcOEt) to give the title compound (not totally pure) as a light brown foam (114 mg) which was used for the next step without further purification. ESP $[M+H]^+$: 347.6

Intermediate N212

2-Cyclopentyl-9-oxo-4-phenyl-6,7,8,9-tetrahydro-5H-pyrido[2,3-c]azepine-3-carbonitrile

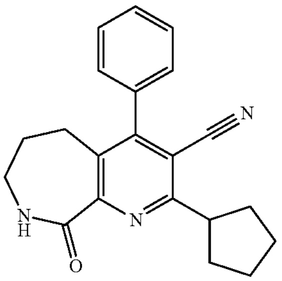 [SMILES: N#Cc1c(C2CCCC2)nc2c(c1-c1ccccc1)CCCNC2=O]

3-(Piperidin-1-yl)-6,7-dihydro-1H-azepin-2(5H)-one (3 g), benzaldehyde (1.64 g), 3-cyclopentyl-3-oxopropanenitrile (2.12 g) and ammonium acetate (5.95 g) were mixed with toluene (45.0 ml) and refluxed for 90 min while water was removed using a Dean-Stark-trap. The reaction mixture was evaporated. The residual brown semisolid was suspended in acetone (75.0 ml). After slow addition of a solution of ceric ammonium nitrate (16.9 g) in water (30.0 ml) the reaction mixture was stirred 30 min at rt. The reaction mixture was diluted with water and ethyl acetate and separated, extracted once more with ethyl acetate. The organic layers were washed once with water, dried over sodium sulphate and evaporated. The residual red-brown gum was purified by chromatography ($SiO_2$, 0-100% EtOAc in heptane) followed by trituration with isopropyl ether to give the title compound (1.25 g) as an off-white solid. ESP $[M+H]^+$: 332.6

As a side product there was obtained 2-cyclopentyl-5-oxo-4-phenyl-6,7,8,9-tetrahydro-5H-pyrido[3,2-c]azepine-3-carbonitrile (1.04 g).

Intermediates N269 and N270

(R)-4-(3-chlorophenyl)-2-(2-(methoxymethyl)tetrahydrofuran-2-yl)-6,6-dimethyl-5,6,7,8-tetrahydroquinoline-3-carbonitrile and (S)-4-(3-chlorophenyl)-2-(2-(methoxymethyl)tetrahydrofuran-2-yl)-6,6-dimethyl-5,6,7,8-tetrahydroquinoline-3-carbonitrile

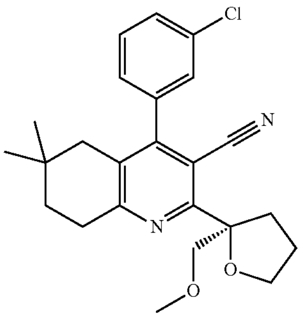

and

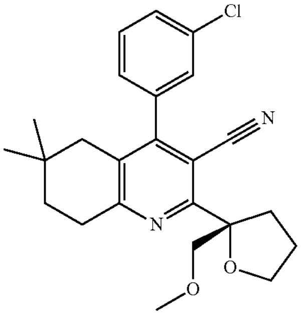

Intermediate N269R was separated into the enantiomers using chiral chromatography (Reprosil Chiral NR, 10% EtOH in heptane) to give the title compounds as colorless solids.

N269 First-eluting enantiomer (−), ESP $[M+H]^+$: 411.5

N270 Second-eluting enantiomer (+), ESP $[M+H]^+$: 411.5

Example A

A compound of formula (I) can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula (I) can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

The invention claimed is:

1. Compounds of formula (I)

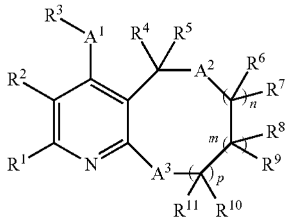

(I)

wherein $R^1$ is alkyl, haloalkyl, cycloalkyl, substituted cycloalkyl, alkoxy, alkoxyalkyl, alkoxyalkoxy, alkoxycarbonyl, alkoxycarbonylalkyl, carboxy, carboxyalkyl, haloalkyl, haloalkoxy, haloalkoxyalkyl, cycloalkoxy, substituted cycloalkoxy, cycloalkoxylalkyl, substituted cycloalkoxyalkyl, hydroxyalkyl, aryl, substituted aryl, heterocycloalkyl, substituted heterocycloalkyl, heterocycloalkoxy, substituted heterocycloalkoxy, heterocycloalkylalkoxy, substituted heterocycloalkylalkoxy, heteroaryl, substituted heteroaryl, amino, substituted amino, aminocarbonyl or substituted aminocarbonyl, wherein substituted cycloalkyl, substituted cycloalkoxy, substituted cycloalkoxyalkyl, substituted aryl, substituted heterocycloalkyl, substituted heterocycloalkoxy, substituted heterocycloalkylalkoxy and substituted heteroaryl are substituted with one to three substituents independently selected from hydroxy, oxo, halogen, alkyl, cycloalkyl, haloalkyl, alkylcycloalkyl, cycloalkylalkyl, alkylcycloalkylalkyl, hydroxyalkyl, alkylsulfonyl, alkylsulfonylalkyl, alkoxycarbonyl, alkoxy and alkoxyalkyl and wherein substituted amino and substituted aminocarbonyl are substituted on the nitrogen atom with one to two substituents independently selected from alkyl, cycloalkyl, haloalkyl, alkylcycloalkyl, cycloalkylalkyl, alkylcycloalkylalkyl, hydroxyalkyl and alkoxyalkyl;

$R^2$ is —COOH, tetrazol-5-yl, [1,3,4]oxadiazol-2-on-5-yl, [1,3,4]oxadiazole-2-thion-5-yl, [1,2,4]oxadiazol-5-on-3-yl, [1,2,4]oxadiazole-5-thion-3-yl, [1,2,3,5]oxathiadiazole-2-oxide-4-yl, [1,2,4]thiadiazol-5-on-3-yl, isoxazol-3-ol-5-yl, 5-alkylisoxazol-3-ol-4-yl, 5-cycloalkylisoxazol-3-ol-4-yl, furazan-3-ol-4-yl, 5-alkylsulfonylamino-[1,3,4]oxadiazol-2-yl, 5-cycloalkylsulfonylamino-[1,3,4]oxadiazol-2-yl, 5-alkylsulfonylamino-[1,2,4]triazol-3-yl, 5-cycloalkylsulfonylamino-[1,2,4]triazol-3-yl, 5-alkylisothiazol-3-ol-4-yl, 5-cycloalkylisothiazol-3-ol-4-yl, [1,2,5]thiadiazol-3-ol-4-yl, 1,4-dihydro-tetrazol-5-on-1-yl, tetrazol-5-ylcarbamoyl, tetrazole-5-carbonyl, [1,2,4]oxadiazolidine-3,5-dion-2-y, [1,2,4]oxadiazol-5-on-3-yl, 2,4-dihydro-[1,2,4]triazol-3-on-5-sulfanyl, [1,2,4]triazole-3-sulfanyl, [1,2,4]triazole-3-sulfinyl, [1,2,4]triazole-3-sulfonyl, 4-alkyl-pyrazol-1-ol-5-yl, 4-cycloalkyl-pyrazol-1-ol-5-yl, 4-alkyl-[1,2,3]triazol-1-ol-5-yl, 4-cycloalkyl-[1,2,3]triazol-1-ol-5-yl, 5-alkyl-imidazol-1-ol-2-yl, 5-cycloalkyl-imidazol-1-ol-2-yl, 4-alkyl-imidazol-1-ol-5-yl, 4-cycloalkyl-imidazol-1-ol-5-yl, 4-alkyl-1,1-dioxo-1$\lambda^6$-[1,2,5]thiadiazolidin-3-on-5-yl, 4,4-dialkyl-1,1-dioxo-1$\lambda^6$-[1,2,5]thiadiazolidin-3-on-5-yl, 4-cycloalkyl-1,1-dioxo-1$\lambda^6$-[1,2,5]thiadiazolidin-3-on-5-yl, 4,4-dicycloalkyl-1,1-dioxo-1$\lambda^6$-[1,2,5]thiadiazolidin-3-on-5-yl, thiazolidine-2,4-dion-5-yl, oxazolidine-2,4-dion-5-yl, 3-[1-hydroxy-meth-(E)-ylidene]-pyrrolidine-2,4-dion-1-yl, 3-[1-hydroxy-meth-(Z)-ylidene]-pyrrolidine-2,4-dion-1-yl, 5-methyl-4-hydroxyfuran-2-on-3-yl, 5,5-dialkyl-4-hydroxyfuran-2-on-3-yl, 5-cycloalkyl-4-hydroxyfuran-2-on-3-yl, 5,5-dicycloalkyl-4-hydroxyfuran-2-on-3-yl, 3-hydroxycyclobut-3-ene-1,2-dion-4-yl or 3-hydroxycyclobut-3-ene-1,2-dion-4-amino;

$R^3$ is phenyl, substituted phenyl, substituted dihydropyridinyl, heteroaryl or substituted heteroaryl, wherein substituted phenyl, substituted dihydropyridinyl and substituted heteroaryl are substituted with one to three substituents independently selected from hydroxy, oxo, halogen, alkyl, cycloalkyl, haloalkyl, haloalkoxy, alkylcycloalkyl, cycloalkylalkyl, alkylcycloalkylalkyl, hydroxyalkyl, hydroxyalkoxy, alkoxy, alkoxyalkyl, alkylsulfonyl, amino and amino substituted on the nitrogen atom with one to two substituents independently selected from alkyl, cycloalkyl, haloalkyl, alkylcycloalkyl, cycloalkylalkyl, alkylcycloalkylalkyl, hydroxyalkyl and alkoxyalkyl;

$A^1$ is a bond or $CR^{12}R^{13}$;

$A^2$ is —$CR^{14}R^{15}$—, —$NR^{16}$—, —O—, —S—, —S(O)— or —$S(O)_2$—;

$A^3$ is —$CR^{17}R^{18}$—, —C(O)$NR^{19}$—, —$NR^{19}$—, —O—, —S—, —S(O)— or —$S(O)_2$—;

$R^4$, $R^5$, $R^6$, $R^7$, $R^8$, $R^9$, $R^{10}$, $R^{11}$, $R^{14}$, $R^{15}$, $R^{17}$ and $R^{18}$ are independently selected from H, halogen, alkyl, alkoxy, cycloalkyl, cycloalkylalkoxy, haloalkoxy and haloalkyl;

$R^{12}$ and $R^{13}$ are independently selected from hydrogen, alkyl, cycloalkyl and haloalkyl;

$R^{16}$ and $R^{19}$ are independently selected from hydrogen, alkyl, cycloalkyl, haloalkyl and alkylcarbonyl;

n, m and p are independently selected from zero and 1;

or pharmaceutically acceptable salts.

2. The compound of claim 1, wherein $R^1$ is alkyl, cycloalkyl, substituted cycloalkyl, alkoxy, alkoxyalkyl, alkoxyalkoxy, alkoxycarbonylalkyl, carboxyalkyl, haloalkyl, haloalkoxy, substituted aryl, heterocycloalkyl, substituted heterocycloalkyl, heterocycloalkoxy, substituted heterocycloalkylalkoxy, heteroaryl, substituted heteroaryl, amino or substituted amino, wherein substituted cycloalkyl, substituted aryl, substituted heterocycloalkyl, substituted heterocycloalkylalkoxy and substituted heteroaryl are substituted with one to three substituents independently selected from halogen, alkyl, haloalkyl, hydoxyalkyl, alkyl sulfonyl alkyl, alkoxycarbonyl and alkoxyalkyl and wherein substituted amino is substituted on the nitrogen atom with two alkyl.

3. The compound of claim 1, wherein $R^1$ is cycloalkyl, substituted cycloalkyl, heterocycloalkyl, substituted heterocycloalkyl, heterocycloalkylalkoxy or substituted amino, wherein substituted cycloalkyl and substituted heterocycloalkyl are substituted with one alkyl or alkoxyalkyl and wherein substituted amino is substituted on the nitrogen atom with two alkyl.

4. The compound of claim 1, wherein $R^1$ is cyclopentyl, substituted cyclopentyl, tetrahydrofuranyl, substituted tetrahydrofuranyl, tetrahydrofuranyloxy, piperidinyl or substituted amino, wherein substituted cyclopentyl and substituted tetrahydrofuranyl are substituted with one alkyl or alkoxyalkyl and wherein substituted amino is substituted on the nitrogen atom with two alkyl.

5. The compound of claim 1, wherein $R^2$ is —COOH, tetrazol-5-yl or [1,3,4]oxadiazol-2-thion-5-yl.

6. The compound of claim 1, wherein $R^2$ is tetrazol-5-yl.

7. The compound of claim 1, wherein $R^3$ is phenyl, substituted phenyl, substituted dihydropyridinyl, heteroaryl or substituted heteroaryl, wherein substituted phenyl, substituted dihydropyridinyl and substituted heteroaryl are substituted with one to three substituents independently selected from hydroxy, oxo, halogen, alkyl, cycloalkyl, haloalkyl, haloalkoxy, hydroxyalkoxy, alkoxy, alkylsulfonyl and amino substituted on the nitrogen atom with one to two substituents independently selected from alkyl, cycloalkyl, haloalkyl, alkylcycloalkyl, cycloalkylalkyl, alkylcycloalkylalkyl, hydroxyalkyl and alkoxyalkyl.

8. The compound of claim 1, wherein $R^3$ is phenyl, substituted phenyl or substituted heteroaryl, wherein substituted phenyl and substituted heteroaryl are substituted with one to three substituents independently selected from halogen and alkyl.

9. The compound of claim 1, wherein $R^3$ is phenyl, substituted phenyl, substituted pyrazolyl or substituted pyridinyl, wherein substituted phenyl, substituted pyrazolyl and substituted pyridinyl are substituted with one to three substituents independently selected from halogen and alkyl.

10. The compound of claim 1, wherein $R^3$ is substituted pyrazolyl or substituted pyridinyl, wherein substituted pyrazolyl and substituted pyridinyl are substituted with one alkyl.

11. The compound of claim 1, wherein $R^3$ is pyridinyl substituted with one alkyl or halogen.

12. The compound of claim 1, wherein $A^1$ is a bond.

13. The compound of claim 1, wherein $A^2$ is —$CR^{14}R^{15}$—, —$NR^{16}$—, —O— and —S—.

14. The compound of claim 1, wherein $A^2$ is —$CR^{14}R^{15}$.

15. The compound of claim 1, wherein $A^3$ is —$CR^{17}R^{18}$—, —C(O)$NR^{19}$ or —$NR^{19}$.

16. The compound of claim 1, wherein $A^3$ is —$CR^{17}R^{18}$—.

17. The compound of claim 1, wherein n is 1.

18. The compound of claim 1, wherein p is zero.

19. The compound of claim 1, wherein $R^4$, $R^5$, $R^6$, $R^7$, $R^8$, $R^9$, $R^{10}$ and $R^{11}$ are H.

20. The compound of claim 1, wherein $R^{14}$ and $R^{15}$ are independently selected from H, halogen and alkyl.

21. The compound of claim 1, wherein $R^{17}$ and $R^{18}$ are independently selected from H and alkyl.

22. The compound of claim 1, wherein $R^{16}$ is haloalkyl or alkylcarbonyl.

23. The compound of claim 1, wherein $R^{19}$ is alkyl or alkylcarbonyl.

24. The compound of claim 1, selected from 2-isopropyl-6,8-dimethyl-4-phenyl-5,6,7,8-tetrahydro-1,8-naphthyridine-3-carboxylic acid;
8-acetyl-2-isopropyl-6-methyl-4-phenyl-5,6,7,8-tetrahydro-1,8-naphthyridine-3-carboxylic acid;
8-ethyl-2-isopropyl-6-methyl-4-phenyl-5,6,7,8-tetrahydro-1,8-naphthyridine-3-carboxylic acid;
4-(3-chlorophenyl)-2-cyclohexyl-8-ethyl-5,6,7,8-tetrahydro-1,8-naphthyridine-3-carboxylic acid;
2-cyclohexyl-8-ethyl-4-phenyl-5,6,7,8-tetrahydro-1,8-naphthyridine-3-carboxylic acid;
2-cyclopentyl-8-ethyl-4-phenyl-5,6,7,8-tetrahydro-1,8-naphthyridine-3-carboxylic acid;
2-cyclopentyl-8-ethyl-6-methyl-4-phenyl-5,6,7,8-tetrahydro-1,8-naphthyridine-3-carboxylic acid;
2-cyclopentyl-6,8-dimethyl-4-phenyl-5,6,7,8-tetrahydro-1,8-naphthyridine-3-carboxylic acid;
2-isopropyl-6-methyl-4-phenyl-5,6,7,8-tetrahydroquinoline-3-carb oxylic acid;
6-ethyl-2-isopropyl-4-phenyl-5,6,7,8-tetrahydroquinoline-3-carboxylic acid;
2-isopropyl-6,6-dimethyl-4-phenyl-5,6,7,8-tetrahydroquinoline-3-carboxylic acid;
2-cyclopentyl-4-(6-methoxypyridin-2-yl)-6,7,8,9-tetrahydro-5H-cyclohepta[b]pyridine-3-carboxylic acid;
2-cyclopentyl-4-(6-oxo-1,6-dihydropyridin-2-yl)-6,7,8,9-tetrahydro-5H-cyclohepta[b]pyridine-3-carboxylic acid;
4-phenyl-2-(piperidin-1-yl)-6,7,8,9-tetrahydro-5H-cyclohepta[b]pyridine-3-carboxylic acid;
2-(2-methylpyrrolidin-1-yl)-4-phenyl-6,7,8,9-tetrahydro-5H-cyclohepta[b]pyridine-3-carboxylic acid;
6-methyl-4-phenyl-2-(piperidin-1-yl)-5,6,7,8-tetrahydroquinoline-3-carboxylic acid;
2-(diethylamino)-4-phenyl-6,7,8,9-tetrahydro-5H-cyclohepta[b]pyridine-3-carboxylic acid;
6-methyl-2-(2-methylpyrrolidin-1-yl)-4-phenyl-5,6,7,8-tetrahydroquinoline-3-carboxylic acid;
2-(diethylamino)-6-methyl-4-phenyl-5,6,7,8-tetrahydroquinoline-3-carboxylic acid;
4-(3-chlorophenyl)-6-methyl-2-(pyrrolidin-1-yl)-5,6,7,8-tetrahydroquinoline-3-carboxylic acid;
4-phenyl-2-(piperidin-1-yl)-6,7-dihydro-5H-cyclopenta[b]pyridine-3-carboxylic acid;
2-(diethylamino)-4-phenyl-6,7-dihydro-5H-cyclopenta[b]pyridine-3-carboxylic acid;
4-(3-chlorophenyl)-6-methyl-2-(piperidin-1-yl)-5,6,7,8-tetrahydroquinoline-3-carboxylic acid;
5-(6-methyl-4-phenyl-2-(piperidin-1-yl)-5,6,7,8-tetrahydroquinolin-3-yl)-1,3,4-oxadiazole-2(3H)-thione;
6-methyl-4-phenyl-2-(piperidin-1-yl)-3-(2H-tetrazol-5-yl)-5,6,7,8-tetrahydroquinoline;
N,N-diethyl-6-methyl-4-phenyl-3-(2H-tetrazol-5-yl)-5,6,7,8-tetrahydroquinolin-2-amine;
4-phenyl-2-(piperidin-1-yl)-3-(2H-tetrazol-5-yl)-6-(trifluoromethyl)-5,6,7,8-tetrahydroquinoline;
N,N-diethyl-4-phenyl-3-(2H-tetrazol-5-yl)-6-(trifluoromethyl)-5,6,7,8-tetrahydroquinolin-2-amine;
6-methyl-4-(1-methyl-1H-pyrazol-5-yl)-2-(piperidin-1-yl)-3-(2H-tetrazol-5-yl)-5,6,7,8-tetrahydroquinoline;
4-phenyl-2-(piperidin-1-yl)-3-(2H-tetrazol-5-yl)-6,7,8,9-tetrahydro-5H-cyclohepta[b]pyridine;
N,N-diethyl-4-phenyl-3-(2H-tetrazol-5-yl)-6,7,8,9-tetrahydro-5H-cyclohepta[b]pyridin-2-amine;
4-(3-chlorophenyl)-2-(piperidin-1-yl)-3-(1H-tetrazol-5-yl)-6, 7,8,9-tetrahydro-5H-cyclohepta[b]pyridine;
4-(3-chlorophenyl)-N,N-diethyl-3-(1H-tetrazol-5-yl)-6,7,8,9-tetrahydro-5H-cyclohepta[b]pyridin-2-amine;
4-(1-methyl-1H-pyrazol-5-yl)-2-(piperidin-1-yl)-3-(1H-tetrazol-5-yl)-6,7,8,9-tetrahydro-5H-cyclohepta[b]pyridine;
4-(4-fluorophenyl)-6-methyl-2-(piperidin-1-yl)-3-(1H-tetrazol-5-yl)-5,6,7,8-tetrahydroquinoline;
4-(4-fluorophenyl)-2-(piperidin-1-yl)-3-(1H-tetrazol-5-yl)-'7,8-dihydro-5H-pyrano[4,3-b]pyridine;
4-(1-methyl-1H-pyrazol-5-yl)-2-(2-methylpyrrolidin-1-yl)-3-(1H-tetrazol-5-yl)-6,7,8,9-tetrahydro-5H-cyclohepta[b]pyridine;
4-(5-chlorothiophen-2-yl)-N,N-diethyl-3-(1H-tetrazol-5-yl)-6,7,8,9-tetrahydro-5H-cyclohepta[b]pyridin-2-amine;
4-(5-chlorothiophen-2-yl)-2-(piperidin-1-yl)-3-(1H-tetrazol-5-yl)-6,7,8,9-tetrahydro-5H-cyclohepta[b]pyridine;
N,N-diethyl-4-(1-methyl-1H-pyrazol-5-yl)-3-(1H-tetrazol-5-yl)-6,7,8,9-tetrahydro-5H-cyclohepta[b]pyridin-2-amine;
5-methyl-3-(2-(piperidin-1-yl)-3-(1H-tetrazol-5-yl)-6,7,8,9-tetrahydro-5H-cyclohepta[b]pyridin-4-yl)isoxazole;
N,N-diethyl-4-(5-methylisoxazol-3-yl)-3-(1H-tetrazol-5-yl)-6,7,8,9-tetrahydro-5H-cyclohepta[b]pyridin-2-amine;
4-(1-methyl-1H-pyrazol-5-yl)-2-(2-methylpyrrolidin-1-yl)-3-(1H-tetrazol-5-yl)-6,7,8,9-tetrahydro-5H-cyclohepta[b]pyridine;
2-(piperidin-1-yl)-4-(pyridin-4-yl)-3-(1H-tetrazol-5-yl)-6,7,8,9-tetrahydro-5H-cyclohepta[b]pyridine;
N,N-diethyl-4-(pyridin-4-yl)-3-(1H-tetrazol-5-yl)-6,7,8,9-tetrahydro-5H-cyclohepta[b]pyridin-2-amine;
4-(5-methylfuran-2-yl)-2-(piperidin-1-yl)-3-(1H-tetrazol-5-yl)-6,7,8,9-tetrahydro-5H-cyclohepta[b]pyridine;
N,N-diethyl-4-(5-methylfuran-2-yl)-3-(1H-tetrazol-5-yl)-6,7,8,9-tetrahydro-5H-cyclohepta[b]pyridin-2-amine;
4-(1,5-dimethyl-1H-pyrazol-4-yl)-2-(piperidin-1-yl)-3-(1H-tetrazol-5-yl)-6,7,8,9-tetrahydro-5H-cyclohepta[b]pyridine;
4-(1,5-dimethyl-1H-pyrazol-4-yl)-N,N-diethyl-3-(1H-tetrazol-5-yl)-6,7,8,9-tetrahydro-5H-cyclohepta[b]pyridin-2-amine;
4-(5-chlorothiophen-2-yl)-2-(3-fluoropiperidin-1-yl)-3-(1H-tetrazol-5-yl)-6,7,8,9-tetrahydro-5H-cyclohepta[b]pyridine;
4-(5-chlorothiophen-2-yl)-2-(3,3-difluoropiperidin-1-yl)-3-(1H-tetrazol-5-yl)-6,7,8,9-tetrahydro-5H-cyclohepta[b]pyridine;
4-(5-chlorothiophen-2-yl)-2-(4,4-difluoropiperidin-1-yl)-3-(1H-tetrazol-5-yl)-6,7,8,9-tetrahydro-5H-cyclohepta[b]pyridine;
4-(5-chlorothiophen-2-yl)-2-(4-fluoropiperidin-1-yl)-3-(1H-tetrazol-5-yl)-6,7,8,9-tetrahydro-5H-cyclohepta[b]pyridine;
4-(5-chlorothiophen-2-yl)-3-(1H-tetrazol-5-yl)-2-(4-(trifluoromethyl)piperidin-1-yl)-6,7,8,9-tetrahydro-5H-cyclohepta[b]pyridine;

4-(5-chlorothiophen-2-yl)-2-(3,3-difluoroazetidin-1-yl)-3-(1H-tetrazol-5-yl)-6,7,8,9-tetrahydro-5H-cyclohepta[b]pyridine;

N,N-diethyl-4-(4-methylthiazol-5-yl)-3-(1H-tetrazol-5-yl)-6,7,8,9-tetrahydro-5H-cyclohepta[b]pyridin-2-amine;

4-methyl-5-(2-(piperidin-1-yl)-3-(1H-tetrazol-5-yl)-6,7,8,9-tetrahydro-5H-cyclohepta[b]pyridin-4-yl)thiazole;

N,N-diethyl-4-(1-methyl-1H-pyrazol-5-yl)-3-(1H-tetrazol-5-yl)-5,6,7,8,9,10-hexahydrocycloocta[b]pyridin-2-amine;

4-(5-chlorothiophen-2-yl)-2-(3,3-difluoropyrrolidin-1-yl)-3-(1H-tetrazol-5-yl)-6,7,8,9-tetrahydro-5H-cyclohepta[b]pyridine;

4-(1-methyl-1H-pyrazol-5-yl)-2-(piperidin-1-yl)-3-(1H-tetrazol-5-yl)-5,6,7,8,9,10-hexahydrocycloocta[b]pyridine;

diethyl-[4-pyrimidin-5-yl-3-(1H-tetrazol-5-yl)-6,7,8,9-tetrahydro-5H-cyclohepta[b]pyridin-2-yl]-amine;

N,N-diethyl-4-(3-fluoropyridin-4-yl)-3-(1H-tetrazol-5-yl)-6,7,8,9-tetrahydro-5H-cyclohepta[b]pyridin-2-amine;

N,N-diethyl-4-(2-methoxypyridin-4-yl)-3-(1H-tetrazol-5-yl)-6,7,8,9-tetrahydro-5H-cyclohepta[b]pyridin-2-amine;

4-phenyl-3-(1H-tetrazol-5-yl)-6,7,8,9-tetrahydro-5H-cyclohepta[b]pyridin-2-amine;

2-propyl-4-(pyridin-4-yl)-3-(1H-tetrazol-5-yl)-6,7,8,9-tetrahydro-5H-cyclohepta[b]pyridine;

4-(1-methyl-1H-pyrazol-5-yl)-2-(pentan-3-yl)-3-(1H-tetrazol-5-yl)-6,7,8,9-tetrahydro-5H-cyclohepta[b]pyridine;

4-(3-chlorophenyl)-2-cyclobutyl-3-(1H-tetrazol-5-yl)-6,7,8,9-tetrahydro-5H-cyclohepta[b]pyridine;

2-cyclohexyl-4-pyridin-4-yl-3-(1H-tetrazol-5-yl)-6,7,8,9-tetrahydro-H-cyclohepta[b]pyridine;

4-(3-chloro-phenyl)-2-cyclopentyl-3-(1H-tetrazol-5-yl)-6,7,8,9-tetrahydro-H-cyclohepta[b]pyridine;

2-cyclohexyl-4-(2-methylpyridin-4-yl)-3-(1H-tetrazol-5-yl)-6,7,8,9-tetrahydro-5H-cyclohepta[b]pyridine;

5-(2-cyclohexyl-3-(1H-tetrazol-5-yl)-6,7,8,9-tetrahydro-5H-cyclohepta[b]pyridin-4-yl)pyridin-2(1H)-one;

5-(2-cyclohexyl-3-(1H-tetrazol-5-yl)-6,7,8,9-tetrahydro-5H-cyclohepta[b]pyridin-4-yl)-1-ethylpyridin-2(1H)-one;

5-(2-cyclohexyl-3-(1H-tetrazol-5-yl)-6,7,8,9-tetrahydro-5H-cyclohepta[b]pyridin-4-yl)-1-methylpyridin-2(1H)-one;

2-cyclohexyl-4-(1-methyl-1H-pyrazol-5-yl)-3-(1H-tetrazol-5-yl)-6,7,8,9-tetrahydro-5H-cyclohepta[b]pyridine;

2-cyclopentyl-4-(pyridin-4-yl)-3-(1H-tetrazol-5-yl)-6,7,8,9-tetrahydro-5H-cyclohepta[b]pyridine;

2-cyclopentyl-4-(1-methyl-1H-pyrazol-5-yl)-3-(1H-tetrazol-5-yl)-6,7,8,9-tetrahydro-5H-cyclohepta[b]pyridine;

1-(4-(3-chlorophenyl)-2-cyclobutyl-3-(1H-tetrazol-5-yl)-7,8-dihydro-1,6-naphthyridin-6(5H)-yl)ethanone;

2-cyclopentyl-4-(6-methoxypyridin-2-yl)-3-(1H-tetrazol-5-yl)-6,7,8,9-tetrahydro-5H-cyclohepta[b]pyridine;

4-phenyl-2-(tetrahydro-2H-pyran-2-yl)-3-(1H-tetrazol-5-yl)-6,7,8,9-tetrahydro-5H-cyclohepta[b]pyridine;

2-cyclopentyl-4-(2-methylpyridin-4-yl)-3-(1H-tetrazol-5-yl)-6,7,8,9-tetrahydro-5H-cyclohepta[b]pyridine;

4-phenyl-2-(tetrahydrofuran-3-yl)-3-(1H-tetrazol-5-yl)-6,7,8,9-tetrahydro-5H-cyclohepta[b]pyridine;

2-cyclopentyl-4-(2-methoxypyridin-4-yl)-3-(1H-tetrazol-5-yl)-6,7,8,9-tetrahydro-5H-cyclohepta[b]pyridine;

2-cyclohexyl-4-phenyl-3-(1H-tetrazol-5-yl)-6,7,8,9-tetrahydro-5H-cyclohepta[b]pyridine;

2-cyclopentyl-4-phenyl-3-(1H-tetrazol-5-yl)-6,7,8,9-tetrahydro-5H-cyclohepta[b]pyridine;

4-phenyl-2-(tetrahydrofuran-2-yl)-3-(1H-tetrazol-5-yl)-6,7,8,9-tetrahydro-5H-cyclohepta[b]pyridine;

2-cyclohexyl-4-(3-fluoropyridin-4-yl)-3-(1H-tetrazol-5-yl)-6,7,8,9-tetrahydro-5H-cyclohepta[b]pyridine;

2-cyclopentyl-4-(3-fluoropyridin-4-yl)-3-(1H-tetrazol-5-yl)-6,7,8,9-tetrahydro-5H-cyclohepta[b]pyridine;

4-phenyl-2-(tetrahydro-2H-pyran-4-yl)-3-(1H-tetrazol-5-yl)-6,7,8,9-tetrahydro-5H-cyclohepta[b]pyridine;

2-cyclohexyl-4-(2-methylpyrimidin-4-yl)-3-(1H-tetrazol-5-yl)-6,7,8,9-tetrahydro-5H-cyclohepta[b]pyridine;

5-(2-cyclobutyl-3-(1H-tetrazol-5-yl)-6,7,8,9-tetrahydro-5H-cyclohepta[b]pyridin-4-yl)-1-methylpyridin-2(1H)-one;

2-cyclohexyl-4-(pyrimidin-4-yl)-3-(1H-tetrazol-5-yl)-6,7,8,9-tetrahydro-5H-cyclohepta[b]pyridine;

2-cyclopentyl-4-(pyrimidin-4-yl)-3-(1H-tetrazol-5-yl)-6,7,8,9-tetrahydro-5H-cyclohepta[b]pyridine;

2-cyclopentyl-4-(2-methylpyrimidin-4-yl)-3-(1H-tetrazol-5-yl)-6,7,8,9-tetrahydro-5H-cyclohepta[b]pyridine;

2-(1-(methoxymethyl)cyclopentyl)-4-(2-methylpyridin-4-yl)-3-(1H-tetrazol-5-yl)-6,7,8,9-tetrahydro-5H-cyclohepta[b]pyridine;

2-cyclopentyl-4-(pyridazin-4-yl)-3-(1H-tetrazol-5-yl)-6,7,8,9-tetrahydro-5H-cyclohepta[b]pyridine;

2-cyclopentyl-4-(6-methylpyridin-2-yl)-3-(1H-tetrazol-5-yl)-6,7,8,9-tetrahydro-5H-cyclohepta[b]pyridine;

2-cyclopentyl-4-(pyridin-2-yl)-3-(1H-tetrazol-5-yl)-6,7,8,9-tetrahydro-5H-cyclohepta[b]pyridine;

2-isopropyl-4-(2-isopropylpyridin-4-yl)-3-(1H-tetrazol-5-yl)-6,7,8,9-tetrahydro-5H-cyclohepta[b]pyridine;

2-cyclopentyl-4-(pyrimidin-2-yl)-3-(1H-tetrazol-5-yl)-6,7,8,9-tetrahydro-5H-cyclohepta[b]pyridine;

2-(2-(2-cyclopentyl-3-(1H-tetrazol-5-yl)-6,7,8,9-tetrahydro-5H-cyclohepta[b]pyridin-4-yl)phenoxy)ethanol;

2-cyclopentyl-4-(2-isopropylpyrimidin-4-yl)-3-(1H-tetrazol-5-yl)-6,7,8,9-tetrahydro-5H-cyclohepta[b]pyridine;

2-isopropyl-4-(2-isopropylpyrimidin-4-yl)-3-(1H-tetrazol-5-yl)-6,7,8,9-tetrahydro-5H-cyclohepta[b]pyridine;

4-(2-chloropyridin-4-yl)-2-cyclopentyl-3-(1H-tetrazol-5-yl)-6,7,8,9-tetrahydro-5H-cyclohepta[b]pyridine;

2-(1-(methoxymethyl)cyclopentyl)-4-(2-methoxypyridin-4-yl)-3-(1H-tetrazol-5-yl)-6,7,8,9-tetrahydro-5H-cyclohepta[b]pyridine;

4-(2-isopropylpyridin-4-yl)-2-(pentan-3-yl)-3-(1H-tetrazol-5-yl)-6,7,8,9-tetrahydro-5H-cyclohepta[b]pyridine;

4-(1-methyl-1H-pyrazol-5-yl)-2-(pentan-3-yl)-3-(2H-tetrazol-5-yl)-6-(trifluoromethyl)-5,6,7,8-tetrahydroquinoline;

2-cyclohexyl-4-(2-methylpyridin-4-yl)-3-(2H-tetrazol-5-yl)-6-(trifluoromethyl)-5,6,7,8-tetrahydroquinoline;

2-cyclohexyl-4-(1-methyl-1H-pyrazol-5-yl)-3-(2H-tetrazol-5-yl)-6-(trifluoromethyl)-5,6,7,8-tetrahydroquinoline;

2-cyclohexyl-6-methyl-4-(1-methyl-1H-pyrazol-5-yl)-3-(2H-tetrazol-5-yl)-5,6,7,8-tetrahydroquinoline;

2-cyclohexyl-6-methyl-4-(2-methylpyridin-4-yl)-3-(2H-tetrazol-5-yl)-5,6,7,8-tetrahydroquinoline;

2-cyclopentyl-4-(1-methyl-1H-pyrazol-5-yl)-3-(2H-tetrazol-5-yl)-6-(trifluoromethyl)-5,6,7,8-tetrahydroquinoline;
2-cyclopentyl-6,6-difluoro-4-phenyl-3-(2H-tetrazol-5-yl)-5,6,7,8-tetrahydroquinoline;
2-cyclopentyl-6-methyl-4-(2-methylpyridin-4-yl)-3-(2H-tetrazol-5-yl)-5,6,7,8-tetrahydroquinoline;
4-(2-cyclohexyl-3-(2H-tetrazol-5-yl)-6-(trifluoromethyl)-5,6,7,8-tetrahydroquinolin-4-yl)-3,5-dimethylisoxazole;
4-(2-cyclohexyl-6-methyl-3-(2H-tetrazol-5-yl)-5,6,7,8-tetrahydroquinolin-4-yl)-3,5-dimethylisoxazole;
2-cyclopentyl-4-(2-methylpyridin-4-yl)-3-(2H-tetrazol-5-yl)-6-(trifluoromethyl)-5,6,7,8-tetrahydroquinoline;
2-cyclopentyl-4-phenyl-3-(2H-tetrazol-5-yl)-6-(2,2,2-trifluoroethyl)-5,6,7,8-tetrahydro-1,6-naphthyridine;
2-cyclopentyl-6,6-dimethyl-4-(2-methylpyridin-4-yl)-3-(2H-tetrazol-5-yl)-5,6,7,8-tetrahydroquinoline;
2-cyclopentyl-6-methoxy-4-(2-methylpyridin-4-yl)-3-(2H-tetrazol-5-yl)-5,6,7,8-tetrahydroquinoline;
6-methyl-4-(2-methylpyridin-4-yl)-2-tert-pentyl-3-(2H-tetrazol-5-yl)-5,6,7,8-tetrahydroquinoline;
2-cyclopentyl-4-(2-methylpyridin-4-yl)-3-(2H-tetrazol-5-yl)-5,6,7,8-tetrahydroquinoline;
2-cyclohexyl-4-(2-methylpyridin-4-yl)-3-(2H-tetrazol-5-yl)-5,6,7,8-tetrahydroquinoline;
2-(1-methoxy-2-methylpropan-2-yl)-6-methyl-4-(2-methylpyridin-4-yl)-3-(2H-tetrazol-5-yl)-5,6,7,8-tetrahydroquinoline;
2-cyclopentyl-4-(2-methylpyridin-4-yl)-3-(2H-tetrazol-5-yl)-6, 7-dihydro-5H-cyclopenta[b]pyridine;
2-cyclohexyl-4-(2-methylpyridin-4-yl)-3-(2H-tetrazol-5-yl)-6, 7-dihydro-5H-cyclopenta[b]pyridine;
2-tert-butyl-4-phenyl-3-(1H-tetrazol-5-yl)-6,7,8,9-tetrahydro-5H-cyclohepta[b]pyridine;
2-tert-butyl-4-(3-fluorophenyl)-3-(1H-tetrazol-5-yl)-6,7,8,9-tetrahydro-5H-cyclohepta[b]pyridine;
2-tert-butyl-3-(1H-tetrazol-5-yl)-4-(4-(trifluoromethyl)phenyl)-6,7,8,9-tetrahydro-5H-cyclohepta[b]pyridine;
2-tert-butyl-3-(1H-tetrazol-5-yl)-4-(3-(trifluoromethyl)phenyl)-6,7,8,9-tetrahydro-5H-cyclohepta[b]pyridine;
2-tert-butyl-4-(2-methylpyridin-4-yl)-3-(1H-tetrazol-5-yl)-6,7,8,9-tetrahydro-5H-cyclohepta[b]pyridine;
2-(3,3-difluorocyclobutyl)-4-phenyl-3-(1H-tetrazol-5-yl)-6,7,8,9-tetrahydro-5H-cyclohepta[b]pyridine;
2-tert-butyl-4-(4-fluoro-phenyl)-3-(1H-tetrazol-5-yl)-6,7,8,9-tetrahydro-5H-cyclohepta[b]pyridine;
4-(2-tert-butyl-3-(1H-tetrazol-5-yl)-6,7,8,9-tetrahydro-5H-cyclohepta[b]pyridin-4-yl)oxazole;
2-tert-butyl-4-(1-methyl-1H-pyrazol-3-yl)-3-(1H-tetrazol-5-yl)-6,7,8,9-tetrahydro-5H-cyclohepta[b]pyridine;
2-tert-butyl-4-(4-methyl-1H-pyrazol-5-yl)-3-(1H-tetrazol-5-yl)-6,7,8,9-tetrahydro-5H-cyclohepta[b]pyridine;
2-tert-butyl-4-(3-cyclopropyl-1H-pyrazol-5-yl)-3-(1H-tetrazol-5-yl)-6,7,8,9-tetrahydro-5H-cyclohepta[b]pyridine;
4-(2-tert-butyl-3-(1H-tetrazol-5-yl)-6,7,8,9-tetrahydro-5H-cyclohepta[b]pyridin-4-yl)-2-methyloxazole;
2-tert-butyl-4-(4-chloro-1H-pyrazol-3-yl)-3-(1H-tetrazol-5-yl)-6,7,8,9-tetrahydro-5H-cyclohepta[b]pyridine;
2-tert-butyl-3-(1H-tetrazol-5-yl)-4-(4-(trifluoromethyl)-1H-imidazol-2-yl)-6,7,8,9-tetrahydro-5H-cyclohepta[b]pyridine;
2-tert-butyl-3-(1H-tetrazol-5-yl)-4-(1H-1,2,3-triazol-5-yl)-6,7,8,9-tetrahydro-5H-cyclohepta[b]pyridine;
2-tert-butyl-4-(2-butyl-1H-imidazol-4-yl)-3-(1H-tetrazol-5-yl)-6,7,8,9-tetrahydro-5H-cyclohepta[b]pyridine;
2-furan-2-yl-4-phenyl-3-(1H-tetrazol-5-yl)-6,7,8,9-tetrahydro-5H-cyclohepta[b]pyridine;
2-sec-butyl-4-phenyl-3-(1H-tetrazol-5-yl)-6,7,8,9-tetrahydro-5H-cyclohepta[b]pyridine;
2-(3-fluorophenyl)-4-phenyl-3-(1H-tetrazol-5-yl)-6,7,8,9-tetrahydro-5H-cyclohepta[b]pyridine; or,
2-sec-butyl-4-(2-methylpyridin-4-yl)-3-(1H-tetrazol-5-yl)-6,7,8,9-tetrahydro-5H-cyclohepta[b]pyridine;
and pharmaceutically acceptable salts thereof.

25. The compound of claim 1, selected from
4-phenyl-2-(R)-tetrahydro-furan-2-yl-3-(1H-tetrazol-5-yl)-6,7,8,9-tetrahydro-5H-cyclohepta[b]pyridine;
4-phenyl-2-(S)-tetrahydro-furan-2-yl-3-(1H-tetrazol-5-yl)-6,7,8,9-tetrahydro-5H-cyclohepta[b]pyridine;
(R)-4-(2-chloropyridin-4-yl)-2-(tetrahydrofuran-2-yl)-3-(1H-tetrazol-5-yl)-6,7,8,9-tetrahydro-5H-cyclohepta[b]pyridine;
(S)-4-(2-chloropyridin-4-yl)-2-(tetrahydrofuran-2-yl)-3-(1H-tetrazol-5-yl)-6,7,8,9-tetrahydro-5H-cyclohepta[b]pyridine;
4-phenyl-2-(tetrahydrofuran-2-yl)-3-(1H-tetrazol-5-yl)-5,6,7,8,9,10-hexahydrocycloocta[b]pyridine;
(S)-4-phenyl-2-(tetrahydrofuran-2-yl)-3-(1H-tetrazol-5-yl)-5,6,7,8,9,10-hexahydrocycloocta[b]pyridine;
(R)-4-phenyl-2-(tetrahydrofuran-2-yl)-3-(1H-tetrazol-5-yl)-5,6,7,8,9,10-hexahydrocycloocta[b]pyridine;
2-(2-methyltetrahydrofuran-2-yl)-4-phenyl-3-(1H-tetrazol-5-yl)-6,7,8,9-tetrahydro-5H-cyclohepta[b]pyridine;
2-((S)-2-methyl-tetrahydro-furan-2-yl)-4-phenyl-3-(1H-tetrazol-5-yl)-6,7,8,9-tetrahydro-5H-cyclohepta[b]pyridine;
2-((R)-2-methyl-tetrahydro-furan-2-yl)-4-phenyl-3-(1H-tetrazol-5-yl)-6,7,8,9-tetrahydro-5H-cyclohepta[b]pyridine;
4-(3-methoxyphenyl)-2-(2-methyltetrahydrofuran-2-yl)-3-(1H-tetrazol-5-yl)-6,7,8,9-tetrahydro-5H-cyclohepta[b]pyridine;
4-(3-methoxy-phenyl)-2-((S)-2-methyl-tetrahydro-furan-2-yl)-3-(1H-tetrazol-5-yl)-6,7,8,9-tetrahydro-5H-cyclohepta[b]pyridine;
4-(3-methoxy-phenyl)-2-((R)-2-methyl-tetrahydro-furan-2-yl)-3-(1H-tetrazol-5-yl)-6,7,8,9-tetrahydro-5H-cyclohepta[b]pyridine;
4-(2-methylpyridin-4-yl)-2-(2-methyltetrahydrofuran-2-yl)-3-(1H-tetrazol-5-yl)-6,7,8,9-tetrahydro-5H-cyclohepta[b]pyridine;
2-[(2S)-2-methyloxolan-2-yl]-4-(2-methylpyridin-4-yl)-3-(1H-tetrazol-5-yl)-6,7,8,9-tetrahydro-5H-cyclohepta[b]pyridine;
2-[(2R)-2-methyloxolan-2-yl]-4-(2-methylpyridin-4-yl)-3-(1H-tetrazol-5-yl)-6,7,8,9-tetrahydro-5H-cyclohepta[b]pyridine;
4-(3-chlorophenyl)-2-(2-methyltetrahydrofuran-2-yl)-3-(1H-tetrazol-5-yl)-6,7,8,9-tetrahydro-5H-cyclohepta[b]pyridine;
4-(3-chloro-phenyl)-2-((S)-2-methyl-tetrahydro-furan-2-yl)-3-(1H-tetrazol-5-yl)-6,7,8,9-tetrahydro-5H-cyclohepta[b]pyridine;
4-(3-chloro-phenyl)-2-((R)-2-methyl-tetrahydro-furan-2-yl)-3-(1H-tetrazol-5-yl)-6,7,8,9-tetrahydro-5H-cyclohepta[b]pyridine;
2-(1-methylcyclopentyl)-4-(2-methylpyridin-4-yl)-3-(1H-tetrazol-5-yl)-6,7,8,9-tetrahydro-5H-cyclohepta[b]pyridine;

2-(1-methylcyclopentyl)-4-phenyl-3-(1H-tetrazol-5-yl)-6,7,8,9-tetrahydro-5H-cyclohepta[b]pyridine;
4-(2-methoxypyridin-4-yl)-2-(1-methylcyclopentyl)-3-(1H-tetrazol-5-yl)-6,7,8,9-tetrahydro-5H-cyclohepta[b]pyridine;
4-(2-(1-methylcyclopentyl)-3-(1H-tetrazol-5-yl)-6,7,8,9-tetrahydro-5H-cyclohepta[b]pyridin-4-yl)pyridin-2(1H)-one;
4-(3-chloro-phenyl)-2-(1-methyl-cyclopentyl)-3-(1H-tetrazol-5-yl)-6,7,8,9-tetrahydro-5H-cyclohepta[b]pyridine;
4-(1-methyl-1H-pyrazol-5-yl)-2-(1-methylcyclohexyl)-3-(1H-tetrazol-5-yl)-6,7,8,9-tetrahydro-5H-cyclohepta[b]pyridine;
2-(1-methylcyclohexyl)-4-(2-methylpyridin-4-yl)-3-(1H-tetrazol-5-yl)-6,7,8,9-tetrahydro-5H-cyclohepta[b]pyridine;
2-(1-methoxymethyl-cyclopentyl)-4-(2-methyl-2H-pyrazol-3-yl)-3-(1H-tetrazol-5-yl)-6,7,8,9-tetrahydro-5H-cyclohepta[b]pyridine;
4-(3-fluoropyridin-4-yl)-2-(1-(methoxymethyl)cyclopentyl)-3-(1H-tetrazol-5-yl)-6,7,8,9-tetrahydro-5H-cyclohepta[b]pyridine;
2-(1-(methoxymethyl)cyclopentyl)-4-(4-methyl-1H-pyrazol-3-yl)-3-(1H-tetrazol-5-yl)-6,7,8,9-tetrahydro-5H-cyclohepta[b]pyridine;
4-(1H-indol-4-yl)-2-(1-(methoxymethyl)cyclopentyl)-3-(1H-tetrazol-5-yl)-6,7,8,9-tetrahydro-5H-cyclohepta[b]pyridine;
4-(2-chloropyridin-4-yl)-2-(1-(methoxymethyl)cyclopentyl)-3-(1H-tetrazol-5-yl)-6,7,8,9-tetrahydro-5H-cyclohepta[b]pyridine;
4-(2-ethylpyridin-4-yl)-2-(1-(methoxymethyl)cyclopentyl)-3-(1H-tetrazol-5-yl)-6,7,8,9-tetrahydro-5H-cyclohepta[b]pyridine;
3-(2-(1-(methoxymethyl)cyclopentyl)-3-(1H-tetrazol-5-yl)-6,7,8,9-tetrahydro-5H-cyclohepta[b]pyridin-4-yl)-2-methylphenol;
4-(2-(1-(methoxymethyl)cyclopentyl)-3-(1H-tetrazol-5-yl)-6,7,8,9-tetrahydro-5H-cyclohepta[b]pyridin-4-yl)-2-methyloxazole;
4-(1H-indazol-4-yl)-2-(1-(methoxymethyl)cyclopentyl)-3-(1H-tetrazol-5-yl)-6,7,8,9-tetrahydro-5H-cyclohepta[b]pyridine;
2-(1-(methoxymethyl)cyclopentyl)-3-(1H-tetrazol-5-yl)-4-(2-(trifluoromethyl)pyridin-4-yl)-6,7,8,9-tetrahydro-5H-cyclohepta[b]pyridine;
2-(1-(methoxymethyl)cyclopentyl)-3-(1H-tetrazol-5-yl)-4-(2-(2,2,2-trifluoroethoxy)pyridin-4-yl)-6,7,8,9-tetrahydro-5H-cyclohepta[b]pyridine;
2-(1-(methoxymethyl)cyclopentyl)-4-phenyl-3-(1H-tetrazol-5-yl)-6,7,8,9-tetrahydro-5H-cyclohepta[b]pyridine;
4-(2-ethoxypyridin-4-yl)-2-(1-(methoxymethyl)cyclopentyl)-3-(1H-tetrazol-5-yl)-6,7,8,9-tetrahydro-5H-cyclohepta[b]pyridine;
4-(4-fluoro-3-methoxyphenyl)-2-(1-(methoxymethyl)cyclopentyl)-3-(1H-tetrazol-5-yl)-6,7,8,9-tetrahydro-5H-cyclohepta[b]pyridine;
4-(4-fluorophenyl)-2-(1-(methoxymethyl)cyclopentyl)-3-(1H-tetrazol-5-yl)-6,7,8,9-tetrahydro-5H-cyclohepta[b]pyridine;
2-(1-(methoxymethyl)cyclopentyl)-4-(3-methoxyphenyl)-3-(1H-tetrazol-5-yl)-6,7,8,9-tetrahydro-5H-cyclohepta[b]pyridine;
4-(2-fluoro-5-methoxyphenyl)-2-(1-(methoxymethyl)cyclopentyl)-3-(1H-tetrazol-5-yl)-6,7,8,9-tetrahydro-5H-cyclohepta[b]pyridine;
4-(3-chloro-phenyl)-2-(1-methoxymethyl-cyclopentyl)-3-(1H-tetrazol-5-yl)-6,7,8,9-tetrahydro-5H-cyclohepta[b]pyridine;
2-(3-(methoxymethyl)pentan-3-yl)-4-(1-methyl-1H-pyrazol-5-yl)-3-(1H-tetrazol-5-yl)-6,7,8,9-tetrahydro-5H-cyclohepta[b]pyridine;
2-(3-(methoxymethyl)pentan-3-yl)-4-phenyl-3-(1H-tetrazol-5-yl)-6,7,8,9-tetrahydro-5H-cyclohepta[b]pyridine;
2-cyclopentyl-4-(2-ethylpyridin-4-yl)-3-(1H-tetrazol-5-yl)-6,7,8,9-tetrahydro-5H-cyclohepta[b]pyridine;
4-(2-cyclopentyl-3-(1H-tetrazol-5-yl)-6,7,8,9-tetrahydro-5H-cyclohepta[b]pyridin-4-yl)-N-methylpyridin-2-amine;
2-cyclopentyl-3-(1H-tetrazol-5-yl)-4-(2-(trifluoromethyl)pyridin-4-yl)-6,7,8,9-tetrahydro-5H-cyclohepta[b]pyridine;
4-(1-methyl-1H-pyrazol-5-yl)-2-(3-methylpentan-3-yl)-3-(1H-tetrazol-5-yl)-6,7,8,9-tetrahydro-5H-cyclohepta[b]pyridine;
4-(2-ethylpyridin-4-yl)-2-isopropyl-3-(1H-tetrazol-5-yl)-6,7,8,9-tetrahydro-5H-cyclohepta[b]pyridine;
2-isopropyl-3-(1H-tetrazol-5-yl)-4-(2-(2,2,2-trifluoroethoxy)pyridin-4-yl)-6,7,8,9-tetrahydro-5H-cyclohepta[b]pyridine;
4-(2-ethoxypyridin-4-yl)-2-isopropyl-3-(1H-tetrazol-5-yl)-6,7,8,9-tetrahydro-5H-cyclohepta[b]pyridine;
2-(1-methoxycyclopentyl)-4-phenyl-3-(1H-tetrazol-5-yl)-6,7,8,9-tetrahydro-5H-cyclohepta[b]pyridine;
2-(1-methoxycyclopentyl)-4-phenyl-3-(1H-tetrazol-5-yl)-5,6,7,8-tetrahydroquinoline;
2-(1-methoxycyclopentyl)-4-(2-methoxypyridin-4-yl)-3-(1H-tetrazol-5-yl)-6,7,8,9-tetrahydro-5H-cyclohepta[b]pyridine;
4-(2-chloropyridin-4-yl)-2-(1-methoxycyclopentyl)-3-(1H-tetrazol-5-yl)-6,7,8,9-tetrahydro-5H-cyclohepta[b]pyridine;
2-(1-methoxycyclopentyl)-4-(2-methylpyridin-4-yl)-3-(1H-tetrazol-5-yl)-6,7,8,9-tetrahydro-5H-cyclohepta[b]pyridine;
(1-(4-phenyl-3-(1H-tetrazol-5-yl)-6,7,8,9-tetrahydro-5H-cyclohepta[b]pyridin-2-yl)cyclopentyl)methanol;
(1-(4-phenyl-3-(1H-tetrazol-5-yl)-5,6,7,8-tetrahydroquinolin-2-yl)cyclopentyl)methanol;
(1-(4-(2-methylpyridin-4-yl)-3-(1H-tetrazol-5-yl)-6,7,8,9-tetrahydro-5H-cyclohepta[b]pyridin-2-yl)cyclopentyl)methanol;
(1-(4-(3-chlorophenyl)-3-(1H-tetrazol-5-yl)-6,7,8,9-tetrahydro-5H-cyclohepta[b]pyridin-2-yl)cyclopentyl)methanol;
(1-(4-(4-fluorophenyl)-3-(1H-tetrazol-5-yl)-6,7,8,9-tetrahydro-5H-cyclohepta[b]pyridin-2-yl)cyclopentyl)methanol;
(S)-tert-butyl 2-(4-phenyl-3-(1H-tetrazol-5-yl)-6,7,8,9-tetrahydro-5H-cyclohepta[b]pyridin-2-yl)pyrrolidine-1-carboxylate;
(S)-4-phenyl-2-(pyrrolidin-2-yl)-3-(1H-tetrazol-5-yl)-6,7,8,9-tetrahydro-5H-cyclohepta[b]pyridine 2,2,2-trifluoroacetate;
2-cyclopentyl-4-phenyl-3-(1H-tetrazol-5-yl)-7,8-dihydro-5H-pyrido[2,3-c]azepin-9(6H)-one;
2-(1-methoxy-2-methylpropan-2-yl)-6,6-dimethyl-4-(1-methyl-1H-pyrazol-5-yl)-3-(2H-tetrazol-5-yl)-5,6,7,8-tetrahydroquinoline;

6,6-dimethyl-4-(1-methyl-1H-pyrazol-5-yl)-2-tert-pentyl-3-(2H-tetrazol-5-yl)-5,6,7,8-tetrahydroquinoline;

2-(1-methoxy-2-methylpropan-2-yl)-6,6-dimethyl-4-(2-methylpyridin-4-yl)-3-(2H-tetrazol-5-yl)-5,6,7,8-tetrahydroquinoline;

2-(1-(methoxymethyl)cyclopentyl)-4-phenyl-3-(2H-tetrazol-5-yl)-5,6,7,8-tetrahydroquinoline;

6,6-difluoro-2-(1-(methoxymethyl)cyclopentyl)-4-phenyl-3-(2H-tetrazol-5-yl)-5,6,7,8-tetrahydroquinoline;

6,6-difluoro-2-(1-methoxymethyl-cyclohexyl)-4-phenyl-3-(1H-tetrazol-5-yl)-5,6,7,8-tetrahydro-quinoline;

6,6-difluoro-2-(1-(methoxymethyl)cyclopentyl)-4-(2-methylpyridin-4-yl)-3-(2H-tetrazol-5-yl)-5,6,7,8-tetrahydroquinoline;

2-(4-methyltetrahydro-2H-pyran-4-yl)-4-phenyl-3-(2H-tetrazol-5-yl)-5,6,7,8-tetrahydroquinoline;

6,6-difluoro-2-(4-methyltetrahydro-2H-pyran-4-yl)-4-phenyl-3-(2H-tetrazol-5-yl)-5,6,7,8-tetrahydroquinoline;

2-(1-(methoxymethyl)cyclopentyl)-6-methyl-4-(2-methylpyridin-4-yl)-3-(2H-tetrazol-5-yl)-5,6,7,8-tetrahydroquinoline;

2-(1-(methoxymethyl)cyclohexyl)-4-phenyl-3-(2H-tetrazol-5-yl)-5,6,7,8-tetrahydroquinoline;

6,6-difluoro-2-(1-(methoxymethyl)cyclopentyl)-4-(1-methyl-1H-pyrazol-5-yl)-3-(2H-tetrazol-5-yl)-5,6,7,8-tetrahydroquinoline;

2-(1-(methoxymethyl)cyclopentyl)-6,6-dimethyl-4-(1-methyl-1H-pyrazol-5-yl)-3-(2H-tetrazol-5-yl)-5,6,7,8-tetrahydroquinoline;

2-(2-methyltetrahydrofuran-2-yl)-4-phenyl-3-(2H-tetrazol-5-yl)-5,6,7,8-tetrahydroquinoline;

6,6-difluoro-2-(2-methyltetrahydrofuran-2-yl)-4-phenyl-3-(2H-tetrazol-5-yl)-5,6,7,8-tetrahydroquinoline;

6,6-dimethyl-2-(2-methyltetrahydrofuran-2-yl)-4-phenyl-3-(2H-tetrazol-5-yl)-5,6,7,8-tetrahydroquinoline;

4-(1-methyl-1H-pyrazol-5-yl)-2-(2-methyltetrahydrofuran-2-yl)-3-(2H-tetrazol-5-yl)-5,6,7,8-tetrahydroquinoline;

6,6-dimethyl-4-(1-methyl-1H-pyrazol-5-yl)-2-(2-methyltetrahydrofuran-2-yl)-3-(2H-tetrazol-5-yl)-5,6,7,8-tetrahydroquinoline;

(R)-2-(2-methyltetrahydrofuran-2-yl)-4-phenyl-3-(2H-tetrazol-5-yl)-5,6,7,8-tetrahydroquinoline;

(S)-2-(2-methyltetrahydrofuran-2-yl)-4-phenyl-3-(2H-tetrazol-5-yl)-5,6,7,8-tetrahydroquinoline;

(R)-6,6-difluoro-2-(2-methyltetrahydrofuran-2-yl)-4-phenyl-3-(2H-tetrazol-5-yl)-5,6,7,8-tetrahydroquinoline;

(S)-6,6-difluoro-2-(2-methyltetrahydrofuran-2-yl)-4-phenyl-3-(2H-tetrazol-5-yl)-5,6,7,8-tetrahydroquinoline;

(R)-6,6-dimethyl-2-(2-methyltetrahydrofuran-2-yl)-4-phenyl-3-(2H-tetrazol-5-yl)-5,6,7,8-tetrahydroquinoline;

(S)-6,6-dimethyl-2-(2-methyltetrahydrofuran-2-yl)-4-phenyl-3-(2H-tetrazol-5-yl)-5,6,7,8-tetrahydroquinoline;

2-(1-(methoxymethyl)cyclopentyl)-4-(1-methyl-1H-pyrazol-5-yl)-3-(2H-tetrazol-5-yl)-5,6,7,8-tetrahydroquinoline;

2-(1-(methoxymethyl)cyclohexyl)-4-(1-methyl-1H-pyrazol-5-yl)-3-(2H-tetrazol-5-yl)-5,6,7,8-tetrahydroquinoline;

2-(1-(methoxymethyl)cyclohexyl)-6,6-dimethyl-4-(1-methyl-1H-pyrazol-5-yl)-3-(2H-tetrazol-5-yl)-5,6,7,8-tetrahydroquinoline;

6,6-difluoro-2-(1-(methoxymethyl)cyclohexyl)-4-(1-methyl-1H-pyrazol-5-yl)-3-(2H-tetrazol-5-yl)-5,6,7,8-tetrahydroquinoline;

6,6-difluoro-4-(1-methyl-1H-pyrazol-5-yl)-2-(2-methyltetrahydrofuran-2-yl)-3-(2H-tetrazol-5-yl)-5,6,7,8-tetrahydroquinoline;

2-(2-(methoxymethyl)tetrahydrofuran-2-yl)-4-phenyl-3-(2H-tetrazol-5-yl)-5,6,7,8-tetrahydroquinoline;

2-(1-(methoxymethyl)cyclohexyl)-4-(1-methyl-1H-pyrazol-4-yl)-3-(2H-tetrazol-5-yl)-5,6,7,8-tetrahydroquinoline;

2-(2-(methoxymethyl)tetrahydrofuran-2-yl)-6,6-dimethyl-4-phenyl-3-(2H-tetrazol-5-yl)-5,6,7,8-tetrahydroquinoline;

6,6-difluoro-2-(2-(methoxymethyl)tetrahydrofuran-2-yl)-4-phenyl-3-(2H-tetrazol-5-yl)-5,6,7,8-tetrahydroquinoline;

2-(2-ethyltetrahydrofuran-2-yl)-4-phenyl-3-(2H-tetrazol-5-yl)-5,6,7,8-tetrahydroquinoline;

2-(2-ethyltetrahydrofuran-2-yl)-6,6-dimethyl-4-phenyl-3-(2H-tetrazol-5-yl)-5,6,7,8-tetrahydroquinoline;

2-(2-ethyltetrahydrofuran-2-yl)-6,6-difluoro-4-phenyl-3-(2H-tetrazol-5-yl)-5,6,7,8-tetrahydroquinoline;

(R)-2-(2-(methoxymethyl)tetrahydrofuran-2-yl)-4-phenyl-3-(2H-tetrazol-5-yl)-5,6,7,8-tetrahydroquinoline;

(S)-2-(2-(methoxymethyl)tetrahydrofuran-2-yl)-4-phenyl-3-(2H-tetrazol-5-yl)-5,6,7,8-tetrahydroquinoline;

(R)-6,6-difluoro-2-(2-(methoxymethyl)tetrahydrofuran-2-yl)-4-phenyl-3-(2H-tetrazol-5-yl)-5,6,7,8-tetrahydroquinoline;

(S)-6,6-difluoro-2-(2-(methoxymethyl)tetrahydrofuran-2-yl)-4-phenyl-3-(2H-tetrazol-5-yl)-5,6,7,8-tetrahydroquinoline;

(R)-2-(2-(methoxymethyl)tetrahydrofuran-2-yl)-6,6-dimethyl-4-phenyl-3-(2H-tetrazol-5-yl)-5,6,7,8-tetrahydroquinoline;

(S)-2-(2-(methoxymethyl)tetrahydrofuran-2-yl)-6,6-dimethyl-4-phenyl-3-(2H-tetrazol-5-yl)-5,6,7,8-tetrahydroquinoline;

2-(2-ethyltetrahydrofuran-2-yl)-4-(1-methyl-1H-pyrazol-5-yl)-3-(2H-tetrazol-5-yl)-5,6,7,8-tetrahydroquinoline;

2-(1-(methoxymethyl)cyclopentyl)-4-(1-methyl-1H-pyrazol-4-yl)-3-(2H-tetrazol-5-yl)-5,6,7,8-tetrahydroquinoline;

4-(3-chlorophenyl)-2-(2-(methoxymethyl)tetrahydrofuran-2-yl)-3-(2H-tetrazol-5-yl)-5,6,7,8-tetrahydroquinoline;

4-(3-chlorophenyl)-2-(2-methyltetrahydrofuran-2-yl)-3-(2H-tetrazol-5-yl)-5,6,7,8-tetrahydroquinoline;

2-(2-(methoxymethyl)tetrahydrofuran-2-yl)-4-(3-methoxyphenyl)-3-(2H-tetrazol-5-yl)-5,6,7,8-tetrahydroquinoline;

4-(4-fluoro-3-methoxyphenyl)-2-(2-(methoxymethyl)tetrahydrofuran-2-yl)-3-(2H-tetrazol-5-yl)-5,6,7,8-tetrahydroquinoline;

2-(1-(methyl sulfonylmethyl)cyclopentyl)-4-phenyl-3-(2H-tetrazol-5-yl)-5,6,7,8-tetrahydroquinoline;

(R)-4-(4-fluoro-3-methoxyphenyl)-2-(2-(methoxymethyl)tetrahydrofuran-2-yl)-3-(2H-tetrazol-5-yl)-5,6,7,8-tetrahydroquinoline;

(S)-4-(4-fluoro-3-methoxyphenyl)-2-(2-(methoxymethyl) tetrahydrofuran-2-yl)-3-(2H-tetrazol-5-yl)-5,6,7,8-tetrahydroquinoline;

2-(1-(methoxymethyl)cyclopentyl)-4-(3-(methylsulfonyl) phenyl)-3-(2H-tetrazol-5-yl)-5,6,7,8-tetrahydroquinoline;

2-(1-(methoxymethyl)cyclopentyl)-4-(3-methoxyphenyl)-3-(2H-tetrazol-5-yl)-5,6,7,8-tetrahydroquinoline;

4-(2-fluoro-5-methoxyphenyl)-2-(2-(methoxymethyl)tetrahydrofuran-2-yl)-3-(2H-tetrazol-5-yl)-5,6,7,8-tetrahydroquinoline;

4-(2-fluoro-5-methoxyphenyl)-2-(2-(methoxymethyl)tetrahydrofuran-2-yl)-3-(2H-tetrazol-5-yl)-5,6,7,8-tetrahydroquinoline;

2-(1-(ethoxymethyl)cyclopentyl)-4-phenyl-3-(2H-tetrazol-5-yl)-5,6,7,8-tetrahydroquinoline;

(R)-4-(3-chlorophenyl)-2-(2-(methoxymethyl)tetrahydrofuran-2-yl)-6,6-dimethyl-3-(2H-tetrazol-5-yl)-5,6,7,8-tetrahydroquinoline;

(S)-4-(3-chlorophenyl)-2-(2-(methoxymethyl)tetrahydrofuran-2-yl)-6,6-dimethyl-3-(2H-tetrazol-5-yl)-5,6,7,8-tetrahydroquinoline;

2-(3,3-difluorocyclobutyl)-4-(1-methyl-1H-pyrazol-4-yl)-3-(1H-tetrazol-5-yl)-6,7,8,9-tetrahydro-5H-cyclohepta[b]pyridine;

2-(1,5-dimethyl-1H-pyrazol-4-yl)-4-phenyl-3-(2H-tetrazol-5-yl)-6,7,8,9-tetrahydro-5H-cyclohepta[b]pyridine;

2-tert-butyl-4-(1-methyl-1H-pyrazol-4-yl)-3-(1H-tetrazol-5-yl)-6,7,8,9-tetrahydro-5H-cyclohepta[b]pyridine;

2-(3,3-difluorocyclobutyl)-4-(2-methylpyridin-4-yl)-3-(1H-tetrazol-5-yl)-6,7,8,9-tetrahydro-5H-cyclohepta[b]pyridine;

2-sec-butyl-4-(1-methyl-1H-pyrazol-4-yl)-3-(1H-tetrazol-5-yl)-6,7,8,9-tetrahydro-5H-cyclohepta[b]pyridine;

2-tert-butyl-6,6-difluoro-4-(2-methyl-pyridin-4-yl)-3-(1H-tetrazol-5-yl)-5,6,7,8-tetrahydro-quinoline;

2-tert-butyl-6,6-difluoro-4-(1-methyl-1H-pyrazol-4-yl)-3-(1H-tetrazol-5-yl)-5,6,7,8-tetrahydro-quinoline;

2-tert-butyl-6,6-difluoro-4-(2-methyl-2H-pyrazol-3-yl)-3-(1H-tetrazol-5-yl)-5,6,7,8-tetrahydro-quinoline;

2-tert-butyl-4-phenyl-3-(1H-tetrazol-5-yl)-7, 8-dihydro-5H-thiopyrano[4,3-b]pyridine;

2-tert-butyl-8, 8-dimethyl-4-phenyl-3-(1H-tetrazol-5-yl)-5,6,7,8-tetrahydroquinoline;

2-tert-butyl-7,7-dimethyl-4-phenyl-3-(1H-tetrazol-5-yl)-6,7-dihydro-5H-cyclopenta[b]pyridine;

2-tert-butyl-8, 8-dimethyl-4-(2-methylpyridin-4-yl)-3-(1H-tetrazol-5-yl)-5,6,7,8-tetrahydroquinoline;

2-tert-butyl-8, 8-dimethyl-4-(1-methyl-1H-pyrazol-4-yl)-3-(1H-tetrazol-5-yl)-5,6,7,8-tetrahydroquinoline;

2-(1-(methoxymethyl)cyclobutyl)-4-phenyl-3-(1H-tetrazol-5-yl)-6,7,8,9-tetrahydro-5H-cyclohepta[b]pyridine;

2-(1-(methoxymethyl)cyclobutyl)-4-(2-methylpyridin-4-yl)-3-(1H-tetrazol-5-yl)-6,7,8,9-tetrahydro-5H-cyclohepta[b]pyridine;

2-(1-(methoxymethyl)cyclobutyl)-4-(1-methyl-1H-pyrazol-4-yl)-3-(1H-tetrazol-5-yl)-6,7,8,9-tetrahydro-5H-cyclohepta[b]pyridine;

2-(perfluoroethyl)-4-phenyl-3-(1H-tetrazol-5-yl)-6,7,8,9-tetrahydro-5H-cyclohepta[b]pyridine;

2-tert-butyl-8, 8-dimethyl-4-(1-methyl-1H-pyrazol-5-yl)-3-(1H-tetrazol-5-yl)-5,6,7,8-tetrahydroquinoline;

2,4-bis(2-methylpyridin-4-yl)-3-(1H-tetrazol-5-yl)-6,7,8,9-tetrahydro-5H-cyclohepta[b]pyridine;

2-isopropoxy-4-phenyl-3-(1H-tetrazol-5-yl)-6,7,8,9-tetrahydro-5H-cyclohepta[b]pyridine;

2-methoxy-4-phenyl-3-(1H-tetrazol-5-yl)-6,7,8,9-tetrahydro-5H-cyclohepta[b]pyridine;

2-ethoxy-4-phenyl-3-(1H-tetrazol-5-yl)-6,7,8,9-tetrahydro-5H-cyclohepta[b]pyridine;

(S)-4-phenyl-2-(tetrahydrofuran-3-yloxy)-6,7,8,9-tetrahydro-5H-cyclohepta[b]pyridine-3-carbonitrile;

(R)-4-phenyl-2-(tetrahydrofuran-3-yloxy)-6,7,8,9-tetrahydro-5H-cyclohepta[b]pyridine-3-carbonitrile;

2-ethoxy-4-(1-methyl-1H-pyrazol-4-yl)-3-(1H-tetrazol-5-yl)-6,7,8,9-tetrahydro-5H-cyclohepta[b]pyridine;

2-isopropoxy-4-(1-methyl-1H-pyrazol-4-yl)-3-(1H-tetrazol-5-yl)-6,7,8,9-tetrahydro-5H-cyclohepta[b]pyridine;

2-ethoxy-4-(2-methylpyridin-4-yl)-3-(1H-tetrazol-5-yl)-6,7,8,9-tetrahydro-5H-cyclohepta[b]pyridine;

2-(2-methoxyethoxy)-4-phenyl-3-(1H-tetrazol-5-yl)-6,7,8,9-tetrahydro-5H-cyclohepta[b]pyridine;

4-phenyl-2-((tetrahydrofuran-2-yl)methoxy)-3-(1H-tetrazol-5-yl)-6,7,8,9-tetrahydro-5H-cyclohepta[b]pyridine;

2-(3-fluoropropoxy)-4-phenyl-3-(1H-tetrazol-5-yl)-6,7,8,9-tetrahydro-5H-cyclohepta[b]pyridine;

2-(2,2-difluoroethoxy)-4-phenyl-3-(1H-tetrazol-5-yl)-6,7,8,9-tetrahydro-5H-cyclohepta[b]pyridine;

(S)-4-phenyl-2-(tetrahydrofuran-3-yloxy)-3-(1H-tetrazol-5-yl)-5,6,7,8-tetrahydroquinoline;

4-(2-methylpyridin-4-yl)-2-(tetrahydro-2H-pyran-4-yloxy)-3-(1H-tetrazol-5-yl)-6,7,8,9-tetrahydro-5H-cyclohepta[b]pyridine;

(S)-4-(2-methylpyridin-4-yl)-2-(tetrahydrofuran-3-yloxy)-3-(1H-tetrazol-5-yl)-6,7,8,9-tetrahydro-5H-cyclohepta[b]pyridine;

(S)-4-(2-methylpyridin-4-yl)-2-(tetrahydrofuran-3-yloxy)-3-(1H-tetrazol-5-yl)-5,6,7,8-tetrahydroquinoline;

2-(2-methoxyethoxy)-3-(1H-tetrazol-5-yl)-4-(4-(trifluoromethyl)phenyl)-6,7,8,9-tetrahydro-5H-cyclohepta[b]pyridine;

4-(3-fluorophenyl)-2-(2-methoxyethoxy)-3-(1H-tetrazol-5-yl)-6,7,8,9-tetrahydro-5H-cyclohepta[b]pyridine;

(S)-4-(3-fluorophenyl)-2-(tetrahydrofuran-3-yloxy)-3-(1H-tetrazol-5-yl)-5,6,7,8-tetrahydroquinoline;

4-(3,5-difluorophenyl)-2-(2-methoxyethoxy)-3-(1H-tetrazol-5-yl)-6,7,8,9-tetrahydro-5H-cyclohepta[b]pyridine;

(S)-4-(3-fluorophenyl)-2-(tetrahydrofuran-3-yloxy)-3-(1H-tetrazol-5-yl)-6,7,8,9-tetrahydro-5H-cyclohepta[b]pyridine;

(S)-4-(3, 5-difluorophenyl)-2-(tetrahydrofuran-3-yloxy)-3-(1H-tetrazol-5-yl)-6,7,8,9-tetrahydro-5H-cyclohepta[b]pyridine;

4-(2-fluorophenyl)-2-((S)-tetrahydrofuran-3-yloxy)-3-(1H-tetrazol-5-yl)-6,7,8,9-tetrahydro-5H-cyclohepta[b]pyridine;

4-(2-fluorophenyl)-2-(2-methoxyethoxy)-3-(1H-tetrazol-5-yl)-6,7,8,9-tetrahydro-5H-cyclohepta[b]pyridine;

(S)-2-(tetrahydrofuran-3-yloxy)-3-(1H-tetrazol-5-yl)-4-(thiophen-2-yl)-6,7,8,9-tetrahydro-5H-cyclohepta[b]pyridine;

2-(3-fluoropropoxy)-3-(1H-tetrazol-5-yl)-4-(thiophen-2-yl)-6,7,8,9-tetrahydro-5H-cyclohepta[b]pyridine;

(S)-2-(tetrahydrofuran-3-yloxy)-3-(1H-tetrazol-5-yl)-4-(thiophen-3-yl)-6,7,8,9-tetrahydro-5H-cyclohepta[b]pyridine;

4-phenyl-2-(tetrahydro-2H-pyran-4-yloxy)-3-(1H-tetrazol-5-yl)-6,7,8,9-tetrahydro-5H-cyclohepta[b]pyridine;

2-(1-methylcyclopentyl)-4-phenyl-6,7,8,9-tetrahydro-5H-cyclohepta[b]pyridine-3-carboxylic acid;

4-(3-chlorophenyl)-2-(1-methylcyclopentyl)-6,7,8,9-tetrahydro-5H-cyclohepta[b]pyridine-3-carboxylic acid;

4-(1-methyl-1H-pyrazol-5-yl)-2-(1-methylcyclohexyl)-6,7,8,9-tetrahydro-5H-cyclohepta[b]pyridine-3-carboxylic acid;

2-(1-methylcyclohexyl)-4-phenyl-6,7,8,9-tetrahydro-5H-cyclohepta[b]pyridine-3-carboxylic acid;

2-cyclohexyl-4-phenyl-6,7,8,9-tetrahydro-5H-cyclohepta[b]pyridine-3-carboxylic acid;

2-(1-methylcyclohexyl)-4-(2-methylpyridin-4-yl)-6,7,8,9-tetrahydro-5H-cyclohepta[b]pyridine-3-carboxylic acid;

2-cyclohexyl-4-(2-methylpyridin-4-yl)-6,7,8,9-tetrahydro-5H-cyclohepta[b]pyridine-3-carboxylic acid;

2-cyclopentyl-4-phenyl-5,6,7,8-tetrahydroquinoline-3-carboxylic acid;

2-(1-(methoxymethyl)cyclopentyl)-6-pentyl-4-phenyl-3-(1H-tetrazol-5-yl)-5,6,7,8-tetrahydroquinoline;

tert-butyl 2-methyl-2-(4-(2-methylpyridin-4-yl)-3-(1H-tetrazol-5-yl)-6,7,8,9-tetrahydro-5H-cyclohepta[b]pyridin-2-yl)propanoate; or, 2-methyl-2-(4-(2-methylpyridin-4-yl)-3-(1H-tetrazol-5-yl)-6,7,8,9-tetrahydro-5H-cyclohepta[b]pyridin-2-yl)propanoic acid;

and pharmaceutically acceptable salts thereof.

26. The compound of claim 1, selected from 6-methyl-4-(1-methyl-1H-pyrazol-5-yl)-2-(piperidin-1-yl)-3-(2H-tetrazol-5-yl)-5,6,7,8-tetrahydroquinoline;

4-(3-chlorophenyl)-N,N-diethyl-3-(1H-tetrazol-5-yl)-6,7,8,9-tetrahydro-5H-cyclohepta[b]pyridin-2-amine;

2-cyclopentyl-4-(2-methylpyridin-4-yl)-3-(1H-tetrazol-5-yl)-6,7,8,9-tetrahydro-5H-cyclohepta[b]pyridine;

4-phenyl-2-(tetrahydrofuran-2-yl)-3-(1H-tetrazol-5-yl)-6,7,8,9-tetrahydro-5H-cyclohepta[b]pyridine;

2-(1-(methoxymethyl)cyclopentyl)-4-(2-methylpyridin-4-yl)-3-(1H-tetrazol-5-yl)-6,7,8,9-tetrahydro-5H-cyclohepta[b]pyridine;

2-cyclopentyl-6,6-difluoro-4-phenyl-3-(2H-tetrazol-5-yl)-5,6,7,8-tetrahydroquinoline;

2-cyclopentyl-6-methyl-4-(2-methylpyridin-4-yl)-3-(2H-tetrazol-5-yl)-5,6,7,8-tetrahydroquinoline; or, 2-cyclopentyl-6,6-dimethyl-4-(2-methylpyridin-4-yl)-3-(2H-tetrazol-5-yl)-5,6,7,8-tetrahydroquinoline;

and pharmaceutically acceptable salts thereof.

27. The compound of claim 1, selected from 2-((R)-2-methyl-tetrahydro-furan-2-yl)-4-phenyl-3-(1H-tetrazol-5-yl)-6,7,8,9-tetrahydro-5H-cyclohepta[b]pyridine;

2-(1-methylcyclopentyl)-4-(2-methylpyridin-4-yl)-3-(1H-tetrazol-5-yl)-6,7,8,9-tetrahydro-5H-cyclohepta[b]pyridine;

4-(2-chloropyridin-4-yl)-2-(1-(methoxymethyl)cyclopentyl)-3-(1H-tetrazol-5-yl)-6,7,8,9-tetrahydro-5H-cyclohepta[b]pyridine;

(R)-6,6-dimethyl-2-(2-methyltetrahydrofuran-2-yl)-4-phenyl-3-(2H-tetrazol-5-yl)-5,6,7,8-tetrahydroquinoline;

(R)-2-(2-(methoxymethyl)tetrahydrofuran-2-yl)-4-phenyl-3-(2H-tetrazol-5-yl)-5,6,7,8-tetrahydroquinoline;

(S)-4-phenyl-2-(tetrahydrofuran-3-yloxy)-6,7,8,9-tetrahydro-5H-cyclohepta[b]pyridine-3-carbonitrile; or, 2-(1-methylcyclohexyl)-4-(2-methylpyridin-4-yl)-6,7,8,9-tetrahydro-5H-cyclohepta[b]pyridine-3-carboxylic acid;

and pharmaceutically acceptable salts thereof.

28. A process to prepare a compound of claim 1 comprising the reaction of a compound of formula (II) in the presence of a compound of formula (XXV), wherein M is sodium, trialkyltin or trialkylsilyl

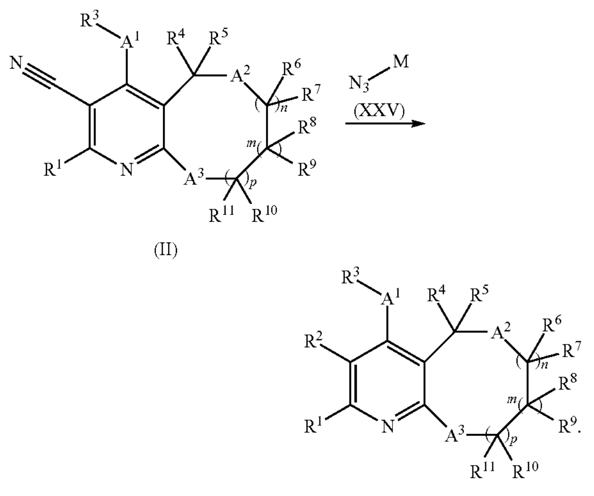

(II)

(I)

29. A pharmaceutical composition comprising a compound of claim 1 and a therapeutically inert carrier.

30. A compound of claim 1, when manufactured according to a process of claim 28.

* * * * *